(12) United States Patent
Galarza et al.

(10) Patent No.: US 11,389,522 B2
(45) Date of Patent: *Jul. 19, 2022

(54) FLAVIVIRUS AND ALPHA VIRUS VIRUS-LIKE PARTICLES (VLPS)

(71) Applicant: TechnoVax, Inc., Elmsford, NY (US)

(72) Inventors: Jose M. Galarza, Elmsford, NY (US); Helene Boigard, Elmsford, NY (US); George Martin, Elmsford, NY (US)

(73) Assignee: TECHNOVAX, INC., Elmsford, NY (US)

( * ) Notice: Subject to any disclaimer, the term of this patent is extended or adjusted under 35 U.S.C. 154(b) by 5 days.

This patent is subject to a terminal disclaimer.

(21) Appl. No.: 17/013,156

(22) Filed: Sep. 4, 2020

(65) Prior Publication Data
US 2020/0397887 A1    Dec. 24, 2020

Related U.S. Application Data

(63) Continuation of application No. 15/738,240, filed as application No. PCT/US2016/039011 on Jun. 23, 2016, now Pat. No. 10,799,575.

(60) Provisional application No. 62/292,936, filed on Feb. 9, 2016, provisional application No. 62/184,738, filed on Jun. 25, 2015.

(51) Int. Cl.
| | |
|---|---|
| *A61K 39/12* | (2006.01) |
| *A61K 39/145* | (2006.01) |
| *A61P 31/14* | (2006.01) |
| *C07K 14/005* | (2006.01) |
| *C12N 7/00* | (2006.01) |
| *C12N 9/50* | (2006.01) |
| *A61K 39/00* | (2006.01) |

(52) U.S. Cl.
CPC ............ *A61K 39/12* (2013.01); *A61K 39/145* (2013.01); *A61P 31/14* (2018.01); *C07K 14/005* (2013.01); *C12N 7/00* (2013.01); *C12N 9/506* (2013.01); *A61K 2039/5258* (2013.01); *C12N 2770/24023* (2013.01); *C12N 2770/24034* (2013.01); *C12N 2770/24134* (2013.01); *Y02A 50/30* (2018.01)

(58) Field of Classification Search
CPC combination set(s) only.
See application file for complete search history.

(56) References Cited

U.S. PATENT DOCUMENTS

| | | | | |
|---|---|---|---|---|
| 8,691,961 B1 * | 4/2014 | Puffer | ............ | C12N 7/00 536/23.72 |
| 2006/0280757 A1 | 12/2006 | Khromykh | | |
| 2008/0118528 A1 | 5/2008 | Liang et al. | | |
| 2010/0297174 A1 | 11/2010 | Garcia-Sastre et al. | | |
| 2011/0293649 A1 | 12/2011 | Bachmann et al. | | |
| 2012/0128713 A1 | 5/2012 | Pugachev et al. | | |
| 2016/0074501 A1 | 3/2016 | Akahata et al. | | |

OTHER PUBLICATIONS

International Search Report and Written Opinion in corresponding International Patent Application No. PCT/US2016/039011, dated Nov. 29, 2016. 8 pages.
International Preliminary Report on Patentability in corresponding International Patent Application No. PCT/US2016/039011, dated Dec. 26, 2017. 5 pages.
Amberg et al. "Mutagenesis of the NS2B-NS3-mediated cleavage site in the flavivirus capsid protein demonstrates a requirement for coordinated processing." Journal of virology 73.10 (1999): 8083-8094.
Konishi et al. "Dengue type 2 virus subviral extracellular particles produced by a stably transfected mammalian cell ine and their evaluation for a subunit vaccine." Vaccine 20.7-8 (2002): 1058-1067.
Li et al. "The serine protease and RNA-stimulated nucleoside Iriphosphalase and RNA helicase functional domains of dengue virus type 2 NS3 converge within a region of 20 amino acids." Journal of virology 73.4 (1999): 3108-3116.
Lobigs. "Flavivirus premembrane protein cleavage and spike heterodimer secretion require the function of the viral proteinase NS3." Proceedings of the National Academy of Sciences 90.13 (1993): 6218-6222.
Purdy et al. "Secretion of noninfectious dengue virus-like particles and identification of amino acids in the stem region involved in intracellular retention of envelope protein." Virology 333.2 (2005): 239-250.
Wang et al. "Efficient assembly and secretion of recombinant subviral particles of the four dengue serotypes using native prM and E proteins." PLoS One 4.12 (2009): e8325.
Zhang et al. "Vaccination with dengue virus-like particles induces humeral and cellular immune responses in mice." Virology journal 8.1(2011):333.
Yoshii et al. "Construction and application of chimeric virus-like particles of tick-borne encephalitis virus and mosquito-borne Japanese encephalitis virus." Journal of General Virology (2008), 89, 200-211.
Henn MR, et al. Polyprotein [Dengue virus 2]. GenBank: ACW82881. 1, Pub. Sep. 30, 2009.
Metz SW, Pijlman GP, "Arbovirus vaccines; opportunities for the baculovirus-insect cell expression system." J Invertebr Pathol. Jul. 2011;107 Suppl:S16-30.

* cited by examiner

*Primary Examiner* — Rachel B Gill
(74) *Attorney, Agent, or Firm* — Leason Ellis LLP

(57) ABSTRACT

Flavivirus virus-like particles (VLPs) are provided that display on their surfaces antigenic flavivirus proteins. The VLPs include at least one flavivirus structural protein and at least one non-structural flavivirus protein. A DNA construct that includes sequences encoding flavivirus viral proteins used to assemble the flavivirus VLP is also provided. A method of producing flavivirus VLPs by introducing one or more the DNA constructs into a host cell is also provided. An immunogenic composition that includes the flavivirus VLP is also provided.

18 Claims, 12 Drawing Sheets

Specification includes a Sequence Listing.

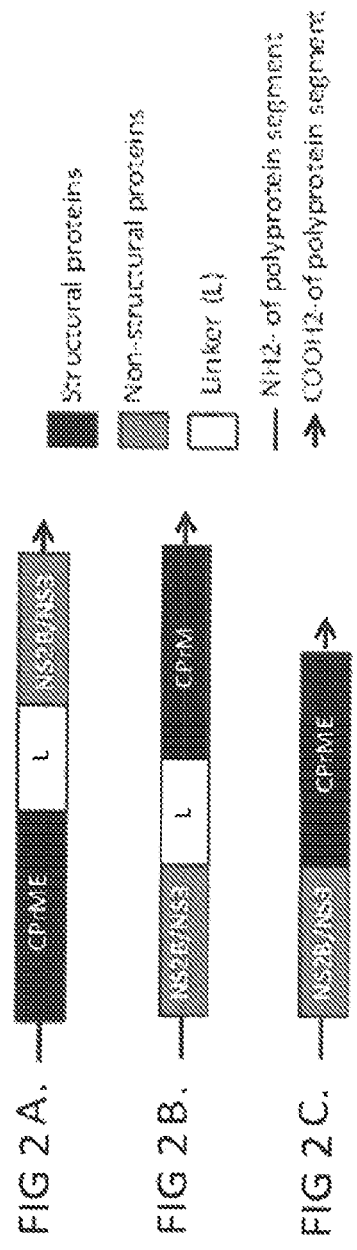

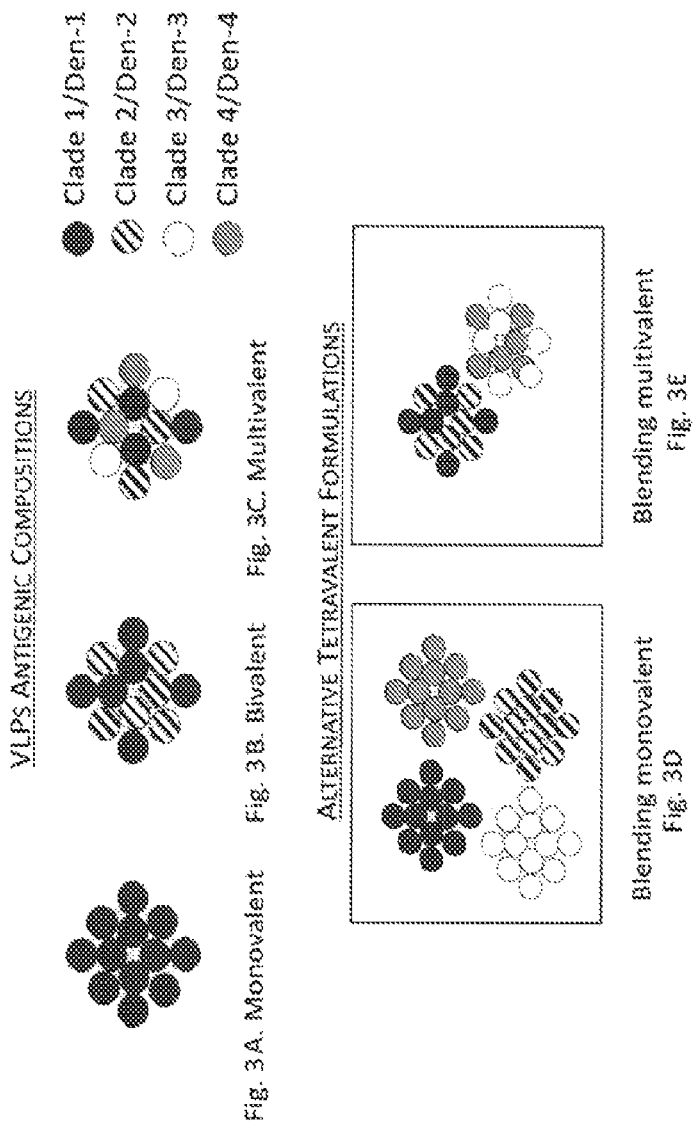

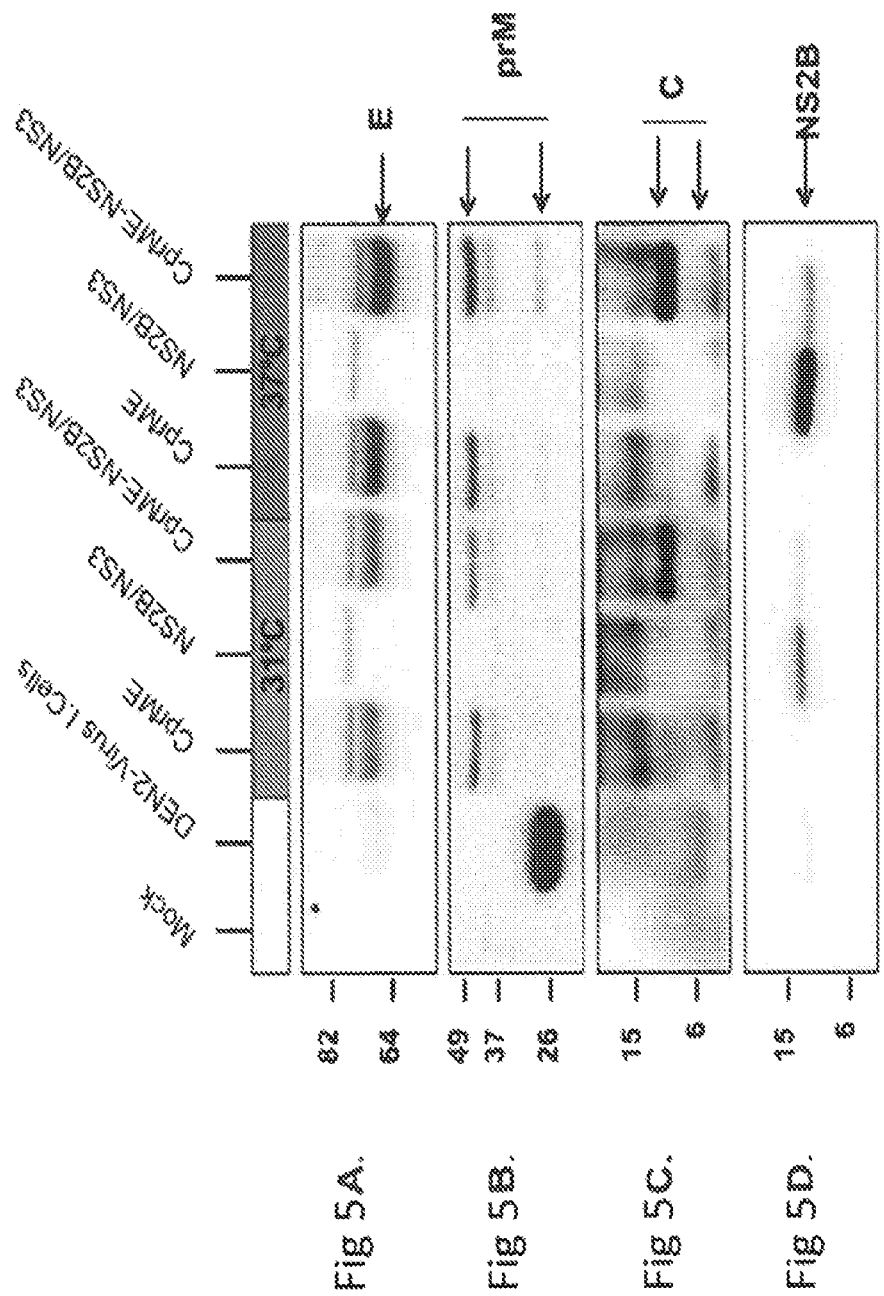

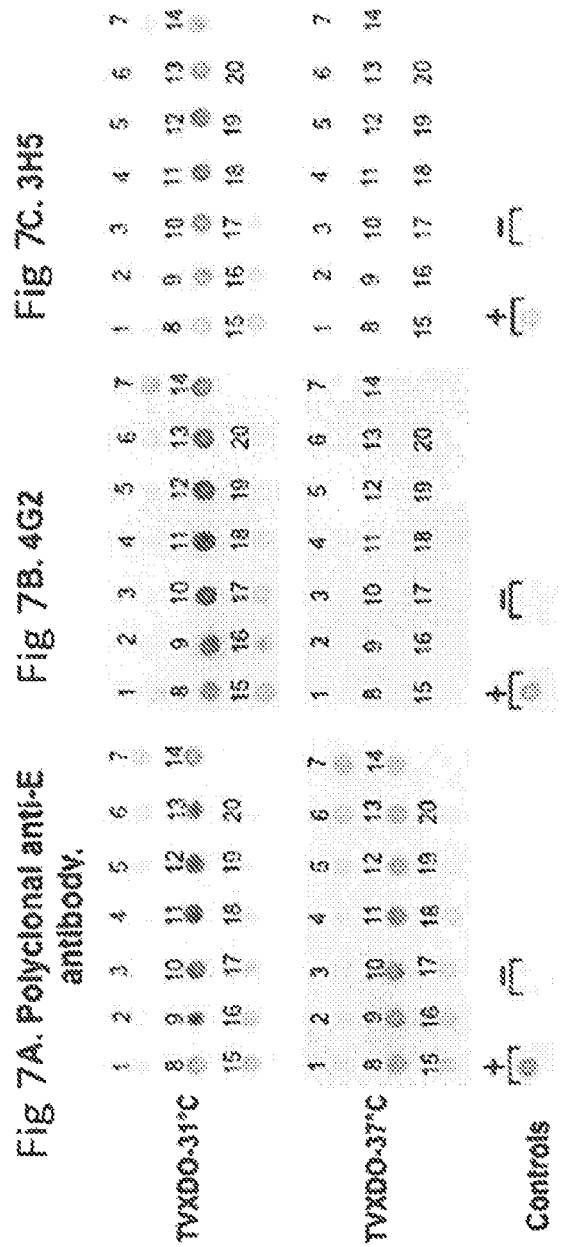

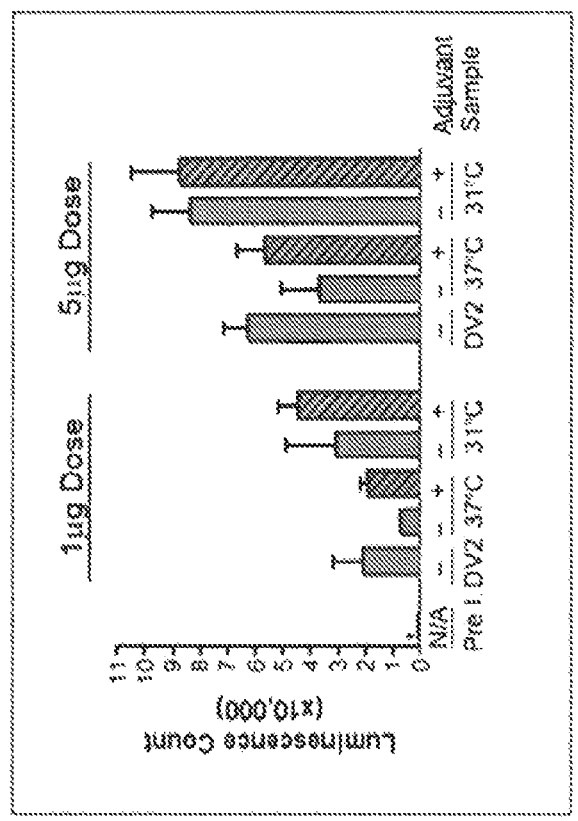
Figure 9
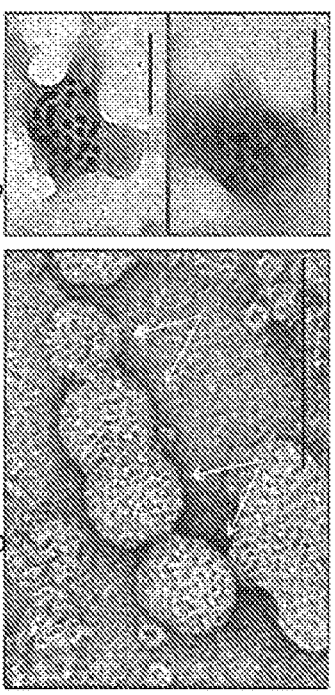
Figure 8A
Figure 8B

Figure 10

| | Neutralizing Titers Elicited by DENV-2 VLP Vaccine and Inactivated Virus | | |
|---|---|---|---|
| | Dose (µg) | Adjuvant | PRNT₅₀ |
| Pre Immune Pre-Immune | | | < 25 |
| Group 1 | 1 | | < 25 |
| Group 2 DENV-2 VLP 37°C | 1 | + | 57 |
| Group 3 | 5 | | < 25 |
| Group 4 | 5 | + | 382 |
| Group 5 | 1 | | 99 |
| Group 6 DENV-2 VLP 31°C | 1 | + | 371 |
| Group 7 | 5 | | 196 |
| Group 8 | 5 | + | 1067 |
| Group 9 Inactivated DEN-2 Virus | 1 | | 158 |
| Group 10 | 5 | | 201 |
| NIBSC- Human Pre-Immune Serum Control | | | < 25 |
| NIBSC- Human anti-DENV-2 Serum Control | | | 297 |

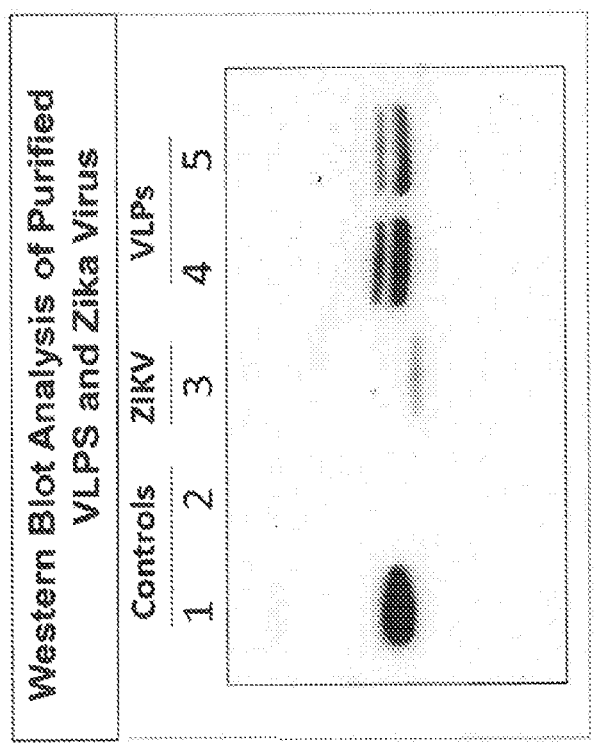

SEQUENCE LISTING

<160> NUMBER OF SEQ ID NOS: 48

<210> SEQ ID NO 1
<211> LENGTH: 2325
<212> TYPE: DNA
<213> ORGANISM: Dengue virus 2

<400> SEQUENCE: 1
atgaataacc aacggaaaaa ggcgaaaaac acgcctttca atatgctgaa acgcgagaga      60
aaccgcgtgt cgactgtgca acagctgaca aagagattct cacttggaat gctgcaggga     120
cgaggaccat taaaactgtt catggccctg gtggcgttcc ttcgtttcct aacaatccca    180

```
ccaacagcag ggatattgaa gagatgggga acaattaaaa aatcaaaagc tattaatgtt    240
ttgagagggt tcaggaaaga gattggaagg atgctgaaca tcttgaatag agacgcaga     300 tctgcaggca tgatcattat gctgattcca acagtgatgg cgttccattt aaccacacgt    360 aacgagaac cacacatgat cgtcagcaga caagagaaag ggaaaagtct tctgtttaaa     420
acagaggatg gcgtgaacat gtgtaccctc atggccatgg accttggtga attgtgtgaa    480
gacacaatca cgtacaagtg tccccttctc aggcagaatg agccagaaga catagactgt    540
tggtgcaact ctacgtccac gtgggtaact tatgggacgt gtaccaccat gggagaacat    600
agaagagaaa aaagatcagt ggcactcgtt ccacatgtgg gaatgggact ggagacacga    660
actgaaacat ggatgtcatc agaaggggcc tggaaacatg tccagagaat gaaacttgg     720 atcttgagac atccaggctt caccatgatg gcagcaatcc tggcatacac catagga acg    780 acacatttcc aaagagccct gattttcatc ttactgacag ctgtcactcc ttcaatgaca    840
atgcgttgca taggaatgtc aaatagagac tttgtggaag gggtttcagg aggaagctgg    900
gttgacatag tcttagaaca tggaagctgt gtgacgacga tggcaaaaaa caaaccaaca    960
ttggattttg aactgataaa aacagaagcc aaacagcctg ccacccta agg gaagtactgt    1020 atagaggcaa agctaaccaa cacaacaaca gaatctcgct gcccaacaca aggggaaccc    1080
agcctaaatg aagagcagga caaaaggttc gtctgcaaac actccatggt agacagagga    1140
tggggaaatg gatgtggact atttggaaag ggaggcattg tgacctgtgc tatgttcaga    1200
tgcaaaaaga catggaagg aaaagttgtg caaccagaaa acttggaata caccattgtg    1260
ataacacctc actcagggga gagcatgca gtcggaaatg acacaggaaa acatggcaag    1320
gaaatcaaaa taacaccaca gagttccatc acagaagcag aattgacagg ttatggcact    1380
gtcacaatgg agtgctctcc aagaacgggc ctcgacttca atgagatggt gttgctgcag    1440
atggaaaata aagcttggct ggtgcacagg caatggttcc tagacctgcc gttaccatgg    1500
ttgcccggag cggacacaca agggtcaaat tggatacaga aagagacatt ggtcactttc    1560
aaaaatcccc atgcgaagaa acaggatgtt gttgttttag gatcccaaga aggggccatg    1620
cacacagcac ttacagggc cacagaaatc caaatgtcat caggaaactt actcttcaca    1680
ggacatctca gtgcaggct gagaatggaa aagctacagc tcaaaggaat gtcatactct    1740
atgtgcacag gaaagtttaa agttgtgaag gaaatagcag aaacacaaca tggaacaata    1800
gttatcagag tgcaatatga aggggacggc tctccatgca agatccctt tgagataatg    1860 gatttggaaa aaagacatgt cttaggtcgc ctgattacag tcaacccaat tgtgacagaa    1920
aaagatagcc cagtcaacat agaagcagaa cctccattcg agacagcta catcatcata    1980 ggagtagagc cggacaact gaagctcaac tggtttaaga aggaagttc tatcggccaa    2040 atgtttgaga caacaatgag ggggcgaag agaatggcca ttttaggtga cacagcctgg    2100 gatttttggat ccttgggagg agtgtttaca tctataggaa aggctctcca ccaagtcttt    2160
ggagcaatct atggagctgc cttcagtggg gttcatgga ctatgaaaat cctcatagga     2220
gtcattatca catggatagg aatgaattca cgcagcacct cactgtctgt gacactagta    2280
ttggtgggaa ttgtgacact gtatttggga gtcatggtgc aggcc                    2325
```

<210> SEQ ID NO 2
<211> LENGTH: 775
<212> TYPE: PRT
<213> ORGANISM: Dengue virus 2

<400> SEQUENCE: 2

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Glu Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415
```

Tyr Thr Ile Val Ile Thr Pro His Ser Gly Glu His Ala Val Gly
                420                 425                 430

Asn Asp Thr Gly Lys His Gly Lys Glu Ile Lys Ile Thr Pro Gln Ser
            435                 440                 445

Ser Ile Thr Glu Ala Glu Leu Thr Gly Tyr Gly Thr Val Thr Met Glu
        450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Leu Gly Ser Gln Glu Gly Ala Met His Thr Ala Leu
530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Ile Gly Gln Met Phe Glu Thr Thr Met Arg Gly
        675                 680                 685

Ala Lys Arg Met Ala Ile Leu Gly Asp Thr Ala Trp Asp Phe Gly Ser
690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser
            740                 745                 750

Thr Ser Leu Ser Val Thr Leu Val Leu Val Gly Ile Val Thr Leu Tyr
        755                 760                 765

Leu Gly Val Met Val Gln Ala
    770                 775

<210> SEQ ID NO 3
<211> LENGTH: 2328
<212> TYPE: DNA
<213> ORGANISM: Dengue virus 2

<400> SEQUENCE: 3
atgaataacc aacggaaaaa ggcgaaaaac acgcctttca atatgctgaa acgcgagaga      60

```
aaccgcgtgt cgactgtgca acagctgaca aagagattct cacttggaat gctgcaggga    120
cgaggaccat taaaactgtt catggccctg gtggcgttcc ttcgtttcct aacaatccca    180
ccaacagcag ggatattgaa gagatgggga acaattaaaa aatcaaaagc tattaatgtt    240
ttgagagggt tcaggaaaga gattggaagg atgctgaaca tcttgaatag agacgcaga     300 tctgcaggca tgatcattat gctgattcca acagtgatgg cgttccattt aaccacacgt    360
aacgagaaac cacacatgat cgtcagcaga caagagaaag gaaaagtct tctgtttaaa     420 acagaggatg gcgtgaacat gtgtaccctc atggccatgg accttggtga attgtgtgaa    480
gacacaatca cgtacaagtg tccccttctc aggcagaatg agccagaaga catagactgt    540
tggtgcaact ctacgtccac gtgggtaact tatgggacgt gtaccaccat gggagaacat    600
agaagagcaa aaagatcagt ggcactcgtt ccacatgtgg gaatgggact ggagacacga    660
actgaaacat ggatgtcatc agaaggggcc tggaaacatg tccagagaat gaaacttgg    720 atcttgagac atccaggctt caccatgatg gcagcaatcc tggcatacac cataggaacg    780
acacatttcc aaagagccct gattttcatc ttactgacag ctgtcactcc ttcaatgaca    840
atgcgttgca taggaatgtc aaatagagac tttgtggaag gggtttcagg aggaagctgg    900
gttgacatag tcttagaaca tggaagctgt gtgacgacga tggcaaaaaa caaaccaaca    960
ttggattttg aactgataaa aacagaagcc aaacagcctg ccaccctaag gaagtactgt   1020
atagaggcaa agctaaccaa cacaacaaca gaatctcgct gcccaacaca aggggaaccc   1080
agcctaaatg aagagcagga caaaaggttc gtctgcaaac actccatggt agacagagga   1140
tggggaaatg gatgtggact atttggaaag ggaggcattg tgacctgtgc tatgttcaga   1200
tgcaaaaaga acatggaagg aaaagttgtg caaccagaaa acttggaata caccattgtg   1260
ataacacctc actcagggga gagcatgca gtcggaaatg acacaggaaa acatggcaag   1320
gaaatcaaaa taacaccaca gagttccatc acagaagcag aattgacagg ttatggcact   1380
gtcacaatgg agtgctctcc aagaacgggc ctcgacttca tgagatggt gttgctgcag   1440 atggaaaata aagcttggct ggtgcacagg caatggttcc tagacctgcc gttaccatgg   1500 ttgcccgag cggacacaca agggtcaaat tggatacaga aagagacatt ggtcactttc   1560
aaaaatcccc atgcgaagaa acaggatgtt gttgttttag gatcccaaga agggcatg    1620 cacacagcac ttcaggggc cacagaaatc caaatgtcat caggaaactt actcttcaca   1680
ggacatctca gtgcaggct gagaatggac aagctacagc tcaaaggaat gtcatactct   1740
atgtgcacag gaaagtttaa agttgtgaag gaaatagcag aaacacaaca tggaacaata   1800
gttatcagag tgcaatatga agggacggc tctccatgca agatccctt tgagataatg    1860 gatttggaaa aagacatgt cttaggtcgc ctgattacag tcaacccaat tgtgacagaa    1920
aaagatagcc cagtcaacat agaagcagaa cctccattcg agacagcta tcatcatca   1980 ggagtagagc cggacaact gaagctcaac tggtttaaga aggaagttc tttgggccaa   2040 gccttggaga caacaatgag ggggcgaag agattggcca ttttaggtga cacagcctgg   2100 gatttggat ccttgggagg agtgtttaca tctataggaa aggctctcca ccaagtcttt   2160
ggagcaatct atggagctgc cttcagtggg gtttcatgga ctatgaaaat cctcatagga   2220
gtcattatca catggatagg aatgaattca cgcagcacct cactgtctgt gacactagta   2280
ttggtgggaa ttgtgacact gtatttggga gtcatggtgc aggcctag               2328

<210> SEQ ID NO 4
```

<211> LENGTH: 2328
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 4

| | |
|---|---|
| atgaacaacc agcgcaagaa ggccaaaaac actccgttca atatgctcaa gagagagcgc | 60 |
| aatcgggttt ctacggtaca gcagctgacg aagagattct ccctgggcat gctgcaaggt | 120 |
| cgcggaccac tgaagctgtt catggcccctt gttgcatttc ttaggttttct tacaattccc | 180 |
| cccactgctg gaatcctgaa gcggtggggc accatcaaaa agtccaaggc tattaatgtc | 240 |
| ctcaggggggt tcaggaaaga gattgggcgg atgctgaaca tccttaatag acgcagacgg | 300 |
| tccgctggca tgataatcat gctgatccca accgtcatgg ccttccacct gactacccga | 360 |
| aatggagagc cccacatgat cgtgagcaga caagagaagg ggaagagtct cctgttcaag | 420 |
| acagaagatg gcgtgaacat gtgcacactg atggccatgg atctcggcga actgtgtgaa | 480 |
| gacactatca cctacaaatg ccctctcctc cgccaaaatg aaccagaaga tattgactgt | 540 |
| tggtgtaatt caacaagtac atgggtgacc tatggcacct gtaccaccat gggtgaacat | 600 |
| cgacgggcga agagaagtgt ggccctcgtc cctcatgtcg gcatggggtt ggagaccaga | 660 |
| acagaaacct ggatgagctc cgagggcgcc tggaaaacg tgcagcggat cgaaacatgg | 720 |
| attttgcggc accctggatt tactatgatg gctgccattc tggcttacac aataggcacc | 780 |
| acacactttc agcgggcgct tatctttatc ctcctgacag cagtaacacc ctctatgacc | 840 |
| atgaggtgca tcgggatgtc aaaccgggac tttgttgagg gggtcagcgg tggatcttgg | 900 |
| gtggatatcg tgctggaaca cggatcttgc gtgaccacca tggcaaagaa taagcccaca | 960 |
| cttgattttg aattgattaa aaccgaggca aaacagccag ccactcttcg caaatactgc | 1020 |
| atcgaggcca agctgaccaa cacaaccaca gaatcccgat gccctaccca aggtgagcct | 1080 |
| tctcttaacg aagagcagga caaacggttc gtgtgtaagc attccatggt ggacaggggg | 1140 |
| tgggggaatg gatgcgggct cttcgggaag ggcgggatcg tcacatgtgc aatgtttaga | 1200 |
| tgtaagaaaa atatggaagg caaagttgtg cagccagaga atctggaata tactattgtg | 1260 |
| ataacgcctc actcaggtga agagcacgct gtaggcaacg ataccggcaa gcacggaaag | 1320 |
| gaaatcaaga taactccaca gtcaagcatc acggaagctg agttgacagg tacggcact | 1380 |
| gtcaccatgg agtgcagccc acgcactggt ctggacttca atgagatggt gcttctccag | 1440 |
| atggaaaaca agcctggct ggttcatagg caatggtttc ttgatcttcc tttgccctgg | 1500 |
| ctgcctggag cagatacaca gggttctaat tggatccaaa aggaaaccct tgtgaccttc | 1560 |
| aagaacccgc atgcaaagaa gcaggatgtg gtggtcctcg gctctcagga gggagccatg | 1620 |
| cacaccgccc ttaccggagc cacagagatc cagatgagct ctggtaacct cctctttacc | 1680 |
| gggcatctga gtgtcgcct tagaatggat aaactgcagc tcaaaggtat gtcctacagc | 1740 |
| atgtgcacag gtaaattcaa agtggtgaag gaaatagctg agactcagca cggcacaatc | 1800 |
| gtcatccgag ttcaatatga gggtgacgga agcccatgta aaatcccttt cgaaattatg | 1860 |
| gacctggaaa acgccacgt gctgggccga cttatcactg ttaatcccat agtcacagag | 1920 |
| aaggactctc cagttaacat cgaggccgag cctcccttcg ggactccta tcatcatc | 1980 |
| ggcgttgaac ctgccaatt gaagctgaac tggttcaaaa agggttcctc actgggacag | 2040 |
| gccttcgaaa cgacaatgag aggcgcaaag agactggcta tcctcggcga tacagcatgg | 2100 |

```
gacttcgggt ccctgggagg agtattcaca agcataggga aggccctgca ccaagtgttc    2160
ggtgcgatct atggtgcggc cttctcagga gtcagttgga ccatgaagat tctgattggc    2220
gtcataatta cgtggattgg tatgaattca aggtctacat ctttgtccgt gactctggtc    2280
ctggtgggaa ttgtgacttt gtatctcggc gtgatggtgc aagcctag                2328
```

<210> SEQ ID NO 5
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
                20                  25                  30

Phe Ser Leu Gly Met Leu Gln Gly Arg Gly Pro Leu Lys Leu Phe Met
            35                  40                  45

Ala Leu Val Ala Phe Leu Arg Phe Leu Thr Ile Pro Pro Thr Ala Gly
        50                  55                  60

Ile Leu Lys Arg Trp Gly Thr Ile Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Asn Gly Glu Pro His Met Ile Val
        115                 120                 125

Ser Arg Gln Glu Lys Gly Lys Ser Leu Leu Phe Lys Thr Glu Asp Gly
    130                 135                 140

Val Asn Met Cys Thr Leu Met Ala Met Asp Leu Gly Glu Leu Cys Glu
145                 150                 155                 160

Asp Thr Ile Thr Tyr Lys Cys Pro Leu Leu Arg Gln Asn Glu Pro Glu
                165                 170                 175

Asp Ile Asp Cys Trp Cys Asn Ser Thr Ser Thr Trp Val Thr Tyr Gly
            180                 185                 190

Thr Cys Thr Thr Met Gly Glu His Arg Arg Ala Lys Arg Ser Val Ala
        195                 200                 205

Leu Val Pro His Val Gly Met Gly Leu Glu Thr Arg Thr Glu Thr Trp
    210                 215                 220

Met Ser Ser Glu Gly Ala Trp Lys His Val Gln Arg Ile Glu Thr Trp
225                 230                 235                 240

Ile Leu Arg His Pro Gly Phe Thr Met Met Ala Ala Ile Leu Ala Tyr
                245                 250                 255

Thr Ile Gly Thr Thr His Phe Gln Arg Ala Leu Ile Phe Ile Leu Leu
            260                 265                 270

Thr Ala Val Thr Pro Ser Met Thr Met Arg Cys Ile Gly Met Ser Asn
        275                 280                 285

Arg Asp Phe Val Glu Gly Val Ser Gly Gly Ser Trp Val Asp Ile Val
    290                 295                 300

Leu Glu His Gly Ser Cys Val Thr Thr Met Ala Lys Asn Lys Pro Thr
305                 310                 315                 320
```

-continued

Leu Asp Phe Glu Leu Ile Lys Thr Glu Ala Lys Gln Pro Ala Thr Leu
                325                 330                 335

Arg Lys Tyr Cys Ile Glu Ala Lys Leu Thr Asn Thr Thr Thr Glu Ser
            340                 345                 350

Arg Cys Pro Thr Gln Gly Glu Pro Ser Leu Asn Glu Glu Gln Asp Lys
        355                 360                 365

Arg Phe Val Cys Lys His Ser Met Val Asp Arg Gly Trp Gly Asn Gly
    370                 375                 380

Cys Gly Leu Phe Gly Lys Gly Ile Val Thr Cys Ala Met Phe Arg
385                 390                 395                 400

Cys Lys Lys Asn Met Glu Gly Lys Val Val Gln Pro Glu Asn Leu Glu
                405                 410                 415

Tyr Thr Ile Val Ile Thr Pro His Ser Gly Glu Glu His Ala Val Gly
            420                 425                 430

Asn Asp Thr Gly Lys His Gly Lys Glu Ile Lys Ile Thr Pro Gln Ser
        435                 440                 445

Ser Ile Thr Glu Ala Glu Leu Thr Gly Tyr Gly Thr Val Thr Met Glu
    450                 455                 460

Cys Ser Pro Arg Thr Gly Leu Asp Phe Asn Glu Met Val Leu Leu Gln
465                 470                 475                 480

Met Glu Asn Lys Ala Trp Leu Val His Arg Gln Trp Phe Leu Asp Leu
                485                 490                 495

Pro Leu Pro Trp Leu Pro Gly Ala Asp Thr Gln Gly Ser Asn Trp Ile
            500                 505                 510

Gln Lys Glu Thr Leu Val Thr Phe Lys Asn Pro His Ala Lys Lys Gln
        515                 520                 525

Asp Val Val Val Leu Gly Ser Gln Glu Gly Ala Met His Thr Ala Leu
    530                 535                 540

Thr Gly Ala Thr Glu Ile Gln Met Ser Ser Gly Asn Leu Leu Phe Thr
545                 550                 555                 560

Gly His Leu Lys Cys Arg Leu Arg Met Asp Lys Leu Gln Leu Lys Gly
                565                 570                 575

Met Ser Tyr Ser Met Cys Thr Gly Lys Phe Lys Val Val Lys Glu Ile
            580                 585                 590

Ala Glu Thr Gln His Gly Thr Ile Val Ile Arg Val Gln Tyr Glu Gly
        595                 600                 605

Asp Gly Ser Pro Cys Lys Ile Pro Phe Glu Ile Met Asp Leu Glu Lys
    610                 615                 620

Arg His Val Leu Gly Arg Leu Ile Thr Val Asn Pro Ile Val Thr Glu
625                 630                 635                 640

Lys Asp Ser Pro Val Asn Ile Glu Ala Glu Pro Pro Phe Gly Asp Ser
                645                 650                 655

Tyr Ile Ile Ile Gly Val Glu Pro Gly Gln Leu Lys Leu Asn Trp Phe
            660                 665                 670

Lys Lys Gly Ser Ser Leu Gly Gln Ala Phe Glu Thr Thr Met Arg Gly
        675                 680                 685

Ala Lys Arg Leu Ala Ile Leu Gly Asp Thr Ala Trp Asp Phe Gly Ser
    690                 695                 700

Leu Gly Gly Val Phe Thr Ser Ile Gly Lys Ala Leu His Gln Val Phe
705                 710                 715                 720

Gly Ala Ile Tyr Gly Ala Ala Phe Ser Gly Val Ser Trp Thr Met Lys
                725                 730                 735

Ile Leu Ile Gly Val Ile Ile Thr Trp Ile Gly Met Asn Ser Arg Ser

```
                 740              745              750
Thr Ser Leu Ser Val Thr Leu Val Leu Val Gly Ile Val Thr Leu Tyr
         755              760              765
Leu Gly Val Met Val Gln Ala
         770              775

<210> SEQ ID NO 6
<211> LENGTH: 2244
<212> TYPE: DNA
<213> ORGANISM: Dengue virus 2

<400> SEQUENCE: 6
agctggccat taaatgaggc tatcatggca gtcgggatgg tgagcatttt agccagttct      60
ctcctaaaaa atgatattcc catgacagga ccattagtgg ctggagggct cctcactgtg     120
tgctacgtgc tcactggacg atcggccgat ttggaactgg agagagcagc cgatgtcaaa     180
tgggaagacc aggcagagat atcaggaagc agtccaatcc tgtcaataac aatatcagaa     240
gatggtagca tgtcgataaa aaatgaagag gaagaacaaa cactgaccat actcattaga     300
acaggattgc tggtgatctc aggacttttt cctgtatcaa taccaatcac ggcagcagca     360
tggtacctgt gggaagtgaa gaaacaacgg ccggagtat tgtgggatgt tccttcaccc     420
ccacccatgg gaaaggctga actggaagat ggagcctata gaattaagca aaaagggatt     480
cttggatatt cccagatcgg agccggagtt tacaaagaag aacattcca tacaatgtgg     540 catgtcacac gtggcgctgt tctaatgcat aaaggaaaga ggattgaacc atcatgggcg     600
gacgtcaaga aagacctaat atcatatgga ggaggctgga gttagaagg agaatggaag     660 gaaggagaag aagtccaggt attggcactg agcctggaa aaaatccaag agccgtccaa     720
acgaaacctg gtcttttcaa accaacgcc ggaacaatag tgctgtatc tctggacttt     780 tctcctggaa cgtcaggatc tccaattatc gacaaaaaag gaaaagttgt gggtctttat     840
ggtaatggtt tgttacaag gagtggagca tatgtgagtg ctatagccca gactgaaaaa     900
agcattgaag acaacccaga gatcgaagat gacattttcc gaaagagaag actgaccatc     960 atggaccctcc acccaggagc gggaaagacg aagagatacc ttccggccat agtcagagaa    1020
gctataaaac ggggtttgag aacattaatc ttggccccca ctagagttgt ggcagctgaa    1080
atggaggaag cccttagagg acttccaata agataccaga ccccagccat cagagctgag    1140 cacaccggc gggagattgt ggacctaatg tgtcatgcca catttaccat gaggctgcta    1200
tcaccagtta gagtgccaaa ctacaacctg attatcatgg acgaagccca tttcacagac    1260
ccagcaagta tagcagctag gaggatacatc tcaactcgag tggagatggg tgaggcagct    1320
gggattttta tgacagccac tccccgggga agcagagacc catttcctca gagcaatgca    1380
ccaatcatag atgaagaaag agaaatccct gaacgttcgt ggaattccgg acatgaatgg    1440
gtcacggatt ttaagggaa gactgtttgg ttcgttccaa gtataaaagc aggaaatgat    1500
atagcagctt gcctgaggaa aaatggaaag aaagtgatac aactcagtag gaagaccttt    1560
gattctgagt atgtcaagac tagaaccaat gattgggact tcgtggttac aactgacatt    1620
tcagaaatgg gtgccaattt caaggctgag agggttatga ccccagacg ctgcatgaaa    1680 ccagtcatac taacagatgg tgaagagcgg gtgattctgg caggacctat gccagtgacc    1740
cactctagtg cagcacaaag aagagggaga ataggaagaa atccaaaaaa tgagaatgac    1800
cagtacatat acatgggga acctctggaa aatgatgaag actgtgcaca ctggaaagaa    1860
gctaaaatgc tcctagataa catcaacacg ccagaaggaa tcattcctag catgttcgaa    1920
```

```
ccagagcgtg aaaaggtgga tgccattgat ggcgaatacc gcttgagagg agaagcaagg   1980
aaaacctttg tagacttaat gagaagagga gacctaccag tctggttggc ctacagagtg   2040
gcagctgaag gcatcaacta cgcagacaga aggtggtgtt ttgatggagt caagaacaac   2100
caaatcctag aagaaaacgt ggaagttgaa atctggacaa agaaggggaa aggaagaaa    2160 ttgaaaccca gatggttgga tgctaggatc tattctgacc cactggcgct aaaagaattt   2220
aaggaatttg cagccggaag aaag                                          2244
```

<210> SEQ ID NO 7
<211> LENGTH: 748
<212> TYPE: PRT
<213> ORGANISM: Dengue virus 2

<400> SEQUENCE: 7

```
Met Ser Trp Pro Leu Asn Glu Ala Ile Met Ala Val Gly Met Val Ser
1               5                   10                  15

Ile Leu Ala Ser Ser Leu Leu Lys Asn Asp Ile Pro Met Thr Gly Pro
            20                  25                  30

Leu Val Ala Gly Gly Leu Leu Thr Val Cys Tyr Val Leu Thr Gly Arg
        35                  40                  45

Ser Ala Asp Leu Glu Leu Glu Arg Ala Ala Asp Val Lys Trp Glu Asp
    50                  55                  60

Gln Ala Glu Ile Ser Gly Ser Ser Pro Ile Leu Ser Ile Thr Ile Ser
65                  70                  75                  80

Glu Asp Gly Ser Met Ser Ile Lys Asn Glu Glu Glu Glu Gln Thr Leu
                85                  90                  95

Thr Ile Leu Ile Arg Thr Gly Leu Leu Val Ile Ser Gly Leu Phe Pro
            100                 105                 110

Val Ser Ile Pro Ile Thr Ala Ala Ala Trp Tyr Leu Trp Glu Val Lys
        115                 120                 125

Lys Gln Arg Ala Gly Val Leu Trp Asp Val Pro Ser Pro Pro Pro Met
130                 135                 140

Gly Lys Ala Glu Leu Glu Asp Gly Ala Tyr Arg Ile Lys Gln Lys Gly
145                 150                 155                 160

Ile Leu Gly Tyr Ser Gln Ile Gly Ala Gly Val Tyr Lys Glu Gly Thr
                165                 170                 175

Phe His Thr Met Trp His Val Thr Arg Gly Ala Val Leu Met His Lys
            180                 185                 190

Gly Lys Arg Ile Glu Pro Ser Trp Ala Asp Val Lys Lys Asp Leu Ile
        195                 200                 205

Ser Tyr Gly Gly Gly Trp Lys Leu Glu Gly Glu Trp Lys Glu Gly Glu
    210                 215                 220

Glu Val Gln Val Leu Ala Leu Glu Pro Gly Lys Asn Pro Arg Ala Val
225                 230                 235                 240

Gln Thr Lys Pro Gly Leu Phe Lys Thr Asn Ala Gly Thr Ile Gly Ala
                245                 250                 255

Val Ser Leu Asp Phe Ser Pro Gly Thr Ser Gly Ser Pro Ile Ile Asp
            260                 265                 270

Lys Lys Gly Lys Val Val Gly Leu Tyr Gly Asn Gly Val Val Thr Arg
        275                 280                 285

Ser Gly Ala Tyr Val Ser Ala Ile Ala Gln Thr Glu Lys Ser Ile Glu
    290                 295                 300

Asp Asn Pro Glu Ile Glu Asp Asp Ile Phe Arg Lys Arg Arg Leu Thr
```

```
                305                 310                 315                 320
        Ile Met Asp Leu His Pro Gly Ala Gly Lys Thr Lys Arg Tyr Leu Pro
                        325                 330                 335

Ala Ile Val Arg Glu Ala Ile Lys Arg Gly Leu Arg Thr Leu Ile Leu
                        340                 345                 350

Ala Pro Thr Arg Val Val Ala Ala Glu Met Glu Glu Ala Leu Arg Gly
                        355                 360                 365

Leu Pro Ile Arg Tyr Gln Thr Pro Ala Ile Arg Ala Glu His Thr Gly
                        370                 375                 380

Arg Glu Ile Val Asp Leu Met Cys His Ala Thr Phe Thr Met Arg Leu
        385                 390                 395                 400

Leu Ser Pro Val Arg Val Pro Asn Tyr Asn Leu Ile Ile Met Asp Glu
                        405                 410                 415

Ala His Phe Thr Asp Pro Ala Ser Ile Ala Ala Arg Gly Tyr Ile Ser
                        420                 425                 430

Thr Arg Val Glu Met Gly Glu Ala Ala Gly Ile Phe Met Thr Ala Thr
                        435                 440                 445

Pro Pro Gly Ser Arg Asp Pro Phe Pro Gln Ser Asn Ala Pro Ile Ile
                        450                 455                 460

Asp Glu Glu Arg Glu Ile Pro Glu Arg Ser Trp Asn Ser Gly His Glu
        465                 470                 475                 480

Trp Val Thr Asp Phe Lys Gly Lys Thr Val Trp Phe Val Pro Ser Ile
                        485                 490                 495

Lys Ala Gly Asn Asp Ile Ala Ala Cys Leu Arg Lys Asn Gly Lys Lys
                        500                 505                 510

Val Ile Gln Leu Ser Arg Lys Thr Phe Asp Ser Glu Tyr Val Lys Thr
                        515                 520                 525

Arg Thr Asn Asp Trp Asp Phe Val Val Thr Thr Asp Ile Ser Glu Met
                        530                 535                 540

Gly Ala Asn Phe Lys Ala Glu Arg Val Ile Asp Pro Arg Arg Cys Met
        545                 550                 555                 560

Lys Pro Val Ile Leu Thr Asp Gly Glu Glu Arg Val Ile Leu Ala Gly
                        565                 570                 575

Pro Met Pro Val Thr His Ser Ser Ala Ala Gln Arg Arg Gly Arg Ile
                        580                 585                 590

Gly Arg Asn Pro Lys Asn Glu Asn Asp Gln Tyr Ile Tyr Met Gly Glu
                        595                 600                 605

Pro Leu Glu Asn Asp Glu Asp Cys Ala His Trp Lys Glu Ala Lys Met
                        610                 615                 620

Leu Leu Asp Asn Ile Asn Thr Pro Glu Gly Ile Ile Pro Ser Met Phe
        625                 630                 635                 640

Glu Pro Glu Arg Glu Lys Val Asp Ala Ile Asp Gly Glu Tyr Arg Leu
                        645                 650                 655

Arg Gly Glu Ala Arg Lys Thr Phe Val Asp Leu Met Arg Arg Gly Asp
                        660                 665                 670

Leu Pro Val Trp Leu Ala Tyr Arg Val Ala Ala Glu Gly Ile Asn Tyr
                        675                 680                 685

Ala Asp Arg Arg Trp Cys Phe Asp Gly Val Lys Asn Asn Gln Ile Leu
                        690                 695                 700

Glu Glu Asn Val Glu Val Glu Ile Trp Thr Lys Glu Gly Glu Arg Lys
        705                 710                 715                 720

Lys Leu Lys Pro Arg Trp Leu Asp Ala Arg Ile Tyr Ser Asp Pro Leu
                        725                 730                 735
```

Ala Leu Lys Glu Phe Lys Glu Phe Ala Ala Gly Arg
            740                 745

<210> SEQ ID NO 8
<211> LENGTH: 939
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
atgagttggc ctctgaacga ggcaataatg gcggtgggga tggtgagcat acttgcatca      60
agcctgctga agaacgacat ccctatgact ggtcccctgg tggccggcgg cctgctgacg     120
gtctgttatg tgctgaccgg caggtccgca gacttggagc tggaaagggc tgccgacgtc     180
aagtgggagg accaggccga atttcagga agcagtccca tcctgagtat cacaatttcc     240
gaggacggtt caatgtccat caagaatgaa gaggaagagc agacactgac catactgatt     300
cgcaccggcc tgcttgttat tagtggcttg ttccctgtat ctatccctat cactgccgcc     360
gcctggtatc tctgggaagt aaagaagcag cgggcaggcg tactctggga tgtgccttcc     420
cccccaccta tgggaaaggc ggaactggag gacggtgcat accgcattaa gcaaaaaggc     480
atcctcggat acagccagat cggagccggg gtgtataaag aaggaacctt tcatactatg     540
tggcacgtga ctagaggggc ggtgcttatg cataagggta aaaggattga accatcctgg     600
gcagatgtga aaaagacct gatctcctac ggggtggct ggaagctgga aggggaatgg      660
aaggaaggag aggaggttca ggtccttgcc ctggaaccag gtaagaatcc ccgcgccgtg     720
cagacaaagc cgggcgcttt caagactaat gcgggaacca tcggagctgt ctccttggat     780
ttcagcccag gcacctccgg ttctcccatc atcgacaaaa agggcaaagt cgttgggctc     840
tatgggaatg gggtggtgac gcgctcagga gcctatgttt ctgcaatagc tcagaccgag     900
aagtcaatcg aagataaccc ggaaatcgaa gatgattag                            939
```

<210> SEQ ID NO 9
<211> LENGTH: 312
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Ser Trp Pro Leu Asn Glu Ala Ile Met Ala Val Gly Met Val Ser
1               5                  10                  15

Ile Leu Ala Ser Ser Leu Leu Lys Asn Asp Ile Pro Met Thr Gly Pro
            20                  25                  30

Leu Val Ala Gly Gly Leu Leu Thr Val Cys Tyr Val Leu Thr Gly Arg
        35                  40                  45

Ser Ala Asp Leu Glu Leu Glu Arg Ala Ala Asp Val Lys Trp Glu Asp
    50                  55                  60

Gln Ala Glu Ile Ser Gly Ser Ser Pro Ile Leu Ser Ile Thr Ile Ser
65                  70                  75                  80

Glu Asp Gly Ser Met Ser Ile Lys Asn Glu Glu Glu Glu Gln Thr Leu
                85                  90                  95

Thr Ile Leu Ile Arg Thr Gly Leu Leu Val Ile Ser Gly Leu Phe Pro
            100                 105                 110

Val Ser Ile Pro Ile Thr Ala Ala Ala Trp Tyr Leu Trp Glu Val Lys
            115                 120                 125

Lys Gln Arg Ala Gly Val Leu Trp Asp Val Pro Ser Pro Pro Pro Met
130                 135                 140

Gly Lys Ala Glu Leu Glu Asp Gly Ala Tyr Arg Ile Lys Gln Lys Gly
145                 150                 155                 160

Ile Leu Gly Tyr Ser Gln Ile Gly Ala Gly Val Tyr Lys Glu Gly Thr
                165                 170                 175

Phe His Thr Met Trp His Val Thr Arg Gly Ala Val Leu Met His Lys
            180                 185                 190

Gly Lys Arg Ile Glu Pro Ser Trp Ala Asp Val Lys Lys Asp Leu Ile
            195                 200                 205

Ser Tyr Gly Gly Gly Trp Lys Leu Glu Gly Glu Trp Lys Glu Gly Glu
            210                 215                 220

Glu Val Gln Val Leu Ala Leu Glu Pro Gly Lys Asn Pro Arg Ala Val
225                 230                 235                 240

Gln Thr Lys Pro Gly Ala Phe Lys Thr Asn Ala Gly Thr Ile Gly Ala
                245                 250                 255

Val Ser Leu Asp Phe Ser Pro Gly Thr Ser Gly Ser Pro Ile Ile Asp
            260                 265                 270

Lys Lys Gly Lys Val Val Gly Leu Tyr Gly Asn Gly Val Val Thr Arg
            275                 280                 285

Ser Gly Ala Tyr Val Ser Ala Ile Ala Gln Thr Glu Lys Ser Ile Glu
            290                 295                 300

Asp Asn Pro Glu Ile Glu Asp Asp
305                 310

<210> SEQ ID NO 10
<211> LENGTH: 396
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atgagttggc ctctgaacga ggcaataatg gcggtgggga tggtgagcat acttgcatca      60
agcctgctga gaacgacat ccctatgact ggtccctgg tggccggcgg cctgctgacg       120
gtctgttatg tgctgaccgg caggtccgca gacttggagc tggaaagggc tgccgacgtc     180
aagtgggagg accaggccga aatttcagga agcagtccca tcctgagtat cacaatttcc     240
gaggacggtt caatgtccat caagaatgaa gaggaagagc agacactgac catactgatt     300
cgcaccggcc tgcttgttat tagtggcttg ttccctgtat ctatccctat cactgccgcc     360
gcctggtatc tctgggaagt aaagaagcag cggtag                               396

<210> SEQ ID NO 11
<211> LENGTH: 131
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Ser Trp Pro Leu Asn Glu Ala Ile Met Ala Val Gly Met Val Ser
1               5                   10                  15

Ile Leu Ala Ser Ser Leu Leu Lys Asn Asp Ile Pro Met Thr Gly Pro

```
            20                  25                  30
Leu Val Ala Gly Gly Leu Leu Thr Val Cys Tyr Val Leu Thr Gly Arg
        35                  40                  45

Ser Ala Asp Leu Glu Leu Glu Arg Ala Ala Asp Val Lys Trp Glu Asp
    50                  55                  60

Gln Ala Glu Ile Ser Gly Ser Ser Pro Ile Leu Ser Ile Thr Ile Ser
65                  70                  75                  80

Glu Asp Gly Ser Met Ser Ile Lys Asn Glu Glu Glu Gln Thr Leu
                85                  90                  95

Thr Ile Leu Ile Arg Thr Gly Leu Leu Val Ile Ser Gly Leu Phe Pro
            100                 105                 110

Val Ser Ile Pro Ile Thr Ala Ala Ala Trp Tyr Leu Trp Glu Val Lys
        115                 120                 125

Lys Gln Arg
    130

<210> SEQ ID NO 12
<211> LENGTH: 546
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
gcaggcgtac tctgggatgt gccttccccc ccacctatgg gaaaggcgga actggaggac      60
ggtgcatacc gcattaagca aaaggcatc ctcggataca gccagatcgg agccggggtg     120
tataaagaag gaacctttca tactatgtgg cacgtgacta gagggggcggt gcttatgcat    180 aagggtaaaa ggattgaacc atcctgggca gatgtgaaaa agacctgat ctcctacggg     240 ggtggctgga agctggaagg ggaatggaag gaaggagagg aggttcaggt ccttgccctg    300
gaaccaggta agaatccccg cgccgtgcag acaaagccgg gcgctttcaa gactaatgcg    360
ggaaccatcg gagctgtctc cttggatttc agcccaggca cctccggttc tcccatcatc    420
gacaaaaagg gcaaagtcgt tgggctctat gggaatgggg tggtgacgcg ctcaggagcc    480
tatgtttctg caatagctca gaccgagaag tcaatcgaag ataacccgga aatcgaagat    540
gattag                                                                546

<210> SEQ ID NO 13
<211> LENGTH: 181
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ala Gly Val Leu Trp Asp Val Pro Ser Pro Pro Met Gly Lys Ala
1               5                   10                  15

Glu Leu Glu Asp Gly Ala Tyr Arg Ile Lys Gln Lys Gly Ile Leu Gly
            20                  25                  30

Tyr Ser Gln Ile Gly Ala Gly Val Tyr Lys Glu Gly Thr Phe His Thr
        35                  40                  45

Met Trp His Val Thr Arg Gly Ala Val Leu Met His Lys Gly Lys Arg
    50                  55                  60

Ile Glu Pro Ser Trp Ala Asp Val Lys Lys Asp Leu Ile Ser Tyr Gly
65                  70                  75                  80
```

```
Gly Gly Trp Lys Leu Glu Gly Glu Trp Lys Glu Gly Glu Val Gln
            85                  90                  95

Val Leu Ala Leu Glu Pro Gly Lys Asn Pro Arg Ala Val Gln Thr Lys
            100                 105                 110

Pro Gly Ala Phe Lys Thr Asn Ala Gly Thr Ile Gly Ala Val Ser Leu
            115                 120                 125

Asp Phe Ser Pro Gly Thr Ser Gly Ser Pro Ile Ile Asp Lys Lys Gly
            130                 135                 140

Lys Val Val Gly Leu Tyr Gly Asn Gly Val Val Thr Arg Ser Gly Ala
145                 150                 155                 160

Tyr Val Ser Ala Ile Ala Gln Thr Glu Lys Ser Ile Glu Asp Asn Pro
                165                 170                 175

Glu Ile Glu Asp Asp
            180

<210> SEQ ID NO 14
<211> LENGTH: 1069
<212> TYPE: DNA
<213> ORGANISM: Dengue virus 2

<400> SEQUENCE: 14
gatagtggtt gcgttgtgag ctggaaaaac aaagaactga atgtggcag tgggattttc      60
atcacagaca acgtgcacac atggacagaa caatacaagt ccaaccaga tccccttca     120
aaactagctt cagctatcca gaaagcccat gaagagggca tttgtggaat ccgctcagta    180
acaagactgg agaatctgat gtggaaacaa ataacaccag aattgaatca cattctatca    240
gaaaatgagg tgaagttaac tattatgaca ggagacatca aggaatcat gcaggcagga    300
aaacgatctc tgcggcctca gcccactgag ctgaagtatt catggaaaac atggggcaaa    360
gcaaaaatgc tctctacaga gtctcataac cagaccttc tcattgatgg ccccgaaaca    420
gcagaatgcc ccaacacaaa tagagcttgg aattcgttgg aagttgaaga ctatggcttt    480
ggagtattca ccaccaatat atggctaaaa ttgaaagaaa acaggatgt attctgcgac    540
tcaaaactca tgtcagcggc cataaaagac aacagagccg tccatgccga tatgggttat    600
tggatagaaa gtgcactcaa tgacacatgg aagatagaga agcctctttt cattgaagtt    660
aaaaactgcc actggccaaa atcacacacc ctctggagca atggagtgct agaaagtgag    720
atgataattc caaagaatct cgctggacca gtgtctcaac acaactatag accaggctac    780
catacacaaa taacaggacc atggcatcta ggtaagcttg agatggactt tgatttctgt    840
gatggaacaa cagtggtagt gactgaggac tgcggaaata gaggaccctc tttgagaaca    900
accactgcct ctggaaaact cataacagaa tggtgctgcc gatcttgcac attaccaccg    960
ctaagataca gaggtgagga tgggtgctgg tacgggatgg aaatcagacc attgaaggag   1020
aaagaagaga atttggtcaa ctccttggtc acagctggac atgggcagg                1069

<210> SEQ ID NO 15
<211> LENGTH: 356
<212> TYPE: PRT
<213> ORGANISM: Dengue virus 2

<400> SEQUENCE: 15

Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30
```

Lys Phe Gln Pro Glu Ser Pro Ser Lys Leu Ala Ser Ala Ile Gln Lys
             35                  40                  45

Ala His Glu Glu Gly Ile Cys Gly Ile Arg Ser Val Thr Arg Leu Glu
         50                  55                  60

Asn Leu Met Trp Lys Gln Ile Thr Pro Glu Leu Asn His Ile Leu Ser
 65                  70                  75                  80

Glu Asn Glu Val Lys Leu Thr Ile Met Thr Gly Asp Ile Lys Gly Ile
                 85                  90                  95

Met Gln Ala Gly Lys Arg Ser Leu Arg Pro Gln Pro Thr Glu Leu Lys
             100                 105                 110

Tyr Ser Trp Lys Thr Trp Gly Lys Ala Lys Met Leu Ser Thr Glu Ser
             115                 120                 125

His Asn Gln Thr Phe Leu Ile Asp Gly Pro Glu Thr Ala Glu Cys Pro
         130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Lys Glu Lys Gln Asp
                 165                 170                 175

Val Phe Cys Asp Ser Lys Leu Met Ser Ala Ala Ile Lys Asp Asn Arg
            180                 185                 190

Ala Val His Ala Asp Met Gly Tyr Trp Ile Glu Ser Ala Leu Asn Asp
            195                 200                 205

Thr Trp Lys Ile Glu Lys Ala Ser Phe Ile Glu Val Lys Asn Cys His
        210                 215                 220

Trp Pro Lys Ser His Thr Leu Trp Ser Asn Gly Val Leu Glu Ser Glu
225                 230                 235                 240

Met Ile Ile Pro Lys Asn Leu Ala Gly Pro Val Ser Gln His Asn Tyr
                245                 250                 255

Arg Pro Gly Tyr His Thr Gln Ile Thr Gly Pro Trp His Leu Gly Lys
            260                 265                 270

Leu Glu Met Asp Phe Asp Phe Cys Asp Gly Thr Thr Val Val Val Thr
            275                 280                 285

Glu Asp Cys Gly Asn Arg Gly Pro Ser Leu Arg Thr Thr Thr Ala Ser
        290                 295                 300

Gly Lys Leu Ile Thr Glu Trp Cys Cys Arg Ser Cys Thr Leu Pro Pro
305                 310                 315                 320

Leu Arg Tyr Arg Gly Glu Asp Gly Cys Trp Tyr Gly Met Glu Ile Arg
                325                 330                 335

Pro Leu Lys Glu Lys Glu Glu Asn Leu Val Asn Ser Leu Val Thr Ala
            340                 345                 350

Gly His Gly Gln
        355

<210> SEQ ID NO 16
<211> LENGTH: 654
<212> TYPE: DNA
<213> ORGANISM: Dengue virus 2

<400> SEQUENCE: 16
gacatgggca gggtcgacaa cttttcacta ggagtcttgg gaatggcatt gttcctggag      60
gaaatgctta ggacccgagt aggaacgaaa catgcaatac tactagttgc agtttctttt     120
gtgacattga tcacagggaa catgtccttt agagacctgg aagagtgat ggttatggta      180 ggcgccacta tgacggatga cataggtatg ggcgtgactt atcttgccct actagcagcc     240

```
ttcaaagtca gaccaacttt tgcagctgga ctactcttga gaaagctgac ctccaaggaa    300
ttgatgatga ctactatagg aattgtactc ctctcccaga gcaccatacc agagaccatt    360
cttgagttga ctgatgcgtt agccttaggc atgatggtcc tcaaaatggt gagaaatatg    420
gaaaagtatc aattggcagt gactatcatg gctatcttgt gcgtcccaaa cgcagtgata    480
ttacaaaacg catggaaagt gagttgcaca atattggcag tggtgtccgt ttccccactg    540
ctcttaacat cctcacagca aaaaacagat tggataccat tagcattgac gatcaaaggt    600
ctcaatccaa cagctatttt tctaacaacc ctctcaagaa ccagcaagaa aagg          654
```
<210> SEQ ID NO 17
<211> LENGTH: 218
<212> TYPE: PRT
<213> ORGANISM: Dengue virus 2

<400> SEQUENCE: 17
```

Gly His Gly Gln Val Asp Asn Phe Ser Leu Gly Val Leu Gly Met Ala
1               5                   10                  15

Leu Phe Leu Glu Glu Met Leu Arg Thr Arg Val Gly Thr Lys His Ala
            20                  25                  30

Ile Leu Leu Val Ala Val Ser Phe Val Thr Leu Ile Thr Gly Asn Met
        35                  40                  45

Ser Phe Arg Asp Leu Gly Arg Val Met Val Met Val Gly Ala Thr Met
    50                  55                  60

Thr Asp Asp Ile Gly Met Gly Val Thr Tyr Leu Ala Leu Leu Ala Ala
65                  70                  75                  80

Phe Lys Val Arg Pro Thr Phe Ala Ala Gly Leu Leu Leu Arg Lys Leu
                85                  90                  95

Thr Ser Lys Glu Leu Met Met Thr Thr Ile Gly Ile Val Leu Leu Ser
            100                 105                 110

Gln Ser Thr Ile Pro Glu Thr Ile Leu Glu Leu Thr Asp Ala Leu Ala
        115                 120                 125

Leu Gly Met Met Val Leu Lys Met Val Arg Asn Met Glu Lys Tyr Gln
    130                 135                 140

Leu Ala Val Thr Ile Met Ala Ile Leu Cys Val Pro Asn Ala Val Ile
145                 150                 155                 160

Leu Gln Asn Ala Trp Lys Val Ser Cys Thr Ile Leu Ala Val Val Ser
                165                 170                 175

Val Ser Pro Leu Leu Leu Thr Ser Ser Gln Gln Lys Thr Asp Trp Ile
            180                 185                 190

Pro Leu Ala Leu Thr Ile Lys Gly Leu Asn Pro Thr Ala Ile Phe Leu
        195                 200                 205

Thr Thr Leu Ser Arg Thr Ser Lys Lys Arg
    210                 215

```
<210> SEQ ID NO 18
<211> LENGTH: 1854
<212> TYPE: DNA
<213> ORGANISM: Dengue virus 2

<400> SEQUENCE: 18

```
gccggagtat tgtgggatgt tccttcaccc ccacccatgg gaaaggctga actggaagat     60
ggagcctata gaattaagca aaaagggatt cttggatatt cccagatcgg agccggagtt    120
tacaaagaag gaacattcca tacaatgtgg catgtcacac gtggcgctgt tctaatgcat    180
```

| | |
|---|---|
| aaaggaaaga ggattgaacc atcatgggcg gacgtcaaga aagacctaat atcatatgga | 240 |
| ggaggctgga agttagaagg agaatggaag gaaggagaag aagtccaggt attggcactg | 300 |
| gagcctggaa aaaatccaag agccgtccaa acgaaacctg gtcttttcaa aaccaacgcc | 360 |
| ggaacaatag gtgctgtatc tctggacttt tctcctggaa cgtcaggatc tccaattatc | 420 |
| gacaaaaaag gaaaagttgt gggtctttat ggtaatggtg ttgttacaag gagtggagca | 480 |
| tatgtgagtg ctatagccca gactgaaaaa agcattgaag acaacccaga gatcgaagat | 540 |
| gacattttcc gaaagagaag actgaccatc atggacctcc acccaggagc gggaaagacg | 600 |
| aagagatacc ttccggccat agtcagagaa gctataaaac gggggtttga gacattaatc | 660 |
| ttggcccccca ctagagttgt ggcagctgaa atggaggaag cccttagagg acttccaata | 720 |
| agataccaga ccccagccat cagagctgag cacaccgggc gggagattgt ggacctaatg | 780 |
| tgtcatgcca catttaccat gaggctgcta tcaccagtta gagtgccaaa ctacaacctg | 840 |
| attatcatgg acgaagccca tttcacagac ccagcaagta tagcagctag aggatacatc | 900 |
| tcaactcgag tggagatggg tgaggcagct gggatttta tgacagccac tcccccggga | 960 |
| agcagagacc catttcctca gagcaatgca ccaatcatag atgaagaaag agaaatccct | 1020 |
| gaacgttcgt ggaattccgg acatgaatgg gtcacggatt ttaaagggaa gactgtttgg | 1080 |
| ttcgttccaa gtataaaagc aggaaatgat atagcagctt gcctgaggaa aaatggaaag | 1140 |
| aaagtgatac aactcagtag gaagaccttt gattctgagt atgtcaagac tagaaccaat | 1200 |
| gattgggact cgtggttac aactgacatt tcagaaatgg gtgccaattt caaggctgag | 1260 |
| agggttatag accccagacg ctgcatgaaa ccagtcatac taacagatgg tgaagagcgg | 1320 |
| gtgattctgg caggacctat gccagtgacc cactctagtg cagcacaaag aagagggaga | 1380 |
| ataggaagaa atccaaaaaa tgagaatgac cagtacatat acatggggga acctctggaa | 1440 |
| aatgatgaag actgtgcaca ctggaaagaa gctaaaatgc tcctagataa catcaacacg | 1500 |
| ccagaaggaa tcattcctag catgttcgaa ccagagcgtg aaaaggtgga tgccattgat | 1560 |
| ggcgaatacc gcttgagagg agaagcaagg aaaaccctttg tagacttaat gagaagagga | 1620 |
| gacctaccag tctggttggc ctacagagtg gcagctgaag gcatcaacta cgcagacaga | 1680 |
| aggtggtgtt ttgatggagt caagaacaac caaatcctag aagaaacgt ggaagttgaa | 1740 |
| atctggacaa agaaggggga aaggaagaaa ttgaaaccca gatggttgga tgctaggatc | 1800 |
| tattctgacc cactggcgct aaaagaattt aaggaatttg cagccggaag aaag | 1854 |

<210> SEQ ID NO 19
<211> LENGTH: 495
<212> TYPE: PRT
<213> ORGANISM: Dengue virus 2

<400> SEQUENCE: 19

Met Arg Cys Ile Gly Met Ser Asn Arg Asp Phe Val Glu Gly Val Ser
1               5                   10                  15

Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
        35                  40                  45

Glu Ala Lys Gln Pro Ala Thr Leu Arg Lys Tyr Cys Ile Glu Ala Lys
    50                  55                  60

Leu Thr Asn Thr Thr Thr Glu Ser Arg Cys Pro Thr Gln Gly Glu Pro
65                  70                  75                  80

-continued

Ser Leu Asn Glu Glu Gln Asp Lys Arg Phe Val Cys Lys His Ser Met
            85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Glu Gly Lys
            115                 120                 125

Val Val Gln Pro Glu Asn Leu Glu Tyr Thr Ile Val Ile Thr Pro His
130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
                165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
            210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
                245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
                325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
370                 375                 380

Gly Gln Leu Lys Leu Asn Trp Phe Lys Lys Gly Ser Ser Leu Gly Gln
385                 390                 395                 400

Ala Phe Glu Thr Thr Met Arg Gly Ala Lys Arg Leu Ala Ile Leu Gly
                405                 410                 415

Asp Thr Ala Trp Asp Phe Gly Ser Leu Gly Gly Val Phe Thr Ser Ile
            420                 425                 430

Gly Lys Ala Leu His Gln Val Phe Gly Ala Ile Tyr Gly Ala Ala Phe
            435                 440                 445

Ser Gly Val Ser Trp Thr Met Lys Ile Leu Ile Gly Val Ile Ile Thr
450                 455                 460

Trp Ile Gly Met Asn Ser Arg Ser Thr Ser Leu Ser Val Thr Leu Val
465                 470                 475                 480

Leu Val Gly Ile Val Thr Leu Tyr Leu Gly Val Met Val Gln Ala
                485                 490                 495

```
<210> SEQ ID NO 20
<211> LENGTH: 2382
<212> TYPE: DNA
<213> ORGANISM: Zika virus
<400> SEQUENCE: 20
atgaaaaacc caaaaaagaa atccggagga ttccggattg tcaatatgct aaaacgcgga 60
gtagcccgtg tgagcccctt tgggggcttg aagaggctgc cagccggact tctgctgggt 120
catgggccca tcaggatggt cttggcgatt ctagcctttt tgagattcac ggcaatcaag 180
ccatcactgg gtctcatcaa tagatggggt tcagtgggga aaaaagaggc tatggaaata 240
ataaagaagt tcaagaaaga tctggctgcc atgctgagaa taatcaatgc taggaaggag 300
aagaagagac gaggcgcaga tactagtgtc ggaattgttg gcctcctgct gaccacagct 360
atggcagcgg aggtcactag acgtgggagt gcatactata tgtacttgga cagaaacgac 420
gctggggagg ccatatcttt tccaaccaca ttggggatga ataagtgtta tatacagatc 480
atggatcttg gacacatgtg tgatgccacc atgagctatg aatgccctat gctggatgag 540
ggggtggaac cagatgacgt cgattgttgg tgcaacacga cgtcaacttg ggttgtgtac 600
ggaacctgcc atcacaaaaa aggtgaagca cggagatcta gaagagctgt gacgctcccc 660
tcccattcca ctaggaagct gcaaacgcgg tcgcaaacct ggttggaatc aagagaatac 720
acaaagcact tgattagagt cgaaaattgg atattcagga accctggctt cgcgttagca 780
gcagctgcca tcgcttggct tttgggaagc tcaacgagcc aaaaagtcat atacttggtc 840
atgatactgc tgattgcccc ggcatacagc atcaggtgca taggagtcag caatagggac 900
tttgtggaag gtatgtcagg tgggacttgg gttgatgttg tcttggaaca tggaggttgt 960
gtcaccgtaa tggcacagga caaaccgact gtcgacatag agctggttac aacaacagtc 1020
agcaacatgg cggaggtaag atcctactgc tatgaggcat caatatcgga catggcttcg 1080
gacagccgct gcccaacaca aggtgaagcc taccttgaca agcaatcaga cactcaatat 1140
gtctgcaaaa gaacgttagt ggacagaggc tggggaaatg gatgtggact tttggcaaa 1200
gggagcctgg tgacatgcgc taagtttgca tgctccaaga aaatgaccgg gaagagcatc 1260
cagccagaga atctggagta ccggataatg ctgtcagttc atggctccca gcacagtggg 1320
atgatcgtta atgacacagg acatgaaact gatgagaata gagcgaaggt tgagataacg 1380
cccaattcac caagagccga agccaccctg gggggttttg gaagcctagg acttgattgt 1440
gaaccgagga caggccttga cttttcagat ttgtattact tgactatgaa taacaagcac 1500
tggttggttc acaaggagtg gttccacgac attccattac cttggcacgc tggggcagac 1560
accggaactc cacactggaa caacaaagaa gcactggtag agttcaagga cgcacatgcc 1620
aaaaggcaaa ctgtcgtggt tctagggagt caagaaggag cagttcacac ggcccttgct 1680
ggagctctgg aggctgagat ggatggtgca aagggaaggc tgtcctctgg ccacttgaaa 1740
tgtcgcctga aaatggataa acttagattg aagggcgtgt catactcctt gtgtaccgca 1800
gcgttcacat tcaccaagat cccggctgaa acactgcacg ggacagtcac agtggaggta 1860
cagtacgcag ggacagatgg accttgcaag gttccagctc agatggcggt ggacatgcaa 1920
actctgaccc cagttgggag gttgataacc gctaaccccg taatcactga aagcactgag 1980
aactctaaga tgatgctgga acttgatcca ccatttgggg actcttacat tgtcatagga 2040
gtcggggaga agaagatcac ccaccactgg cacaggagtg gcagcaccat tggaaaagca 2100
tttgaagcca ctgtgagagg tgccaagaga atggcagtct tgggagacac agcctgggac 2160
```

| | |
|---|---|
| tttggatcag ttggaggcgc tctcaactca ttgggcaagg gcatccatca aatttttgga | 2220 |
| gcagctttca aatcattgtt tggaggaatg tcctggttct cacaaattct cattggaacg | 2280 |
| ttgctgatgt ggttgggtct gaacacaaag aatggatcta tttcccttat gtgcttggcc | 2340 |
| ttaggggag tgttgatctt cttatccaca gctgtctctg ct | 2382 |

```
<210> SEQ ID NO 21
<211> LENGTH: 2385
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
```

| | |
|---|---|
| atgaagaacc ccaagaagaa gtccggcggc ttccggatcg tgaacatgct gaagagaggc | 60 |
| gtggccagag tcagccccct cggcggactg aaaagactgc ctgccggact gctgctgggc | 120 |
| cacggcccta ttagaatggt gctggccatc ctggcctttc tgcggttcac cgccatcaag | 180 |
| ccctccctgg gcctgatcaa cagatggggc agcgtgggca agaaagaagc catggaaatc | 240 |
| atcaagaagt tcaagaaaga cctggccgcc atgctgcgga tcatcaacgc ccggaaagag | 300 |
| aagaagcgca gaggcgccga tacctccgtg ggcattgtgg gcctgctgct gacaacagcc | 360 |
| atggccgccg aagtgaccag aagaggcagc gcctactaca tgtacctgga ccggaatgac | 420 |
| gccggcgagg ccatcagctt tccaaccacc ctgggcatga caagtgcta catccagatc | 480 |
| atggacctgg ccacatgtg cgacgccaca atgagctacg agtgccccat gctggacgag | 540 |
| ggcgtggaac ccgacgatgt ggactgctgg tgcaacacca ccagcacctg ggtggtgtac | 600 |
| ggcacctgtc accacaagaa gggcgaagcc cgcagatcca cgggccgt gacactgcct | 660 |
| agccacagca ccagaaagct gcagaccaga agccagacct ggctgaaaag cagagagtac | 720 |
| accaagcacc tgatccgggt ggaaaactgg atcttccgga accccggctt tgccctggcc | 780 |
| gctgctgcta ttgcttggct gctgggaagc agcaccagcc agaaagtgat ctacctggtc | 840 |
| atgatcctgc tgatcgcccc tgcctacagc atccggtgca tcggcgtgtc caaccgggac | 900 |
| ttcgtggaag gcatgagcgg cggcacatgg gtggacgtgg tgctgaaca cggcggctgt | 960 |
| gtgaccgtga tggcccagga taagcccacc gtggacatcg agctggtcac caccaccgtg | 1020 |
| tccaatatgg ccgaagtgcg gagctactgc tacgaggcca gcatcagcga catggccagc | 1080 |
| gacagcagat gccctacaca gggcgaggcc tacctggaca gcagtccga cacccagtac | 1140 |
| gtgtgcaagc ggaccctggt ggacagaggc tggggcaatg gctgcggcct gtttggcaag | 1200 |
| ggcagcctcg tgacctgcgc caagttcgcc tgcagcaaga agatgaccgg caagagcatc | 1260 |
| cagcccgaga acctggaata ccggatcatg ctgagcgtgc acggcagcca gcactccggc | 1320 |
| atgatcgtga atgacaccgg ccacgagaca gacgagaacc gggccaaggt ggaaatcacc | 1380 |
| cctaacagcc ctagagccga ggccacactg gcggctttg atctctgg cctggactgc | 1440 |
| gagccccgga ccggcctgga tttcagcgac ctgtactacc tgaccatgaa caacaagcac | 1500 |
| tggctggtcc acaaagagtg gttccacgac atccctctgc cctggcatgc cggcgctgat | 1560 |
| acaggcaccc ctcactggaa caacaaagag gccctggtcg agttcaagga cgcccacgcc | 1620 |
| aagaggcaga cagtggtggt cctgggatct caggaaggcg ccgtccatac agctctggct | 1680 |
| ggcgccctgg aagccgagat ggatggcgct aagggcagac tgtccagcgg ccacctgaag | 1740 |
| tgccggctga agatggacaa gctgcggctg aagggcgtgt cctacagcct gtgtaccgcc | 1800 |

-continued

```
gccttcacct tcaccaagat ccccgccgag acactgcacg gcaccgtgac cgtggaagtg    1860
cagtatgccg gcaccgatgg cccatgcaag gtgccagctc agatggccgt ggatatgcag    1920
accctgaccc ctgtgggccg gctgatcacc gccaatcctg tgatcaccga gagcaccgag    1980
aacagcaaga tgatgctgga actgaccct ccattcggcg acagctacat cgtgatcgga    2040
gtgggcgaga agaagatcac ccaccactgg cacagaagcg gcagcaccat cggcaaggcc    2100
ttcgaggcta cagtgcgggg agccaagaga atggccgtgc tggcgatac cgcctgggat    2160 tttggttctg tgggcggagc cctgaacagc ctgggcaagg gaatccacca gatcttcgga    2220
gccgccttta agagcctgtt cggcggcatg tcctggttca gccagatcct gatcggcacc    2280
ctgctgatgt ggctgggact gaacaccaag aacggcagca tctccctgat gtgcctggcc    2340
ctgggcggcg tgctgatctt tctgagcaca gccgtgtccg cctga                   2385
```

```
<210> SEQ ID NO 22
<211> LENGTH: 794
<212> TYPE: PRT
<213> ORGANISM: Zika virus

<400> SEQUENCE: 22

Met Lys Asn Pro Lys Lys Ser Gly Gly Phe Arg Ile Val Asn Met
1               5                   10                  15

Leu Lys Arg Gly Val Ala Arg Val Ser Pro Phe Gly Gly Leu Lys Arg
                20                  25                  30

Leu Pro Ala Gly Leu Leu Gly His Gly Pro Ile Arg Met Val Leu
            35                  40                  45

Ala Ile Leu Ala Phe Leu Arg Phe Thr Ala Ile Lys Pro Ser Leu Gly
        50                  55                  60

Leu Ile Asn Arg Trp Gly Ser Val Gly Lys Lys Glu Ala Met Glu Ile
65                  70                  75                  80

Ile Lys Lys Phe Lys Lys Asp Leu Ala Ala Met Leu Arg Ile Ile Asn
                85                  90                  95

Ala Arg Lys Glu Lys Lys Arg Arg Gly Ala Asp Thr Ser Val Gly Ile
            100                 105                 110

Val Gly Leu Leu Leu Thr Thr Ala Met Ala Ala Glu Val Thr Arg Arg
        115                 120                 125

Gly Ser Ala Tyr Tyr Met Tyr Leu Asp Arg Asn Asp Ala Gly Glu Ala
    130                 135                 140

Ile Ser Phe Pro Thr Thr Leu Gly Met Asn Lys Cys Tyr Ile Gln Ile
145                 150                 155                 160

Met Asp Leu Gly His Met Cys Asp Ala Thr Met Ser Tyr Glu Cys Pro
                165                 170                 175

Met Leu Asp Glu Gly Val Glu Pro Asp Asp Val Asp Cys Trp Cys Asn
            180                 185                 190

Thr Thr Ser Thr Trp Val Val Tyr Gly Thr Cys His His Lys Lys Gly
        195                 200                 205

Glu Ala Arg Arg Ser Arg Arg Ala Val Thr Leu Pro Ser His Ser Thr
    210                 215                 220

Arg Lys Leu Gln Thr Arg Ser Gln Thr Trp Leu Glu Ser Arg Glu Tyr
225                 230                 235                 240

Thr Lys His Leu Ile Arg Val Glu Asn Trp Ile Phe Arg Asn Pro Gly
                245                 250                 255

Phe Ala Leu Ala Ala Ala Ile Ala Trp Leu Leu Gly Ser Ser Thr
            260                 265                 270
```

-continued

```
Ser Gln Lys Val Ile Tyr Leu Val Met Ile Leu Leu Ile Ala Pro Ala
            275                 280                 285
Tyr Ser Ile Arg Cys Ile Gly Val Ser Asn Arg Asp Phe Val Glu Gly
        290                 295                 300
Met Ser Gly Gly Thr Trp Val Asp Val Val Leu Glu His Gly Gly Cys
305                 310                 315                 320
Val Thr Val Met Ala Gln Asp Lys Pro Thr Val Asp Ile Glu Leu Val
                325                 330                 335
Thr Thr Thr Val Ser Asn Met Ala Glu Val Arg Ser Tyr Cys Tyr Glu
            340                 345                 350
Ala Ser Ile Ser Asp Met Ala Ser Asp Ser Arg Cys Pro Thr Gln Gly
        355                 360                 365
Glu Ala Tyr Leu Asp Lys Gln Ser Asp Thr Gln Tyr Val Cys Lys Arg
    370                 375                 380
Thr Leu Val Asp Arg Gly Trp Gly Asn Gly Cys Gly Leu Phe Gly Lys
385                 390                 395                 400
Gly Ser Leu Val Thr Cys Ala Lys Phe Ala Cys Ser Lys Lys Met Thr
                405                 410                 415
Gly Lys Ser Ile Gln Pro Glu Asn Leu Glu Tyr Arg Ile Met Leu Ser
            420                 425                 430
Val His Gly Ser Gln His Ser Gly Met Ile Val Asn Asp Thr Gly His
        435                 440                 445
Glu Thr Asp Glu Asn Arg Ala Lys Val Glu Ile Thr Pro Asn Ser Pro
    450                 455                 460
Arg Ala Glu Ala Thr Leu Gly Gly Phe Gly Ser Leu Gly Leu Asp Cys
465                 470                 475                 480
Glu Pro Arg Thr Gly Leu Asp Phe Ser Asp Leu Tyr Tyr Leu Thr Met
                485                 490                 495
Asn Asn Lys His Trp Leu Val His Lys Glu Trp Phe His Asp Ile Pro
            500                 505                 510
Leu Pro Trp His Ala Gly Ala Asp Thr Gly Thr Pro His Trp Asn Asn
        515                 520                 525
Lys Glu Ala Leu Val Glu Phe Lys Asp Ala His Ala Lys Arg Gln Thr
    530                 535                 540
Val Val Val Leu Gly Ser Gln Glu Gly Ala Val His Thr Ala Leu Ala
545                 550                 555                 560
Gly Ala Leu Glu Ala Glu Met Asp Gly Ala Lys Gly Arg Leu Ser Ser
                565                 570                 575
Gly His Leu Lys Cys Arg Leu Lys Met Asp Lys Leu Arg Leu Lys Gly
            580                 585                 590
Val Ser Tyr Ser Leu Cys Thr Ala Ala Phe Thr Phe Thr Lys Ile Pro
        595                 600                 605
Ala Glu Thr Leu His Gly Thr Val Thr Val Glu Val Gln Tyr Ala Gly
    610                 615                 620
Thr Asp Gly Pro Cys Lys Val Pro Ala Gln Met Ala Val Asp Met Gln
625                 630                 635                 640
Thr Leu Thr Pro Val Gly Arg Leu Ile Thr Ala Asn Pro Val Ile Thr
                645                 650                 655
Glu Ser Thr Glu Asn Ser Lys Met Met Leu Glu Leu Asp Pro Pro Phe
            660                 665                 670
Gly Asp Ser Tyr Ile Val Ile Gly Val Gly Glu Lys Lys Ile Thr His
        675                 680                 685
His Trp His Arg Ser Gly Ser Thr Ile Gly Lys Ala Phe Glu Ala Thr
```

-continued

```
    690                 695                 700

Val Arg Gly Ala Lys Arg Met Ala Val Leu Gly Asp Thr Ala Trp Asp
705                 710                 715                 720

Phe Gly Ser Val Gly Gly Ala Leu Asn Ser Leu Gly Lys Gly Ile His
                725                 730                 735

Gln Ile Phe Gly Ala Ala Phe Lys Ser Leu Phe Gly Gly Met Ser Trp
            740                 745                 750

Phe Ser Gln Ile Leu Ile Gly Thr Leu Leu Met Trp Leu Gly Leu Asn
        755                 760                 765

Thr Lys Asn Gly Ser Ile Ser Leu Met Cys Leu Ala Leu Gly Gly Val
    770                 775                 780

Leu Ile Phe Leu Ser Thr Ala Val Ser Ala
785                 790

<210> SEQ ID NO 23
<211> LENGTH: 2241
<212> TYPE: DNA
<213> ORGANISM: Zika virus

<400> SEQUENCE: 23
agctggcccc ctagcgaagt actcacagct gttggcctga tatgcgcatt ggctggaggg      60
ttcgccaagg cagatataga gatggctggg cccatggccg cggtcggtct gctaattgtc     120
agttacgtgg tctcaggaaa gagtgtggac atgtacattg aaagagcagg tgacatcaca     180
tgggaaaaag atgcggaagt cactggaaac agtccccggc tcgatgtggc gctagatgag     240
agtggtgatt tctccctggt ggaggatgac ggtcccccca tgagagagat catactcaag     300
gtggtcctga tgaccatctg tggcatgaac ccaatagcca taccctttgc agctggagcg     360
tggtacgtat acgtgaagac tggaaaaagg agtggtgctc tatgggatgt gcctgctccc     420
aaggaagtaa aaaaggggga gaccacagat ggagtgtaca gagtaatgac tcgtagactg     480
ctaggttcaa cacaagttgg agtgggagtt atgcaagagg gggtctttca cactatgtgg     540
cacgtcacaa aaggatccgc gctgagaagc ggtgaaggga gacttgatcc atactgggga     600
gatgtcaagc aggatctggt gtcatactgt ggtccatgga agctagatgc cgcctgggac     660
gggcacagcg aggtgcagct cttggccgtg ccccccggag agagagcgag gaacatccag     720
actctgcccg gaatatttaa gacaaaggat ggggacattg gagcggttgc gctggattac     780
ccagcaggaa cttcaggatc tccaatccta gacaagtgtg ggagagtgat aggactttat     840
ggcaatgggg tcgtgatcaa aaatgggagt tatgttagtg ccatcaccca agggaggagg     900
gaggaagaga ctcctgttga gtgcttcgag ccttcgatgc tgaagaagaa gcagctaact     960
gtcttagact tgcatcctgg agctgggaaa accaggagag ttcttcctga aatagtccgt    1020
gaagccataa aaacaagact ccgtactgtg atcttagctc caaccagggt tgtcgctgct    1080
gaaatggagg aagcccttag agggcttcca gtgcgttata tgacaacagc agtcaatgtc    1140
acccactctg gaacagaaat cgtcgactta atgtgccatg ccaccttcac ttcacgtcta    1200
ctacagccaa tcagagtccc caactataat ctgtatatta tggatgaggc ccacttcaca    1260
gatccctcaa gtatagcagc aagaggatac atttcaacaa gggttgagat gggcgaggcg    1320
gctgccatct tcatgaccgc cacgccacca ggaacccgtg acgcatttcc ggactccaac    1380
tcaccaatta tggacaccga agtggaagtc ccagagagag cctggagctc aggctttgat    1440
tgggtgacgg atcattctgg aaaaacagtt tggtttgttc caagcgtgag gaacggcaat    1500
gagatcgcag cttgtctgac aaaggctgga aaacgggtca tacagctcag cagaaagact    1560
```

-continued

```
tttgagacag agttccagaa aacaaaacat caagagtggg actttgtcgt gacaactgac    1620
atttcagaga tgggcgccaa ctttaaagct gaccgtgtca tagattccag gagatgccta    1680
aagccggtca tacttgatgg cgagagagtc attctggctg acccatgcc tgtcacacat     1740 gccagcgctg cccagaggag ggggcgcata ggcaggaatc ccaacaaacc tggagatgag    1800
tatctgtatg gaggtgggtg cgcagagact gacgaagacc atgcacactg gcttgaagca    1860
agaatgctcc ttgacaatat ttacctccaa gatggcctca tagcctcgct ctatcgacct    1920
gaggccgaca agtagcagc cattgaggga gagttcaagc ttaggacgga gcaaaggaag      1980
acctttgtgg aactcatgaa agaggagat cttcctgttt ggctggccta tcaggttgca     2040
tctgccggaa taacctacac agatagaaga tggtgctttg atggcacgac caacaacacc    2100
ataatggaag acagtgtgcc ggcagaggtg tggaccagac acggagagaa agagtgctc     2160 aaaccgaggt ggatggacgc cagagtttgt tcagatcatg cggccctgaa gtcattcaag    2220
gagtttgccg ctgggaaaag a                                              2241
```

<210> SEQ ID NO 24
<211> LENGTH: 748
<212> TYPE: PRT
<213> ORGANISM: Zika virus

<400> SEQUENCE: 24

```
Met Ser Trp Pro Pro Ser Glu Val Leu Thr Ala Val Gly Leu Ile Cys
1               5                   10                  15

Ala Leu Ala Gly Gly Phe Ala Lys Ala Asp Ile Glu Met Ala Gly Pro
            20                  25                  30

Met Ala Ala Val Gly Leu Leu Ile Val Ser Tyr Val Val Ser Gly Lys
        35                  40                  45

Ser Val Asp Met Tyr Ile Glu Arg Ala Gly Asp Ile Thr Trp Glu Lys
    50                  55                  60

Asp Ala Glu Val Thr Gly Asn Ser Pro Arg Leu Asp Val Ala Leu Asp
65                  70                  75                  80

Glu Ser Gly Asp Phe Ser Leu Val Glu Asp Asp Gly Pro Pro Met Arg
                85                  90                  95

Glu Ile Ile Leu Lys Val Val Leu Met Thr Ile Cys Gly Met Asn Pro
            100                 105                 110

Ile Ala Ile Pro Phe Ala Ala Gly Ala Trp Tyr Val Tyr Val Lys Thr
        115                 120                 125

Gly Lys Arg Ser Gly Ala Leu Trp Asp Val Pro Ala Pro Lys Glu Val
    130                 135                 140

Lys Lys Gly Glu Thr Thr Asp Gly Val Tyr Arg Val Met Thr Arg Arg
145                 150                 155                 160

Leu Leu Gly Ser Thr Gln Val Gly Val Gly Val Met Gln Glu Gly Val
                165                 170                 175

Phe His Thr Met Trp His Val Thr Lys Gly Ser Ala Leu Arg Ser Gly
            180                 185                 190

Glu Gly Arg Leu Asp Pro Tyr Trp Gly Asp Val Lys Gln Asp Leu Val
        195                 200                 205

Ser Tyr Cys Gly Pro Trp Lys Leu Asp Ala Ala Trp Asp Gly His Ser
    210                 215                 220

Glu Val Gln Leu Leu Ala Val Pro Pro Gly Glu Arg Ala Arg Asn Ile
225                 230                 235                 240

Gln Thr Leu Pro Gly Ile Phe Lys Thr Lys Asp Gly Asp Ile Gly Ala
```

-continued

```
                245                 250                 255
Val Ala Leu Asp Tyr Pro Ala Gly Thr Ser Gly Ser Pro Ile Leu Asp
            260                 265                 270
Lys Cys Gly Arg Val Ile Gly Leu Tyr Gly Asn Gly Val Val Ile Lys
        275                 280                 285
Asn Gly Ser Tyr Val Ser Ala Ile Thr Gln Gly Arg Arg Glu Glu Glu
    290                 295                 300
Thr Pro Val Glu Cys Phe Glu Pro Ser Met Leu Lys Lys Lys Gln Leu
305                 310                 315                 320
Thr Val Leu Asp Leu His Pro Gly Ala Gly Lys Thr Arg Arg Val Leu
                325                 330                 335
Pro Glu Ile Val Arg Glu Ala Ile Lys Thr Arg Leu Arg Thr Val Ile
            340                 345                 350
Leu Ala Pro Thr Arg Val Val Ala Ala Glu Met Glu Glu Ala Leu Arg
        355                 360                 365
Gly Leu Pro Val Arg Tyr Met Thr Thr Ala Val Asn Val Thr His Ser
    370                 375                 380
Gly Thr Glu Ile Val Asp Leu Met Cys His Ala Thr Phe Thr Ser Arg
385                 390                 395                 400
Leu Leu Gln Pro Ile Arg Val Pro Asn Tyr Asn Leu Tyr Ile Met Asp
                405                 410                 415
Glu Ala His Phe Thr Asp Pro Ser Ser Ile Ala Ala Arg Gly Tyr Ile
            420                 425                 430
Ser Thr Arg Val Glu Met Gly Glu Ala Ala Ile Phe Met Thr Ala
        435                 440                 445
Thr Pro Pro Gly Thr Arg Asp Ala Phe Pro Asp Ser Asn Ser Pro Ile
    450                 455                 460
Met Asp Thr Glu Val Glu Val Pro Glu Arg Ala Trp Ser Ser Gly Phe
465                 470                 475                 480
Asp Trp Val Thr Asp His Ser Gly Lys Thr Val Trp Phe Val Pro Ser
                485                 490                 495
Val Arg Asn Gly Asn Glu Ile Ala Ala Cys Leu Thr Lys Ala Gly Lys
            500                 505                 510
Arg Val Ile Gln Leu Ser Arg Lys Thr Phe Glu Thr Glu Phe Gln Lys
        515                 520                 525
Thr Lys His Gln Glu Trp Asp Phe Val Val Thr Thr Asp Ile Ser Glu
    530                 535                 540
Met Gly Ala Asn Phe Lys Ala Asp Arg Val Ile Asp Ser Arg Arg Cys
545                 550                 555                 560
Leu Lys Pro Val Ile Leu Asp Gly Glu Arg Val Ile Leu Ala Gly Pro
                565                 570                 575
Met Pro Val Thr His Ala Ser Ala Ala Gln Arg Arg Gly Arg Ile Gly
            580                 585                 590
Arg Asn Pro Asn Lys Pro Gly Asp Glu Tyr Leu Tyr Gly Gly Gly Cys
        595                 600                 605
Ala Glu Thr Asp Glu Asp His Ala His Trp Leu Glu Ala Arg Met Leu
    610                 615                 620
Leu Asp Asn Ile Tyr Leu Gln Asp Gly Leu Ile Ala Ser Leu Tyr Arg
625                 630                 635                 640
Pro Glu Ala Asp Lys Val Ala Ala Ile Glu Gly Glu Phe Lys Leu Arg
                645                 650                 655
Thr Glu Gln Arg Lys Thr Phe Val Glu Leu Met Lys Arg Gly Asp Leu
            660                 665                 670
```

Pro Val Trp Leu Ala Tyr Gln Val Ala Ser Ala Gly Ile Thr Tyr Thr
                675                 680                 685

Asp Arg Arg Trp Cys Phe Asp Gly Thr Thr Asn Asn Thr Ile Met Glu
    690                 695                 700

Asp Ser Val Pro Ala Glu Val Trp Thr Arg His Gly Glu Lys Arg Val
705                 710                 715                 720

Leu Lys Pro Arg Trp Met Asp Ala Arg Val Cys Ser Asp His Ala Ala
                725                 730                 735

Leu Lys Ser Phe Lys Glu Phe Ala Ala Gly Lys Arg
                740                 745

<210> SEQ ID NO 25
<211> LENGTH: 936
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
atgtcttggc ctccatctga ggtgctgacc gccgtgggac tgatttgtgc cctggctggc     60
ggattcgcca aggccgacat tgagatggcc ggacctatgg ccgctgtggg cctgctgatc    120
gtgtcctacg tggtgtccgg caagagcgtg gacatgtaca tcgagagagc cggcgacatc    180
acctgggaga aggatgccga agtgaccggc aacagcccca gactggatgt ggccctggac    240
gagagcggcg atttcagcct ggtggaagat gacggcccte ccatgcgcga tcatcctg     300
aaggtggtgc tgatgaccat ctgcggaatg aaccctatcg ccatcccctt cgccgctggc    360
gcttggtacg tgtacgtgaa aaccggcaag cggagcggag ccctgtggga cgtgccagcc    420
cctaaagaag tgaagaaggg cgagacaacc gacgcgtgt acagagtgat gaccagacgg    480
ctgctgggca gcacacaagt cggagtggga gtgatgcagg aagggtctt ccacaccatg     540
tggcacgtga ccaagggcag cgccctgaga tctggcgaag gcagactgga cccttactgg    600
ggcgacgtga agcaggacct ggtgtcctac tgcggcccct ggaaactgga tgccgcctgg    660
gatggccaca gcgaagtgca gctgctggct gtgcctcccg cgagagggc cagaaatatc    720
cagaccctgc ccggcatctt caagaccaag gatggcgaca tcggcgccgt ggctctggat    780
taccctgccg gcacatctgg cagccccatc ctggataagt gcggcagagt gatcggcctg    840
tacggcaacg gcgtggtcat caagaacggc agctacgtgt ccgccatcac ccagggcaga    900
cgcgaggaag agacacccgt ggaatgcttc gagtga                              936

<210> SEQ ID NO 26
<211> LENGTH: 311
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met Ser Trp Pro Pro Ser Glu Val Leu Thr Ala Val Gly Leu Ile Cys
1               5                   10                  15

Ala Leu Ala Gly Gly Phe Ala Lys Ala Asp Ile Glu Met Ala Gly Pro
            20                  25                  30

Met Ala Ala Val Gly Leu Leu Ile Val Ser Tyr Val Val Ser Gly Lys
        35                  40                  45

-continued

```
Ser Val Asp Met Tyr Ile Glu Arg Ala Gly Asp Ile Thr Trp Glu Lys
    50                  55                  60

Asp Ala Glu Val Thr Gly Asn Ser Pro Arg Leu Asp Val Ala Leu Asp
65                  70                  75                  80

Glu Ser Gly Asp Phe Ser Leu Val Glu Asp Gly Pro Pro Met Arg
                85                  90                  95

Glu Ile Ile Leu Lys Val Val Leu Met Thr Ile Cys Gly Met Asn Pro
            100                 105                 110

Ile Ala Ile Pro Phe Ala Ala Gly Ala Trp Tyr Val Tyr Val Lys Thr
        115                 120                 125

Gly Lys Arg Ser Gly Ala Leu Trp Asp Val Pro Ala Pro Lys Glu Val
130                 135                 140

Lys Lys Gly Glu Thr Thr Asp Gly Val Tyr Arg Val Met Thr Arg Arg
145                 150                 155                 160

Leu Leu Gly Ser Thr Gln Val Gly Val Gly Val Met Gln Glu Gly Val
                165                 170                 175

Phe His Thr Met Trp His Val Thr Lys Gly Ser Ala Leu Arg Ser Gly
            180                 185                 190

Glu Gly Arg Leu Asp Pro Tyr Trp Gly Asp Val Lys Gln Asp Leu Val
        195                 200                 205

Ser Tyr Cys Gly Pro Trp Lys Leu Asp Ala Ala Trp Asp Gly His Ser
210                 215                 220

Glu Val Gln Leu Leu Ala Val Pro Pro Gly Glu Arg Ala Arg Asn Ile
225                 230                 235                 240

Gln Thr Leu Pro Gly Ile Phe Lys Thr Lys Asp Gly Asp Ile Gly Ala
                245                 250                 255

Val Ala Leu Asp Tyr Pro Ala Gly Thr Ser Gly Ser Pro Ile Leu Asp
            260                 265                 270

Lys Cys Gly Arg Val Ile Gly Leu Tyr Gly Asn Gly Val Val Ile Lys
        275                 280                 285

Asn Gly Ser Tyr Val Ser Ala Ile Thr Gln Gly Arg Arg Glu Glu Glu
    290                 295                 300

Thr Pro Val Glu Cys Phe Glu
305                 310

<210> SEQ ID NO 27
<211> LENGTH: 617
<212> TYPE: PRT
<213> ORGANISM: Dengue virus 2

<400> SEQUENCE: 27

Ala Gly Val Leu Trp Asp Val Pro Ser Pro Pro Met Gly Lys Ala
1               5                   10                  15

Glu Leu Glu Asp Gly Ala Tyr Arg Ile Lys Gln Lys Gly Ile Leu Gly
                20                  25                  30

Tyr Ser Gln Ile Gly Ala Gly Val Tyr Lys Glu Gly Thr Phe His Thr
            35                  40                  45

Met Trp His Val Thr Arg Gly Ala Val Leu Met His Lys Gly Lys Arg
        50                  55                  60

Ile Glu Pro Ser Trp Ala Asp Val Lys Lys Asp Leu Ile Ser Tyr Gly
65                  70                  75                  80

Gly Gly Trp Lys Leu Glu Gly Glu Trp Lys Glu Gly Glu Glu Val Gln
                85                  90                  95

Val Leu Ala Leu Glu Pro Gly Lys Asn Pro Arg Ala Val Gln Thr Lys
            100                 105                 110
```

```
Pro Gly Leu Phe Lys Thr Asn Ala Gly Thr Ile Gly Ala Val Ser Leu
        115                 120                 125

Asp Phe Ser Pro Gly Thr Ser Gly Ser Pro Ile Ile Asp Lys Lys Gly
        130                 135                 140

Lys Val Val Gly Leu Tyr Gly Asn Gly Val Val Thr Arg Ser Gly Ala
145                 150                 155                 160

Tyr Val Ser Ala Ile Ala Gln Thr Glu Lys Ser Ile Glu Asp Asn Pro
                165                 170                 175

Glu Ile Glu Asp Asp Ile Phe Arg Lys Arg Arg Leu Thr Ile Met Asp
                180                 185                 190

Leu His Pro Gly Ala Gly Lys Thr Lys Arg Tyr Leu Pro Ala Ile Val
        195                 200                 205

Arg Glu Ala Ile Lys Arg Gly Leu Arg Thr Leu Ile Leu Ala Pro Thr
        210                 215                 220

Arg Val Val Ala Ala Glu Met Glu Glu Ala Leu Arg Gly Leu Pro Ile
225                 230                 235                 240

Arg Tyr Gln Thr Pro Ala Ile Arg Ala Glu His Thr Gly Arg Glu Ile
                245                 250                 255

Val Asp Leu Met Cys His Ala Thr Phe Thr Met Arg Leu Leu Ser Pro
                260                 265                 270

Val Arg Val Pro Asn Tyr Asn Leu Ile Ile Met Asp Glu Ala His Phe
            275                 280                 285

Thr Asp Pro Ala Ser Ile Ala Ala Arg Gly Tyr Ile Ser Thr Arg Val
        290                 295                 300

Glu Met Gly Glu Ala Ala Gly Ile Phe Met Thr Ala Thr Pro Pro Gly
305                 310                 315                 320

Ser Arg Asp Pro Phe Pro Gln Ser Asn Ala Pro Ile Ile Asp Glu Glu
                325                 330                 335

Arg Glu Ile Pro Glu Arg Ser Trp Asn Ser Gly His Glu Trp Val Thr
                340                 345                 350

Asp Phe Lys Gly Lys Thr Val Trp Phe Val Pro Ser Ile Lys Ala Gly
        355                 360                 365

Asn Asp Ile Ala Ala Cys Leu Arg Lys Asn Gly Lys Lys Val Ile Gln
        370                 375                 380

Leu Ser Arg Lys Thr Phe Asp Ser Glu Tyr Val Lys Thr Arg Thr Asn
385                 390                 395                 400

Asp Trp Asp Phe Val Val Thr Thr Asp Ile Ser Glu Met Gly Ala Asn
                405                 410                 415

Phe Lys Ala Glu Arg Val Ile Asp Pro Arg Arg Cys Met Lys Pro Val
                420                 425                 430

Ile Leu Thr Asp Gly Glu Glu Arg Val Ile Leu Ala Gly Pro Met Pro
        435                 440                 445

Val Thr His Ser Ser Ala Ala Gln Arg Arg Gly Arg Ile Gly Arg Asn
        450                 455                 460

Pro Lys Asn Glu Asn Asp Gln Tyr Ile Tyr Met Gly Glu Pro Leu Glu
465                 470                 475                 480

Asn Asp Glu Asp Cys Ala His Trp Lys Glu Ala Lys Met Leu Leu Asp
                485                 490                 495

Asn Ile Asn Thr Pro Glu Gly Ile Ile Pro Ser Met Phe Glu Pro Glu
                500                 505                 510

Arg Glu Lys Val Asp Ala Ile Asp Gly Glu Tyr Arg Leu Arg Gly Glu
        515                 520                 525
```

Ala Arg Lys Thr Phe Val Asp Leu Met Arg Arg Gly Asp Leu Pro Val
530                 535                 540

Trp Leu Ala Tyr Arg Val Ala Ala Glu Gly Ile Asn Tyr Ala Asp Arg
545                 550                 555                 560

Arg Trp Cys Phe Asp Gly Val Lys Asn Asn Gln Ile Leu Glu Asn
        565                 570                 575

Val Glu Val Glu Ile Trp Thr Lys Gly Glu Arg Lys Lys Leu Lys
            580                 585                 590

Pro Arg Trp Leu Asp Ala Arg Ile Tyr Ser Asp Pro Leu Ala Leu Lys
        595                 600                 605

Glu Phe Lys Glu Phe Ala Ala Gly Arg
    610                 615

<210> SEQ ID NO 28
<211> LENGTH: 1311
<212> TYPE: DNA
<213> ORGANISM: Dengue virus 2

<400> SEQUENCE: 28
attttccgaa agagaagact gaccatcatg gacctccacc caggagcggg aaagacgaag      60
agataccttc cggccatagt cagagaagct ataaaacggg gtttgagaac attaatcttg     120
gcccccacta gagttgtggc agctgaaatg gaggaagccc ttagaggact ccaataaga     180
taccagaccc cagccatcag agctgagcac accgggcggg agattgtgga cctaatgtgt     240
catgccacat ttaccatgag gctgctatca ccagttagag tgccaaacta caacctgatt     300
atcatggacg aagcccattt cacagaccca gcaagtatag cagctagagg atacatctca     360
actcgagtgg agatgggtga ggcagctggg atttttatga cagccactcc cccgggaagc     420
agagacccat ttcctcagag caatgcacca atcatagatg aagaaagaga atccctgaa     480
cgttcgtgga attccggaca tgaatgggtc acggatttta aagggaagac tgtttggttc     540
gttccaagta taaaagcagg aaatgatata gcagcttgcc tgaggaaaaa tggaaagaaa     600
gtgatacaac tcagtaggaa gacctttgat tctgagtatg tcaagactag aaccaatgat     660
tgggacttcg tggttacaac tgacatttca gaaatgggtg ccaatttcaa ggctgagagg     720
gttatagacc ccagacgctg catgaaacca gtcatactaa cagatggtga agagcgggtg     780
attctggcag acctatgcc agtgacccac tctagtgcag cacaagaag gggagaata     840
ggaagaaatc caaaaatga aatgaccag tacatataca tgggggaacc tctggaaaat     900
gatgaagact gtgcacactg gaagaagct aaaatgctcc tagataacat caacacgcca     960
gaaggaatca ttcctagcat gttcgaacca gagcgtgaaa aggtggatgc cattgatggc    1020
gaataccgct tgagaggaga agcaaggaaa acctttgtag acttaatgag aagaggagac    1080
ctaccagtct ggttggccta cagagtggca gctgaaggca tcaactacgc agacagaagg    1140
tggtgttttg atggagtcaa gaacaaccaa atcctagaag aaacgtgga agttgaaatc    1200
tggacaaaag aagggaaag gaagaaattg aaacccagat ggttggatgc taggatctat    1260
tctgacccac tggcgctaaa agaatttaag gaatttgcag ccggaagaaa g             1311

<210> SEQ ID NO 29
<211> LENGTH: 436
<212> TYPE: PRT
<213> ORGANISM: Dengue virus 2

<400> SEQUENCE: 29

Ile Phe Arg Lys Arg Arg Leu Thr Ile Met Asp Leu His Pro Gly Ala

-continued

```
 1               5                   10                  15
Gly Lys Thr Lys Arg Tyr Leu Pro Ala Ile Val Arg Glu Ala Ile Lys
                 20                  25                  30

Arg Gly Leu Arg Thr Leu Ile Leu Ala Pro Thr Arg Val Val Ala Ala
                 35                  40                  45

Glu Met Glu Glu Ala Leu Arg Gly Leu Pro Ile Arg Tyr Gln Thr Pro
                 50                  55                  60

Ala Ile Arg Ala Glu His Thr Gly Arg Glu Ile Val Asp Leu Met Cys
 65                  70                  75                  80

His Ala Thr Phe Thr Met Arg Leu Leu Ser Pro Val Arg Val Pro Asn
                 85                  90                  95

Tyr Asn Leu Ile Ile Met Asp Glu Ala His Phe Thr Asp Pro Ala Ser
                100                 105                 110

Ile Ala Ala Arg Gly Tyr Ile Ser Thr Arg Val Glu Met Gly Glu Ala
                115                 120                 125

Ala Gly Ile Phe Met Thr Ala Thr Pro Pro Gly Ser Arg Asp Pro Phe
                130                 135                 140

Pro Gln Ser Asn Ala Pro Ile Ile Asp Glu Glu Arg Glu Ile Pro Glu
145                 150                 155                 160

Arg Ser Trp Asn Ser Gly His Glu Trp Val Thr Asp Phe Lys Gly Lys
                165                 170                 175

Thr Val Trp Phe Val Pro Ser Ile Lys Ala Gly Asn Asp Ile Ala Ala
                180                 185                 190

Cys Leu Arg Lys Asn Gly Lys Lys Val Ile Gln Leu Ser Arg Lys Thr
                195                 200                 205

Phe Asp Ser Glu Tyr Val Lys Thr Arg Thr Asn Asp Trp Asp Phe Val
210                 215                 220

Val Thr Thr Asp Ile Ser Glu Met Gly Ala Asn Phe Lys Ala Glu Arg
225                 230                 235                 240

Val Ile Asp Pro Arg Arg Cys Met Lys Pro Val Ile Leu Thr Asp Gly
                245                 250                 255

Glu Glu Arg Val Ile Leu Ala Gly Pro Met Pro Val Thr His Ser Ser
                260                 265                 270

Ala Ala Gln Arg Arg Gly Arg Ile Gly Arg Asn Pro Lys Asn Glu Asn
                275                 280                 285

Asp Gln Tyr Ile Tyr Met Gly Glu Pro Leu Glu Asn Asp Glu Asp Cys
                290                 295                 300

Ala His Trp Lys Glu Ala Lys Met Leu Leu Asp Asn Ile Asn Thr Pro
305                 310                 315                 320

Glu Gly Ile Ile Pro Ser Met Phe Glu Pro Glu Arg Glu Lys Val Asp
                325                 330                 335

Ala Ile Asp Gly Glu Tyr Arg Leu Arg Gly Glu Ala Arg Lys Thr Phe
                340                 345                 350

Val Asp Leu Met Arg Arg Gly Asp Leu Pro Val Trp Leu Ala Tyr Arg
                355                 360                 365

Val Ala Ala Glu Gly Ile Asn Tyr Ala Asp Arg Arg Trp Cys Phe Asp
                370                 375                 380

Gly Val Lys Asn Asn Gln Ile Leu Glu Glu Asn Val Glu Val Glu Ile
385                 390                 395                 400

Trp Thr Lys Glu Gly Glu Arg Lys Lys Leu Lys Pro Arg Trp Leu Asp
                405                 410                 415

Ala Arg Ile Tyr Ser Asp Pro Leu Ala Leu Lys Glu Phe Lys Glu Phe
                420                 425                 430
```

Ala Ala Gly Arg
        435

<210> SEQ ID NO 30
<211> LENGTH: 939
<212> TYPE: DNA
<213> ORGANISM: Dengue virus 2

<400> SEQUENCE: 30

| atgagctggc | cattaaatga | ggctatcatg | gcagtcggga | tggtgagcat | tttagccagt | 60 |
| tctctcctaa | aaatgatat  | tcccatgaca | ggaccattag | tggctggagg | gctcctcact | 120 |
| gtgtgctacg | tgctcactgg | acgatcggcc | gatttggaac | tggagagagc | agccgatgtc | 180 |
| aaatgggaag | accaggcaga | gatatcagga | agcagtccaa | tcctgtcaat | aacaatatca | 240 |
| gaagatggta | gcatgtcgat | aaaaaatgaa | gaggaagaac | aaacactgac | catactcatt | 300 |
| agaacaggat | tgctggtgat | ctcaggactt | tttcctgtat | caataccaat | cacggcagca | 360 |
| gcatggtacc | tgtgggaagt | gaagaaacaa | cgggccggag | tattgtggga | tgttccttca | 420 |
| cccccaccca | tgggaaaggc | tgaactggaa | gatggagcct | atagaattaa | gcaaaaaggg | 480 |
| attcttggat | attcccagat | cggagccgga | gtttacaaag | aaggaacatt | ccatacaatg | 540 |
| tggcatgtca | cacgtggcgc | tgttctaatg | cataaggaa  | agaggattga | accatcatgg | 600 |
| gcggacgtca | agaaagacct | aatatcatat | ggaggaggct | ggaagttaga | aggagaatgg | 660 |
| aaggaaggag | aagaagtcca | ggtattggca | ctggagcctg | aaaaaatcc  | aagagccgtc | 720 |
| caaacgaaac | ctggtgcctt | caaaaccaac | gccggaacaa | taggtgctgt | atctctggac | 780 |
| tttctcctg  | aacgtcagg  | atctccaatt | atcgacaaaa | aggaaaagt  | tgtgggtctt | 840 |
| tatggtaatg | tgttgttac  | aaggagtgga | gcatatgtga | gtgctatagc | ccagactgaa | 900 |
| aaaagcattg | aagacaaccc | agagatcgaa | gatgactag  |            |            | 939 |

<210> SEQ ID NO 31
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

| atgaacaacc | agcgcaagaa | ggccaaaaac | actccgttca | atatgctcaa | gagagagcgc | 60 |
| aatcgggttt | ctacggtaca | gcagctgacg | aagagattct | ccctgggcat | gctgcaaggt | 120 |
| cgcggaccac | tgaagctgtt | catggcccct | gttgcatttc | ttaggttct  | tacaattccc | 180 |
| cccactgctg | gaatcctgaa | gcggtggggc | accatcaaaa | agtccaaggc | tattaatgtc | 240 |
| ctcaggggt  | tcaggaaaga | gattgggcgg | atgctgaaca | tccttaatag | acgcagacgg | 300 |
| tccgctggca | tgataatcat | gctgatccca | accgtcatgg | cc         |            | 342 |

<210> SEQ ID NO 32
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Asn Asn Gln Arg Lys Lys Ala Lys Asn Thr Pro Phe Asn Met Leu

```
            1               5                  10                 15
Lys Arg Glu Arg Asn Arg Val Ser Thr Val Gln Gln Leu Thr Lys Arg
             20                  25                  30

Phe Ser Leu Gly Met Leu Gln Gly Arg Gly Pro Leu Lys Leu Phe Met
             35                  40                  45

Ala Leu Val Ala Phe Leu Arg Phe Leu Thr Ile Pro Pro Thr Ala Gly
             50                  55                  60

Ile Leu Lys Arg Trp Gly Thr Ile Lys Lys Ser Lys Ala Ile Asn Val
 65                  70                  75                  80

Leu Arg Gly Phe Arg Lys Glu Ile Gly Arg Met Leu Asn Ile Leu Asn
                 85                  90                  95

Arg Arg Arg Arg Ser Ala Gly Met Ile Ile Met Leu Ile Pro Thr Val
                100                 105                 110

Met Ala
```

<210> SEQ ID NO 33
<211> LENGTH: 1983
<212> TYPE: DNA
<213> ORGANISM: Dengue virus 1

<400> SEQUENCE: 33

| | | | | | |
|---|---|---|---|---|---|
| ttccatctga | ccacccgagg | gggagagccg | cacatgatag | ttagcaagca | ggaaagagga | 60 |
| aaatcacttt | tgtttaagac | ctctgcaggt | gtcaacatgt | gcacccttat | tgcaatggat | 120 |
| ttgggagagt | tatgtgagga | cacaatgacc | tacaaatgcc | cccggatcac | tgagacggaa | 180 |
| ccagatgacg | ttgactgttg | gtgcaatgcc | acggagacat | gggtgaccta | tggaacatgt | 240 |
| tctcaaactg | gtgaacaccg | acgagacaaa | cgttccgtcg | cactggcacc | acacgtaggg | 300 |
| cttggtctag | aaacaagaac | cgaaacgtgg | atgtcctctg | aaggcgcttg | gaaacaaata | 360 |
| caaaaagtgg | agacctgggc | tctgagacac | ccaggattca | cggtgatagc | ccttttctct | 420 |
| gcacatgcca | taggaacatc | catcacccag | aaagggatca | tttttatttt | gctgatgctg | 480 |
| gtaactccat | ccatggccat | gcggtgcgtg | ggaataggca | acagagactt | cgtggaagga | 540 |
| ctgtcaggag | ctacgtgggt | ggatgtggta | ctggagcatg | gaagttgcgt | cactaccatg | 600 |
| gcaaaagaca | accaacact | ggacattgaa | ctcttgaaga | cggaggtcac | aaaccctgcc | 660 |
| gtcctgcgca | aactgtgcat | tgaagctaaa | atatcaaaca | ccaccaccga | ttcgagatgt | 720 |
| ccaacacaag | gagaagccac | gctggtggaa | gaacaggaca | cgaactttgt | gtgtcgacga | 780 |
| acgttcgtgg | acagaggctg | gggcaatggt | tgtgggctat | cggaaaaagg | tagcttaata | 840 |
| acgtgtgcta | agtttaagtg | tgtgacaaaa | ctggaaggaa | agatagtcca | atatgaaaac | 900 |
| ttaaaatatt | cagtgatagt | caccgtacac | actggagacc | agcaccaagt | ggaaatgag | 960 |
| accacagaac | atggaacaac | tgcaaccata | cacctcaag | ctcccacgtc | ggaaatacag | 1020 |
| ctgacagact | acgagctct | aacattggat | tgttcaccta | gaacagggct | agactttaat | 1080 |
| gagatggtgt | tgttgacaat | ggaaaaaaaa | tcatggctcg | tccacaaaca | atggtttcta | 1140 |
| gacttaccac | tgccttggac | ctcggggct | tcaacatccc | aagagacttg | aatagacaa | 1200 |
| gacttgctgg | tcacatttaa | gacagctcat | gcaaaaaagc | aggaagtagt | cgtactagga | 1260 |
| tcacaagaag | gagcaatgca | cactgcgttg | actggagcga | cagaaatcca | aacgtctgga | 1320 |
| acgacaacaa | ttttttgcagg | acacctgaaa | tgcagactaa | aaatggataa | actgactta | 1380 |
| aaagggatgt | catatgtaat | gtgcacaggg | tcattcaagt | tagagaagga | agtggctgag | 1440 |
| acccagcatg | gaactgttct | agtgcaggtt | aaatacgaag | gaacagatgc | accatgcaag | 1500 |

-continued

```
atcccttct cgtcccaaga tgagaaggga gtaacccaga atgggagatt gataacagcc   1560
aaccccatag tcactgacaa agaaaaacca gtcaacattg aagcggagcc acctttggt   1620 gagagctaca ttgtggtagg agcaggtgaa aaagctttga aactaagctg gttcaagaag   1680
ggaagcagta tagggaaaat gtttgaagca actgcccgtg agcacgaag atggccatc    1740 ctgggagaca ctgcatggga cttcggttct ataggagggg tgttcacgtc tgtgggaaaa   1800
ctgatacacc agatttttgg gactgcgtat ggagttttgt tcagcggtgt ttcttggacc   1860
atgaagatag aatagggat tctgctgaca tggctaggat taaactcaag gagcacgtcc    1920 cttttcaatga cgtgtatcgc agttggcatg gtcacgctgt acctaggagt catggttcag   1980
gcg                                                                 1983
```

<210> SEQ ID NO 34
<211> LENGTH: 650
<212> TYPE: PRT
<213> ORGANISM: Dengue virus 1

<400> SEQUENCE: 34

```
Met Ile Val Ser Lys Gln Glu Arg Gly Lys Ser Leu Leu Phe Lys Thr
1               5                   10                  15

Ser Ala Gly Val Asn Met Cys Thr Leu Ile Ala Met Asp Leu Gly Glu
            20                  25                  30

Leu Cys Glu Asp Thr Met Thr Tyr Lys Cys Pro Arg Ile Thr Glu Thr
        35                  40                  45

Glu Pro Asp Asp Val Asp Cys Trp Cys Asn Ala Thr Glu Thr Trp Val
    50                  55                  60

Thr Tyr Gly Thr Cys Ser Gln Thr Gly Glu His Arg Arg Asp Lys Arg
65                  70                  75                  80

Ser Val Ala Leu Ala Pro His Val Gly Leu Gly Leu Glu Thr Arg Thr
                85                  90                  95

Glu Thr Trp Met Ser Ser Glu Gly Ala Trp Lys Gln Ile Gln Lys Val
            100                 105                 110

Glu Thr Trp Ala Leu Arg His Pro Gly Phe Thr Val Ile Ala Leu Phe
        115                 120                 125

Leu Ala His Ala Ile Gly Thr Ser Ile Thr Gln Lys Gly Ile Ile Phe
    130                 135                 140

Ile Leu Leu Met Leu Val Thr Pro Ser Met Ala Met Arg Cys Val Gly
145                 150                 155                 160

Ile Gly Asn Arg Asp Phe Val Glu Gly Leu Ser Gly Ala Thr Trp Val
                165                 170                 175

Asp Val Val Leu Glu His Gly Ser Cys Val Thr Thr Met Ala Lys Asp
            180                 185                 190

Lys Pro Thr Leu Asp Ile Glu Leu Leu Lys Thr Glu Val Thr Asn Pro
        195                 200                 205

Ala Val Leu Arg Lys Leu Cys Ile Glu Ala Lys Ile Ser Asn Thr Thr
    210                 215                 220

Thr Asp Ser Arg Cys Pro Thr Gln Gly Glu Ala Thr Leu Val Glu Glu
225                 230                 235                 240

Gln Asp Thr Asn Phe Val Cys Arg Arg Thr Phe Val Asp Arg Gly Trp
                245                 250                 255

Gly Asn Gly Cys Gly Leu Phe Gly Lys Gly Ser Leu Ile Thr Cys Ala
            260                 265                 270

Lys Phe Lys Cys Val Thr Lys Leu Glu Gly Lys Ile Val Gln Tyr Glu
```

```
                275                 280                 285
Asn Leu Lys Tyr Ser Val Ile Val Thr Val His Thr Gly Asp Gln His
    290                 295                 300
Gln Val Gly Asn Glu Thr Thr Glu His Gly Thr Thr Ala Thr Ile Thr
305                 310                 315                 320
Pro Gln Ala Pro Thr Ser Glu Ile Gln Leu Thr Asp Tyr Gly Ala Leu
                325                 330                 335
Thr Leu Asp Cys Ser Pro Arg Thr Gly Leu Asp Phe Asn Glu Met Val
            340                 345                 350
Leu Leu Thr Met Glu Lys Lys Ser Trp Leu Val His Lys Gln Trp Phe
            355                 360                 365
Leu Asp Leu Pro Leu Pro Trp Thr Ser Gly Ala Ser Thr Ser Gln Glu
        370                 375                 380
Thr Trp Asn Arg Gln Asp Leu Leu Val Thr Phe Lys Thr Ala His Ala
385                 390                 395                 400
Lys Lys Gln Glu Val Val Leu Gly Ser Gln Glu Gly Ala Met His
                405                 410                 415
Thr Ala Leu Thr Gly Ala Thr Glu Ile Gln Thr Ser Gly Thr Thr Thr
            420                 425                 430
Ile Phe Ala Gly His Leu Lys Cys Arg Leu Lys Met Asp Lys Leu Thr
        435                 440                 445
Leu Lys Gly Met Ser Tyr Val Met Cys Thr Gly Ser Phe Lys Leu Glu
        450                 455                 460
Lys Glu Val Ala Glu Thr Gln His Gly Thr Val Leu Val Gln Val Lys
465                 470                 475                 480
Tyr Glu Gly Thr Asp Ala Pro Cys Lys Ile Pro Phe Ser Ser Gln Asp
                485                 490                 495
Glu Lys Gly Val Thr Gln Asn Gly Arg Leu Ile Thr Ala Asn Pro Ile
            500                 505                 510
Val Thr Asp Lys Glu Lys Pro Val Asn Ile Glu Ala Glu Pro Pro Phe
        515                 520                 525
Gly Glu Ser Tyr Ile Val Val Gly Ala Gly Glu Lys Ala Leu Lys Leu
        530                 535                 540
Ser Trp Phe Lys Lys Gly Ser Ser Ile Gly Lys Met Phe Glu Ala Thr
545                 550                 555                 560
Ala Arg Gly Ala Arg Arg Met Ala Ile Leu Gly Asp Thr Ala Trp Asp
                565                 570                 575
Phe Gly Ser Ile Gly Gly Val Phe Thr Ser Val Gly Lys Leu Ile His
            580                 585                 590
Gln Ile Phe Gly Thr Ala Tyr Gly Val Leu Phe Ser Gly Val Ser Trp
        595                 600                 605
Thr Met Lys Ile Gly Ile Gly Ile Leu Leu Thr Trp Leu Gly Leu Asn
        610                 615                 620
Ser Arg Ser Thr Ser Leu Ser Met Thr Cys Ile Ala Val Gly Met Val
625                 630                 635                 640
Thr Leu Tyr Leu Gly Val Met Val Gln Ala
                645                 650

<210> SEQ ID NO 35
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide
```

<400> SEQUENCE: 35

```
atgaacaacc agcgcaagaa ggccaaaaac actccgttca atatgctcaa gagagagcgc    60
aatcgggttt ctacggtaca gcagctgacg aagagattct ccctgggcat gctgcaaggt   120
cgcggaccac tgaagctgtt catggccctt gttgcatttc ttaggtttct tacaattccc   180
cccactgctg gaatcctgaa gcggtggggc accatcaaaa agtccaaggc tattaatgtc   240
ctcaggggt tcaggaaaga gattgggcgg atgctgaaca tccttaatag acgcagacgg   300
tccgctggca tgataatcat gctgatccca accgtcatgg cctttcacct gaccactagg   360
ggcggtgagc cacatatgat agttagtaaa caggaaaggg gtaaaagtct gcttttttaaa   420
acttccgccg gcgtaaatat gtgcacactg atagccatgg acttgggcga gctttgcgag   480
gataccatga catacaaatg cccccggatc acagagacaa aaccagacga tgttgactgc   540
tggtgcaacg ccaccgagac ttgggttaca tacgggactt gcagccaaac gggagaacat   600
agacgcgcaa agagatctgt agcccttgcc ccacacgtag gactgggact cgagacaaga   660
acagaaacct ggatgagtag tgaaggcgct tggaaacaga tccaaaaggt ggaaacttgg   720
gctctgcgac accctgggtt cacagtgatc gcattgtttt tggcccatgc aataggaact   780
tctatcacac agaaaggcat tatcttcatc ctgctgatgt tggttacacc ttcaatggcc   840
atgaggtgcg tcggtatcgg aaacagagat ttcgtggaag ggctgagcgg ggctacctgg   900
gtggatgtcg tcctcgaaca cggatcatgt gtcacgacta tggcaaaaga taagcctacc   960
ctcgatattg agctgttgaa gaccgaggtt actaaccctg ctgtgctgcg caaactgtgt  1020
attgaagcaa agatttctaa cacaacaacc gacagtagat gccccactca gggagaagcc  1080
acgctggtgg aagagcagga caccaacttt gtatgtagaa gaaccttcgt cgatcgcgga  1140
tgggggaacg ggtgcggact cttcggaaaa ggatccctga ttacttgtgc aaaattcaaa  1200
tgcgtgacta aacttgaagg caaaatcgta cagtacgaaa atttgaagta ctctgttatc  1260
gttaccgttc atacgggaga tcaacaccag gttgggaacg agaccaccga acacggcact  1320
accgcaacga ttacacctca agcccctact tccgaaatac aactcaccga ctatggcgcc  1380
cttacactgg actgttcacc acgcactgga ctggacttca cgaaatggt cctcctgaca  1440
atggaaaaga aaagctggct tgtacacaag caatggttct tggacctgcc gctcccatgg  1500
acgagtggcg cgagtactag ccaggagacc tggaaccggc aggaccttct ggtaacattc  1560
aagacagcac acgctaaaaa acaagaggtg gtcgttcttg gatcccaaga gggtgcaatg  1620
cacacagccc tcacaggtgc aaccgagatc cagacttccg gaactaccac tatctttgca  1680
ggccatctca aatgcagact gaaaatggat aaacttacac tcaaggggat gtcatatgtc  1740
atgtgtacgg ggtctttaa acttgaaaag gaggtcgctg aaacacaaca cggaactgtt  1800
ctggtgcaag tcaaatacga aggtacggat gctccctgta aaattccctt cagctctcag  1860
gacgaaaaag gtgttactca gaatggtagg ctgattaccg ctaatccaat tgtaaccgat  1920
aaggagaaac ccgtgaatat tgaggcagag ccccccttcg gtgaatctta tattgtagtt  1980
ggagcaggag agaaggccct taaactcagt tggttcaaga agggatcttc cctcggaaaa  2040
gcatttgaag ctacggctcg gggagcgcgc aggctggcta tccttgggga cacggcatgg  2100
gactttggaa gcattggtgg cgtctttaca tccgtgggaa agttgataca ccaaatcttc  2160
gggaccgcgt acggcgtgct cttttcagga gtctcttgga ctatgaagat cggaattggc  2220
atactcttga cctggcttgg cttgaattcc cggtctactt ctttgagtat gacttgcatt  2280
```
gctgttggca tggtcactct ctacctcggc gtgatggtgc aggcctag          2328

<210> SEQ ID NO 36
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Thr Thr Arg Gly Gly Glu Pro His Met Ile Val
        115                 120                 125

Ser Lys Gln Glu Arg Gly Lys Ser Leu Leu Phe Lys Thr Ser Ala Gly
    130                 135                 140

Val Asn Met Cys Thr Leu Ile Ala Met Asp Leu Gly Glu Leu Cys Glu
145                 150                 155                 160

Asp Thr Met Thr Tyr Lys Cys Pro Arg Ile Thr Glu Thr Glu Pro Asp
                165                 170                 175

Asp Val Asp Cys Trp Cys Asn Ala Thr Glu Thr Trp Val Thr Tyr Gly
            180                 185                 190

Thr Cys Ser Gln Thr Gly Glu His Arg Arg Asp Lys Arg Ser Val Ala
        195                 200                 205

Leu Ala Pro His Val Gly Leu Gly Leu Glu Thr Arg Thr Glu Thr Trp
    210                 215                 220

Met Ser Ser Glu Gly Ala Trp Lys Gln Ile Gln Lys Val Glu Thr Trp
225                 230                 235                 240

Ala Leu Arg His Pro Gly Phe Thr Val Ile Ala Leu Phe Leu Ala His
                245                 250                 255

Ala Ile Gly Thr Ser Ile Thr Gln Lys Gly Ile Ile Phe Ile Leu Leu
            260                 265                 270

Met Leu Val Thr Pro Ser Met Ala Met Arg Cys Val Gly Ile Gly Asn
        275                 280                 285

Arg Asp Phe Val Glu Gly Leu Ser Gly Ala Thr Trp Val Asp Val Val
    290                 295                 300

Leu Glu His Gly Ser Cys Val Thr Thr Met Ala Lys Asp Lys Pro Thr
305                 310                 315                 320

Leu Asp Ile Glu Leu Leu Lys Thr Glu Val Thr Asn Pro Ala Val Leu
                325                 330                 335

Arg Lys Leu Cys Ile Glu Ala Lys Ile Ser Asn Thr Thr Thr Asp Ser
            340                 345                 350
```

```
Arg Cys Pro Thr Gln Gly Glu Ala Thr Leu Val Glu Gln Asp Thr
            355                 360                 365
Asn Phe Val Cys Arg Arg Thr Phe Val Asp Arg Gly Trp Gly Asn Gly
        370                 375                 380
Cys Gly Leu Phe Gly Lys Gly Ser Leu Ile Thr Cys Ala Lys Phe Lys
385                 390                 395                 400
Cys Val Thr Lys Leu Glu Gly Lys Ile Val Gln Tyr Glu Asn Leu Lys
                405                 410                 415
Tyr Ser Val Ile Val Thr Val His Thr Gly Asp Gln His Gln Val Gly
                420                 425                 430
Asn Glu Thr Thr Glu His Gly Thr Thr Ala Thr Ile Thr Pro Gln Ala
            435                 440                 445
Pro Thr Ser Glu Ile Gln Leu Thr Asp Tyr Gly Ala Leu Thr Leu Asp
    450                 455                 460
Cys Ser Pro Arg Thr Gly Leu Asp Phe Asn Glu Met Val Leu Leu Thr
465                 470                 475                 480
Met Glu Lys Lys Ser Trp Leu Val His Lys Gln Trp Phe Leu Asp Leu
                485                 490                 495
Pro Leu Pro Trp Thr Ser Gly Ala Ser Thr Ser Gln Glu Thr Trp Asn
            500                 505                 510
Arg Gln Asp Leu Leu Val Thr Phe Lys Thr Ala His Ala Lys Lys Gln
        515                 520                 525
Glu Val Val Val Leu Gly Ser Gln Glu Gly Ala Met His Thr Ala Leu
    530                 535                 540
Thr Gly Ala Thr Glu Ile Gln Thr Ser Gly Thr Thr Thr Ile Phe Ala
545                 550                 555                 560
Gly His Leu Lys Cys Arg Leu Lys Met Asp Lys Leu Thr Leu Lys Gly
                565                 570                 575
Met Ser Tyr Val Met Cys Thr Gly Ser Phe Lys Leu Glu Lys Glu Val
            580                 585                 590
Ala Glu Thr Gln His Gly Thr Val Leu Val Gln Val Lys Tyr Glu Gly
        595                 600                 605
Thr Asp Ala Pro Cys Lys Ile Pro Phe Ser Ser Gln Asp Glu Lys Gly
    610                 615                 620
Val Thr Gln Asn Gly Arg Leu Ile Thr Ala Asn Pro Ile Val Thr Asp
625                 630                 635                 640
Lys Glu Lys Pro Val Asn Ile Glu Ala Glu Pro Pro Phe Gly Glu Ser
                645                 650                 655
Tyr Ile Val Val Gly Ala Gly Glu Lys Ala Leu Lys Leu Ser Trp Phe
            660                 665                 670
Lys Lys Gly Ser Ser Leu Gly Lys Ala Phe Glu Ala Thr Ala Arg Gly
        675                 680                 685
Ala Arg Arg Leu Ala Ile Leu Gly Asp Thr Ala Trp Asp Phe Gly Ser
    690                 695                 700
Ile Gly Gly Val Phe Thr Ser Val Gly Lys Leu Ile His Gln Ile Phe
705                 710                 715                 720
Gly Thr Ala Tyr Gly Val Leu Phe Ser Gly Val Ser Trp Thr Met Lys
                725                 730                 735
Ile Gly Ile Gly Ile Leu Leu Thr Trp Leu Gly Leu Asn Ser Arg Ser
            740                 745                 750
Thr Ser Leu Ser Met Thr Cys Ile Ala Val Gly Met Val Thr Leu Tyr
        755                 760                 765
Leu Gly Val Met Val Gln Ala
```

770          775

<210> SEQ ID NO 37
<211> LENGTH: 1977
<212> TYPE: DNA
<213> ORGANISM: Dengue virus 3

<400> SEQUENCE: 37

```
ttccacttaa cttcacgaga tggagagccg cgcatgattg tggggaagaa tgaaagaggg      60
aaatccctac tttttaagac agcttctgga atcaacatgt gcacactcat agccatggac     120
ttgggagaga tgtgtgatga cacggtcact tacaaatgcc cccacattgc cgaagtggaa     180
cctgaagaca ttgactgctg gtgcaacctt acatcgacat gggtgactta tggaacgtgc     240
aatcaagctg gggagcacag acgcgacaag agatcagtgg cgttagctcc ccatgtcggc     300
atgggactgg acacacgcac ccaaacctgg atgtcggctg aaggagcttg agacaagtc     360
gagaaggtag agacatgggc ccttaggcac ccagggttca ccatactagc tctatttctt     420
gcccattaca taggcacttc cttgacccag aaagtggtta tttttatact actaatactg     480
gtcactccat ccatggcaat gagatgcgtg ggagtaggaa acagagattt tgtggaaggt     540
ctatcgggag ctacgtgggt tgacgtggtg ctcgagcacg gtgggtgtgt gaccaccatg     600
gctaagaaca agcccacgct ggacatagac cttcagaaga ccgaggccac ccaactggcc     660
accctaagga agttatgcat tgagggaaaa attaccaaca taacaactga ctcaaggtgt     720
cctacccagg gggaagcgat tttacctgag gagcaggacc agaactacgt atgtaagcat     780
acatacgtgg atagagctg gggaaacggt tgtggtttgt ttggaaaagg aagcttggtg     840
acatgcgcga aatttcaatg cttagaatca atagaggaa agtggtgca acatgagaac     900
ctcaaataca ctgtcatcat tacagtgcac acaggagacc aacaccaggt gggaaatgaa     960
acgcagggag tcacggctga taacacccc caggcatcaa ccgttgaagc tatcttgcct    1020
gaatatggaa cccttgggct agaatgctca ccacggacag ttttggattt caatgaaatg    1080
atcttattga caatgaagaa caaagcatgg atggtacata caatggttc ctttgacctc    1140
cccctaccat ggacatcagg agctacaaca gagacaccaa cttggaacag aaagagctt    1200
cttgtgacat tcaaaaatgc acatgcaaaa aagcaagaag tagttgtcct tggatcgcaa    1260
gagggagcaa tgcacacagc gctgacagga gctacagaga tccaaaactc aggaggcaca    1320
agcatttttg ccgggcactt gaaatgtaga cttaagatgg acaaattgga actcaagggg    1380
atgagctatg caatgtgctt gaacacctt gtgttaaga agaagtctc cgagacgcag    1440
catgggacaa tactcattaa ggttgagtac aaaggggaag atgcaccttg caagattcct    1500
ttctccacgg aggatggaca agggaaagct cacaatggta gactgatcac agccaaccca    1560
gtggtgacca agaaggagga gcctgtcaac attgaggctg aacctccttt tggggaaagt    1620
aacatagtga ttggaattgg agacaaagcc ttgaaaatta ctggtacaa gaagggaagc    1680
tcgattggga agatgttcga ggccactgcc agaggtgcaa ggcgcatggc catcttggga    1740
gacacagcct gggactttgg atcagtgggt ggtgtcttga attcattagg gaaaatggtc    1800
caccaaatat ttggaagtgc ttacacagcc ctgtttagtg gagtctcatg gataatgaaa    1860
attggaatag gtgtcctctt aacctggata gggttgaatt caaaaacac ttccatgtca    1920
tttttcatgta ttgcgatagg aattattaca ctctatctgg gagccgtggt acaagct     1977
```

<210> SEQ ID NO 38
<211> LENGTH: 2322

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 38

| | | | | | |
|---|---|---|---|---|---|
| atgaacaacc | agcgcaagaa | ggccaaaaac | actccgttca | atatgctcaa | gagagagcgc | 60 |
| aatcgggttt | ctacggtaca | gcagctgacg | aagagattct | ccctgggcat | gctgcaaggt | 120 |
| cgcggaccac | tgaagctgtt | catggccctt | gttgcatttc | ttaggtttct | tacaattccc | 180 |
| cccactgctg | gaatcctgaa | gcggtggggc | accatcaaaa | agtccaaggc | tattaatgtc | 240 |
| ctcagggggt | tcaggaaaga | gattgggcgg | atgctgaaca | tccttaatag | acgcagacgg | 300 |
| tccgctggca | tgataatcat | gctgatccca | accgtcatgg | cctttcatct | gacttctcga | 360 |
| gatggagagc | ctcgcatgat | cgttggcaag | aatgagcgcg | gcaaaagtct | cctgttcaaa | 420 |
| acggcctctg | gaattaatat | gtgtaccttg | attgctatgg | atctgggaga | gatgtgtgat | 480 |
| gataccgtta | cctacaagtg | cccgcacatt | gctgaggttg | agcctgaaga | catagactgc | 540 |
| tggtgcaact | tgacaagtac | gtgggtcacc | tacgggacct | gcaaccaagc | cggcgagcac | 600 |
| aggcgcgcaa | agagatccgt | tgcgctggcg | ccacacgtag | gaatgggcct | ggacactcgc | 660 |
| actcagactt | ggatgtctgc | tgagggcgcc | tggcggcagg | tagagaaagt | agagacatgg | 720 |
| gctctcaggc | acccaggatt | taccattctg | gctctgtttt | tggcccacta | tatcggcacc | 780 |
| tccctcactc | agaaggtcgt | cattttcata | ctcctgatac | tcgtgacccc | ttctatggcc | 840 |
| atgcggtgtg | tcggggtcgg | caatagggac | ttcgtggaag | gattgagtgg | cgcaacttgg | 900 |
| gtcgatgtcg | tgctggaaca | tggaggttgt | gtaactacta | tggcgaagaa | taaaccaact | 960 |
| ctggacatcg | agctgcaaaa | gactgaggca | acacaacttg | caactcttag | aaagctgtgt | 1020 |
| atcgaaggca | aaataactaa | tatcaccaca | gattccagat | gtcccaccca | ggggaagct | 1080 |
| atcctgccag | aggagcagga | ccagaattac | gtgtgtaagc | atacctatgt | ggatcggggc | 1140 |
| tgggggaatg | gatgtggcct | cttcggtaag | ggttccctcg | tgacgtgcgc | gaaattccag | 1200 |
| tgtttggaat | ccatagaagg | caaagtagta | caacacgaaa | acctcaaata | tacagttatt | 1260 |
| atcactgttc | acaccgggga | ccagcaccaa | gtagggaatg | agacacaggg | cgttacagcc | 1320 |
| gaaattactc | cacaagccag | tacagtcgag | gctattctgc | ctgaatatgg | tactttggga | 1380 |
| ctcgaatgct | caccgcggac | cggactggac | tttaacgaaa | tgatactgct | gacaatgaag | 1440 |
| aacaaggcct | ggatggtaca | ccgccaatgg | ttctttgacc | tgccactgcc | atggacatcc | 1500 |
| ggtgcaacaa | ctgaaactcc | tacatggaac | cgaaaagaac | tgctcgtcac | ttttaagaat | 1560 |
| gcccatgcta | aaaacagga | ggttgtcgta | ttgggttctc | aggaaggcgc | aatgcatact | 1620 |
| gctcttacag | gggccaccga | gatacaaaat | tcaggggaa | ccagcatctt | cgcagggcac | 1680 |
| ttgaagtgta | ggctgaaaat | ggacaagctg | gagctcaagg | gaatgagtta | cgccatgtgc | 1740 |
| ctcaacacgt | ttgttctgaa | aaaggaggtc | agcgagacag | agcacggaac | aatactgatt | 1800 |
| aaggttgagt | ataaggaga | agatgccccc | tgcaaaattc | ctttcagcac | cgaagacggg | 1860 |
| caagggaaag | cacacaacgg | acgcctgatt | actgccaatc | ccgtcgtcac | taagaaggag | 1920 |
| gaaccagtga | atattgaggc | cgaaccacct | tttgggaat | ctaacattgt | aattgggatt | 1980 |
| ggagacaaag | cattgaagat | aaattggtac | aagaagggtt | catctctggg | caaggctttc | 2040 |
| gaggccacag | cgagaggggc | aagacgactg | gccattttgg | gggatacagc | ttgggacttc | 2100 |
| ggtagcgtcg | gcggagtgct | gaactccctg | gggaaaatgg | tgcaccagat | attcggttcc | 2160 |

```
gcctacactg cgctgttctc tggggttagt tggattatga aaatcggtat cggagtgctg    2220
ctcacgtgga tcggactcaa cagtaagaac acctctatgt catttagttg tatcgcaatt    2280
ggaatcatta ccttgtatct gggagccgtc gtgcaagcct ag                       2322
```

<210> SEQ ID NO 39
<211> LENGTH: 659
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Phe His Leu Thr Ser Arg Asp Gly Glu Pro Arg Met Ile Val Gly Lys
1               5                   10                  15

Asn Glu Arg Gly Lys Ser Leu Leu Phe Lys Thr Ala Ser Gly Ile Asn
            20                  25                  30

Met Cys Thr Leu Ile Ala Met Asp Leu Gly Glu Met Cys Asp Asp Thr
        35                  40                  45

Val Thr Tyr Lys Cys Pro His Ile Ala Glu Val Glu Pro Glu Asp Ile
    50                  55                  60

Asp Cys Trp Cys Asn Leu Thr Ser Thr Trp Val Thr Tyr Gly Thr Cys
65                  70                  75                  80

Asn Gln Ala Gly Glu His Arg Arg Ala Lys Arg Ser Val Ala Leu Ala
                85                  90                  95

Pro His Val Gly Met Gly Leu Asp Thr Arg Thr Gln Thr Trp Met Ser
            100                 105                 110

Ala Glu Gly Ala Trp Arg Gln Val Glu Lys Val Glu Thr Trp Ala Leu
        115                 120                 125

Arg His Pro Gly Phe Thr Ile Leu Ala Leu Phe Leu Ala His Tyr Ile
    130                 135                 140

Gly Thr Ser Leu Thr Gln Lys Val Val Ile Phe Ile Leu Leu Ile Leu
145                 150                 155                 160

Val Thr Pro Ser Met Ala Met Arg Cys Val Gly Val Gly Asn Arg Asp
                165                 170                 175

Phe Val Glu Gly Leu Ser Gly Ala Thr Trp Val Asp Val Val Leu Glu
            180                 185                 190

His Gly Gly Cys Val Thr Thr Met Ala Lys Asn Lys Pro Thr Leu Asp
        195                 200                 205

Ile Glu Leu Gln Lys Thr Glu Ala Thr Gln Leu Ala Thr Leu Arg Lys
    210                 215                 220

Leu Cys Ile Glu Gly Lys Ile Thr Asn Ile Thr Thr Asp Ser Arg Cys
225                 230                 235                 240

Pro Thr Gln Gly Glu Ala Ile Leu Pro Glu Glu Gln Asp Gln Asn Tyr
                245                 250                 255

Val Cys Lys His Thr Tyr Val Asp Arg Gly Trp Gly Asn Gly Cys Gly
            260                 265                 270

Leu Phe Gly Lys Gly Ser Leu Val Thr Cys Ala Lys Phe Gln Cys Leu
        275                 280                 285

Glu Ser Ile Glu Gly Lys Val Val Gln His Glu Asn Leu Lys Tyr Thr
    290                 295                 300

Val Ile Ile Thr Val His Thr Gly Asp Gln His Gln Val Gly Asn Glu
305                 310                 315                 320

Thr Gln Gly Val Thr Ala Glu Ile Thr Pro Gln Ala Ser Thr Val Glu
```

```
            325                 330                 335
Ala Ile Leu Pro Glu Tyr Gly Thr Leu Gly Leu Glu Cys Ser Pro Arg
            340                 345                 350

Thr Gly Leu Asp Phe Asn Glu Met Ile Leu Leu Thr Met Lys Asn Lys
        355                 360                 365

Ala Trp Met Val His Arg Gln Trp Phe Phe Asp Leu Pro Leu Pro Trp
    370                 375                 380

Thr Ser Gly Ala Thr Thr Glu Thr Pro Thr Trp Asn Arg Lys Glu Leu
385                 390                 395                 400

Leu Val Thr Phe Lys Asn Ala His Ala Lys Lys Gln Glu Val Val Val
                405                 410                 415

Leu Gly Ser Gln Glu Gly Ala Met His Thr Ala Leu Thr Gly Ala Thr
            420                 425                 430

Glu Ile Gln Asn Ser Gly Gly Thr Ser Ile Phe Ala Gly His Leu Lys
        435                 440                 445

Cys Arg Leu Lys Met Asp Lys Leu Glu Leu Lys Gly Met Ser Tyr Ala
    450                 455                 460

Met Cys Leu Asn Thr Phe Val Leu Lys Lys Glu Val Ser Glu Thr Gln
465                 470                 475                 480

His Gly Thr Ile Leu Ile Lys Val Glu Tyr Lys Gly Glu Asp Ala Pro
                485                 490                 495

Cys Lys Ile Pro Phe Ser Thr Glu Asp Gly Gln Gly Lys Ala His Asn
            500                 505                 510

Gly Arg Leu Ile Thr Ala Asn Pro Val Val Thr Lys Lys Glu Glu Pro
        515                 520                 525

Val Asn Ile Glu Ala Glu Pro Pro Phe Gly Glu Ser Asn Ile Val Ile
    530                 535                 540

Gly Ile Gly Asp Lys Ala Leu Lys Ile Asn Trp Tyr Lys Lys Gly Ser
545                 550                 555                 560

Ser Leu Gly Lys Ala Phe Glu Ala Thr Ala Arg Gly Ala Arg Arg Leu
                565                 570                 575

Ala Ile Leu Gly Asp Thr Ala Trp Asp Phe Gly Ser Val Gly Gly Val
            580                 585                 590

Leu Asn Ser Leu Gly Lys Met Val His Gln Ile Phe Gly Ser Ala Tyr
        595                 600                 605

Thr Ala Leu Phe Ser Gly Val Ser Trp Ile Met Lys Ile Gly Ile Gly
    610                 615                 620

Val Leu Leu Thr Trp Ile Gly Leu Asn Ser Lys Asn Thr Ser Met Ser
625                 630                 635                 640

Phe Ser Cys Ile Ala Ile Gly Ile Ile Thr Leu Tyr Leu Gly Ala Val
                645                 650                 655

Val Gln Ala

<210> SEQ ID NO 40
<211> LENGTH: 1983
<212> TYPE: DNA
<213> ORGANISM: Dengue virus 4

<400> SEQUENCE: 40
ttccacttat cgtcaagaga cggcgaaccc ctcatgatag tagcgaaaca cgaaaggggg      60
agacctcttt tgtttaagac aacggaagga atcaacagat gcactctcat tgccatggac     120
gtgggtgaaa tgtgtgagga caccgtcaca tataaatgcc ccctactggt caacactgag     180
cctgaagaca ttgattgctg gtgcaactcc acatccactt gggtcacgta tggaacgtgt     240
```

-continued

```
acccagagtg gggaacggag acgggagaag cgctcagtgg cactggcacc acattcagga     300
atgggattgg aaaccaggac agagacgtgg atgtcatcgg aggggggcatg gaaacatgcc    360
cagagagtgg agagctggat acttagaaat ccaggatttg cactcttggc aggatttatg    420
gcttacatga ttggacagac aggaattcaa cgaacagtct tctttgtcct catgatgttg    480
gtcgctccat cctatggaat gcgatgcgtg ggagtgggga atagagattt tgtggaagga    540
gtctcaggag aacatggggt cgacctggtg ctggaacacg gaggatgtgt acaaccatg     600
gcacagggaa agccaacctt ggattttgaa ttgatcaaga caacagcaaa ggaggtagct    660
ctattaagaa cttattgcat agaggcctca atatcaaaca taaccacggc aacaagatgt    720
ccaacacaag gagaacctta tcttaaagag gaacaagacc agcagtacat ttgcagaaga    780
gacgtggtag acagaggatg gggtaatggc tgtggcctat ttggaaaagg aggagttgta    840
acatgcgcaa agttttcatg ctcggggaaa ataacaggca acctggtcca agttgaaaac    900
cttgaataca cagtggttgt gacagttcat aatgggatg cccacgcagt gggaaacagc    960
acgtccaatc atggagtaac aaccacaata accccccagt caccatcggt agaagttaaa    1020
ctaccagatt atgggaact gacactcgat tgcgaaccca ggtccggaat cgactttaac    1080
gaaatgatcc tgatgaaaat gaaggaaaa acatggcttg tgcacaaaca atggttctta    1140
gatctacccc tgccatggac agcaggagct gacacatcag aagtccattg gaattataaa    1200
gagagaatgg tgacgttcaa agtacctcat gccaagagac aggatgtcac agtgctagga    1260
tcccaggaag gagccatgca ctctgccctc actggagcta cggaggtgga ttctggtgac    1320
ggaaaccaca tgtttgcagg gcacctaaag tgcaaagtgc gcatggaaaa attgaggatc    1380
aagggaatgt catacacgat gtgctcagga aagttttcca tcgacaagga atggcagaa    1440
acgcagcacg ggacaacagt ggtgaaggtc aagtatgaag gcactggggc tccatgcaaa    1500
attccaatag aaataaaaga catgaataag gaaaaagtgg ttggacgcat tatttcatct    1560
attcccttg ctgaaaacac caacagcata accaatattg aactcgaacc ccccttggg     1620
gacagctaca tagtgatagg cgctggagac agtgcattga cactccattg gtttaggaag    1680
ggaagttcta tcgggaagat gtttgagtcc acttatagag gtgcaaaaag aatggccatt    1740
ttggggtgaaa cagcatggga ttttggctcc gttggtggat tgtttacatc attagggaaa    1800
gctgtgcatc aggttttggg cagtgtctac acaacaatgt tggggggagt ctcatggatg    1860
atcagaattc tcattgggat tttagtattg tggatcggca cgaactcaag aaacacttca    1920
atggcaatgt catgcatagc tgttggagga atcaccttat ttcttggttt tacggtccaa    1980
gca                                                                  1983
```

<210> SEQ ID NO 41
<211> LENGTH: 650
<212> TYPE: PRT
<213> ORGANISM: Dengue virus 4

<400> SEQUENCE: 41

```
Met Ile Val Ala Lys His Glu Arg Gly Arg Pro Leu Leu Phe Lys Thr
1               5                   10                  15

Thr Glu Gly Ile Asn Arg Cys Thr Leu Ile Ala Met Asp Val Gly Glu
            20                  25                  30

Met Cys Glu Asp Thr Val Thr Tyr Lys Cys Pro Leu Leu Val Asn Thr
        35                  40                  45

Glu Pro Glu Asp Ile Asp Cys Trp Cys Asn Ser Thr Ser Thr Trp Val
```

```
           50                  55                  60
Thr Tyr Gly Thr Cys Thr Gln Ser Gly Glu Arg Arg Glu Lys Arg
65                      70                  75                  80

Ser Val Ala Leu Ala Pro His Ser Gly Met Gly Leu Glu Thr Arg Thr
                    85                  90                  95

Glu Thr Trp Met Ser Ser Glu Gly Ala Trp Lys His Ala Gln Arg Val
                100                 105                 110

Glu Ser Trp Ile Leu Arg Asn Pro Gly Phe Ala Leu Leu Ala Gly Phe
            115                 120                 125

Met Ala Tyr Met Ile Gly Gln Thr Gly Ile Gln Arg Thr Val Phe Phe
130                 135                 140

Val Leu Met Met Leu Val Ala Pro Ser Tyr Gly Met Arg Cys Val Gly
145                 150                 155                 160

Val Gly Asn Arg Asp Phe Val Glu Gly Val Ser Gly Gly Thr Trp Val
                165                 170                 175

Asp Leu Val Leu Glu His Gly Gly Cys Val Thr Thr Met Ala Gln Gly
                180                 185                 190

Lys Pro Thr Leu Asp Phe Glu Leu Ile Lys Thr Thr Ala Lys Glu Val
                195                 200                 205

Ala Leu Leu Arg Thr Tyr Cys Ile Glu Ala Ser Ile Ser Asn Ile Thr
210                 215                 220

Thr Ala Thr Arg Cys Pro Thr Gln Gly Glu Pro Tyr Leu Lys Glu Glu
225                 230                 235                 240

Gln Asp Gln Gln Tyr Ile Cys Arg Arg Asp Val Val Asp Arg Gly Trp
                245                 250                 255

Gly Asn Gly Cys Gly Leu Phe Gly Lys Gly Val Val Thr Cys Ala
                260                 265                 270

Lys Phe Ser Cys Ser Gly Lys Ile Thr Gly Asn Leu Val Gln Val Glu
                275                 280                 285

Asn Leu Glu Tyr Thr Val Val Val Thr Val His Asn Gly Asp Ala His
                290                 295                 300

Ala Val Gly Asn Ser Thr Ser Asn His Gly Val Thr Thr Ile Thr
305                 310                 315                 320

Pro Arg Ser Pro Ser Val Glu Val Lys Leu Pro Asp Tyr Gly Glu Leu
                325                 330                 335

Thr Leu Asp Cys Glu Pro Arg Ser Gly Ile Asp Phe Asn Glu Met Ile
                340                 345                 350

Leu Met Lys Met Lys Gly Lys Thr Trp Leu Val His Lys Gln Trp Phe
                355                 360                 365

Leu Asp Leu Pro Leu Pro Trp Thr Ala Gly Ala Asp Thr Ser Glu Val
                370                 375                 380

His Trp Asn Tyr Lys Glu Arg Met Val Thr Phe Lys Val Pro His Ala
385                 390                 395                 400

Lys Arg Gln Asp Val Thr Val Leu Gly Ser Gln Glu Gly Ala Met His
                405                 410                 415

Ser Ala Leu Thr Gly Ala Thr Glu Val Asp Ser Gly Asp Gly Asn His
                420                 425                 430

Met Phe Ala Gly His Leu Lys Cys Lys Val Arg Met Glu Lys Leu Arg
                435                 440                 445

Ile Lys Gly Met Ser Tyr Thr Met Cys Ser Gly Lys Phe Ser Ile Asp
                450                 455                 460

Lys Glu Met Ala Glu Thr Gln His Gly Thr Thr Val Val Lys Val Lys
465                 470                 475                 480
```

```
Tyr Glu Gly Thr Gly Ala Pro Cys Lys Ile Pro Ile Glu Ile Lys Asp
                485                 490                 495

Met Asn Lys Glu Lys Val Val Gly Arg Ile Ile Ser Ser Ile Pro Phe
            500                 505                 510

Ala Glu Asn Thr Asn Ser Ile Thr Asn Ile Glu Leu Glu Pro Pro Phe
            515                 520                 525

Gly Asp Ser Tyr Ile Val Ile Gly Ala Gly Asp Ser Ala Leu Thr Leu
            530                 535                 540

His Trp Phe Arg Lys Gly Ser Ser Ile Gly Lys Met Phe Glu Ser Thr
545                 550                 555                 560

Tyr Arg Gly Ala Lys Arg Met Ala Ile Leu Gly Glu Thr Ala Trp Asp
                565                 570                 575

Phe Gly Ser Val Gly Gly Leu Phe Thr Ser Leu Gly Lys Ala Val His
            580                 585                 590

Gln Val Phe Gly Ser Val Tyr Thr Thr Met Phe Gly Gly Val Ser Trp
            595                 600                 605

Met Ile Arg Ile Leu Ile Gly Ile Leu Val Leu Trp Ile Gly Thr Asn
            610                 615                 620

Ser Arg Asn Thr Ser Met Ala Met Ser Cys Ile Ala Val Gly Gly Ile
625                 630                 635                 640

Thr Leu Phe Leu Gly Phe Thr Val Gln Ala
                645                 650

<210> SEQ ID NO 42
<211> LENGTH: 2328
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
atgaacaacc agcgcaagaa ggccaaaaac actccgttca atatgctcaa gagagagcgc      60
aatcgggttt ctacggtaca gcagctgacg aagagattct ccctgggcat gctgcaaggt     120
cgcggaccac tgaagctgtt catggccctt gttgcatttc ttaggtttct tacaattccc     180
cccactgctg gaatcctgaa gcggtggggc accatcaaaa agtccaaggc tattaatgtc     240 ctcaggggt tcaggaaaga gattggcgg atgctgaaca tccttaatag acgcagacgg     300
tccgctggca tgataatcat gctgatccca accgtcatgg cctttcatct cagctcccgc     360
gatggagaac ctttgatgat agtcgcaaaa cacgaacggg gcaggccact gcttttcaag     420
actactgaag gcatcaaccg ctgcaccctg atcgcaatgg acgtgggtga gatgtgcgag     480
gataccgtga cttataagtg cccacttctc gtaaacacag agccagaaga cattgattgt     540
tggtgcaatt ctacctctac ctgggtaacc tatggaactt gcacacaaag cggagaaagg     600
agaagagcca agcggagcgt tgctctggca ccgcattccg gaatgggact gaaactaga      660 acagaaactt ggatgagtag cgaaggagcc tggaaacatg cccaacgggt ggaaagctgg     720
attctgcgca accctggatt cgcactgctt gccggttta tggcatacat gattggacag     780
accggaatcc agagaaccgt tttctttgta ctgatgatgc tggtggctcc ctcttatgga     840
atgcgatgtg tcggcgtggg caatcgagat tttgtggaag gggtcagcgg gggcacttgg     900
gtggacctcg tgctggagca tggaggatgc gttacaacca tggcccaagg aaaacctaca     960
cttgattttg aactgataaa gacaacagct aaggaagtag ccctgttgcg cacctactgt    1020
```

```
atcgaagcta gtatctctaa catcactaca gcaacacggt gcccaactca gggagaaccc    1080
tatttgaagg aggagcaaga tcagcagtat atctgtcgcc gagatgtcgt ggaccgagga    1140
tgggggaacg gctgcgggct ttttggaaaa ggaggcgtcg tgacctgtgc taaattcagt    1200
tgttcaggaa agattacggg gaacctcgtg caggtggaga acctggaata cacggtggta    1260
gtaacagttc ataatgggga cgcacacgcc gtaggaaata gcacctccaa ccacggcgtt    1320
accactacaa ttacacctag aagcccttcc gtggaagtta agctgcctga ttatggggag    1380
ctcacccttg attgcgagcc cagaagtggc attgacttta cgaaatgat actcatgaag     1440 atgaaaggaa aaacctggct ggtacataaa cagtggttcc tcgaccttcc gctcccatgg    1500
acagcaggag ccgacacctc cgaggttcat tggaattaca agagagaat ggttactttc     1560 aaggtgccac atgcgaagcg ccaggatgtg acagtactgg gatcccaaga aggcgccatg    1620
cactctgccc tgacaggcgc tactgagtg gactccggcg atggaaatca catgttcgcg     1680
ggccatctga agtgtaaagt aaggatggag aagctgcgaa tcaaggaat gtcctatacg     1740 atgtgttcag gtaagttttc tattgacaaa gaaatggcag aaacccaaca tggtactact    1800
gtggtgaagg tgaaatatga aggaactgga gctccatgta aataccgat cgagatcaaa     1860 gacatgaata aggagaaagt tgtgggaaga atcataagca gcattccttt tgctgagaat    1920
actaactcta tcacaaatat agaacttgaa cctccgttcg gtgattccta catagtaatc    1980
ggagccggcg attcagcact tactctgcac tggttcagaa aaggaagttc actcggaaag    2040
gcttttgagt caacatatag gggcgcaaag agacttgcaa ttcttgggga aacagcttgg    2100
gatttcggga gcgtcggtgg tctgtttact tcccttggaa aggcggttca tcaagtgttt    2160
ggctcagtat acaccacaat gtttggggga gtgagttgga tgatccgcat tcttatcggt    2220
atacttgtgc tgtggattgg aacaaattca agaaatacca gtatggcaat gtcatgtatt    2280
gctgtggggg ggataacttt gtttctcggg tttaccgtgc aggcatag               2328
```

<210> SEQ ID NO 43
<211> LENGTH: 775
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Met Asn Asn Gln Arg Lys Lys Ala Lys Asn Thr Pro Phe Asn Met Leu
1               5                   10                  15

Lys Arg Glu Arg Asn Arg Val Ser Thr Val Gln Gln Leu Thr Lys Arg
            20                  25                  30

Phe Ser Leu Gly Met Leu Gln Gly Arg Gly Pro Leu Lys Leu Phe Met
        35                  40                  45

Ala Leu Val Ala Phe Leu Arg Phe Leu Thr Ile Pro Pro Thr Ala Gly
    50                  55                  60

Ile Leu Lys Arg Trp Gly Thr Ile Lys Lys Ser Lys Ala Ile Asn Val
65                  70                  75                  80

Leu Arg Gly Phe Arg Lys Glu Ile Gly Arg Met Leu Asn Ile Leu Asn
                85                  90                  95

Arg Arg Arg Arg Ser Ala Gly Met Ile Ile Met Leu Ile Pro Thr Val
            100                 105                 110

Met Ala Phe His Leu Ser Ser Arg Asp Gly Glu Pro Leu Met Ile Val
        115                 120                 125
```

-continued

```
Ala Lys His Glu Arg Gly Arg Pro Leu Leu Phe Lys Thr Thr Glu Gly
    130                 135                 140

Ile Asn Arg Cys Thr Leu Ile Ala Met Asp Val Gly Glu Met Cys Glu
145                 150                 155                 160

Asp Thr Val Thr Tyr Lys Cys Pro Leu Leu Val Asn Thr Glu Pro Glu
                165                 170                 175

Asp Ile Asp Cys Trp Cys Asn Ser Thr Ser Thr Trp Val Thr Tyr Gly
            180                 185                 190

Thr Cys Thr Gln Ser Gly Glu Arg Arg Ala Lys Arg Ser Val Ala
        195                 200                 205

Leu Ala Pro His Ser Gly Met Gly Leu Glu Thr Arg Thr Glu Thr Trp
    210                 215                 220

Met Ser Ser Glu Gly Ala Trp Lys His Ala Gln Arg Val Glu Ser Trp
225                 230                 235                 240

Ile Leu Arg Asn Pro Gly Phe Ala Leu Leu Ala Gly Phe Met Ala Tyr
                245                 250                 255

Met Ile Gly Gln Thr Gly Ile Gln Arg Thr Val Phe Phe Val Leu Met
            260                 265                 270

Met Leu Val Ala Pro Ser Tyr Gly Met Arg Cys Val Gly Val Gly Asn
        275                 280                 285

Arg Asp Phe Val Glu Gly Val Ser Gly Gly Thr Trp Val Asp Leu Val
    290                 295                 300

Leu Glu His Gly Gly Cys Val Thr Thr Met Ala Gln Gly Lys Pro Thr
305                 310                 315                 320

Leu Asp Phe Glu Leu Ile Lys Thr Thr Ala Lys Glu Val Ala Leu Leu
                325                 330                 335

Arg Thr Tyr Cys Ile Glu Ala Ser Ile Ser Asn Ile Thr Thr Ala Thr
            340                 345                 350

Arg Cys Pro Thr Gln Gly Glu Pro Tyr Leu Lys Glu Glu Gln Asp Gln
        355                 360                 365

Gln Tyr Ile Cys Arg Arg Asp Val Val Asp Arg Gly Trp Gly Asn Gly
    370                 375                 380

Cys Gly Leu Phe Gly Lys Gly Val Val Thr Cys Ala Lys Phe Ser
385                 390                 395                 400

Cys Ser Gly Lys Ile Thr Gly Asn Leu Val Gln Val Glu Asn Leu Glu
                405                 410                 415

Tyr Thr Val Val Val Thr Val His Asn Gly Asp Ala His Ala Val Gly
            420                 425                 430

Asn Ser Thr Ser Asn His Gly Val Thr Thr Thr Ile Thr Pro Arg Ser
        435                 440                 445

Pro Ser Val Glu Val Lys Leu Pro Asp Tyr Gly Glu Leu Thr Leu Asp
    450                 455                 460

Cys Glu Pro Arg Ser Gly Ile Asp Phe Asn Glu Met Ile Leu Met Lys
465                 470                 475                 480

Met Lys Gly Lys Thr Trp Leu Val His Lys Gln Trp Phe Leu Asp Leu
                485                 490                 495

Pro Leu Pro Trp Thr Ala Gly Ala Asp Thr Ser Glu Val His Trp Asn
            500                 505                 510

Tyr Lys Glu Arg Met Val Thr Phe Lys Val Pro His Ala Lys Arg Gln
        515                 520                 525

Asp Val Thr Val Leu Gly Ser Gln Glu Gly Ala Met His Ser Ala Leu
    530                 535                 540

Thr Gly Ala Thr Glu Val Asp Ser Gly Asp Gly Asn His Met Phe Ala
```

Gly His Leu Lys Cys Lys Val Arg Met Glu Lys Leu Arg Ile Lys Gly
545                 550                 555                 560

Met Ser Tyr Thr Met Cys Ser Gly Lys Phe Ser Ile Asp Lys Glu Met
        565                 570                 575

Ala Glu Thr Gln His Gly Thr Val Val Lys Val Lys Tyr Glu Gly
            580                 585                 590

Thr Gly Ala Pro Cys Lys Ile Pro Ile Glu Ile Lys Asp Met Asn Lys
    595                 600                 605

Glu Lys Val Val Gly Arg Ile Ile Ser Ser Ile Pro Phe Ala Glu Asn
610                 615                 620

Thr Asn Ser Ile Thr Asn Ile Glu Leu Glu Pro Pro Phe Gly Asp Ser
625                 630                 635                 640

Tyr Ile Val Ile Gly Ala Gly Asp Ser Ala Leu Thr Leu His Trp Phe
            645                 650                 655

Arg Lys Gly Ser Ser Leu Gly Lys Ala Phe Glu Ser Thr Tyr Arg Gly
    660                 665                 670

Ala Lys Arg Leu Ala Ile Leu Gly Glu Thr Ala Trp Asp Phe Gly Ser
675                 680                 685

Val Gly Gly Leu Phe Thr Ser Leu Gly Lys Ala Val His Gln Val Phe
690                 695                 700

Gly Ser Val Tyr Thr Thr Met Phe Gly Gly Val Ser Trp Met Ile Arg
705                 710                 715                 720

Ile Leu Ile Gly Ile Leu Val Leu Trp Ile Gly Thr Asn Ser Arg Asn
            725                 730                 735

Thr Ser Met Ala Met Ser Cys Ile Ala Val Gly Gly Ile Thr Leu Phe
    740                 745                 750

Leu Gly Phe Thr Val Gln Ala
755                 760                 765

770                 775

<210> SEQ ID NO 44
<211> LENGTH: 930
<212> TYPE: DNA
<213> ORGANISM: Zika virus

<400> SEQUENCE: 44
agctggcccc ctagcgaagt actcacagct gttggcctga tatgcgcatt ggctggaggg    60
ttcgccaagg cagatataga gatggctggg cccatggccg cggtcggtct gctaattgtc   120
agttacgtgg tctcaggaaa gagtgtggac atgtacattg aaagagcagg tgacatcaca   180
tgggaaaaag atgcggaagt cactggaaac agtccccggc tcgatgtggc gctagatgag   240
agtggtgatt ctccctggt ggaggatgac ggtcccccca tgagagagat catactcaag   300
gtggtcctga tgaccatctg tggcatgaac ccaatagcca tacccttgc agctggagcg   360
tggtacgtat acgtgaagac tggaaaaagg agtggtgctc tatgggatgt gcctgctccc   420
aaggaagtaa aaaggggga gaccacagat ggagtgtaca gagtaatgac tcgtagactg   480
ctaggttcaa cacaagttgg agtgggagtt atgcaagagg gggtcttta cactatgtgg   540
cacgtcacaa aaggatccgc gctgagaagc ggtgaaggga acttgatcc atactgggga   600
gatgtcaagc aggatctggt gtcatactgt ggtccatgga agctagatgc cgcctgggac   660
gggcacagcg aggtgcagct cttggccgtg ccccccggag agagagcgag gaacatccag   720
actctgcccg gaatatttaa gacaaaggat ggggacattg agcggttgc gctggattac   780
ccagcaggaa cttcaggatc tccaatccta gacaagtgtg ggagagtgat aggactttat   840

```
                                          -continued ggcaatgggg tcgtgatcaa aaatgggagt tatgttagtg ccatcaccca agggaggagg    900
gaggaagaga ctcctgttga gtgcttcgag                                    930

<210> SEQ ID NO 45
<211> LENGTH: 1311
<212> TYPE: DNA
<213> ORGANISM: Zika virus

<400> SEQUENCE: 45
ccttcgatgc tgaagaagaa gcagctaact gtcttagact tgcatcctgg agctgggaaa     60
accaggagag ttcttcctga atagtccgt gaagccataa aaacaagact ccgtactgtg    120
atcttagctc caaccagggt tgtcgctgct gaaatggagg aagcccttag agggcttcca    180
gtgcgttata tgcaacagc agtcaatgtc acccactctg gaacagaaat cgtcgactta    240
atgtgccatg ccaccttcac ttcacgtcta ctacagccaa tcagagtccc caactataat    300
ctgtatatta tggatgaggc ccacttcaca gatccctcaa gtatagcagc aagaggatac    360
atttcaacaa gggttgagat gggcgaggcg gctgccatct tcatgaccgc cacgccacca    420
ggaacccgtg acgcatttcc ggactccaac tcaccaatta tggacaccga agtggaagtc    480
ccagagagag cctggagctc aggctttgat tgggtgacgg atcattctgg aaaaacagtt    540
tggtttgttc caagcgtgag gaacggcaat gagatcgcag cttgtctgac aaaggctgga    600
aaacgggtca tacagctcag cagaaagact tttgagacag agttccagaa aacaaaacat    660
caagagtggg actttgtcgt gacaactgac atttcagaga tgggcgccaa ctttaaagct    720
gaccgtgtca tagattccag gagatgccta aagccggtca tacttgatgg cgagagagtc    780
attctggctg acccatgcc tgtcacacat gccagcgctg cccagaggag ggggcgcata    840
ggcaggaatc ccaacaaacc tggagatgag tatctgtatg gaggtgggtg cgcagagact    900
gacgaagacc atgcacactg gcttgaagca agaatgctcc ttgacaatat ttacctccaa    960
gatggcctca tagcctcgct ctatcgacct gaggccgaca agtagcagc cattgaggga   1020
gagttcaagc ttaggacgga gcaaaggaag acctttgtgg aactcatgaa aagaggagat   1080
cttcctgttt ggctggccta tcaggttgca tctgccggaa taacctacac agatagaaga   1140
tggtgctttg atggcacgac caacaacacc ataatggaag acagtgtgcc ggcagaggtg   1200
tggaccagac acggagagaa aagagtgctc aaaccgaggt ggatggacgc cagagtttgt   1260
tcagatcatg cggccctgaa gtcattcaag gagtttgccg ctgggaaaag a            1311

<210> SEQ ID NO 46
<211> LENGTH: 437
<212> TYPE: PRT
<213> ORGANISM: Zika virus

<400> SEQUENCE: 46

Pro Ser Met Leu Lys Lys Lys Gln Leu Thr Val Leu Asp Leu His Pro
 1               5                  10                  15

Gly Ala Gly Lys Thr Arg Arg Val Leu Pro Glu Ile Val Arg Glu Ala
            20                  25                  30

Ile Lys Thr Arg Leu Arg Thr Val Ile Leu Ala Pro Thr Arg Val Val
        35                  40                  45

Ala Ala Glu Met Glu Glu Ala Leu Arg Gly Leu Pro Val Arg Tyr Met
    50                  55                  60

Thr Thr Ala Val Asn Val Thr His Ser Gly Thr Glu Ile Val Asp Leu
65                  70                  75                  80
```

Met Cys His Ala Thr Phe Thr Ser Arg Leu Leu Gln Pro Ile Arg Val
                85                  90                  95
Pro Asn Tyr Asn Leu Tyr Ile Met Asp Glu Ala His Phe Thr Asp Pro
            100                 105                 110
Ser Ser Ile Ala Ala Arg Gly Tyr Ile Ser Thr Arg Val Glu Met Gly
            115                 120                 125
Glu Ala Ala Ile Phe Met Thr Ala Thr Pro Pro Gly Thr Arg Asp
130                 135                 140
Ala Phe Pro Asp Ser Asn Ser Pro Ile Met Asp Thr Glu Val Glu Val
145                 150                 155                 160
Pro Glu Arg Ala Trp Ser Ser Gly Phe Asp Trp Val Thr Asp His Ser
            165                 170                 175
Gly Lys Thr Val Trp Phe Val Pro Ser Val Arg Asn Gly Asn Glu Ile
            180                 185                 190
Ala Ala Cys Leu Thr Lys Ala Gly Lys Arg Val Ile Gln Leu Ser Arg
            195                 200                 205
Lys Thr Phe Glu Thr Glu Phe Gln Lys Thr Lys His Gln Glu Trp Asp
210                 215                 220
Phe Val Val Thr Thr Asp Ile Ser Glu Met Gly Ala Asn Phe Lys Ala
225                 230                 235                 240
Asp Arg Val Ile Asp Ser Arg Arg Cys Leu Lys Pro Val Ile Leu Asp
                245                 250                 255
Gly Glu Arg Val Ile Leu Ala Gly Pro Met Pro Val Thr His Ala Ser
            260                 265                 270
Ala Ala Gln Arg Arg Gly Arg Ile Gly Arg Asn Pro Asn Lys Pro Gly
            275                 280                 285
Asp Glu Tyr Leu Tyr Gly Gly Gly Cys Ala Glu Thr Asp Glu Asp His
            290                 295                 300
Ala His Trp Leu Glu Ala Arg Met Leu Leu Asp Asn Ile Tyr Leu Gln
305                 310                 315                 320
Asp Gly Leu Ile Ala Ser Leu Tyr Arg Pro Glu Ala Asp Lys Val Ala
                325                 330                 335
Ala Ile Glu Gly Glu Phe Lys Leu Arg Thr Glu Gln Arg Lys Thr Phe
            340                 345                 350
Val Glu Leu Met Lys Arg Gly Asp Leu Pro Val Trp Leu Ala Tyr Gln
            355                 360                 365
Val Ala Ser Ala Gly Ile Thr Tyr Thr Asp Arg Arg Trp Cys Phe Asp
370                 375                 380
Gly Thr Thr Asn Asn Thr Ile Met Glu Asp Ser Val Pro Ala Glu Val
385                 390                 395                 400
Trp Thr Arg His Gly Glu Lys Arg Val Leu Lys Pro Arg Trp Met Asp
                405                 410                 415
Ala Arg Val Cys Ser Asp His Ala Ala Leu Lys Ser Phe Lys Glu Phe
            420                 425                 430
Ala Ala Gly Lys Arg
            435

<210> SEQ ID NO 47
<211> LENGTH: 495
<212> TYPE: PRT
<213> ORGANISM: Dengue virus 2

<400> SEQUENCE: 47

Met Arg Cys Ile Gly Met Ser Asn Arg Asp Phe Val Glu Gly Val Ser

```
1               5                   10                  15
Gly Gly Ser Trp Val Asp Ile Val Leu Glu His Gly Ser Cys Val Thr
            20                  25                  30

Thr Met Ala Lys Asn Lys Pro Thr Leu Asp Phe Glu Leu Ile Lys Thr
            35                  40                  45

Glu Ala Lys Gln Pro Ala Thr Leu Arg Lys Tyr Cys Ile Glu Ala Lys
            50                  55                  60

Leu Thr Asn Thr Thr Thr Glu Ser Arg Cys Pro Thr Gln Gly Glu Pro
65                  70                  75                  80

Ser Leu Asn Glu Glu Gln Asp Lys Arg Phe Val Cys Lys His Ser Met
            85                  90                  95

Val Asp Arg Gly Trp Gly Asn Gly Cys Gly Leu Phe Gly Lys Gly Gly
            100                 105                 110

Ile Val Thr Cys Ala Met Phe Arg Cys Lys Lys Asn Met Glu Gly Lys
            115                 120                 125

Val Val Gln Pro Glu Asn Leu Glu Tyr Thr Ile Val Ile Thr Pro His
            130                 135                 140

Ser Gly Glu Glu His Ala Val Gly Asn Asp Thr Gly Lys His Gly Lys
145                 150                 155                 160

Glu Ile Lys Ile Thr Pro Gln Ser Ser Ile Thr Glu Ala Glu Leu Thr
            165                 170                 175

Gly Tyr Gly Thr Val Thr Met Glu Cys Ser Pro Arg Thr Gly Leu Asp
            180                 185                 190

Phe Asn Glu Met Val Leu Leu Gln Met Glu Asn Lys Ala Trp Leu Val
            195                 200                 205

His Arg Gln Trp Phe Leu Asp Leu Pro Leu Pro Trp Leu Pro Gly Ala
            210                 215                 220

Asp Thr Gln Gly Ser Asn Trp Ile Gln Lys Glu Thr Leu Val Thr Phe
225                 230                 235                 240

Lys Asn Pro His Ala Lys Lys Gln Asp Val Val Val Leu Gly Ser Gln
            245                 250                 255

Glu Gly Ala Met His Thr Ala Leu Thr Gly Ala Thr Glu Ile Gln Met
            260                 265                 270

Ser Ser Gly Asn Leu Leu Phe Thr Gly His Leu Lys Cys Arg Leu Arg
            275                 280                 285

Met Asp Lys Leu Gln Leu Lys Gly Met Ser Tyr Ser Met Cys Thr Gly
            290                 295                 300

Lys Phe Lys Val Val Lys Glu Ile Ala Glu Thr Gln His Gly Thr Ile
305                 310                 315                 320

Val Ile Arg Val Gln Tyr Glu Gly Asp Gly Ser Pro Cys Lys Ile Pro
            325                 330                 335

Phe Glu Ile Met Asp Leu Glu Lys Arg His Val Leu Gly Arg Leu Ile
            340                 345                 350

Thr Val Asn Pro Ile Val Thr Glu Lys Asp Ser Pro Val Asn Ile Glu
            355                 360                 365

Ala Glu Pro Pro Phe Gly Asp Ser Tyr Ile Ile Ile Gly Val Glu Pro
            370                 375                 380

Gly Gln Leu Lys Leu Asn Trp Phe Lys Lys Gly Ser Ser Ile Gly Gln
385                 390                 395                 400

Met Phe Glu Thr Thr Met Arg Gly Ala Lys Arg Met Ala Ile Leu Gly
            405                 410                 415

Asp Thr Ala Trp Asp Phe Gly Ser Leu Gly Gly Val Phe Thr Ser Ile
            420                 425                 430
```

```
Gly Lys Ala Leu His Gln Val Phe Gly Ala Ile Tyr Gly Ala Ala Phe
        435                 440                 445

Ser Gly Val Ser Trp Thr Met Lys Ile Leu Ile Gly Val Ile Ile Thr
    450                 455                 460

Trp Ile Gly Met Asn Ser Arg Ser Thr Ser Leu Ser Val Thr Leu Val
465                 470                 475                 480

Leu Val Gly Ile Val Thr Leu Tyr Leu Gly Val Met Val Gln Ala
            485                 490                 495

<210> SEQ ID NO 48
<211> LENGTH: 648
<212> TYPE: PRT
<213> ORGANISM: Dengue virus 3

<400> SEQUENCE: 48

Met Ile Val Gly Lys Asn Glu Arg Gly Lys Ser Leu Leu Phe Lys Thr
1               5                   10                  15

Ala Ser Gly Ile Asn Met Cys Thr Leu Ile Ala Met Asp Leu Gly Glu
            20                  25                  30

Met Cys Asp Asp Thr Val Thr Tyr Lys Cys Pro His Ile Ala Glu Val
        35                  40                  45

Glu Pro Glu Asp Ile Asp Cys Trp Cys Asn Leu Thr Ser Thr Trp Val
    50                  55                  60

Thr Tyr Gly Thr Cys Asn Gln Ala Gly Glu His Arg Arg Asp Lys Arg
65                  70                  75                  80

Ser Val Ala Leu Ala Pro His Val Gly Met Gly Leu Asp Thr Arg Thr
                85                  90                  95

Gln Thr Trp Met Ser Ala Glu Gly Ala Trp Arg Gln Val Glu Lys Val
            100                 105                 110

Glu Thr Trp Ala Leu Arg His Pro Gly Phe Thr Ile Leu Ala Leu Phe
        115                 120                 125

Leu Ala His Tyr Ile Gly Thr Ser Leu Thr Gln Lys Val Val Ile Phe
    130                 135                 140

Ile Leu Leu Ile Leu Val Thr Pro Ser Met Ala Met Arg Cys Val Gly
145                 150                 155                 160

Val Gly Asn Arg Asp Phe Val Glu Gly Leu Ser Gly Ala Thr Trp Val
                165                 170                 175

Asp Val Val Leu Glu His Gly Gly Cys Val Thr Thr Met Ala Lys Asn
            180                 185                 190

Lys Pro Thr Leu Asp Ile Glu Leu Gln Lys Thr Glu Ala Thr Gln Leu
        195                 200                 205

Ala Thr Leu Arg Lys Leu Cys Ile Glu Gly Lys Ile Thr Asn Ile Thr
    210                 215                 220

Thr Asp Ser Arg Cys Pro Thr Gln Gly Glu Ala Ile Leu Pro Glu Glu
225                 230                 235                 240

Gln Asp Gln Asn Tyr Val Cys Lys His Thr Tyr Val Asp Arg Gly Trp
                245                 250                 255

Gly Asn Gly Cys Gly Leu Phe Gly Lys Gly Ser Leu Val Thr Cys Ala
            260                 265                 270

Lys Phe Gln Cys Leu Glu Ser Ile Glu Gly Lys Val Val Gln His Glu
        275                 280                 285

Asn Leu Lys Tyr Thr Val Ile Ile Thr Val His Thr Gly Asp Gln His
    290                 295                 300

Gln Val Gly Asn Glu Thr Gln Gly Val Thr Ala Glu Ile Thr Pro Gln
```

```
305                 310                 315                 320
Ala Ser Thr Val Glu Ala Ile Leu Pro Glu Tyr Gly Thr Leu Gly Leu
                325                 330                 335

Glu Cys Ser Pro Arg Thr Gly Leu Asp Phe Asn Glu Met Ile Leu Leu
                340                 345                 350

Thr Met Lys Asn Lys Ala Trp Met Val His Arg Gln Trp Phe Phe Asp
                355                 360                 365

Leu Pro Leu Pro Trp Thr Ser Gly Ala Thr Thr Glu Thr Pro Thr Trp
        370                 375                 380

Asn Arg Lys Glu Leu Leu Val Thr Phe Lys Asn Ala His Ala Lys Lys
385                 390                 395                 400

Gln Glu Val Val Val Leu Gly Ser Gln Glu Gly Ala Met His Thr Ala
                405                 410                 415

Leu Thr Gly Ala Thr Glu Ile Gln Asn Ser Gly Gly Thr Ser Ile Phe
                420                 425                 430

Ala Gly His Leu Lys Cys Arg Leu Lys Met Asp Lys Leu Glu Leu Lys
                435                 440                 445

Gly Met Ser Tyr Ala Met Cys Leu Asn Thr Phe Val Leu Lys Lys Glu
        450                 455                 460

Val Ser Glu Thr Gln His Gly Thr Ile Leu Ile Lys Val Glu Tyr Lys
465                 470                 475                 480

Gly Glu Asp Ala Pro Cys Lys Ile Pro Phe Ser Thr Glu Asp Gly Gln
                485                 490                 495

Gly Lys Ala His Asn Gly Arg Leu Ile Thr Ala Asn Pro Val Val Thr
                500                 505                 510

Lys Lys Glu Glu Pro Val Asn Ile Glu Ala Glu Pro Pro Phe Gly Glu
        515                 520                 525

Ser Asn Ile Val Ile Gly Ile Gly Asp Lys Ala Leu Lys Ile Asn Trp
        530                 535                 540

Tyr Lys Lys Gly Ser Ser Ile Gly Lys Met Phe Glu Ala Thr Ala Arg
545                 550                 555                 560

Gly Ala Arg Arg Met Ala Ile Leu Gly Asp Thr Ala Trp Asp Phe Gly
                565                 570                 575

Ser Val Gly Gly Val Leu Asn Ser Leu Gly Lys Met Val His Gln Ile
                580                 585                 590

Phe Gly Ser Ala Tyr Thr Ala Leu Phe Ser Gly Val Ser Trp Ile Met
                595                 600                 605

Lys Ile Gly Ile Gly Val Leu Leu Thr Trp Ile Gly Leu Asn Ser Lys
        610                 615                 620

Asn Thr Ser Met Ser Phe Ser Cys Ile Ala Ile Gly Ile Ile Thr Leu
625                 630                 635                 640

Tyr Leu Gly Ala Val Val Gln Ala
                645
```

FLAVIVIRUS AND ALPHA VIRUS VIRUS-LIKE PARTICLES (VLPS)

CROSS REFERENCE TO RELATED APPLICATIONS

This application is a continuation of U.S. application Ser. No. 15/738,240, filed on Dec. 20, 2017, which is U.S. National Stage Application under 35 U.S.C. § 371 of International Patent Application No. PCT/US2016/039011 filed on Jun. 23, 2016, which claims priority to U.S. Provisional Application No. 62/184,738, filed Jun. 25, 2015, and U.S. Provisional Application No. 62/292,936, filed Feb. 9, 2016, the disclosures of which are hereby incorporated by reference in their respective entireties.

STATEMENT AS TO FEDERALLY SPONSORED RESEARCH

This work was supported in part by a Qualifying Therapeutic Discovery Project Grant form Health and Human Service (HHS) for the Development of a Multivalent Dengue Virus-Like Particle (VLP) Vaccine to TechnoVax, Inc. The U.S. Government may have certain rights in this invention.

TECHNICAL FIELD

The present invention relates to compositions comprising flavivirus (e.g., dengue or Zika) and/or alphavirus (e.g., chikungunya) virus-like particles (VLPs) and to methods of making and using these VLPs, including the creation and production of virus-like particle (VLP) based vaccines (e.g., for dengue, Zika, and/or chikungunya) as well as its use for diagnostic and therapeutic indications. In particular, the present disclosure includes strategies and methods used for the development of novel monovalent or multivalent vaccines that are able to protect humans against infection with one or more clades or antigenic variants of the flavivirus (dengue, Zika) and/or alphavirus viruses. Also described herein are VLP production methods that produce VLPs that display certain antigenic configurations. These VLPs feature conformational epitopes relevant for the generation of an enhanced neutralizing immune response to the virus. Single particle monovalent, bivalent, or multivalent (e.g., tetravalent, for example for the 4 dengue serotypes) VLPs are assembled and used to formulate vaccine compositions, which allows for immunization and subsequent protection against one or more clades or antigenically distinct virus (e.g. Asian clade, South America clade, etc. for Zika; 1, 2, 3, or 4 for dengue serotypes). Furthermore, VLPs are also used for the diagnosis of infection or for therapeutic indications. VLP vaccines can be produced in suspension culture of eukaryotic cells and released into the culture medium. After purification, concentration, and formulation the vaccine can be administered by any suitable route, for example, via either mucosal or parenteral routes, and induce an immune response able to protect against any or all of the Zika, dengue, chikungunya virus clades, antigenic variants or serotypes. VLPs comprising combinations of Zika, dengue and/or chickungunya and methods of providing immune responses to additional viruses are also provided.

BACKGROUND

Flaviviruses such as dengue and Zika and alphaviruses such as chikungunya are the causative agents of infections in humans and birth defects when pregnant women are infected with Zika. Zika fever disease results from an infection with Zika virus (ZIKV), which is transmitted to human by the bite of an infected *Aedes* mosquito (*A. aegypti, A. albopictus* and polynesiensis). Zika virus was isolated for the first time in the Zika Forest in Uganda from a Rhesus monkey in 1947 and later from humans in 1952. ZIKV belongs to the flavivirus genus within the Flaviviridae family. Members of this family possess a single stranded positive sense RNA genome (~10,794 nucleotides long) that encodes only one open reading frame (ORF) translated into a single polyprotein which is cleaved by both cellular and virus-encoded proteases into three structural proteins (C, prM and E) and seven non-structural proteins (NS1, NS2A, NS2B, NS3, NS4A, NS4B and NS5.) that enables virus replication. Zika virus protein processing and maturation appears to be similar to that of other members of the family and it occurs through the secretory pathway beginning with the self-cleavage of NS3 protease with its cofactor NS2B. Then, the NS2B/NS3 complex cleaves the cytoplasmic tail of the C protein and host cell signalases and proteases perform other cleavages within the polyprotein.

During replication and virus morphogenesis, which occurs in closed association with intracellular membranes, nascent virions are assembled and transported through the secretory pathway and released at the cell surface. Enveloped virions are composed of a cell-derived lipid bilayer encapsulating the C-protein wrapped viral RNA genome and studded with multiple copies of the proteins E and M. During maturation within the secretary pathway (trans-Golgi network) the precursor prM protein is cleaved by the host cell's furin protease to produce the small M protein and the fragment pr, which is released upon virus egress from the cell. The surface of the virus displays E protein (dimers arranged in head to tail herringbone arrays) as the major antigenic determinant of the virus and mediates receptor binding and fusion during virus entry into cells. Structural studies of an analogous protein of the genus flavivirus reveals three domains, DI, DII and DIII followed by two helices and two transmembrane domains, which anchor this protein to the surface of the virion particle (Crill W D, Chang G-JJ, 2004, Localization and Characterization of Flavivirus Envelope Glycoprotein Cross-Reactive Epitopes. J. Virol 78(24):13975-13986). Therefore, this protein is a major target of the host immune response and a suitable candidate for vaccine development and diagnostic applications.

ZIKV has been transmitted in Africa for many years through a sylvatic cycle between the mosquito vectors and nonhuman primates, with occasional human infections. In recent years, however, epidemics of Zika have resulted from cycles of transmission between vectors and humans spreading the disease beyond the African continent into the French Polynesia and other Pacific regions. Since 2015 a dramatic spread of ZIKV that started in Brazil is taking place in South America and the Caribbean Islands and some sporadic cases of travelers have been identified in the USA and Europe. Although Zika fever appears to cause a mild illness in 1 of 5 people infected, contracting the virus during pregnancy has been associated with birth defects, primarily microcephaly (defective brain development). Furthermore, an increase of cases of Guillain-Barre syndrome has been observed following ZIKV infection. The seriousness of these disorders imposes a tremendous burden on public health and human life. In addition to vectors transmission, ZIKV can also be transmitted by sexual contact, making disease control more difficult.

It has been observed with other flaviviruses that in addition to mature and immature particles (virions that carry uncleaved pr peptide) produced by flavivirus-infected cells; small non-infectious particles composed of M and E are also assembled and released. Furthermore, it was shown that recombinant expression of proteins prM and E from tick-borne encephalitis (TBE) virus was sufficient to drive assembly and budding of this type of particle. Other flavivirus sub-viral particles assembled with prM and E proteins have also been produced in the yeast *Pichia pastoris* expression system as well as in mammalian cells. Vaccine compositions containing these sub-viral particles have been shown to induce neutralizing antibodies and specific cytotoxic T lymphocyte responses in mice.

Dengue fever results from infection with dengue virus, which is transmitted to humans by the bite of infected *Aedes* mosquitoes (*A. aegypti*, *A. albopictus* and *A. polynesiensis*). This mosquitos-borne illness is responsible for 100 million cases of dengue each year worldwide. The World Health Organization (WHO) estimates that two-third of the world human population is at risk of contracting dengue infection. Furthermore, the relentless spread of the mosquito vectors in recent years continues to expand the illness to new regions of the world. Four distinct virus serotypes (DENV1-4) can be transmitted by infected *Aedes* mosquitoes causing an infection characterized by fever, headache, myalgia, arthralgia and, depending on the severity of the infection, may progress to Dengue hemorrhagic fever/Dengue shock syndrome (DHF/DSS) (WHO (2014) Dengue and severe Dengue Fact Sheet N° 117. These life-threatening outcomes are more common following subsequent infections with a dengue virus of a different serotype. The presence of a low concentration of poorly neutralizing antibodies produced after the primary infection, appears to heighten infection of Fc-receptor bearing cells, increasing virus replication and clinical signs by the mechanism of antibody-dependent enhancement (ADE) of disease. This complex interaction between the host-immunity and dengue viruses has hindered the development of a safe and effective dengue vaccine, which has to elicit a robust and balanced neutralizing antibody response against each one of the four virus serotypes in order to avoid potential induction of ADE.

Dengue virus is an enveloped positive sense single-strand RNA virus, which belongs to the flaviviridae family within the Flavivirus genus. The dengue RNA genome (~10.7-Kb) encodes only one open reading frame (ORF) and translates into a single polyprotein cleaved by both cellular and virus-encoded proteases into three structural proteins (C, prM and E) and seven non-structural proteins (NS1, NS2A, NS2B, NS3, NS4A, NS4B and NS5.) that enables virus replication (Lindenbach B D, Rice C M, 2003, Molecular biology of flaviviruses. Adv Virus Res 59:23-61). Protein processing and maturation occur through the secretory pathway and begins with the self-cleavage of NS3 protease with its cofactor NS2b. Then, the NS2B/NS3 complex cleaves the cytoplasmic tail of the C protein and host cell signalases and proteases perform other cleavages within the polyprotein.

During replication and virus morphogenesis, which occurs in closely association with intracellular membranes, nascent virions are assembled and transported through the secretory pathway and released at the cell surface. Enveloped virions are composed of a cell-derived lipid bilayer encapsulating the C-protein wrapped viral RNA genome and studded with multiple copies of the proteins E and M. During maturation within the secretary pathway (trans-Golgi network) the precursor prM protein is cleaved by the host furin protease to produce the small M protein and the fragment pr, which is released upon virus egress from the cell. The surface of the virus displays E protein (dimers ordered in head to tail herringbone arrays) as the major antigenic determinant of the virus and mediates receptor binding and fusion during virus entry. This protein has three domains, DI, DII and DIII followed by two helices and two transmembrane domains, which anchor this protein to the surface of the virion particle (Crill W D, Chang G-JJ, 2004, Localization and Characterization of Flavivirus Envelope Glycoprotein Cross-Reactive Epitopes. *J Virol* 78(24): 13975-13986). Therefore, this protein is a major target for vaccine development. It has been observed that in addition to mature and immature particles (virions that carry uncleaved pr peptide) produced by dengue-infected cells; small non-infectious particles composed of M and E are also assembled and released. Furthermore, it was shown that recombinant expression of proteins prM and E from tick-borne encephalitis (TBE) virus was sufficient to drive assembly and budding of this type of particle. Dengue sub-viral particles assembled with prM and E proteins have also been produced in the yeast *Pichia pastoris* expression system as well as in mammalian cells. Vaccine compositions containing these sub-viral particles have been shown to induce neutralizing antibodies and specific CTL responses in mice.

At this time there is no vaccine or specific treatment to control, combat or prevent ZIKV infection. For their parts, dengue vaccines are being developed using conventional strategies such as chimeric, live-attenuated, and inactivated viruses or DNA and some of these vaccine are far advanced in their development. However, due to a prolong immunization regimen, as well as unbalanced and insufficient immunity against some serotypes raises concern as to whether these vaccines are safe and efficacious. Therefore, new technologies are needed to develop safer and more effective dengue vaccines. The prevention of infection by vaccination represents a critical unmet need to control the spread and the effects of theses diseases globally. Here, we described the formation of virus-like particles as a strategy for flavivirus (Zika and dengue) and/or alphavirus (chickungunya) vaccine development and formulations for an specific virus as example dengue containing four sertoypes or Zika containing one or more antigenic variants as well as combination as dengue, Zika and chikungunya and alternative dual compositions e.g. dengue/Zika or dengue/Chikungunya or Zika/Chikungunya. Furthermore, the VLPs as described herein can be used for diagnostic as well as therapeutic applications.

SUMMARY

Described herein are virus-like particles (VLPs) comprising at least one antigenic flavivirus or alphavirus protein (Zika, dengue or chickungunya). Also described are compositions comprising these VLPs, as well as methods for making and using these VLPs. The VLPs described herein are devoid of viral genetic material and therefore unable to replicate or cause infection; however given their morphological, biochemical and antigenic similarities to wild type virions, VLPs are highly immunogenic and able to elicit robust protective immune responses. Unlike virion inactivated based vaccines, VLPs are not infectious eliminating the need for chemical treatment, thus maintaining the native conformation of structural components and antigenic epitopes.

Thus, the invention describes a novel approach for Zika, dengue and/or chickungunya virus-like particle (VLP)

development. In particular, we describe the creation, development and production of VLP vaccines for Zika, dengue as well as chickungunya that will trigger, upon human immunization, a strong and balanced immune response characterized by the induction of high level of neutralizing antibodies. In certain embodiments, the VLP triggers a high level of neutralizing antibodies against the four-dengue virus serotypes and/or multiple Zika clades concurrently. In other embodiments, the VLP vaccine as a virus specific composition triggers a high level of neutralizing antibodies against either the four-Dengue serotypes, or against a single or multiple Zika clades. In another embodiment, a combination vaccine elicits a high level of neutralizing response against the four-dengue serotypes, Zika clades and chikungunya.

Based on flavivirus subviral particles studies as well as on our own experience in virus-like particle assembly, we have designed a new and more effective strategy for the formation and release of virus-like particles (e.g., dengue and/or Zika). We have found that the co-expression of flavivirus (dengue, Zika) virus structural proteins capsid (C), preMembrane (prM), envelope (E) together with the non-structural protein NS2B/NS3 drives the assembly and release of virus-like particles. The presence of the complex NS2B/NS3 contributes not only to the processing of the polyprotein CprME by its protease functions but also to the particles assembly and release. We also produce VLPs displaying E protein with different reactivites as demonstrated with a monoclonal antibody that recognizes a conformation epitope of the E protein that is shared by other flaviviruses. These different E protein conformations seem to be highly relevant for the elicitation of potent neutralizing antibody in humans.

In one aspect, described herein is a flavivirus (e.g., dengue, Zika, yellow fever, Japanese encephalitis, tick-borne encephalitis, hepatitis C and/or West Nile virus) virus-like particle (VLP) comprising at least one flavivirus structural protein and at least one non-structural flavivirus protein. In certain embodiments, the VLP comprises all of the CPrME proteins. Any CPrME proteins can be employed, including wild-type or mutated (e.g., codon optimized) sequences from any flavivirus species and serotype (dengue 1, 2, 3, 4, Zika, etc.). In an exemplary embodiment, the wild-type nucleotide sequence of CprME of dengue-2 is shown in SEQ ID NO:1, and the amino acid sequence is described in SEQ ID NO:2. Other wild-type CprME sequences are known in the art and may be readily aligned with any of the exemplary Zika or dengue (e.g., dengue-2) sequences disclosed herein. In certain embodiments, the CprME sequence comprises a sequence with one or more mutations (substitutions, additions and/or deletions) as compared to wild-type and/or a codon optimized sequences. See, e.g., SEQ ID NO:3 (mutated) and SEQ ID NO:4 (codon optimized with mutations), which both include the amino acid sequences shown in SEQ ID NO:5. In other embodiments, the VLP consists of less than all of the CPrME proteins (e.g., CPrME, PrME, CME, CPrE or ME), as compared to the full length wild-type or mutated sequences. Similar mutations can be made in any flavivirus CprME protein following the teachings described herein. In any of the assembly of VLPs as described herein the non-structural proteins may comprise NS2B and/or NS3 proteins derived from any flavivirus species or serotype (e.g. an example of wild type nucleotide sequence of NS2B/NS3 is shown in SEQ ID NO:6 and amino acid sequence described in SEQ ID NO:7) or modified (e.g., truncated, mutated and/or codon optimized) proteins (e.g. example of modified NS2B/NS3 nucleotide sequence is shown in SEQ ID NO:8 and amino acid sequence shown in SEQ ID NO:9). NS2B or NS3 may also be used as single proteins the nucleotide sequences (e.g., fragments derived from any flavivirus NS2B/NS3 protein. Exemplary, non-limiting sequences are shown in SEQ ID NO: 10 (NS2B nucleotide sequence), SEQ ID NO:11 (NS2B amino acid sequence), SEQ ID NO:12 (NS3 nucleotide sequence) and SEQ ID NO: 13 (NS3 amino acid). The VLP may be monovalent, bivalent or multiple valent and display on its surface one or more antigenic flavivirus proteins (1, 2, 3, 4 or more proteins): from a single flavivirus, from one or more serotypes (or clades or isolated) of a single flavivirus (e.g., a bivalent or multivalent; from multiple flaviviruses (e.g., dengue and/or Zika and/or alphaviruses), as well as combinations thereof.

Also provided is an immunogenic composition comprising at least one VLP as described herein. In certain embodiments, the immunogenic compositions further comprise an adjuvant. Thus, described herein are flavivirus (e.g., dengue, Zika) virus-like particles (VLP)—also known as subviral particles, recombinant subviral particles, biological nanoparticles, nanoparticles, etc.—utilizing structural (C-prM-E) and non-structural (NS2B/NS3) viral proteins. These VLPs are designed as vaccine or immunogens for protecting against infection with any one of the four-dengue virus serotypes and/or any of the known Zika clades/isolates. In certain embodiments, the VLP also comprises alphavirus antigenic proteins (e.g., chickungunya).

Also provided are DNA constructs comprising sequences encoding flavivirus viral proteins (structural and non-structural) used to assemble the VLP of any of claims 1 to 8. The constructs may further comprise one or more sequences encoding one or more linkers between one or more of the sequences encoding the structural and non-structural proteins (e.g., a linker comprising amino acids corresponding to amino acids 1 to 8 or 9 or 10 of any flavivirus NS1 protein, numbered relative to any flavivirus NS1 protein, for example as shown in SEQ ID NO:15 (amino acid) (SEQ ID NO:14 shows the nucleotide sequence encoding these residues); a linker comprising amino acids corresponding to 186 or 187 or 188 or 189 to amino acids corresponding to 218 or 225 of any flavivirus NS2A protein, numbered relative to any wild-type protein (e.g. as shown in SEQ ID NO:17); a linker comprising amino acid 1 to 8 or 9 or 10 of NS1, amino acids 1 to 24 or 25 or 26 or 27 or 28 or 29 or 30 or 31 or 32 of NS2A, amino acids 186 or 187 or 188 or 189 to 218 or 225 of NS2A; a linker comprising amino acids 1 to 8 or 9 or 10 of NS1 and the second transmembrane domain of NS2B (e.g. nucleotide sequence amino acid sequence SEQ ID NO:11); a linker comprising amino acid 1 to 8 or 9 or 10 of NS1 and the first transmembrane domain of NS2A (e.g., amino acids encoded by nucleotides 51 to 100 of nucleotide sequence, SEQ ID NO: 16 and amino acid sequence SEQ ID NO: 17); and a linker comprising amino acid 1 to 8 or 9 or 10 of NS1 and the C terminal portion of NS2B comprising the second transmembrane domain to the end of the protein. The DNA constructs may comprise the flavivirus protein-encoding sequences in any order (e.g., a full length NS2B (e.g. SEQ ID NO:10): and a full NS3 (e.g. SEQ ID NO: 18) or modified truncated NS2B/NS3 (SEQ ID NO: 8) or wild-type NS2B/NS3 (e.g. SEQ ID NO: 6) operably linked directly to the structural proteins CprME (e.g. SEQ ID NO: 4) in any order). In certain embodiments, the furin protease cleavage site between pr and M protein of the constructs describes herein (e.g., SEQ ID NO:5) is modified by substituting amino acids residues at position P3 with hydrophobic one and/or wherein the NS3 protease active site is modified (e.g. as shown in NS3 alone SEQ ID NO: 13 and NS2B/NS3 SEQ ID NO: 9, which correspond to nucleotide sequences SEQ ID NO: 12 and SEQ ID NO: 8) in such that its enzymatic activity is enhanced. In other embodiments, sequence(s) encoding the E protein (e.g. SEQ ID NO: 47) is (are) modified to enhance VLP assemble and release (e.g., amphipathic helix 1 in the stem domain of the E protein is modified to enhance the hydrophobic properties of one side of the helix; one, two, three or more amino acids in the hydrophobic side of the helix are substituted, for example, at positions corresponding to 398, 401 and/or 412 (e.g., numbered relative to SEQ ID NO:47), including but not limited to I398L, I398M, I398V, I398A or M401A, M401L, M401V, M401I, or M412A, M412L, M412V, M412I; and/or helix 1 and/or helix 2 of the E protein (e.g. as example I398L, M401A, and M412L of SEQ ID NO: 19) are exchanged with the helix sequences of other flaviviruses or analogous motif from other viruses and cellular sources).

In another aspect, methods of generating (assembling) the VLPs described herein are provided. In certain embodiments, such methods and strategies involve mutations, deletions, insertions, gene organization and/or expression conditions to enhance particle morphogenesis and egress from producing cells. Also delineated are strategies for the assembly of VLPs displaying on its surface the E protein of a single serotype (monovalent), or the E protein of two distinct serotypes (bivalent), or the E protein of three distinct serotypes (trivalent) or the E protein of each one of the four-dengue virus serotypes (tetravalent) or again multiple Zika clades. In certain embodiments, combining VLPs with alternative antigenic composition allows for the formulation of a tetravalent vaccine. Furthermore, production of VLP can be attained in suspension cultures of transfected eukaryotic cells following the expression of the selected structural and non-structural genes. Transient or stable transfection methods can be used to introduce into cells the plasmids that direct proteins expression. VLPs are released from the producing cells into the culture medium from where they are collected and purified by different methods such as gradient centrifugation, filtration and chromatography or combination thereof. Thus, also provided is a method of producing a VLP, the method comprising introducing into a host cell (e.g., a eukaryotic cells such as a mammalian, yeast, insect, plant, amphibian and avian cells) one or more DNA constructs as described herein under conditions such that the cells produces the VLP. In certain embodiments, host cell(s) are cultured at temperatures ranging from 25° C. to 33° C. (e.g., 25° C., 26° C., 27° C., 28° C., 29° C., 30° C., 31° C., 32° C. or 33° C.). Also provided are VLPs generated by the methods as described herein as well as a method of generating an immune response to one or more flaviviruses in a subject (e.g., human), the method comprising administering (e.g., mucosally, intradermally, subcutaneously, intramuscularly, or orally) to the subject an effective amount of the VLPs and/or immunogenic compositions as described herein. The methods described herein can result in an immune response that treats and/or prevents (vaccinates) the subject against multiple serotypes or clades of one or more flaviviruses.

In yet another aspect, described herein is the formation of VLPs containing E proteins of different structural conformations resulting from the production at different temperatures (e.g. 37° C. or 31° C.). These VLPs show differential reactivity with a specific monoclonal antibody that recognizes the E protein, reflecting their conformational differences. In addition, VLPs produced at 31° C. elicited stronger titers of neutralizing antibodies than those induced by VLP produced at 37° C. when administered as vaccine to small animal models. A tetravalent VLP based vaccine can be formulated with single tetravalent VLPs (one particle carrying E antigens of all serotypes/clades) or by blending VLP of alternative antigenic compositions. The utility of the VLPs as described herein may include, but it is not limited to, vaccine and immunological use, as adjuvant, and/or immune-modulators, delivery vehicle for heterologous proteins or small molecules and RNA molecules as well as prophylactic and therapeutic applications.

In another aspect of the invention described provides dengue and/or Zika virus-like particles (VLP) (also known as subviral particles), recombinant subviral particles, biological nanoparticles, nanoparticles, etc.—utilizing structural prM-E or C-prM-E and non-structural (NS2B/NS3) viral proteins. These VLPs are designed as vaccine or immunogens for protecting against infection with any one of the dengue and/or Zika virus clades, antigenic variants or serotypes. Furthermore, the flavivirus (e.g., dengue/Zika) vaccine could be combined with one or all of other VLP based vaccine such as dengue, yellow fever, West Nile, or chikungunya, which are viral diseases transmitted by mosquito vectors.

In addition, methods for generating (assembling) the VLPs (e.g., dengue and/or Zika) described herein are provided. In certain embodiments, such methods and strategies involve mutations, deletions, insertions, gene organization arrangements and the conditions under which the VLPs are produced recombinantly to better retain particle resemblance to the virus and enhance egress from the producing cells. Also delineated are strategies for the assembly of VLPs displaying on their surface the E protein of a single clade/antigenic variant or the E protein of two distinct clades/antigenic variants (bivalent), or the E protein of distinct clades/antigenic variants (multivalent). In certain embodiments, combining VLPs with alternative antigenic composition allows for the formulation of a multivalent vaccine. Furthermore, production of VLPs can be attained in suspension cultures of eukaryotic cells following the expression of the selected structural proteins prME or CprME alone or structural and non-structural proteins NS2B/NS3 combined. Transient or stable transfection methods can be used to introduce into cells the plasmids that direct proteins expression. VLPs are released from the producing cells into the culture medium from where they are collected and purified by different methods such as gradient centrifugation, filtration and chromatography or combination thereof.

In yet another aspect, described herein is the formation of VLPs containing E proteins of different structural conformation resulting from the production of the VLPs at different temperatures, one set ranging from 27° C.-to 33° C. (e.g. 31° C.) and a second set ranging from 34° C. to 41° C. (e.g. 37° C.). These VLPs show differential reactivity with a specific monoclonal antibody that recognizes shared epitopes of E protein amongst other flaviviruses and reflects their conformational differences when produced at distinct temperatures. In addition, VLPs produced at 31° C. elicits stronger titers of neutralizing antibodies than those induced by VLP produced at 37° C. when administered as vaccine to small animals. Single or multivalent antigenic VLP based vaccine (Zika, dengue and/or chikunguna) can be formulated (one particle carrying E antigens of several clades or by blending VLP of alternative antigenic compositions). The utility of the these VLPs may include, but it is not limited to, vaccine and immunological use, as adjuvant, and/or immune-modulators, delivery vehicle for heterologous proteins or small molecules as well as prophylactic, therapeutic and diagnostic applications.

Also provided are VLPs produced by any of the methods described herein.

In a still further aspect, provided herein is a method of generating an immune response to a flavivirus and/or alphavirus in a subject, the method comprising administering to the subject (e.g., human) an effective amount of a VLP and/or immunogenic composition as described herein to the subject. In certain embodiments, the composition is administered mucosally, intradermally, subcutaneously, intramuscularly, or orally. In certain embodiments, the methods generate an immune response to multiple strains or subtypes of flaviviruses, thereby providing a "universal" vaccine that protects the subject against infection from various flaviviruses and/or over time (more than one season).

Any of the methods may involve multiple administrations (e.g., a multiple dose schedule).

In another aspect, a packaging cell line is provided for producing VLPs as described herein. The cell line may be stably transfected with one or more polynucleotides encoding structural proteins and upon introduction and expression of the one or more flavivirus protein-encoding sequences not stably transfected into the cell, the VLP is produced by the cell. The packaging cell may be an insect, plant, mammalian, bacterial or fungal cell. In certain embodiments, the packaging cell is a mammalian (e.g., human) cell line.

Thus, the invention includes but is not limited to the following embodiments:

1. A flavivirus virus-like particle (VLP) comprising the proteins CPrME that are assembled following the co-expression of structural and non-structural proteins, wherein said flavivirus is dengue and/or Zika.

2. A flavivirus virus-like particle (VLP) comprising of the structural proteins CPrME that are assembled following the expression of the same structural proteins, wherein said flavivirus is dengue and/or Zika.

3. A flavivirus virus-like particle comprising less than the structural protein CPrME such as PrME or CME or CPrE or ME that are assembled following their expression or co-expressed with the non-structural proteins, wherein said flavivirus is dengue and/or Zika.

4. A virus-like particle of 1, 2 and/or 3, wherein the structural proteins are produced from separate transcription units.

5. A virus-like particle (VLP) of 1, 2, 3 and/or 4 where the non-structural proteins comprise the full length or truncated form of NS3 co-expressed with the full length or truncated forms of NS2B.

6. A DNA construct comprising sequences encoding dengue and/or Zika viral proteins used to assemble VLPs, wherein the structural and non-structural viral proteins are operably linked to form a single segment with a defined order optionally comprising a linker such as a sequence of different portions of the NS1, NS2A and/or NS2B proteins.

7. The DNA construct of 6, wherein the linker comprises amino acids corresponding to amino acids 1 to 8 or 9 or 10 of NS1 connected to a portion of NS2A comprising of amino acids corresponding to 186 or 187 or 188 or 189 to amino acids corresponding to 218 of NS2A.

8. The DNA construct of 6, wherein the linker comprises amino acid 1 to 8 or 9 or 10 of NS1 are connected to a first portion of NS2A comprising amino acid 1 to 24 or 25 or 26 or 27 or 28 or 29 or 30 or 31 or 32 connected to a second portion of NS2A comprising of amino acid 186 or 187 or 188 or 189 to 218 of NS2A.

9. The DNA construct of 6, wherein the linker comprises amino acid 1 to 8 or 9 or 10 of NS1 connected to the second transmembrane domain of NS2B.

10. The DNA construct of 6, wherein the linker comprises amino acid 1 to 8 or 9 or 10 of NS1 connected to the first transmembrane domain of NS2A.

11. The DNA construct of 6, wherein the linker comprises amino acid 1 to 8 or 9 or 10 of NS1 connected to the C terminal portion of NS2B comprising the second transmembrane domain to the end of the protein.

12. The DNA construct of any of 6 through 11, wherein the order of the structural and non-structural segments is inverted and the non-structural segment is operably linked to the structural segment with or without a connecting linker.

13. The DNA construct of 12, wherein the non-structural protein optionally includes a full length NS2B and a full NS3 genetically linked directly to the structural proteins CprME.

14. The DNA construct of 12 and 13, wherein the non-structural proteins comprise a truncated variant of NS3 in which the helicase domain is deleted but the protease domain and its recognizable self-cleavage site located at the carboxyl terminal of the protein is preserved. The self-cleavage site serves as one example of a linker that may be used to connect the non-structural and structural proteins.

15. A DNA construct comprising sequences encoding dengue and/or Zika viral proteins are used to assemble VLPs wherein the furin protease cleavage site between pr and M protein is modified by substituting amino acids residues at position P3 with hydrophobic amino acids.

16. A DNA construct comprising sequences encoding dengue and/or Zika viral proteins are used to assemble VLPs wherein the helices of the E protein are modified to enhance VLP assemble and release.

17. The DNA construct of 16, where the amphipathic helix 1 in the stem domain of the E protein is modified to enhance the hydrophobic properties of one side of the helix.

18. The DNA construct of 16 and/or 17 where one, two, three or more amino acids in the hydrophobic side of the helix are substituted, for example at positions corresponding to 398, 401 and/or 412, including but not limited to I398L, I398M, I398V, I398A or M401A, M401L, M401V, M401I, or M412A, M412L, M412V, M412I.

19. A DNA construct of 16, wherein the helix 1 and/or helix 2 are exchanged with the helix sequences of other flaviviruses or analogous motif from other viruses and cellular sources.

20. A DNA construct comprising sequences encoding flavivirus (Zika, dengue, yellow fever, Japanese encephalitis, West Nile virus etc.) viral proteins used to assemble VLPs wherein the NS3 protease active site is modified in order to enhance its enzymatic activity. Such modification may include but are not limited to the substitution of the amino acid corresponding to leucine at position 115 to a preferred amino acid with a shorter side chain such as alanine.

21. A method of increasing the amount of mature particles produced by a cell, the method comprising enhancing cleavage between pr and M by the furin protease wherein said protease is furnished to the culture media of VLP producing cells, or co expressed with the VLP producing genes or produced constitutively in stably transfected cells used for VLP production.

22. A method of producing VLPs comprising selected gene products (e.g., dengue and/or Zika proteins), the method comprising transiently transfecting a eukaryotic cell with one or more plasmids comprising sequences encoding the selected gene products such that the VLPs are produced by the eukaryotic cell.

23. A method of producing VLPs comprising selected gene products, the method comprising stably integrating with one or more sequences encoding the selected gene products into the genome of a eukaryotic cell such that the VLPs are produced by the eukaryotic cell.

24. The method of 22 and 23, wherein said eukaryotic cell is selected from the group consisting of mammalian, yeast, insect, plant, amphibian and avian cells.

25. A method of producing VLPs with selected gene products and distinct structural conformation of the E, the method comprising transiently or stably transfecting a eukaryotic cell one or more sequences encoding the selected gene products and culturing cells at temperatures ranging from 25° C. to 33° C., in which the optimal temperature is 31° C. such that the VLPs are produced by the eukaryotic cell.

26. The method of 25, wherein said VLP elicits higher neutralizing antibodies titers in humans or animals and are more protective against one or all dengue virus serotypes than those induced by VLPs produced at higher temperature (e.g. 37° C.) when administered to said humans or animals.

27. The method of any of 22 to 26, wherein the VLP is a single bivalent VLP that displays on its surface the E antigen of two dengue virus serotypes (e.g. 1 and 2 or 1 and 3 or 1 and 4 or combination thereof) or a single tetravalent VLP wherein said VLP displays on its surface the E antigen of all four-dengue virus serotype (e.g. 1, 2, 3 and 4) or a single bivalent VLP that displays on its surface the E antigen of two Zika virus clades or a single multivalent VLP wherein said VLP displays on its surface the E antigen of multiple antigenic variants/clades of the Zika virus.

28. A VLP generated by the method of any of 22 to 27.

29. A single bivalent VLP that displays on its surface the E antigen of two dengue virus serotypes (e.g. 1 and 2 or 1 and 3 or 1 and 4 or combination thereof).

30. A single tetravalent VLP wherein said VLP displays on its surface the E antigen of all four-dengue virus serotype (e.g. 1, 2, 3 and 4).

31. A monovalent vaccine comprising at least one of the four-dengue serotypes monovalent.

32. A tetravalent vaccine composed of four monovalent VLPs or two bivalent VLPs wherein said induces strong and balance immune response to all dengue virus serotypes.

33. A single bivalent VLP that displays on its surface the E antigen of two or more flavivirus (Zika, dengue and/or yellow fever, Japanese encephalitis, West Nile virus etc.) virus clades/antigenic variants or combinations thereof.

34. A single multivalent VLP wherein said VLP displays on its surface the E antigen of multiple flavivirus (Zika, dengue and/or yellow fever, Japanese encephalitis, West Nile virus etc.) virus clades/antigenic variants or serotypes.

35. A monovalent VLP vaccine comprising at least one of the clades of flavivirus virus (monovalent).

36. A multivalent vaccine composed of various monovalent VLPs or two bivalent VLPs wherein said induces strong and balance immune response to (i) one or all virus clades/antigenic variants or serotypes of a flavivirus (e.g., Zika) and/or (ii) one or more virus clades/antigenic variants or serotypes of at least one other flavivirus (e.g., dengue and/or yellow fever, Japanese encephalitis, West Nile virus) or Alphavirus chikungunya.

37. The VLP or vaccines of any of 31 to 35, wherein the vaccine also comprises adjuvant.

38. Flavivirus vaccine compositions where the Zika vaccine is blended in bivalent, trivalent, tetravalent or pentavalent formulations and combination thereof with VLPs derived from dengue virus, yellow fever virus, West Nile virus, Japanese encephalitis virus or Alphavirus chikungunya.

39. The VLP or vaccines of any of 29 to 38, wherein the vaccine comprises an adjuvant. In another aspect, described herein is a host cell comprising any of the VLPs as described above. In certain embodiments, the host cell permits assembly and release of a VLP as described herein from one or more vectors encoding the polypeptides of the VLP. In certain embodiments, the eukaryotic cell is selected from the group consisting of a yeast cell, an insect cell, an amphibian cell, an avian cell, a plant cell or a mammalian cell.

BRIEF DESCRIPTION OF THE DRAWINGS

FIGS. 2A through 2C are schematics depicting exemplary arrangements for constructs comprising the genes encoding the structural and non-structural protein utilized for the assembly of virus-like particles.

FIGS. 3A through 3E show exemplary antigenic composition of single VLPs and options for formulating multivalent (e.g., tetravalent) vaccines.

FIG. 4A is a schematic showing the dengue virus genome, which contains a single open reading frame (ORF) that expresses a polyprotein comprised of both structural and non-structural proteins, which arise via several proteolytic cleavages (top panel). In early stages, the complex viral protease NS3 with its cofactor NS2B (1) self-cleaves before cleaving the capsid protein. A host cell signalase is also involved in the maturation of the polyprotein (◇). In a final step, the furin protease (∇) cleaves the pr portion from the M protein to uncover E protein fusion peptide. FIG. 4B depicts the VLP assembly strategy relies on the native properties of the structural genes although key point mutations were introduced to improve protein processing and particle assembly. The furin cleavage site (∇) was mutated at E88A to enhance cleavage at this location. The E protein was mutated as followed I398A, M401A, and M412L to improve the amphipathic properties of the helical domain 1 and enhance trafficking and secretion of E. The viral NS3 protein was truncated maintaining only its N-terminal protease domain that was mutated at L115A to enhance its catalytic activity. The protease domain is kept as a single transcription unit together with its cofactor NS2B.

FIGS. 5A through 5D show dengue VLPs were produced in Expi293™ cells by co-expression of CprME-NS2B/NS3 or CprME alone. Analysis of transfected cells lysates show that capsid protein cleavage was efficient when CprME protease was co-expressed with CprME. The distinct cell lysates (20 μg of total protein per lane) were tested by Western blot using specific antibodies: anti-E (shown in FIG. 5A), anti-pr (shown in FIG. 5B), anti-C (shown in FIG. 5C) and anti-NS2B (shown in FIG. 5D) antibodies.

FIGS. 7A through 7C show analysis of the effect of temperature on the reactivity of the envelope (E) protein display on the surface of the dengue VLP with monoclonal antibodies recognizing conformational epitopes. Samples of gradient purified VLP fractions were applied to nitrocellulose membranes and probed by dot blot with the following antibodies: FIG. 7A shows anti-E polyclonal antibody; FIG. 7B shows 4G2 MAb; and FIG. 7C shows 3H5 MAb. VLPs produced at a lower temperature (31° C.) demonstrate better protein folding of conformational epitopes as shown by reactivity with MAbs 4G2 and 3H3, which also react with DENV-2 virus control.

FIGS. 8A and 8B show electron microscopy study of gradient purified DENV-2 VLP (bar represents 100 nm). FIG. 8A shows negative staining with 2% Uranyl acetate. Arrows point to the dengue VLPs. FIG. 8B shows two particles observed after Immuno-gold staining with 3H5 monoclonal antibody FIG. 9 is a graph showing results of ELISA assays at the indicated conditions. Analysis of anti-DENV specific antibodies (total IgG) in mouse serum (n=4) following immunization with dengue VLP vaccine (TVX-31° C. and TVX37° C.) and inactivated dengue-2 virus control (DENV-2) via chemiluminescent ELISA. Pre-immune sera (Pre I.) show statistical difference (*) (P<0.05) with the immunized groups.

FIG. 10 is a table showing neutralization power of vaccinated mice sera is presented as the reciprocal of serum dilution for which 50% of the virus is neutralized ($PRNT_{50}$). $PRNT_{50}$ is calculated using PROBIT method (Finney, 1952).

FIGS. 11A, 11B and 11C show images of negatively stained zVLPs, which have round shape of ~60 nm diameter. FIGS. 11D, 11E and 11F show images of immuno-gold labeled zVLP using an anti-E specific MAb as primary and a gold labeled (10 nm beads) secondary Ab. Black dots (beads) demonstrates the presence of the E protein on the surface of the particles.

FIG. 13 shows Western blot examination of gradient purified VLPs and Zika virus. The Western blot membrane was probed with an anti-E specific antibody and each lane correspond to the following: (1) Dengue control, 2) mock, (3) Zika virus (ZIKV) fractions 6-9, (4) Zika VLPs fractions 10-12, and (5) Zika VLPs fractions 7-8. The anti-E antibody detected the E protein of VLPs (lanes 4 and 5) and ZIKV (lane 3) as well as dengue control (lane 1).

DETAILED DESCRIPTION

Figure 1:
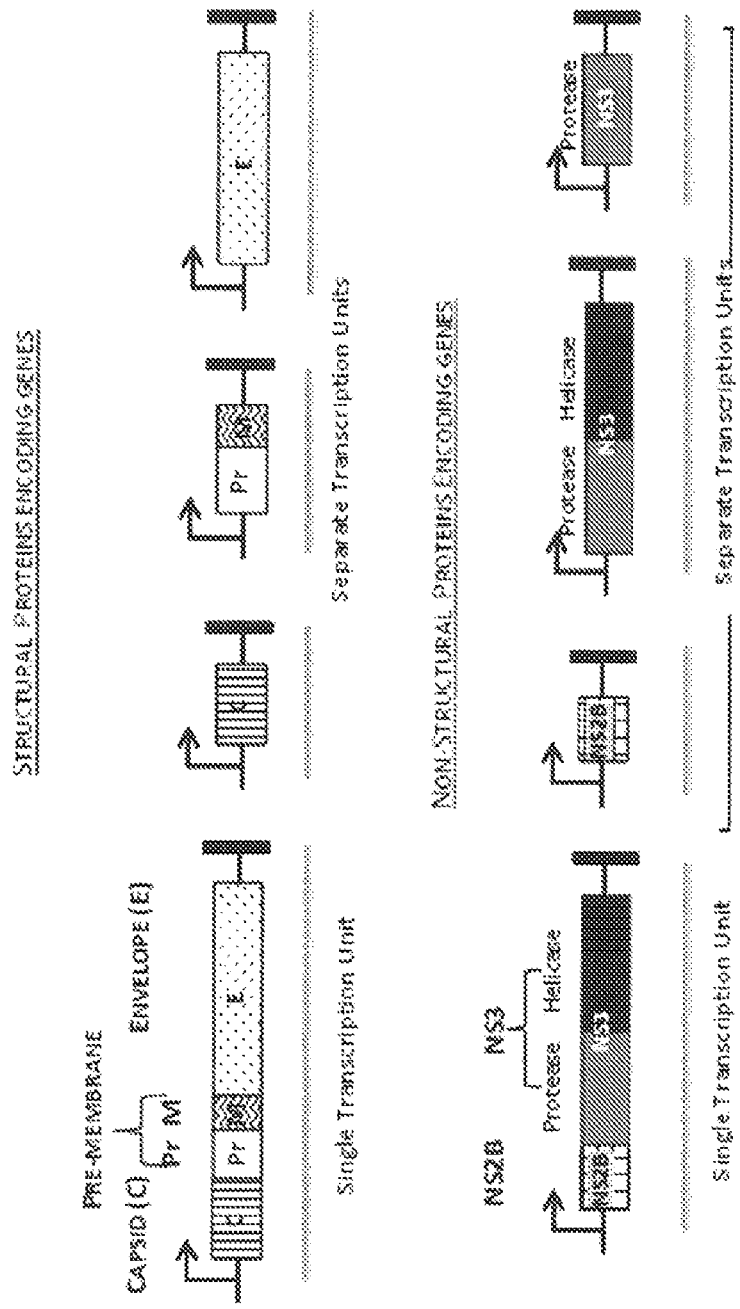
FIG. 1 is a schematic depicting the structural and non-structural genes selected for virus-like particle assembly and their different configurations.

The practice of the present invention will employ, unless otherwise indicated, conventional methods of chemistry, biochemistry, molecular biology, immunology and pharmacology, within the skill of the art. Such techniques are explained fully in the literature. See, e.g., Remington's Pharmaceutical Sciences, 18th Edition (Easton, Pa.: Mack Publishing Company, 1990); Methods In Enzymology (S. Colowick and N. Kaplan, eds., Academic Press, Inc.); and Handbook of Experimental Immunology, Vols. I-IV (D. M. Weir and C. C. Blackwell, eds., 1986, Blackwell Scientific Publications); Sambrook, et al., Molecular Cloning: A Laboratory Manual (2nd Edition, 1989); Short Protocols in Molecular Biology, 4th ed. (Ausubel et al. eds., 1999, John Wiley & Sons); Molecular Biology Techniques: An Intensive Laboratory Course, (Ream et al., eds., 1998, Academic Press); PCR (Introduction to Biotechniques Series), 2nd ed. (Newton & Graham eds., 1997, Springer Verlag); Fundamental Virology, Second Edition (Fields & Knipe eds., 1991, Raven Press, New York).

All publications, patents and patent applications cited herein are hereby incorporated by reference in their entirety.

As used in this specification and the appended claims, the singular forms "a," "an" and "the" include plural references unless the content clearly dictates otherwise. Thus, for example, reference to "a VLP" includes a mixture of two or more such VLPs.

Definitions

As used herein, the terms "sub-viral particle" "virus-like particle", "recombinant subviral particles" or "VLP" refer to a nonreplicating, viral shell. VLPs are generally composed of one or more viral proteins, such as, but not limited to those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art and discussed more fully below. The presence of VLPs following recombinant expression of viral proteins can be detected using conventional techniques known in the art, such as by electron microscopy, biophysical and immunological characterizations, and the like. See, e.g., Baker et al., *Biophys. J.* (1991) 60:1445-1456; Hagensee et al., *J. Virol.* (1994) 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions. Additional methods of VLP purification include but are not limited to chromatographic techniques such as affinity, ion exchange, size exclusion, and reverse phase procedures.

By "particle-forming polypeptide" derived from a particular viral protein is meant a full-length or near full-length viral protein, as well as a fragment thereof, or a viral protein with internal deletions, which has the ability to form VLPs under conditions that favor VLP formation. Accordingly, the polypeptide may comprise the full-length sequence, fragments, truncated and partial sequences, as well as analogs and precursor forms of the reference molecule. The term therefore intends deletions, additions and substitutions to the sequence, so long as the polypeptide retains the ability to form a VLP. Thus, the term includes natural variations of the specified polypeptide since variations in coat proteins often occur between viral isolates. The term also includes deletions, additions and substitutions that do not naturally occur in the reference protein, so long as the protein retains the ability to form a VLP. Preferred substitutions are those which are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids.

An "antigen" refers to a molecule containing one or more epitopes (either linear, conformational or both) that will stimulate a host's immune-system to make a humoral and/or cellular antigen-specific response. The term is used interchangeably with the term "immunogen." Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 7 and 15 amino acids, such as, 9, 10, 12 or 15 amino acids. The term includes polypeptides which include modifications, such as deletions, additions and substitutions (generally conservative in nature) as compared to a native sequence, so long as the protein maintains the ability to elicit an immunological response, as defined herein. These modifications may be deliberate, as through site-directed mutagenesis, or may be accidental, such as through mutations of hosts which produce the antigens.

An "immunological response" to an antigen or composition is the development in a subject of a humoral and/or a cellular immune response to an antigen present in the composition of interest. For purposes of the present disclosure, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells. Hence, an immunological response may include one or more of the following effects: the production of antibodies by B-cells; and/or the activation of suppressor T-cells and/or γΔ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

An "immunogenic composition" is a composition that comprises an antigenic molecule where administration of the composition to a subject results in the development in the subject of a humoral and/or a cellular immune response to the antigenic molecule of interest.

"Substantially purified" general refers to isolation of a substance (compound, polynucleotide, protein, polypeptide, polypeptide composition) such that the substance comprises the majority percent of the sample in which it resides. Typically in a sample a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence are determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements", include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences, and/or sequence elements controlling an open chromatin structure see e.g., McCaughan et al. (1995) PNAS USA 92:5431-5435; Kochetov et al (1998) FEBS Letts. 440:351-355.

A "nucleic acid" molecule can include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when active. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" as used herein to describe a nucleic acid molecule means a polynucleotide of genomic, cDNA, semi-synthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting prokaryotic microorganisms or eukaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

Two or more polynucleotide sequences can be compared by determining their "percent identity." Two or more amino acid sequences likewise can be compared by determining their "percent identity." The percent identity of two sequences, whether nucleic acid or peptide sequences, is generally described as the number of exact matches between two aligned sequences divided by the length of the shorter sequence and multiplied by 100. An approximate alignment for nucleic acid sequences is provided by the local homology algorithm of Smith and Waterman, Advances in Applied Mathematics 2:482-489 (1981). This algorithm can be extended to use with peptide sequences using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov, Nucl. Acids Res. 14(6):6745-6763 (1986). Suitable programs for calculating the percent identity or similarity between sequences are generally known in the art.

A "vector" is capable of transferring gene sequences to target cells (e.g., bacterial plasmid vectors, viral vectors, non-viral vectors, particulate carriers, and liposomes). Typically, "vector construct," "expression vector," and "gene transfer vector," mean any nucleic acid construct capable of directing the expression of one or more sequences of interest in a host cell. Thus, the term includes cloning and expression vehicles, as well as viral vectors. The term is used interchangeable with the terms "nucleic acid expression vector" and "expression cassette."

By "subject" is meant any member of the subphylum chordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The term does not denote a particular age. Thus, both adult and newborn individuals are intended to be covered. The system described above is intended for use in any of the above vertebrate species, since the immune systems of all of these vertebrates operate similarly.

By "pharmaceutically acceptable" or "pharmacologically acceptable" is meant a material which is not biologically or otherwise undesirable, i.e., the material may be administered to an individual in a formulation or composition without causing any unacceptable biological effects or interacting in a deleterious manner with any of the components of the composition in which it is contained.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

As used herein the term "adjuvant" refers to a compound that, when used in combination with a specific immunogen (e.g. a VLP) in a formulation, will augment or otherwise alter or modify the resultant immune response. Modification of the immune response includes intensification or broadening the specificity of either or both antibody and cellular immune responses. Modification of the immune response can also mean decreasing or suppressing certain antigen-specific immune responses.

As used herein an "effective dose" generally refers to that amount of VLPs of the invention sufficient to induce immunity, to prevent and/or ameliorate an infection or to reduce at least one symptom of an infection and/or to enhance the efficacy of another dose of a VLP. An effective dose may refer to the amount of VLPs sufficient to delay or minimize the onset of an infection. An effective dose may also refer to the amount of VLPs that provides a therapeutic benefit in the treatment or management of an infection. Further, an effective dose is the amount with respect to VLPs of the invention alone, or in combination with other therapies, that provides a therapeutic benefit in the treatment or management of an infection. An effective dose may also be the amount sufficient to enhance a subject's (e.g., a human's) own immune response against a subsequent exposure to an infectious agent. Levels of immunity can be monitored, e.g., by measuring amounts of neutralizing secretory and/or serum antibodies, e.g., by plaque neutralization, complement fixation, enzyme-linked immunosorbent, or microneutralization assay. In the case of a vaccine, an "effective dose" is one that prevents disease and/or reduces the severity of symptoms.

As used herein, the term "effective amount" refers to an amount of VLPs necessary or sufficient to realize a desired biologic effect. An effective amount of the composition would be the amount that achieves a selected result, and such an amount could be determined as a matter of routine experimentation by a person skilled in the art. For example, an effective amount for preventing, treating and/or ameliorating an infection could be that amount necessary to cause activation of the immune system, resulting in the development of an antigen specific immune response upon exposure to VLPs of the invention. The term is also synonymous with "sufficient amount."

As used herein, the term "multivalent" refers to VLPs which have multiple antigenic proteins against multiple types or strains of infectious agents.

As used herein the term "immune stimulator" refers to a compound that enhances an immune response via the body's own chemical messengers (cytokines). These molecules comprise various cytokines, lymphokines and chemokines with immunostimulatory, immunopotentiating, and pro-inflammatory activities, such as interferons, interleukins (e.g., IL-1, IL-2, IL-3, L-4, IL-12, IL-13); growth factors (e.g., granulocyte-macrophage (GM)-colony stimulating factor (CSF)); and other immunostimulatory molecules, such as macrophage inflammatory factor, Flt3 ligand, B7.1; B7.2, etc. The immune stimulator molecules can be administered in the same formulation as VLPs of the invention, or can be administered separately. Either the protein or an expression vector encoding the protein can be administered to produce an immunostimulatory effect.

As used herein the term "protective immune response" or "protective response" refers to an immune response mediated by antibodies against an infectious agent, which is exhibited by a vertebrate (e.g., a human), that prevents or ameliorates an infection or reduces at least one symptom thereof. VLPs of the invention can stimulate the production of antibodies that, for example, neutralize infectious agents, blocks infectious agents from entering cells, blocks replication of said infectious agents, and/or protect host cells from infection and destruction. The term can also refer to an immune response that is mediated by T-lymphocytes and/or other white blood cells against an infectious agent, exhibited by a vertebrate (e.g., a human), that prevents or ameliorates flavivirus infection or reduces at least one symptom thereof.

As use herein, the term "antigenic formulation" or "antigenic composition" refers to a preparation which, when administered to a vertebrate, e.g. a mammal, will induce an immune response.

As used herein, the term "vaccine" refers to a formulation which contains VLPs of the present invention, which is in a form that is capable of being administered to a vertebrate and which induces a protective immune response sufficient to induce immunity to prevent and/or ameliorate an infection and/or to reduce at least one symptom of an infection and/or to enhance the efficacy of another dose of VLPs. Typically, the vaccine comprises a conventional saline or buffered aqueous solution medium in which the composition of the present invention is suspended or dissolved. In this form, the composition of the present invention can be used conveniently to prevent, ameliorate, or otherwise treat an infection. Upon introduction into a host, the vaccine is able to provoke an immune response including, but not limited to, the production of antibodies and/or cytokines and/or the activation of cytotoxic T cells, antigen presenting cells, helper T cells, dendritic cells and/or other cellular responses.

General Overview

This invention describes the formation of biological particles (e.g., VLPs) that mimic the structure in size, morphology and biochemical composition of native Zika viruses and other flaviviruses; however, they are devoid of a fully competent viral genome and therefore unable to cause infection or disease. The lack of viral genome and lack of infectivity of the flavivirus (Zika) VLPs eliminate the need of chemical inactivation better preserving therefore their structures, protein conformations and antigenic properties enhancing immunogenicity and potency as vaccine. These biological mimics are identified as virus-like particles (VLPs). VLPs are assembled using genetic information comprising segments of the virus genome encoding selected proteins that may include but not limited to structural and non-structural protein. As shown in FIG. 1, the viral sequences in DNA form can be organized in a single transcription unit (segment) that expresses a single polypeptide or in separate transcription units (segments) each one expressing a single protein.

Virus-Like Particles

The present disclosure relates to flavivirus VLPs, which VLPs carry on their surfaces one or more modified antigenic flavivirus proteins. This VLP, alone or in combination with one or more additional VLPs and/or adjuvants, stimulates an immune response that protects against flavivirus infection.

In one embodiment of the invention, the structural proteins of interest comprise CprME, which after expression leads to the formation of VLPs. In order to enhance assembly and release of these VLPs from the producing cells, non-structural proteins may be co-expressed with the structural proteins (e.g. NS2B/NS3). Exemplary wild-type and mutant CprME nucleotide and amino acid sequences are shown in the "Sequences" Section below (e.g. Zika CprME wild type nucleotide sequence, SEQ ID NO: 20 and codon optimized SEQ ID NO:21 and the amino acid sequence is shown in SEQ ID NO:22). Exemplary of Zika NS2B/NS3 full-length nucleotide sequence (e.g. SEQ ID NO:23) and amino acid sequence (e.g. SEQ ID NO: 24). Also, examples of truncated and codon optimized nucleotide sequence of Zika NS2B/NS3 is shown in SEQ ID NO: 25 and its corresponding amino acid sequence is described in SEQ ID NO: 26. It will be apparent proteins from any Zika serotype or strain can be used in the compositions described herein, for example by alignment with the exemplary Zika sequences disclosed herein.

In any of the VLPs and methods described herein, the non-structural proteins may comprise either a full-length NS3 segment or a truncated version of the segment containing the protease domain, which is localized at the amino terminal of the polypeptide (e.g. truncated version of NS3 comprising aa 1 to aa 181). Exemplary sequences are shown below (e.g. full length amino acid sequence of dengue NS3, SEQ ID NO:27, and truncated aa 1 to aa 181 and mutated, SEQ ID NO:13).

In any of the VLPs or methods described herein, the non-structural protein segment comprising the full length or truncated form of NS3 is co-expressed with the full length or truncated forms of NS2B. Exemplary wild-type and mutant NS3 and/or NS2B nucleotide and amino acid sequences are shown in the "Sequences" section below. (e.g. an example of wild type nucleotide sequence of dengue NS2B/NS3 is shown in SEQ ID NO: 6 and amino acid sequence described in SEQ ID NO: 7). Modified dengue NS2B/NS3 (e.g., truncated, mutated and codon optimized) nucleotide sequence is shown in SEQ ID NO: 8 and amino acid sequence shown in SEQ ID NO: 9. When NS2B or NS3 are used as single proteins the nucleotide sequence is derived from SEQ ID NO: 8 resulting in NS2B nucleotide sequence (e.g. SEQ ID NO: 10) and amino acid sequence (SEQ ID NO: 11) and NS3 nucleotide sequence (e.g. SEQ ID NO: 12) and amino acid (e.g. SEQ ID NO: 13). In certain embodiments, the structural and non-structural proteins may be genetically linked, (as shown in FIG. 2). This is a non-limiting example of a single segment with a defined order using a linker that may encode. Additional exemplary sequences that may be used include but are not limited to a sequence of different portions of the NS1, NS2A and/or NS2B proteins as follows:

Linker 1: amino acids (aa) 1 to 8 or 9 or 10 of NS1 (e.g. nucleotide sequence SEQ ID NO: 14 and amino acid sequence SEQ ID NO: 15) connected to a portion of NS2A comprising of aa 186 or 187 or 188 or 189 to aa 218 of NS2A (e.g. nucleotide sequence SEQ ID NO: 16 and amino acid sequence SEQ ID NO: 17).

Linker 2: aa 1 to 8 or 9 or 10 of NS1 (SEQ ID NO: 14) connected to a first portion of NS2A comprising aa 1 to 24 or 25 or 26 or 27 or 28 or 29 or 30 or 31 or 32 connected to a second portion of NS2A comprising of aa 186 or 187 or 188 or 189 to 218 of NS2A (SEQ ID NO: 16).

Linker 3: aa 1 to 8 or 9 or 10 of NS1 (SEQ ID NO: 14) connected to the second transmembrane domain of NS2B (e.g. nucleotide sequence SEQ ID NO: 10 and amino acid sequence SEQ ID NO: 11)

Linker 4: aa 1 to 8 or 9 or 10 of NS1 (SEQ ID NO: 14) connected to the first transmembrane domain of NS2A (Amino acid 51 to 100 of nucleotide sequence, SEQ ID NO: 16 and amino acid sequence SEQ ID NO: 17)

Linker 5: aa 1 to 8 or 9 or 10 of NS1 (SEQ ID NO: 14) connected to the C terminal portion of NS2B comprising the second transmembrane domain to the end of the protein (e.g. nucleotide sequence SEQ ID NO: 10 and amino acid sequence SEQ ID NO:11).

In still further embodiments, the positional order of the structural and non-structural segments may be inverted (with respect to each other) where the non-structural segment is genetically linked to the structural segment with or without a connecting linker. For example, the non-structural protein may include a full length NS2B and a full NS3 genetically linked directly to the structural proteins CprME. Alternatively, the non-structural proteins may comprise a truncated variant of NS3 in which the helicase domain is deleted but the protease domain and its recognizable self-cleavage site located at the carboxyl terminal of the protein are preserved. The self-cleavage site serves as one example of a linker that may be used to connect the non-structural and structural proteins.

In still further embodiments, the VLPs and methods described herein may include changes in the sequence of the structural and non-structural proteins (e.g., modifications to the nucleotide sequence which result in amino acid modifications), which can be used to enhance the formation and release of the VLP from the producing cells.

For example, the furin protease cleavage site between pr and M protein may be modified to enhance furin activity. The recognition consensus sequence is defined as R-Xaa-L/R-R where amino acids immediately prior to the cleavage site specifies positions P1 (R), P2 L/R, P3 (Xaa) and P4 (R). The naturally occurring acid residue in the cleavage site at position P3 can be substituted, but not limited to, by a hydrophobic residue. Exemplary sequences are shown below in "Sequences" section (e.g SEQ ID NO: 4)

In other embodiments, one or more helices of the E protein may be modified to enhance VLP assemble and release (Purdy D E, Chang G-JJ, 2005, Secretion of noninfectious dengue virus-like particles and identification of amino acids in the stem region involved in intracellular retention of envelope protein, *Virology* 333(2): 239-250).

For example, the amphipathic helix 1 in the stem domain of the E protein may be modified to enhance the hydrophobic properties of one side of helix.

In one exemplary embodiments of this modification: one, two, three or more amino acids in the hydrophobic side of the helix are substituted. These substitutions may occur at positions 398, 401 and/or 412, including but not limited to I398L, I398M, I398V, I398A or M401A, M401L, M401V, M401I, or M412A, M412L, M412V, M412I.

In other embodiments, the helix 1 and/or helix 2 are exchanged with the helix sequences derived from other flaviviruses or other viruses and sources.

In other embodiments, the NS3 protease active site may be modified in order to enhance its enzymatic activity. Non-limiting examples of such modifications include the substitution of amino acid leucine at position 115 (e.g., with an amino acid with a shorter side chain such as glycine or alanine).

In still further embodiments, to boost the protease cleavage between pr and M by furin and therefore increase the amount of mature particles, additional furin enzymes may be furnished throughout the VLP production using any of the methods described below:

One version of this example may include the addition of recombinant furin protein to the VLPs producing cells culture medium.

A second version of this example: an expression plasmid carrying the furin gene as a single transcription unit (segment) may be co-transfected with one or more plasmids expressing the structural and non-structural genes. Another method may include an expression plasmid carrying a single transcription unit (segment) where the furin gene is genetically linked to either structural or non-structural protein or both.

A third version of this example: a cell line stably transfected and selected for its constitutive expression of furin, may be used in VLP production. Alternatively, the furin gene is stably transfected and/or inducible in a cell line already modified to constitutively produce VLPs.

VLP Production

The production of VLPs as described herein may be achieved by any suitable method, including but not limited to transient and/or stable expression of the structural and/or non-structural genes in a suspension culture of eukaryotic cells, typically requiring a period of continued cell culture after which the VLPs are harvested from the culture medium. The VLPs produced as described herein are conveniently prepared using standard recombinant techniques. Polynucleotides encoding the VLP-forming protein(s) are introduced into a host cell and, when the proteins are expressed in the cell, they assembly into VLPs.

Polynucleotide sequences coding for molecules (proteins) that form and/or are incorporated into the VLPs can be obtained using recombinant methods, such as by screening cDNA and genomic libraries from cells expressing the gene, or by deriving the gene from a vector known to include the same. For example, plasmids which contain sequences that encode naturally occurring or altered cellular products may be obtained from a depository such as the A.T.C.C., or from commercial sources. Plasmids containing the nucleotide sequences of interest can be digested with appropriate restriction enzymes, and DNA fragments containing the nucleotide sequences can be inserted into a gene transfer vector using standard molecular biology techniques.

Alternatively, cDNA sequences may be obtained from cells which express or contain the sequences, using standard techniques, such as phenol extraction and PCR of cDNA or genomic DNA. See, e.g., Sambrook et al., supra, for a description of techniques used to obtain and isolate DNA. Briefly, mRNA from a cell which expresses the gene of interest can be reverse transcribed with reverse transcriptase using oligo-dT or random primers. The single stranded cDNA may then be amplified by PCR (see U.S. Pat. Nos. 4,683,202, 4,683,195 and 4,800,159, see also PCR Technology: Principles and Applications for DNA Amplification, Erlich (ed.), Stockton Press, 1989)) using oligonucleotide primers complementary-to sequences on either side of desired sequences.

The nucleotide sequence of interest can also be produced synthetically, rather than cloned, using a DNA synthesizer (e.g., an Applied Biosystems Model 392 DNA Synthesizer, available from ABI, Foster City, Calif.). The nucleotide sequence can be designed with the appropriate codons for the expression product desired. The complete sequence is assembled from overlapping oligonucleotides prepared by standard methods and assembled into a complete coding sequence. See, e.g., Edge (1981) Nature 292:756; Nambair et al. (1984) Science 223:1299; Jay et al. (1984) J. Biol. Chem. 259:6311.

Preferably, the sequences employed to form flavivirus VLPs exhibit between about 60% to 80% (or any value therebetween including 61%, 62%, 63%, 64%, 65%, 66%, 67%, 68%, 69%, 70%, 71%, 72%, 73%, 74%, 75%, 76%, 77%, 78% and 79%) sequence identity to a naturally occurring flavivirus polynucleotide sequence and more preferably the sequences exhibit between about 80% and 100% (or any value therebetween including 81%, 82%, 83%, 84%, 85%, 86%, 87%, 88%, 89%, 90%, 91%, 92%, 93%, 94%, 95%, 96%, 97%, 98% and 99%) sequence identity to a naturally occurring polynucleotide sequence.

Any of the sequences described herein may further include additional sequences. For example, to further to enhance vaccine potency, hybrid molecules are expressed and incorporated into the sub-viral structure. These hybrid molecules are generated by linking, at the DNA level, the sequences coding for the protein genes with sequences coding for an adjuvant or immuno-regulatory moiety. During sub-viral structure formation, these hybrid proteins are incorporated into or onto the particle. The incorporation of one or more polypeptide immunomodulatory polypeptides (e.g., adjuvants describe in detail below) into the sequences described herein into the VLP may enhance potency and therefore reduces the amount of antigen required for stimulating a protective immune response. Alternatively, as described below, one or more additional molecules (polypeptide or small molecules) may be included in the VLP-containing compositions after production of the VLP from the sequences described herein.

These sub-viral structures do not contain infectious viral nucleic acids and they are not infectious eliminating the need for chemical inactivation. Absence of chemical treatment preserves native epitopes and protein conformations enhancing the immunogenic characteristics of the vaccine.

The sequences described herein can be operably linked to each other in any combination. For example, one or more sequences may be expressed from the same promoter and/or from different promoters. As described below, sequences may be included on one or more vectors. Non-limiting examples of vectors that can be used to express sequences that assemble into VLPs as described herein include viral-based vectors (e.g., retrovirus, adenovirus, adeno-associated virus, lentivirus), baculovirus vectors (see, Examples), plasmid vectors, non-viral vectors, mammalians vectors, mammalian artificial chromosomes (e.g., liposomes, particulate carriers, etc.) and combinations thereof. The expression vector(s) typically contain(s) coding sequences and expression control elements which allow expression of the coding regions in a suitable host. Enhancer elements may also be used herein to increase expression levels of the mammalian constructs.

Vaccine formulation is accomplished according to standard procedures, for example as shown in FIG. 3.

Monovalent

Different exemplary strategies are described to assemble monovalent VLPs including:
1. Use homologous clades/antigenic variants for both structural and non-structural proteins
2. Use heterologous clades between the structural proteins and non-structural proteins with the exception of the viral cleavage site within the sequence of the C protein that matches the clade/antigenic variant of the non-structural proteins
3. Use heterologous clades between the structural proteins and non-structural proteins with the exception of the cytoplasmic domain including the viral protease cleavage site of the C protein, which matches the serotype of the non-structural proteins Bivalent Two exemplary strategies to generate a bivalent vaccine:
1. Blending two monovalent VLP in a single formulation.
   1a. Use homologous clades/antigenic variants for both structural and non-structural proteins
   1b. Use heterologous clades/antigenic variants between the structural proteins and non-structural proteins with the exception of the viral cleavage site within the sequence of the C protein that matches the serotype of the non-structural proteins
   1c. Use heterologous clades/antigenic variants between the structural proteins and non-structural proteins with the exception of the cytoplasmic domain including the viral protease cleavage site of the C protein, which matches the serotype of the non-structural proteins (e.g. SEQ. ID NO: 35 and SEQ ID NO: 36, SEQ ID NO: 38, SEQ ID NO: 39 and SEQ ID NO: 42, SEQ ID NO: 43)
2. Assembly of a single bivalent particle VLP. Alternative exemplary approach may be used to build these structures:
   2a. Co-expression of two heterologous set of both structural and non-structural proteins
   2b. Co-expression of two heterologous structural proteins containing the same viral cleavage site within the sequence of the C protein together with non-structural proteins that recognized this viral cleavage site.
   2c. Co-expression of two heterologous structural proteins that share the analogous cytoplasmic domain sequence including the viral protease cleavage site of the C protein together with non-structural proteins that recognize this viral cleavage site Multivalent Several exemplary approaches may be used to create multivalent vaccine formulations:
1. Blending of several single monovalent VLPs as described in the monovalent sections 1, 2 and 3
2. Blending of two single particle bivalents in a sole combination. Assembly of the single particle bivalent is as described in section 2a, 2b and 2c.
3. Assembly of single multivalent particle: To assemble this particle
   3a. Co-expression of several heterologous sets of both structural and non-structural proteins
   3b. Co-expression of several heterologous structural proteins containing the same viral cleavage site within the sequence of the C protein together with non-structural proteins that recognize this viral cleavage site
   3c. Co-expression of several heterologous structural proteins that share the analogous cytoplasmic domain sequence including the viral protease cleavage site of the C protein together with non-structural proteins that recognize this viral cleavage site.

Furthermore, combination vaccine can be created by blending in a single formulation monovalent, bivalent or multivalent compositions of a disease-causing virus (e.g. dengue) with composition of another disease-causing virus such as Zika or chikungunya.

The utility of the VLPs include, but it is not limited to, the generation of immunogenic (vaccine) compositions that when administered to humans are able to treat and/or prevent flavivirus (dengue, Zika) infection, including treatment and/or prevention of infection with one and/or more flavivirus virus clades/antigenic variants or serotypes. Flavivirus VLPs may be used in combination with other flavivirus VLPs (e.g., Zika with dengue, and/or Alpha chikungunya, etc.), including VLPs that include one or more antigenic determinants from two or more flaviviruses and combinations of VLPs that include one or more antigenic determinants from one, two or more flaviviruses with VLPs that includes one or more antigenic determinants from one, two or more flaviviruses (e.g., monovalent, bivalent or multivalent Zika VLP in a pharmaceutical composition with monovalent, bivalent or multivalent Zika, dengue and/or chikungunya VLP). Other utility of the Zika VLP relates to diagnostic and therapeutic applications.

Suitable host cells for producing VLPs as described herein include, but are not limited to, bacterial, mammalian, baculovirus/insect, yeast, plant and *Xenopus* cells. For example, a number of mammalian cell lines are known in the art and include primary cells as well as immortalized cell lines available from the American Type Culture Collection (A.T.C.C.), such as, but not limited to, MDCK, BHK, VERO, MRC-5, WI-38, HT1080, 293, 293T, RD, COS-7, CHO, Jurkat, HUT, SUPT, C8166, MOLT4/clone8, MT-2, MT-4, H9, PM1, CEM, myeloma cells (e.g., SB20 cells) and CEMX174 (such cell lines are available, for example, from the A.T.C.C.).

The immunogenicity of VLP vaccines may be affected by the structural conformation of the E protein displayed on the particles' surface. Changing the temperature of the fermentation process may alter this conformation. In one embodiment, the VLPs are produced at lower temperature (31° C., plus or minus 3 degrees centigrade) than the standard temperature of fermentation of 37° C. VLPs produced at the lower temperature when administered as vaccine may induce higher neutralizing antibody titers than those produced at 37° C.

The VLPs as described herein may be purified following production. Non-limiting examples of suitable purification (isolation) from the cell culture medium procedures include using centrifugation and/or gradient centrifugation under suitable conditions. Other methods of purification may include sequential steps of filtration and/or chromatography procedures including ion exchange, affinity, size exclusion and/or hydrophobic interaction chemistries.

Cell lines expressing one or more of the sequences described above can readily be generated given the disclosure provided herein by stably integrating one or more expression vector constructs encoding the proteins of the VLP. The promoter regulating expression of the stably integrated flavivirus sequences (s) may be constitutive or inducible. Thus, a cell line can be generated in which one or more structural proteins are stably integrated such that, upon introduction of the sequences described herein (e.g., hybrid proteins) into a host cell and expression of the proteins encoded by the polynucleotides, non-replicating viral particles that present antigenic glycoproteins are formed.

In certain embodiments, a mammalian cell line that stably expressed two or more antigenically distinct flavivirus proteins is generated. Sequences encoding structural and/or non-structural proteins can be introduced into such a cell line to produce VLPs as described herein. Alternatively, a cell line that stably produces structural proteins can be generated and sequences encoding the antigenic flavivirus protein(s) from the selected strain(s)/serotype(s)/clade(s) introduced into the cell line, resulting in production of VLPs presenting the desired antigenic glycoproteins.

The parent cell line from which an VLP-producer cell line is derived can be selected from any cell described above, including for example, mammalian, insect, yeast, bacterial cell lines. In a preferred embodiment, the cell line is a mammalian cell line (e.g., 293, RD, COS-7, CHO, BHK, MDCK, MDBK, MRC-5, VERO, HT1080, and myeloma cells). Production of VLPs using mammalian cells provides (i) VLP formation; (ii) correct post translation modifications (glycosylation, palmitylation) and budding; (iii) absence of non-mammalian cell contaminants and (iv) ease of purification.

In addition to creating cell lines, flavivirus-encoding sequences may also be transiently expressed in host cells. Suitable recombinant expression host cell systems include, but are not limited to, bacterial, mammalian, baculovirus/ insect, vaccinia, Semliki Forest virus (SFV), Alphaviruses (such as, Sindbis, Venezuelan Equine Encephalitis (VEE)), Retrovirus vectors (lentivirus), mammalian, yeast and *Xenopus* expression systems, well known in the art. Particularly preferred expression systems are mammalian cell lines, vaccinia, Sindbis, insect and yeast systems.

Many suitable expression systems are commercially available, including, for example, the following: baculovirus expression (Reilly, P. R., et al., BACULOVIRUS EXPRESSION VECTORS: A LABORATORY MANUAL (1992); Beames, et al., Biotechniques 11:378 (1991); Pharmingen; Clontech, Palo Alto, Calif.)), vaccinia expression systems (Earl, P. L., et al., "Expression of proteins in mammalian cells using vaccinia" In Current Protocols in Molecular Biology (F. M. Ausubel, et al. Eds.), Greene Publishing Associates & Wiley Interscience, New York (1991); Moss, B., et al., U.S. Pat. No. 5,135,855, issued Aug. 4, 1992), expression in bacteria (Ausubel, F. M., et al., CURRENT PROTOCOLS IN MOLECULAR BIOLOGY, John Wiley and Sons, Inc., Media Pa.; Clontech), expression in yeast (Rosenberg, S. and Tekamp-Olson, P., U.S. Pat. No. RE35, 749, issued, Mar. 17, 1998, herein incorporated by reference; Shuster, J. R., U.S. Pat. No. 5,629,203, issued May 13, 1997, herein incorporated by reference; Gellissen, G., et al., Antonie Van Leeuwenhoek, 62(1-2):79-93 (1992); Romanos, M. A., et al., Yeast 8(6):423-488 (1992); Goeddel, D. V., Methods in Enzymology 185 (1990); Guthrie, C., and G. R. Fink, Methods in Enzymology 194 (1991)), expression in mammalian cells (Clontech; Gibco-BRL, Ground Island, N.Y.; e.g., Chinese hamster ovary (CHO) cell lines (Haynes, J., et al., Nuc. Acid. Res. 11:687-706 (1983); 1983, Lau, Y. F., et al., Mol. Cell. Biol. 4:1469-1475 (1984); Kaufman, R. J., "Selection and coamplification of heterologous genes in mammalian cells," in Methods in Enzymology, vol. 185, pp 537-566. Academic Press, Inc., San Diego Calif. (1991)), and expression in plant cells (plant cloning vectors, Clontech Laboratories, Inc., Palo-Alto, Calif., and Pharmacia LKB Biotechnology, Inc., Pistcataway, N.J.; Hood, E., et al., J. Bacteriol. 168:1291-1301 (1986); Nagel, R., et al., FEMS Microbiol. Lett. 67:325 (1990); An, et al., "Binary Vectors", and others in Plant Molecular Biology Manual A3:1-19 (1988); Miki, B. L. A., et al., pp. 249-265, and others in Plant DNA Infectious Agents (Hohn, T., et al., eds.) Springer-Verlag, Wien, Austria, (1987); Plant Molecular Biology: Essential Techniques, P. G. Jones and J. M. Sutton, New York, J. Wiley, 1997; Miglani, Gurbachan Dictionary of Plant Genetics and Molecular Biology, New York, Food Products Press, 1998; Henry, R. J., Practical Applications of Plant Molecular Biology, New York, Chapman & Hall, 1997).

When expression vectors containing the altered genes that code for the proteins required for sub-viral structure vaccine formation are introduced into host cell(s) and subsequently expressed at the necessary level, the sub-viral structure vaccine assembles and is then released from the cell surface into the culture media (FIG. 7).

Depending on the expression system and host selected, the VLPs are produced by growing host cells transformed by an expression vector under conditions whereby the particle-forming polypeptide(s) is (are) expressed and VLPs can be formed. The selection of the appropriate growth conditions is within the skill of the art. If the VLPs are formed and retained intracellularly, the cells are then disrupted, using chemical, physical or mechanical means, which lyse the cells yet keep the VLPs substantially intact. Such methods are known to those of skill in the art and are described in, e.g., Protein Purification Applications: A Practical Approach, (E. L. V. Harris and S. Angal, Eds., 1990). Alternatively, VLPs may be secreted and harvested from the surrounding culture media.

The particles are then isolated (or substantially purified) using methods that preserve the integrity thereof, such as, by density gradient centrifugation, e.g., sucrose, potassium tartrate or Iodixanol gradients, PEG-precipitation, pelleting, and the like (see, e.g., Kirnbauer et al. J. Virol. (1993) 67:6929-6936), as well as standard purification techniques including, e.g., ion exchange and gel filtration chromatography, tangential filtration, etc.

Compositions

VLPs produced as described herein can be used to elicit an immune response when administered to a subject. As discussed above, the VLPs can comprise a variety of antigens (e.g., one or more modified flavivirus antigens from one or more flaviviruses and/or one or more strains, serotypes, clades or isolates of a particular flavivirus). Purified VLPs can be administered to a vertebrate subject, usually in the form of vaccine compositions. Combination vaccines may also be used, where such vaccines contain, for example, other proteins derived from other flaviviruses or other organisms and/or gene delivery vaccines encoding such antigens.

VLP immune-stimulating (or vaccine) compositions can include various excipients, adjuvants, carriers, auxiliary substances, modulating agents, and the like. The immune stimulating compositions will include an amount of the VLP/antigen sufficient to mount an immunological response. An appropriate effective amount can be determined by one of skill in the art. Such an amount will fall in a relatively broad range that can be determined through routine trials and will generally be an amount on the order of about 0.1 µg to about 10 (or more) mg, more preferably about 1 µg to about 300 µg, of VLP/antigen.

Sub-viral structure vaccines are purified from the cell culture media and formulated with the appropriate buffers and additives, such as a) preservatives or antibiotics; b) stabilizers, including proteins or organic compounds; c) adjuvants or immuno-modulators for enhancing potency and modulating immune responses (humoral and cellular) to the vaccine; or d) molecules that enhance presentation of vaccine antigens to specifics cell of the immune system. This vaccine can be prepared in a freeze-dried (lyophilized) form in order to provide for appropriate storage and maximize the shelf-life of the preparation. This will allow for stock piling of vaccine for prolonged periods of time maintaining immunogenicity, potency and efficacy.

A carrier is optionally present in the compositions described herein. Typically, a carrier is a molecule that does not itself induce the production of antibodies harmful to the individual receiving the composition. Suitable carriers are typically large, slowly metabolized macromolecules such as proteins, polysaccharides, polylactic acids, polyglycollic acids, polymeric amino acids, amino acid copolymers, lipid aggregates (such as oil droplets or liposomes), and inactive virus particles. Examples of particulate carriers include those derived from polymethyl methacrylate polymers, as well as microparticles derived from poly(lactides) and poly (lactide-co-glycolides), known as PLG. See, e.g., Jeffery et al., Pharm. Res. (1993) 10:362-368; McGee J P, et al., J Microencapsul. 14(2):197-210, 1997; O'Hagan D T, et al., Vaccine 11(2):149-54, 1993. Such carriers are well known to those of ordinary skill in the art.

Additionally, these carriers may function as immunostimulating agents ("adjuvants"). Exemplary adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detoxu); (3) saponin adjuvants, such as Stimulon™. (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), beta chemokines (MIP, 1-alpha, 1-beta Rantes, etc.); (6) detoxified mutants of a bacterial ADP-ribosylating toxin such as a cholera toxin (CT), a pertussis toxin (PT), or an E. coli heat-labile toxin (LT), particularly LT-K63 (where lysine is substituted for the wild-type amino acid at position 63) LT-R72 (where arginine is substituted for the wild-type amino acid at position 72), CT-S109 (where serine is substituted for the wild-type amino acid at position 109), and PT-K9/G129 (where lysine is substituted for the wild-type amino acid at position 9 and glycine substituted at position 129) (see, e.g., International Publication Nos. WO93/13202 and WO92/19265); and (7) other substances that act as immunostimulating agents to enhance the effectiveness of the composition.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetylmuramyl-L-alanyl-D-isogluatminyl-L-alanine-2-(1'-2'-dipalmitoyl-sn-glycero-3-huydroxyphosphoryloxy)-ethylamine (MTP-PE), etc.

Examples of suitable immunomodulatory molecules for use herein include adjuvants described above and the following: IL-1 and IL-2 (Karupiah et al. (1990) J. Immunology 144:290-298, Weber et al. (1987) J. Exp. Med. 166: 1716-1733, Gansbacher et al. (1990) J. Exp. Med. 172:1217-1224, and U.S. Pat. No. 4,738,927-); IL-3 and IL-4 (Tepper et al. (1989) Cell 57:503-512, Golumbek et al. (1991) Science 254:713-716, and U.S. Pat. No. 5,017,691); IL-5 and IL-6 (Brakenhof et al. (1987) J. Immunol. 139:4116-4121, and International Publication No. WO 90/06370); IL-7 (U.S. Pat. No. 4,965,195); IL-8, IL-9, IL-10, IL-11, IL-12, and IL-13 (Cytokine Bulletin, Summer 1994); IL-14 and IL-15; alpha interferon (Finter et al. (1991) *Drugs* 42:749-765, U.S. Pat. Nos. 4,892,743 and 4,966,843, International Publication No. WO 85/02862, Nagata et al. (1980) *Nature* 284:316-320, Familletti et al. (1981) Methods in Enz. 78:387-394, Twu et al. (1989) *Proc. Natl. Acad. Sci. USA* 86:2046-2050, and Faktor et al. (1990) *Oncogene* 5:867-872); β-interferon (Seif et al. (1991) *J. Virol.* 65:664-671); γ-interferons (Watanabe et al. (1989) *Proc. Natl. Acad. Sci. USA* 86:9456-9460, Gansbacher et al. (1990) *Cancer Research* 50:7820-7825, Maio et al. (1989) *Can. Immunol. Immunother.* 30:34-42, and U.S. Pat. Nos. 4,762,791 and 4,727,138); G-CSF (U.S. Pat. Nos. 4,999,291 and 4,810,643); GM-CSF (International Publication No. WO 85/04188); tumor necrosis factors (TNFs) (Jayaraman et al. (1990) *J. Immunology* 144:942-951); CD3 (Krissanen et al. (1987) Immunogenetics 26:258-266); ICAM-1 (Altman et al. (1989) *Nature* 338:512-514, Simmons et al. (1988) *Nature* 331:624-627); ICAM-2, LFA-1, LFA-3 (Wallner et al. (1987) *J. Exp. Med.* 166:923-932); MHC class I molecules, MHC class II molecules, B7.1-β2-microglobulin (Parnes et al. (1981) *Proc. Natl. Acad. Sci. USA* 78:2253-2257); chaperones such as calnexin; and MHC-linked transporter proteins or analogs thereof (Powis et al. (1991) *Nature* 354:528-531). Immunomodulatory factors may also be agonists, antagonists, or ligands for these molecules. For example, soluble forms of receptors can often behave as antagonists for these types of factors, as can mutated forms of the factors themselves.

Nucleic acid molecules that encode the above-described substances, as well as other nucleic acid molecules that are advantageous for use within the present invention, may be readily obtained from a variety of sources, including, for example, depositories such as the American Type Culture Collection, or from commercial sources such as British Bio-Technology Limited (Cowley, Oxford England). Representative examples include BBG 12 (containing the GM-CSF gene coding for the mature protein of 127 amino acids), BBG 6 (which contains sequences encoding gamma interferon), A.T.C.C. Deposit No. 39656 (which contains sequences encoding TNF), A.T.C.C. Deposit No. 20663 (which contains sequences encoding alpha-interferon), A.T.C.C. Deposit Nos. 31902, 31902 and 39517 (which contain sequences encoding beta-interferon), A.T.C.C. Deposit No. 67024 (which contains a sequence which encodes Interleukin-1b), A.T.C.C. Deposit Nos. 39405, 39452, 39516, 39626 and 39673 (which contain sequences encoding Interleukin-2), A.T.C.C. Deposit Nos. 59399, 59398, and 67326 (which contain sequences encoding Interleukin-3), A.T.C.C. Deposit No. 57592 (which contains sequences encoding Interleukin-4), A.T.C.C. Deposit Nos. 59394 and 59395 (which contain sequences encoding Interleukin-5), and A.T.C.C. Deposit No. 67153 (which contains sequences encoding Interleukin-6).

Plasmids encoding one or more of the above-identified polypeptides can be digested with appropriate restriction enzymes, and DNA fragments containing the particular gene of interest can be inserted into a gene transfer vector (e.g., expression vector as described above) using standard molecular biology techniques. (See, e.g., Sambrook et al., supra, or Ausubel et al. (eds) Current Protocols in Molecular Biology, Greene Publishing and Wiley-Interscience).

Administration

The VLPs and compositions comprising these VLPs can be administered to a subject by any mode of delivery, including, for example, by parenteral injection (e.g. subcutaneously, intraperitoneally, intravenously, intramuscularly, or to the interstitial space of a tissue), or by rectal, oral (e.g. tablet, spray), vaginal, topical, transdermal (e.g. see WO99/27961) or transcutaneous (e.g. see WO02/074244 and WO02/064162), intranasal (e.g. see WO03/028760), ocular, aural, pulmonary or other mucosal administration and/or inhalation of powder compositions. Multiple doses can be administered by the same or different routes. In a preferred embodiment, the doses are intranasally administered.

The VLPs (and VLP-containing compositions) can be administered prior to, concurrent with, or subsequent to delivery of other vaccines. Also, the site of VLP administration may be the same or different as other vaccine compositions that are being administered.

Dosage treatment with the VLP composition may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the potency of the modality, the vaccine delivery employed, the need of the subject and be dependent on the judgment of the practitioner.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting. Thus, it will be apparent that while exemplary results are presented with respect to dengue virus, the teachings herein are equally applicable to any flavivirus (e.g. Zika, yellow fever, Japanese encephalitis, hepatitis C, West Nile, tick-borne encephalitis) or alphavirus (e.g. chikungunya).

EXAMPLES

Example 1: Dengue VLP Production

A dengue vaccine capable of rapidly eliciting a robust and balanced immunity against the four virus serotypes after only a few immunizations is greatly needed. We describe a new strategy to develop dengue vaccines based on the assembly of virus-like particles (VLPs) utilizing the structural proteins CprME together with a modified complex of the NS2B/NS3 protease, which enhances particle formation and yield. These VLPs are produced in mammalian cells and resemble native dengue virus as demonstrated by negative staining and immunogold labeling electron microscopy (EM). Realizing that in the mosquito that the virus replicates at a lower temperate than in humans, we found that VLPs produced at a lower temperature (31° C.) were recognized by conformational monoclonal antibodies (MAbs) 4G2 and 3H5, whereas VLPs produced at a higher temperature (37° C.) were not recognized by either MAbs. To evaluate the significance of these conformational discrepancies in vaccine performance, we tested the immunogenicity of VLP vaccines produced at 31° C. or 37° C. in alternative formulations. Mice immunized with the VLP vaccine produced at 31° C. (TVXDO-31° C.) elicited higher titer of neutralizing antibodies as compared to those elicited by equivalent doses of the vaccine produced at 37° C. (TVXDO-37° C.) as well as by inactivated dengue virus vaccine or the titer seen with a human anti-dengue-2 convalescence serum used as a reference. Our results demonstrate that the conformation of the E protein displayed on the VLP vaccine plays a critical role in the induction of highly neutralizing antibodies. These findings will guide development of a tetravalent vaccine capable of eliciting a robust and balanced neutralizing response against four dengue serotypes regardless of background immunity.

Dengue is a mosquito-borne viral disease that affects humans of all ages in tropical and subtropical regions around the world. Due to global expansion of the mosquito vectors (primarily A. aegypti, and A. albopictus) the virus has spread to more than 120 countries, infecting approximately 390 million people annually (1). This dramatic spread of the vector poses a threat to almost half of the world's population with disease outbreaks imposing a hefty public health and economic burden upon all affected areas. Four distinct virus serotypes (DENV1-4) can be transmitted by the bite of an infected Aedes Sp. mosquito causing an infection characterized by fever, headache, myalgia, arthralgia and, depending on the severity of the infection, may progress to Dengue hemorrhagic fever/Dengue shock syndrome (DHF/DSS) (2). Primary infection generates long-term protection against the homologous serotype, but a short-lived defense against heterologous serotypes. A secondary infection with a different serotype can trigger an antibody-dependent enhancement (ADE) of disease that may result in potentially fatal DHF and DSS (3). Currently, there are no specific interventions to treat dengue infections and prophylactic vaccines are the best hope to control the disease. The need to elicit a robust and balanced neutralizing response against the four-dengue serotypes, in order to prevent ADE, has hindered the development of a safe and effective dengue vaccines.

Dengue virus is a positive sense single-stranded RNA virus that belongs to the Flavivirus genus within the Flaviviridae family. There are four distinct identified virus serotypes: DENV-1, DENV-2, DENV-3 and DENV-4. These serotypes appeared independently during endemic cycles of transmission between humans and arthropod vectors (4). The dengue viral genome has a single open reading frame (ORF) encoding a polyprotein that is cleaved co- and post-translationally by cellular and viral proteases into three structural proteins: capsid (C), the premembrane (prM) and the envelope (E) as well as seven non-structural proteins: NS1, NS2A/B, NS3, NS4A/B and NS5 (5). Virus replication and morphogenesis takes place on virus-induced remodeled endoplasmic reticulum (ER) membranes leading to the assembly and budding of complete but immature particles into the ER system. (6). The spiky immature particles undergo an additional furin protease cleavage of prM during trafficking through the ER and the trans-Golgi network (tGN) (7) (FIG. 1A) that together, with a rearrangement of the E protein, turn the virions into smooth mature particles that are released from infected cells.

The surface E protein is the main antigenic determinant of the virus and the target of the immune system. Immunity directed toward the E protein is primarily mediated by neutralizing antibody which, when present, confers protection against dengue (8).

After decades of ceaseless effort, recently a dengue vaccine has reached commercialization stage. This live-attenuated chimeric vaccine is based on the yellow fever virus 17D vaccine strain, which provides the backbone to carry the DENV prM-E structural proteins of each serotype as chimeric viruses. Results of clinical phase III trials in Asia and South America show better results than did the clinical phase II trials, but both present serotype-dependent differences in vaccine efficacy and a lower efficacy in young children. In particular, the response against DENV-2 is suboptimal and after three immunization doses, the vaccination efficacy is only approximately 35% to 50% (9-11). Other vaccine candidates currently in clinical trials include live-attenuated virus vaccines, purified inactivated vaccine, a DNA vaccine, and a subunit vaccine (12, 13). The later vaccine formulation is comprised of four recombinant truncated E proteins and is currently the only recombinant vaccine candidate in clinical trials.

An alternative strategy for vaccine development involves the generation of viral-like particle (VLP) vaccine. These recombinant particles are self-assembling complex structures morphologically similar to wild-type virus but are devoid of viral genetic material and are thereby unable to replicate or cause infection. Flavivirus subviral particles or VLPs were initially detected in the supernatant of flavirius-infected cells (14) and subsequent studies have shown that the sole expression of recombinant prM and E were sufficient to drive the assembly and budding of subviral particles (15-17). These structures provide an attractive strategy for vaccine development because the particulate nature of recombinant VLPs composed of native proteins enhances antigen recognition, presentation and immune stimulation (18-20). Furthermore, the system allows for surface protein engineering to optimize antigen configuration seeking enhancement of the immune response. The proven efficacy and safety of licensed human VLP based vaccines for HBV, HPV and HEV (21-24) provide strong evidence of the value of this approach for vaccine development.

Here, we present data on the assembly of dengue virus-like particles utilizing a unique set of viral structural and non structural (NS) proteins and production conditions in which suspension cultures of mammalian cells render particles with distinct immunological properties which, as vaccines, elicit the production of highly effective neutralizing antibodies. This study describes a new strategy to efficiently develop a VLP based dengue vaccine that is assembled with native dengue protein and manufactured in a mammalian cell suspension culture system suitable for scale up manufacturing.

A. Materials & Methods

Genes and Plasmids Construct

The structural and non structural genes of DENV-2 were chemically synthesized by GeneArt (Life Technology) according to a specifically designed and codon-optimized sequence. DNA fragments were subcloned into the plasmid vector pcDNA3.4 (Life Techhologies) utilizing the NheI/NotI restriction enzyme sites. Specific mutations were introduced in the prM gene G88A, and in the E gene, I398L, M401A, M412L, as described by Purdy and Chang (25).

The non-structural genes of NS2B and viral protease NS3 were synthesized as a single codon optimized unit and subcloned into plasmid vector pcDNA3.4 via XhoI/EcoRV. The mutation L115A was introduced into the synthesized NS3 gene.

Plasmids were amplified in MAX Efficiency® Stbl2™ Competent E. Coli Cells (Life Technologies 10268-019) and purified from the bacteria utilizing an EndoFree Plasmid Maxi Kit (Qiagen).

Virus, Cells, and Antibodies

Cultures of Vero cells (ATCC® CCL-81™) were maintained in VP-SFM media (Life Technologies 11681-020) supplemented with 2 mM L-Glutamine (Life Technologies 25030-081), 2 mM GlutaMAX™ Supplement (Life Technologies 35050-061), 1× Non-essential amino acids solution (Life Technologies 11140-050), 1×ITSE (Invitria 777ITS032) and 500 ng/ml rhEGF (Life Technologies PHG0314).

Dengue virus: DENV-2 Th-36 (ATCC® VR-1810™) was amplified in Vero cells following virus inoculation at a low multiplicity of infection (MO: 0.01). Expi293™ (Life Technologies) cells were expanded in Expi293 medium (Gibco A1435101) and transfected using Expifectamine following the manufacturer's instructions (Life Technologies, A14635). Monoclonal antibody 4G2 is an in-house protein G purified from hybridoma D1-4G2-4-15 culture supernatant (ATCC HB-112). Mouse monoclonal antibody 3H5 was acquired through BEI Resources (NR-2556). Rabbit polyclonal antibodies, anti-C (GTX124247), anti-E (GTX127277), anti-prM (GTX128093) and anti-NS2B (GTX124246) were purchased from GeneTex, CA.

These secondary antibodies anti-mouse and anti-rabbit were both purchased from Pierce Thermo Fisher, MA (#31430 and #31460 respectively).

VLP Production and Purification

Expi293™ cells were transfected with a 1:2 ratio of pcDNA3.4-NS2b/NS3 and pcDNA3.4-CprME at 37° C. and transferred after 4 h post-transfection to incubators set at either 37° C. or 31° C. Transfected cells were harvested 72 hs post-transfection and clarified via two successive centrifugations. The first clarification was performed at 400×g for 10 min at 4° C. followed by a second clarification at 10,000×g for 10 min at 4° C. Clarified supernatant fluid was concentrated by ultracentrifugation for 2 h at 140,000×g at 4° C. The pellet was resuspended with 1×PBSCaMg pH 7.2 (1× phosphate buffered saline supplemented with 1 mM $MgCl_2$; and 1 mM $CaCl_2$)). VLPs were further purified by ultracentrifugation through a 20-60% step sucrose gradient in TN buffer (50 mM Tris-HCl pH 7.2; 150 mM NaCl) for 4 h at 180,000×g at 4° C. using an SW40Ti rotor (Beckman Coulter, CA). The protein content of the collected fractions was analyzed by dot blot using a dengue specific antibody. Selected fractions were combined, dialyzed overnight versus 1×PBS and concentrated by ultracentrifugation for 2 h at 140,000×g at 4° C. The pellet was then suspended in 80 µl of 1×PBSCaMg and loaded onto a second sucrose gradient (20%-60%) in TN buffer. Fractions were collected, analyzed and processed in the same fashion as in the first linear gradient above.

Dot Blot and Western Blot Assays

The cell protein content was analyzed after clarification of transfected Expi293™ cells. The cell pellet was collected and cells were lysed with RIPA buffer (PI-89901, Pierce Thermo Fisher, MA). For Western blotting, cell lysates and concentrated culture supernatants were loaded onto a 10-20% Tris-glycine SDS-PAGE gel (EC61352BOX, Life Technologies, CA). After electrophoresis separation, proteins were electro-transferred from the gel onto a 0.45 m nitrocellulose membrane (Life Technologies LC2001). For dot blot, 3 µl of sample was applied on top of a 0.45 µm nitrocellulose membrane and allowed to dry for 5 min. The nitrocellulose membranes were then treated for 1 h at room temperature with blocking solution (5% non-fat milk 1×TBS 0.1% Tween-20) followed by overnight incubation at room temperature in primary antibody diluted in blocking solution. Membranes were washed three times for 5 min with 1×TBS 0.1% Tween-20 and then incubated for 1.5 h in secondary antibody diluted in blocking solution. Finally, membranes were washed three times with 1×TBS-0.1% Tween-20 and developed with ECL system (WP20005, Life Technologies, CA).

Negative Staining and Immuno-Gold Labeling Electron Microscopy

Gradient purified VLP samples were blotted onto 200-mesh carbon coated grid (EMS CF200-Cu) for 5 min. The grids were then washed and stained with 2% uranyl acetate (EMS 22400-2). Examination of VLPs by immunogold labeling EM was performed as follows: sample coated carbon grids were blocked with 3% BSA in 0.1M Sodium cacodylate buffer for 5 min, followed by incubation for 20 min in primary monoclonal antibody 3H5 diluted in PBS (1:100 dilution). Grids were then washed three times with 0.1M sodium cacodylate buffer and then incubated for 20 min with secondary goat anti-mouse antibody (1:30 dilution). After a final series of three washes with 0.1M Sodium Cacodylate buffer, grids were stained with 2% uranyl acetate solution and examined with a JEOL-1400 electron microscope at the Rockefeller University Imaging Center.

Mouse Immunogenicity Study

Ten groups of 4-week old BALB/c mice were inoculated twice (day 0 and day 24) via the intramuscular (IM) route with VLP vaccines (TVXDO-31° C. or TVXDO37° C.). Groups of mice received doses of either 1 µg or 5 µg of total E protein content and formulated alone or admixed in a 1:1 volume with a squalene-based oil-in-water nano-emulsion AddaVax (InvivoGen, CA). Control groups were immunized with formalin inactivated (0.05%) DENV-2 Th-36 virus at the dose of either 1 µg or 5 µg of total E protein content. Serum samples for immunogenicity evaluation were collected at day 39.

ELISA

ELISA assays were performed in 96-well plates coated with 100 µl/well of formaldehyde inactivated DENV-2 virus (1 g/ml of E protein content) and incubated overnight at 4° C. The plates were washed three times with PBST buffer (phosphate buffered saline plus 0.05% Tween-20) and then blocked with 100 µl of blocking buffer (PBST plus 5% non-fat milk) for one hour at room temperature. Mouse sera were diluted following a 4-fold serial dilution in blocking buffer starting at 1:10; 50 µl of the diluted sera were incubated for 2 h at room temperature. After a set of 6 washes with PBST, plates were incubated for 2 h with 50 µl of HRP-conjugated goat anti-mouse antibody diluted 1:2, 000 in blocking buffer. Subsequently, plates were washed (6×) and developed by adding 50 µl/well of ECL reagent. Light emission was measured at 425 nm using a plate reader (Synergy, H1; BioTek, VT).

Plaque Reduction Neutralization Test (PRNT)

The plaque reduction neutralization test was carried out in Vero cells using dengue virus serotype 2 (DENV-2) and sera from immunized mice according to the method described for the evaluation of vaccine efficacy (26, 27). Briefly, DENV-2 was amplified and titrated in Vero cells using the same plaque visualization procedure described below. Vero cells were seeded in 24 well plates at a density of 5×104 cells per well 24 h prior to the initiation of the test. Control and tests sera were heat inactivated at 56° C. for 30 min. and then two-fold serially diluted in cell culture media supplemented with penicillin and streptomycin. An equal amount of diluted virus to form ~60 plaques per well was added to each serum dilution. The sera-virus mixture was incubated for 1 h at 37° C. in a 5% CO2 environment. Subsequently, each dilution was applied in duplicate wells of an 85% confluent monolayer of Vero cells and incubated for 1 h at 37° C. in a 5% CO2 incubator.

Thereafter, the inoculum was removed and a 3 ml overlay of 2% carboxymethyl cellulose (CMC) in culture medium was added to each well. Plates were then incubated for six days at which time the CMC overlay was removed, cells washed 1× with PBST (phosphate buffer saline plus 0.05% Tween 20) and fixed with cold 80% acetone for 10 min at room temperature (RT). Subsequently, plates were washed 1× with PBST and then incubated with blocking buffer (2.5% non-fat milk in PBS plus 0.5% of Triton X-100) for 1 h in a 37° C. incubator. After one wash, the primary antibody (MAb 4G2) diluted 1/200 in blocking buffer was applied for 2 h at RT, followed by two PBST washes and incubation for 1 h at RT with a goat anti-mouse AP conjugated secondary antibody (1/2000) in blocking buffer. Finally, plates were washed twice with PBST and one time with alkaline phosphate buffer (APB: 100 mM Tris-HCl pH9.0, 150 mMNaCl, 1 mMMgCl2). Viral plaques were detected by adding 100 µl per well of the alkaline phosphate (AP) substrate nitro blue tetrazolium chloride (NTB) and 5-brome-4-chlore-3-indolyl phosphate (BCIP) prepared and used as follows: 33 µl of NTB (50 mg/ml in 70% dimethylformamide) was added to 5 ml of APB, mixed well and then added 16.5 ul of BCIP (50 mg/ml in 100% dimethylformamide) and the mixture was used within 1 h. Plaques were counted and PRNT50s were determined using the PROBIT method (28). The neutralization power calculated is expressed as the reciprocal of the highest serum dilution that neutralizes 50% of the virus. Human pre-immune serum control and human anti-DENV-2 convalescent serum references were obtained from National Institute for Biological Standards and Control (NIBSC), UK.

B. Results

Processing of the structural and non-structural polyproteins and formation of dengue virus-like particles (VLPs)

Figure 4A:
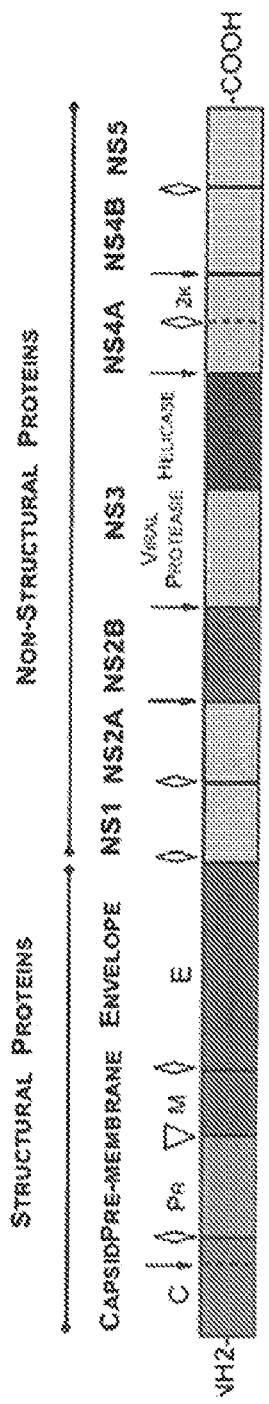
FIGS. 4A and 4B are schematics depicting dengue virus genome and VLP assembly strategy.
Figure 4B:
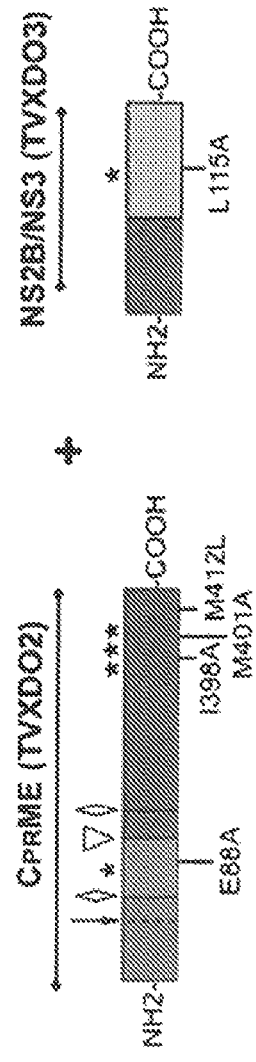

To assemble and release dengue virus-like particles (VLPs), we co-transfected into suspension cultures of Expi293™ human cells two DNA plasmids, one expressing the structural protein CprME and the other the non-structural proteins NS2B/NS3 (FIG. 4B). Expression of this protein combination resulted in the processing of the structural proteins CprME in an analogous fashion as occurs within the whole viral polyprotein (FIG. 4A) and therefore drove the formation and release of dengue VLPs.

The genes encoding CprME (plasmid TVXDO2) and NS2B/NS3 (plasmid TVXDO3) were de novo-synthesized and codon optimized to enhance protein expression in the HEK293 derived human cell line. Both the structural and non-structural protein coding sequences were modified by truncation and substitution mutations to facilitate polyprotein processing and enhance assembly and release of the VLPs. We introduced mutations at positions I398A, M104A and M412L within the amphipathic domain-1 of the E protein to overcome restrictions in the processing and maturation of the dengue polyprotein and thereby enhance VLP yield. (e.g. retention signal in the E protein) (25). We also mutated E88A in the furin recognition sequence of prM protein to enhance furin cleavage at this location. Furthermore, the viral NS3 protease/helicase was truncated retaining only the N-terminal protease domain, which contains the L115A mutation to enhance its catalytic activity. The remaining protease cleavage sites within the CprME polypeptide, however, were preserved in order to maintain a processing pattern analogous to the one occurring in dengue virus infected cells (FIG. 4B).

Western blot analysis of transfected Expi293™ cell lysates showed not only expression of both structural and non-structural proteins but also complete processing of the structural polyprotein. Indeed, the capsid (12 Kda), the prM predicted size (23/8 Kda) and the E protein (64 KDa) demonstrated the appropriate molecular size, as would be expected of a fully processed polyprotein (FIG. 5). The molecular weight of the NS2B protein is similar to the one detected in the DENV-2 cell lysate, suggesting that the self-cleavage between NS2B/NS3Pro occurs efficiently at the corresponding cleavage site (FIG. 2D). The NS3 portion of NS2B/NS3 could not be detected due to the lack of a suitable specific antibody. The efficient self-cleavage of NS2B/NS3Pro and the cleavage of the capsid protein confirm that the amino acids 1 to 183 are sufficient for proper protease activity as described by Li et. al. (29). Our construct contains the substitution mutation L115A in the NS3Pro, which does not appear to interfere with proper protease activity.

To determine whether the NS2B/NS3pro have an effect on VLP production, we transfected Expi293™ cells with the TVXDO2 (CprME) plasmid alone or TVXDO2 together with TVXDO3 (NS2B/NS3pro) plasmid. The culture supernatants were clarified twice and VLPs concentrated by ultracentrifugation. Western blot analysis of concentrated supernatant of TVXDO2 alone showed that small amount of pr/M and E proteins were secreted into the culture medium (FIG. 6). Release of the structural proteins, however, was enhanced when the plasmid TVXDO2 expressing the structural genes (CprME) was co-transfected with the plasmid TVXDO3 that expresses the modified non-structural proteins NS2/NS3pro. There was an increase in the amount of secreted E and prM when NS2B/NS3pro was co-expressed with CprME (FIG. 6). Furthermore, these results revealed interdependence of cleavage between the C-anchored to C and the C anchored to prM, which is in agreement with findings in studies previously reported (30, 31). Thus, this protein combination offers an effective approach for VLP production.

Dot Blot Analysis of VLPs Produced at Different Temperatures

Dengue virus is able to replicate in both mosquitoes and humans, which illustrates the broad temperature range (ambient versus 37° C. respectively) over which the virus can complete its replication cycle. Several studies have shown that higher VLP yields can be obtained when the producing mammalian cell culture is incubated at a lower temperature underlying the significance of a slower assembly process (32, 33). Based on this information, we chose to evaluate the effect of different temperatures on particle formation and surface protein structure by dot blot using specific MAbs recognizing conformation epitopes of the E protein. VLPs were produced at two distinct temperatures 31° C. and 37° C., purified through a linear sucrose gradient (15%-50%) and their sedimentation profile analyzed by dot blot using an anti-E polyclonal antibody. This comparative examination showed that the migration profile of the VLPs produced at both temperatures was similar with the strongest reactivity in fractions 10 to 13, indicating that the differing temperatures did not affect the migration profile of the assembled VLPs (FIG. 7).

To examine the structural conformation of the E protein, we utilized the dot blot method that allows for the study of dengue VLP in its native conformation. The monoclonal antibodies 4G2 and 3H5 that recognize structural epitopes on the E protein were used to search for conformational differences between VLPs produced at 31° C. (TVXDO-31° C.) and 37° C. (TVXDO-37° C.). The MAb 4G2 recognizes a structural epitope in the domain DII of E at the fusion loop comprised of amino acids G104, G106, L107 and W231. The fusion loop of the E protein plays a key role in membrane fusion and therefore in dengue virus cell entry and replication.

Purified VLPs produced at 31° C. (fractions 10-13) demonstrated the strongest reactivity with the MAb 4G2, whereas VLPs produced at 37° C. failed to be recognized by this MAb (FIG. 7). It was evident, therefore, that the recombinant E protein displayed on the VLPs produced at either 31° C. or 37° C. was recognized by the anti-E polyclonal antibody but that only the VLPs produced at 31° C. exhibited the epitope recognized by 4G2 MAb, suggesting a conformational difference between these E proteins.

To further examine the structural features of the VLP E protein, we used a second MAb (3H5) that recognizes a conformation epitope in the domain DIII of the E protein, comprised of amino acid residues K305, P384 which are essential for binding to cellular receptors (34, 35). Dot blot analysis of purified VLPs with the 3H5 MAb showed strong reactivity with TVXDO-31° C. but failed to recognize TVXDO-37° C. (FIG. 7). Thus, equivalent fractions of the two VLP preparations reacted strongly with the anti-E polyclonal antibody, however only the VLPs prepared at 31° C. (TVXDO-31° C.) were recognized by both 3H5 and 4G2 (FIG. 7). TVXDO-31° C. shows closer immunological characteristics to the wild type virus than does the TVXDO-37° C. VLP. All three tested antibodies recognized DENV-2 control. These results support the conclusion that the E protein display on VLPs produced at a lower temperature adopt structures that better exhibit conformational epitopes, which are critical for the induction of neutralizing antibodies.

Electron Microscopy (EM) Examination of DEN-2 VLPs

In view of the conformational differences due to incubation at either 31° C. or 37° C., we carried out a closer examination of purified VLPs by negative staining and electron microscopy to further evaluate the morphology, shape, size and surface composition of the secreted virus-like particles. EM examination of TVXDO-31° C. VLPs (FIG. 8A) showed that they are spherical in shape and with an approximately 50 nm diameter, resembling structural characteristics of mature dengue virus as has been previously shown (36). Immuno-gold labeling EM of dengue-2 VLPs using the conformational-epitope recognized by MAb 3H5 showed surface reactivity and labeling only of TVXDO-31° C. VLP, confirming the assembly and release of particles composed of prM/E that exhibited the conformational epitopes recognized by these MAbs (FIG. 8B). In contrast, the TVXDO-37° C. VLPs did not react with either 4G2 or 3H5.

Immunogenicity Evaluation of VLPs in Mice by ELISA

Figure 6:
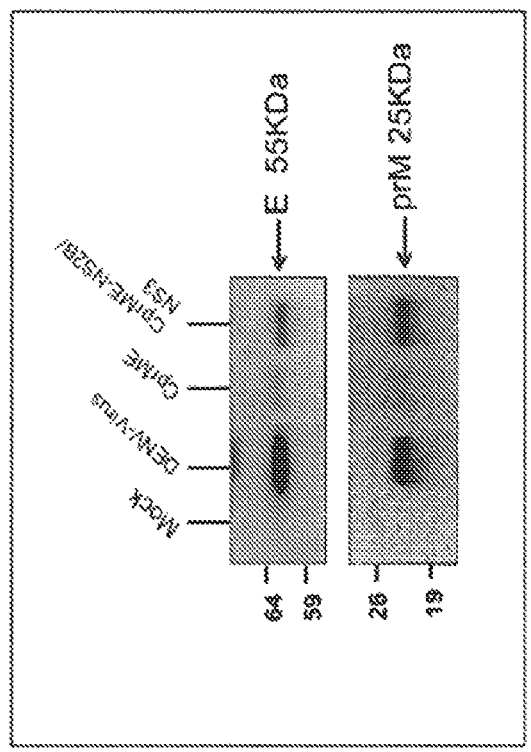
FIG. 6 shows dengue VLP secretion is enhanced by co-expression of CprME and the viral protease complex NS2B/NS3. Expi293™ cells were transfected with CprME alone or CprME together with NS2B/NS3. Cell supernatant from mock transfected or CprME or CprME-NS2B/NS3 transfected cells were purified by ultracentrifugation. Purified VLPs were analyzed via Western blot using 20 g of total protein per lane. Purified DENV-2 virus was used as control (20 µg). The Western blot membranes were probed with (top panel) an anti-E antibody and (bottom panel) an anti-prM antibody.

The recombinant DENV-2 VLPs showed immunological and structural similarities with DENV-2 virus when produced at 31° C. but not at 37° C. To ascertain whether these distinctions play a significant role in the immunogenicity of the VLPs and therefore in their effectiveness as vaccine candidates, we performed immunization studies in BALB/c mice. Groups of mice (n=4) were immunized twice, two weeks apart, via the intramuscular route with either TVXDO-31° C. or TVXDO-37° C. at the dose of 1 µg or 5 µg of total E protein content and formulated with or without adjuvant. Two weeks after the booster immunization, we collected serum samples from vaccine and control mice and assessed the antibody response by measuring total IgG levels by ELISA and neutralizing antibody titers by plaque reduction neutralization assay. Mice immunized with 5 µg of TVXDO-31° C. VLP vaccine with or without adjuvant demonstrated the highest level of IgG production as compared to the equivalent dose and formulations of TVXDO-37° C. vaccine or the inactivated DENV-2 virus control (FIG. 6). Similarly, the TVXDO-31° C. VLP vaccine administered at the dose of 1 µg elicited production of higher IgG levels than the TVXDO-37° C. VLP or inactivated virus vaccine. Although the TVXDO-31° C. VLP vaccine induced the highest IgG levels, in a dose response manner, it was only the 1p g adjuvanted dose that showed a statistically significant difference with the TVXDO-37° C. VLP vaccine (FIG. 9).

Immunogenicity Assessment by Plaque Reduction Neutralization Test (PRNT)

Elicitation of high titers of neutralizing antibody is paramount for dengue protection and therefore we measured the levels of neutralizing antibodies elicited by these vaccines via PRNT. The assay was performed according to the World Health Organization (WHO) guidelines and protocols (26, 27). The PRNT50 of reciprocal dilutions was calculated using the PROBIT methods and compared with pre-immune mouse serum and reference controls (FIG. 10). Both adjuvanted vaccines, at the dose of either 1 µg or 5 µg elicited higher neutralizing titers than the non-adjuvanted preparations. The 1 µg dose of TVXDO-37° C. vaccine, with and without adjuvant induced lower neutralizing antibody titers (PRNT50s: <25 and 57) than an equivalent dose of the inactivated dengue virus control (FIG. 10). However, the adjuvanted 5 µg dose of the TVXDO-37° C. elicited neutralizing titers (PRNT50: 382) that were greater than the one induced by the 5 µg (PRNT50: 201) and 1 µg (PRNT50: 158) doses of the inactivated dengue virus control.

On the other hand, the non-adjuvanted TVXDO-31° C. vaccine at the dose of 1 µg and 5 µg stimulated neutralizing antibody in the PRNT50 ranging from 99 to 196. However, when this vaccine was admixed with adjuvant the potency of the neutralizing response increased 3.7-fold to a PRNT50 of 371 for the 1 µg dose and greater than 5-fold to a PRNT50 of 1067 for the 5 µg dose. The high neutralizing potency stimulated by the adjuvanted 5 µg dose of the TVXDO-31° C. is almost 3-fold greater than the equivalent dose of the TVXDO-37° C. as well as 5.3 fold greater than the inactivated dengue virus control. Furthermore, to better judge the neutralization power elicited by the different vaccine doses, formulations and controls, we performed PRNT50 assays with a standard of human pre-immune and human convalescence DENV-2 sera obtained from the National Institute for Biological Standard and Control, UK (NIBSC). The PRNT50 of human seronegative control was similar to mouse pre-immune sera whereas the neutralizing power of the human convalescent DENV-2 serum (PRNT50: 297), was slightly higher than the high dose (5 µg) of inactivated dengue virus control (PRNT50: 201). On the other hand, the adjuvanted TVXDO-31° C. VLP vaccine at the dose of 1 µg and 5 µg elicited neutralizing antibody responses that were 1.2 fold and 3.6 fold higher than the human convalescence sera control, PRNT50: 371 versus 297 and PRNT50: 1067 versus 297 respectively. Although the TVXDO-37° C. adjuvanted 5 µg dose vaccine performed better than the inactivated DENV-2 and the anti-DENV-2 human serum standard it did not reach the neutralizing power induced by the TVXDO-31° C. vaccine (PRNT: 382 versus PRNT: 1067). These results clearly show that the VLP vaccine produced at lower temperature, TVXDO-31° C., and formulated with adjuvant elicits the strongest anti-DENV-2 neutralizing antibody response, which potency correlated with the amount of antigen and inclusion of adjuvant.

Dengue is an expanding disease due to the increase numbers and geographic spread of the *Aedes* sp. mosquito population that disseminates the virus. The only vaccine approved for DENV is a live attenuated virus that requires a year of multiple immunizations to reach, in many cases, an unbalanced immunity against the four-dengue serotypes (Dengvaxia, Sanofi Pasteur's) (10, 11). Importantly, vaccine efficacy against the most disseminated DENV-2 serotype is only approximately 35% to 50%. Thus, new approaches for developing highly effective and safe dengue vaccines are needed. Here we report a novel strategy that utilizes a new set of structural and non-structural dengue proteins to assemble virus-like particles (VLPs) for dengue vaccine development. Most dengue VLPs have been assembled using the sole expression of prM and E proteins (37) and these attempts have revealed limitations in protein processing and domain restrictions, such as the presence of E retention sequences, which reduce assembly efficacy and yield. Our approach utilizes the complete set of structural proteins (CprME) expressed as a single polypeptide together with a modified NS2B/NS3 protease complex. In order to optimize authentic protein processing, trafficking and particle assembly, we introduced specific mutations, substitutions and a deletion within the structural and non-structural proteins. We mutated the furin recognition site (E88A) in prM protein to enhance cleavage and protein processing as well as introduced changes in the helical domain 1 of the E protein (I398A, M401A, and M412L) to improve its amphipathic properties and thus enhance trafficking and secretion of E. Lack of furin cleavage and retention of the E protein by its helical domains may impede protein transport and the assembly of mature particles. Furthermore, the C-terminal of the NS3 protein was truncated retaining only its N-terminal protease domain that contains a mutation (L115A) to enhance its catalytic activity. The NS3 protease domain was genetically linked to its cofactor NS2B and expressed as a single polypeptide in order to maintain enzymatic activity. We selected this approach rather than replacing C with a heterologous signal peptide for protein translocation into the ER, as has been reported (38, 39) because our optimized CPrME construct spurred significant expression of the structural polyprotein, which was effectively processed by the co-expressed viral protease (NS2B/NS3) and cell host proteases. Co-expression of these proteins in suspension culture of mammalian cells resulted in the assembly and release of dengue virus-like particles (VLPs) into the culture media. Their structures resemble native dengue virus in shape, size and surface antigenic composition as demonstrated by negative staining and immunogold labeling electron microscopy with VLPs produced at 31° C.

Because of the temperature range of dengue virus replication (ambient in the mosquito vector and 37° C. in the human host) and the observation that lower temperature increased the yield of dengue replicons (32, 33), we investigated whether the VLP production temperature enhances yield. This study revealed that lower temperature (31° C.) not only improves VLP yield but also has a significant effect on the antigenic properties of the E protein displayed on the particle surface. VLPs produced at 31° C. were strongly recognized by two distinct MAbs (4G2 and 3H5) that bind the conformational epitopes in domain II (4G2) and domain III (3H5) of the E protein. In contrast, VLPs produced at 37° C. were recognized by neither 4G2 nor 3H5, revealing that the targeted epitopes were not properly folded in two different domains of the E protein. This finding suggests that production temperature has a significant effect on the folding and conformation of the E protein exhibited on the surface of the VLPs. Several studies have demonstrated the effect of different temperatures on dengue virus structures. Detailed cryo-electron microscopy analysis of dengue virus showed that mature virus produced at 28° C. is smooth, however when incubated at temperatures higher than 33° C. it appears bumpy, with an increase in diameter and heterogeneity (40, 41). Although it has been reported that MAbs react differently with dengue virus of distinct conformations (42, 43), the role of dissimilar conformations of E in the elicitation of neutralizing antibodies has not been completely elucidated.

In our vaccine studies, we have shown that VLPs produced at 31° C. elicit higher neutralizing antibody titers than those produced at 37° C. This finding indicates that the TVXDO-31° C. vaccine exhibits a better conformation of E as was initially recognized with the MAbs 4G2 and 3H5. This structure appears to displays a larger repertoire of neutralizing sites, which is evident in the stronger neutralizing response stimulated by this vaccine. Furthermore, the higher neutralizing activity stimulated by the TVXDO-31° C. VLP vaccine cannot be merely attributed to the sites recognized by 4G2 and 3H5 because these antibodies are not highly neutralizing, suggesting that additional epitopes capable of stimulating neutralizing antibodies are also exposed. Neutralizing titers were markedly enhanced with the addition of an adjuvant and the improvement was significantly higher with both doses (1 μg and 5 μg) of TVXDO-31° C. (PRNTs: 371 and 1067) as compared to equivalent doses of the TVXDO-37° C. vaccine (PRNTs: 57 and 382). To provide context to these PRNT results, we tested a human anti-DENV-2 convalescent serum (NIBSC/WHO) and found that it had lower neutralizing titers than that obtained with either dose of the adjuvanted TVXDO-31° C. vaccine or even higher dose of the TVXDO-37° C. vaccine. The difference in neutralizing power between the two VLP vaccines (TVXDO-31° C. and TVXDO-37° C.) at either dose with and without adjuvant illustrates intrinsic distinctions in the antigenic conformation of the E protein of the VLPs with better display, arrangement or frequency of epitopes in the TVXDO-31° C. vaccine. It is even possible that these conformational attributes arise after inoculation as the consequence of molecular breathing at the higher temperature of the recipient host (37° C.). In addition, the display of quaternary epitopes that result from adjacent domains of two surface proteins may further explain why the VLPs produced at 31° C. elicit higher neutralizing titers, since molecular breathing may also impact the quaternary structure of the VLP. Reactivity with MAb 4G2 suggests better E protein folding, which correlates with quaternary epitope display as has been reported (42, 44-46). These results highlight how conformational differences of the major dengue surface antigens affect the elicitation of neutralizing antibodies. Given the significance of the level of neutralizing antibody against dengue needed to achieve protection, these findings may be of great significance in dengue vaccine design and development. While other dengue VLP vaccine studies have reported efficacy, some of these preclinical tests used significantly higher doses than the one used with our VLP vaccine formulations (100 μg versus 5 μg) (38) and the assays used to assess efficacy were not comparable to our PRNTs. Thus, it seems impractical to compare the effectiveness of our TVXDO-31° C. or TVXDO-37° C. with other vaccine constructs. The convalescent human DENV-2 serum standard may provide the best benchmark for comparison.

In summary, this work not only describes a new strategy for VLP based dengue vaccine development but also shows the effect of temperature on the VLP E protein conformation and how these structural dissimilarities dictate the neutralizing antibody response, which is higher with VLP vaccines produced at a lower temperature. These findings hold great promise for the development of a VLP-based dengue vaccine.

Example 2: Zika VLP Production

Emerging viral infections are those that either newly infect the human population such as Zika or rapidly disseminate increasing the geographical range of infection and the number of cases of disease, as is the case with dengue. One of the most effective countermeasures to fight these arthropod transmitted viral infections is prophylactic vaccination. We have developed a flavivirus VLP vaccine platform technology to generate vaccines against these pathogens and using it to produce a Zika vaccine.

Zika fever disease results from an infection with Zika virus (ZIKV), which is transmitted to humans by the bite of an infected *Aedes* mosquito (*A. aegypti, A. albopictus* and polynesiensis). Zika virus was isolated for the first time from a Rhesus monkey in the Zika Forest in Uganda in 1947 and later from humans in 1952 [2].

ZIKV has been transmitted in Africa for many years through a sylvatic cycle between mosquito vectors and nonhuman primates, with occasional human infections [3]. In recent years, however, epidemics of Zika have resulted from cycles of transmission between vectors and humans resulting in the spread of disease beyond the African continent into French Polynesia and other Pacific regions [4-6]. Since 2015 a dramatic spread of ZIKV that began in Brazil is taking place in South America and the Caribbean Islands with the occurrence of sporadic cases in travelers identified in the USA and Europe [7].

Zika infection appears to cause a mild illness in most people infected, however, contracting the virus during pregnancy is associated with birth defects, primarily microcephaly (defective brain development). Furthermore, an increase in cases of Guillain-Barre syndrome has been observed following ZIKV infection. The seriousness of these disorders imposes a tremendous burden on public health. In addition to vector transmission, ZIKV is also likely transmitted via sexual contact [8], this fact taken together with its often asymptomatic nature makes disease control more difficult.

Zika virus is a member of the flavivirus genus within the Flaviviridae family. This is a large group of enveloped viruses including dengue, yellow fever, West Nile, Japanese encephalitis and others that possess a single stranded RNA genome of positive polarity, which serves as mRNA upon the infection of susceptible cells. The ZIKV RNA genome encodes only one open reading frame (ORF, ~10,272 nt) and translates into a single polyprotein that is co- and post-translationally cleaved by cellular and virus-encoded proteases into three structural proteins (C, prM and E) and seven non-structural proteins (NS1, NS2A, NS2B, NS3, NS4A, NS4B and NS5.) that enable virus replication [9, 10]. Flaviviurs replication and morphogenesis occurs closely associated with intracellular membranes and nascent virions are assembled and transported through the secretory pathway and released at the cell surface. Enveloped virions are composed of a cell-derived lipid bilayer encapsulating the C-protein wrapped viral RNA genome and studded with multiple copies of the proteins E and M. During maturation within the secretary pathway the precursor prM protein is cleaved by the host cell furin protease to produce the small M protein and the fragment pr, which is released upon virus egress from the cell. The surface displays E protein as the major antigenic determinant of the virus and mediates receptor binding and fusion during virus entry. Therefore, this protein is a major target for vaccine development [11].

At this time there is no vaccine or specific treatment to control, combat or prevent ZIKV infection. The prevention of infection by vaccination represents a critical unmet need to control the spread and the effects of the disease globally. Development of a ZIKV vaccine is highly significant given the public health concerns raised by the dramatic spread of the disease, its possible effects and unclear epidemiology (birth defects, Guillain-Barre syndrome and sexual transmission).

We implemented our flavivivirus virus-like particle (VLP) vaccine platform technology to create immunoprotective countermeasures against Zika. VLP vaccines are produced in cell-based systems as structural and biochemical mimics of wild-type viruses, however, VLPs lack viral genetic material and are unable to replicate or cause infection. Therefore, vaccine inactivation is not required, better maintaining their antigenic epitopes and enhancing immunogenicity. The strategy to create flavivirus VLPs, and as an example Zika, is based on the simultaneous expression in mammalian cells of the structural proteins CprME together with a modified complex of the non-structural protein NS2B/NS3 protease to maximize assembly and production.

These polypeptides suffice for the efficient self-assembly and release of particles into culture media. Since only sequence information of viral genes is needed and because of the flexibility, speed and safety of the technology, vaccines against emerging viruses such as Zika can be generated rapidly and without risk of disseminating infectious material [12-14]. Furthermore, VLP vaccines can be manufactured via transient transfection of mammalian cells with an expressing plasmid or by using engineered and selected high producer stably transfected cells. This later approach will allow not only for the continuous vaccine production to the desired scale but also for the storage of specific vaccine producing cell lines that can be activated at the time, location and levels required. In addition, this technology allows for the generation of combination vaccines via either blending distinct VLPs in a single formulation or by assembling chimeric VLPs following the co-expressing of E proteins from different pathogens or serotypes.

Results

Figure 11:
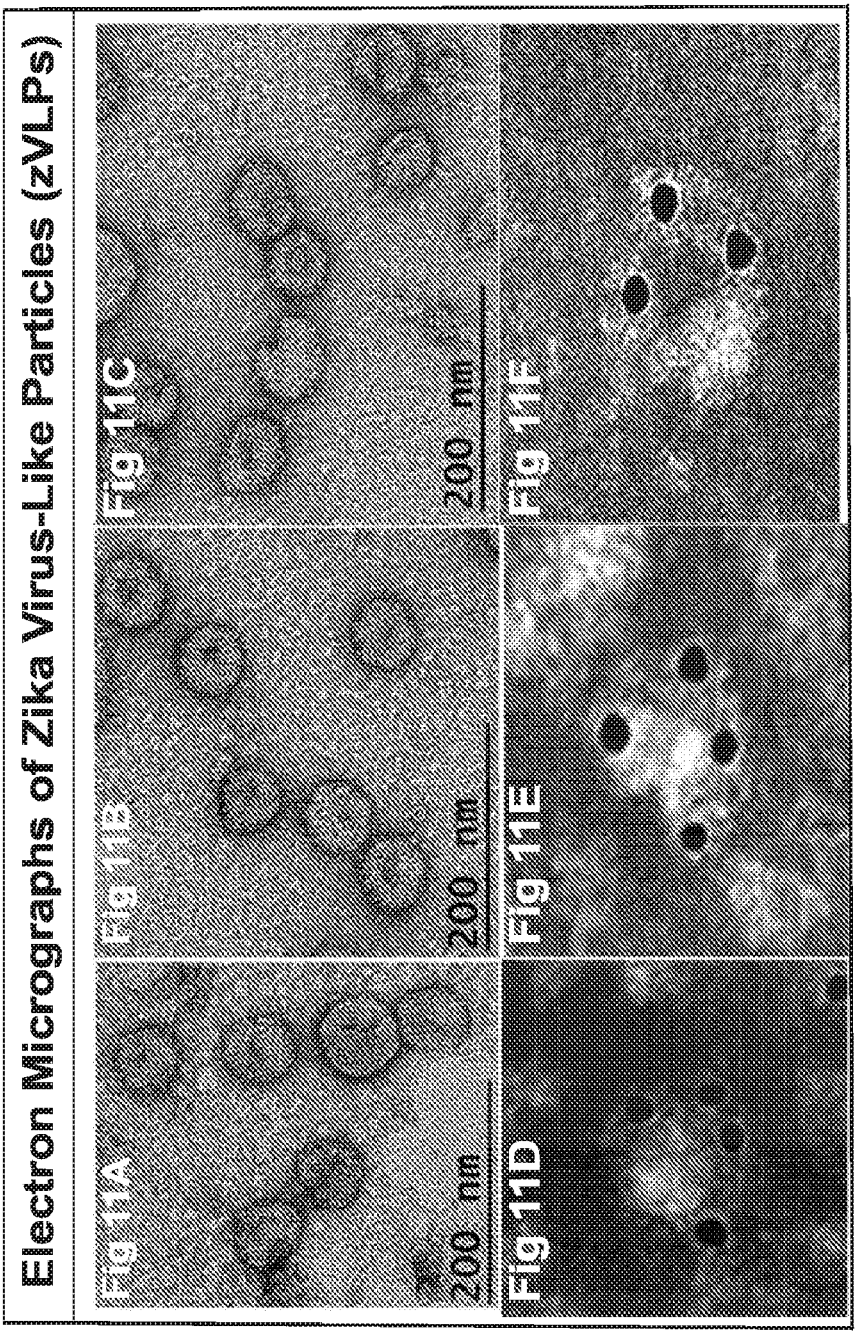
FIGS. 11A through 11F shows electron microscopy studies of Zika VLPs. Zika virus-like particles (zVLPs) were purified by ultracentrifugation through a potassium tartrate (10%-35%)/glycerol (7%-28%) linear gradient and examined by electron microscopy.
Figure 12:
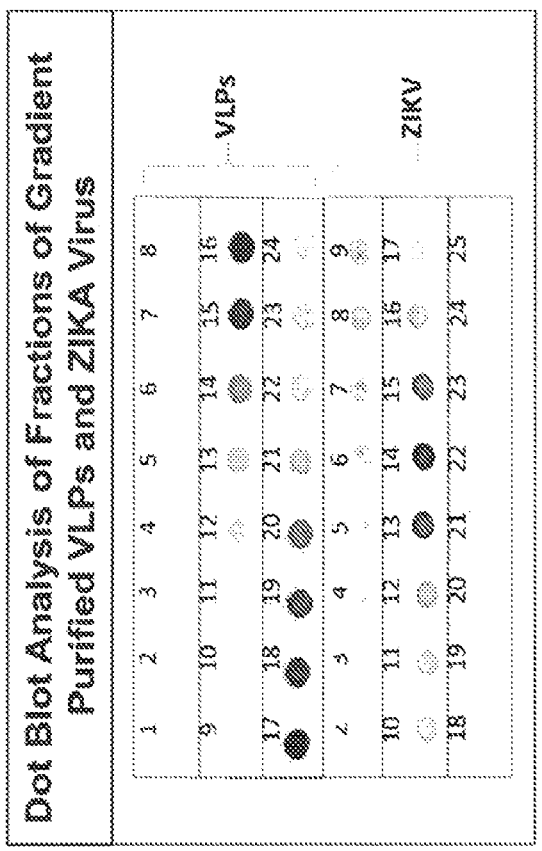
FIG. 12 shows dot blot evaluation of gradient purification profile of Zika virus-like particles (zVLPs) and Zika virus. Aliquots (3 ul) from each fraction of gradient purified VLPs and ZIKA virus were tested by dot blot with an anti-E specific MAb. VLPs were detected in fractions 15 to 20 whereas the ZIKA virus was detected in fractions 13 to 15.

Transient transfection of the structural protein CprME and non-structural protease complex NS2B/NS3 lead to secretion of particles. Purification of ZIKA VLPs by ultracentrifugation through a potassium tartrate (10-35%)/glycerol (7%-30%) linear demonstrates a similar migration pattern as the ZIKV when gradient fractions were probed with an anti-E specific MAb, as shown in FIG. 12. Furthermore, examination of E positive gradient fractions of negative staining electron microscopy (EM) showed the presence of spherical particles (~60 nm diameter) that closely resembled the structure of the wild type ZIKV. (FIGS. 11A, 11B, 11C). To assess whether the E protein was present on the surface of the VLPs, we evaluated the same ZIKA VLP fraction by immune-gold labeling EM using an anti-E MAb as primary and an anti-mouse gold bead conjugated secondary antibodies, respectively.

This study demonstrated that indeed the E protein was detected on the VLPs as shown by the presence of beads on the particles surface (FIGS. 11, 11D, 11E, and 11F). In addition, Western blot analysis of ZIKA VLPs and wild type Zika virus revealed the presence of a correct size E protein in both VLP and virus samples when probed with anti-E antibody, FIG. 13. These data demonstrates that transfected cells release VLPs, which resemble native Zika virus and display the E protein a major antigenic target for the elicitation of neutralizing antibodies.

The immunogenic attributes of alternative ZIKA VLP vaccine formulations are assessed in mice to evaluate the quality and magnitude of ZIKA virus specific neutralizing antibody response.

Based on the high neutralizing antibody titers elicited by a monovalent dengue-2 VLP vaccine, assessed by plaque reduction neutralization assay (PRNT) (FIG. 10), a ZIKA VLP vaccine should also stimulate a robust virus neutralizing antibody response. Vaccine for flaviviruses based on the VLP platform technology offers a safe, effective and scalable system and warrants further development, particularly for the Zika virus problem.

REFERENCES

1. Bhatt S, Gething P W, Brady O J, Messina J P, Farlow A W, Moyes C L, Drake J M, Brownstein J S, Hoen A G, Sankoh O, Myers M F, George D B, Jaenisch T, Wint G R, Simmons C P, Scott T W, Farrar J J, Hay S I. 2013. The global distribution and burden of dengue. Nature 496: 504-507.
2. Martina B E, Koraka P, Osterhaus A D. 2009. Dengue virus pathogenesis: an integrated view. Clin Microbiol Rev 22:564-581.
3. Guzman M G, Vazquez S. 2010. The complexity of antibody-dependent enhancement of dengue virus infection. Viruses 2:2649-2662.
4. Twiddy S S, Holmes E C, Rambaut A. 2003. Inferring the rate and time-scale of dengue virus evolution. Mol Biol Evol 20:122-129.
5. Lindenbach B D, Murray, C. L., Thiel, H-J., Rice, C. M. 2013. Flaviviridae. Fields Virology, Sixth Edition, Lippincott Williams & Wilkins Vol. I, Chapter 25:713-746.
6. Apte-Sengupta S, Sirohi D, Kuhn R J. 2014. Coupling of replication and assembly in flaviviruses. Curr Opin Virol 9:134-142.
7. Umareddy I, Pluquet O, Wang Q Y, Vasudevan S G, Chevet E, Gu F. 2007. Dengue virus serotype infection specifies the activation of the unfolded protein response. Virol J 4:91.
8. Murphy B R, Whitehead S S. 2011. Immune response to dengue virus and prospects for a vaccine. Annu Rev Immunol 29:587-619.
9. Sabchareon A, Wallace D, Sirivichayakul C, Limkittikul K, Chanthavanich P, Suvannadabba S, Jiwariyavej V, Dulyachai W, Pengsaa K, Wartel T A, Moureau A, Saville M, Bouckenooghe A, Viviani S, Tornieporth N G, Lang J. 2012. Protective efficacy of the recombinant, live-attenuated, CYD tetravalent dengue vaccine in Thai schoolchildren: a randomised, controlled phase 2b trial. Lancet 380:1559-1567.
10. Capeding M R, Tran N H, Hadinegoro S R, Ismail H I, Chotpitayasunondh T, Chua M N, Luong C Q, Rusmil K, Wirawan D N, Nallusamy R, Pitisuttithum P, Thisyakorn U, Yoon I K, van der Vliet D, Langevin E, Laot T, Hutagalung Y, Frago C, Boaz M, Wartel T A, Tornieporth N G, Saville M, Bouckenooghe A, Group CYDS. 2014. Clinical efficacy and safety of a novel tetravalent dengue vaccine in healthy children in Asia: a phase 3, randomised, observer-masked, placebo-controlled trial. Lancet 384:1358-1365.
11. Villar L, Dayan G H, Arredondo-Garcia J L, Rivera D M, Cunha R, Deseda C, Reynales H, Costa M S, Morales-Ramirez J O, Carrasquilla G, Rey L C, Dietze R, Luz K, Rivas E, Miranda Montoya M C, Cortes Supelano M, Zambrano B, Langevin E, Boaz M, Tornieporth N, Saville M, Noriega F, Group CYDS. 2015. Efficacy of a tetravalent dengue vaccine in children in Latin America. N Engl J Med 372:113-123.
12. Coller B A, Clements D E, Bett A J, Sagar S L, Ter Meulen J H. 2011. The development of recombinant subunit envelope-based vaccines to protect against dengue virus induced disease. Vaccine 29:7267-7275.
13. Kirkpatrick B D, Whitehead S S, Pierce K K, Tibery C M, Grier P L, Hynes N A, Larsson C J, Sabundayo B P, Talaat K R, Janiak A, Carmolli M P, Luke C J, Diehl S A, Durbin A P. 2016. The live attenuated dengue vaccine TV003 elicits complete protection against dengue in a human challenge model. Sci Transl Med 8:330ra336.
14. Smith T J, Brandt W E, Swanson J L, McCown J M, Buescher E L. 1970. Physical and biological properties of dengue-2 virus and associated antigens. J Virol 5:524-532.
15. Allison S L, Stadler K, Mandl C W, Kunz C, Heinz F X. 1995. Synthesis and secretion of recombinant tick-borne encephalitis virus protein E in soluble and particulate form. J Virol 69:5816-5820.
16. Allison S L, Tao Y J, O'Riordain G, Mandl C W, Harrison S C, Heinz F X. 2003. Two distinct size classes of immature and mature subviral particles from tick-borne encephalitis virus. J Virol 77:11357-11366.
17. Lorenz I C, Kartenbeck J, Mezzacasa A, Allison S L, Heinz F X, Helenius A. 2003. Intracellular assembly and secretion of recombinant subviral particles from tick-borne encephalitis virus. J Virol 77:4370-4382.
18. Frietze K M, Peabody D S, Chackerian B. 2016. Engineering virus-like particles as vaccine platforms. Curr Opin Virol 18:44-49.
19. Lopez-Sagaseta J, Malito E, Rappuoli R, Bottomley M J. 2016. Self-assembling protein nanoparticles in the design of vaccines. Comput Struct Biotechnol J 14:58-68.
20. Kushnir N, Streatfield S J, Yusibov V. 2012. Virus-like particles as a highly efficient vaccine platform: diversity of targets and production systems and advances in clinical development. Vaccine 31:58-83.
21. Valenzuela P, Medina A, Rutter W J, Ammerer G, Hall B D. 1982. Synthesis and assembly of hepatitis B virus surface antigen particles in yeast. Nature 298:347-350.
22. Keating G M, Noble S. 2003. Recombinant hepatitis B vaccine (Engerix-B): a review of its immunogenicity and protective efficacy against hepatitis B. Drugs 63:1021-1051.
23. Joura E A, Leodolter S, Hernandez-Avila M, Wheeler C M, Perez G, Koutsky L A, Garland S M, Harper D M, Tang G W, Ferris D G, Steben M, Jones R W, Bryan J, Taddeo F J, Bautista O M, Esser M T, Sings H L, Nelson M, Boslego J W, Sattler C, Barr E, Paavonen J. 2007. Efficacy of a quadrivalent prophylactic human papillomavirus (types 6, 11, 16, and 18) L1 virus-like-particle vaccine against high-grade vulval and vaginal lesions: a combined analysis of three randomised clinical trials. Lancet 369:1693-1702.
24. Zhang J, Zhang X F, Huang S J, Wu T, Hu Y M, Wang Z Z, Wang H, Jiang H M, Wang Y J, Yan Q, Guo M, Liu X H, Li J X, Yang C L, Tang Q, Jiang R J, Pan H R, Li Y M, Shih J W, Ng M H, Zhu F C, Xia N S. 2015. Long-term efficacy of a hepatitis E vaccine. N Engl J Med 372:914-922.
25. Purdy D E, Chang G J. 2005. Secretion of noninfectious dengue virus-like particles and identification of amino acids in the stem region involved in intracellular retention of envelope protein. Virology 333:239-250.

26. Timiryasova™, Bonaparte M I, Luo P, Zedar R, Hu B T, Hildreth S W. 2013. Optimization and validation of a plaque reduction neutralization test for the detection of neutralizing antibodies to four serotypes of dengue virus used in support of dengue vaccine development. Am J Trop Med Hyg 88:962-970.
27. WHO. 2007. Guidelines for Plaque-Reduction Neutralization Testing of human antibodies to Dengue viruses.
28. Finney D J. 1952. Probit Analysis. Ed, Cambridge, England, Cambridge University Press.
29. Li H, Clum S, You S, Ebner K E, Padmanabhan R. 1999. The serine protease and RNA-stimulated nucleoside triphosphatase and RNA helicase functional domains of dengue virus type 2 NS3 converge within a region of 20 amino acids. J Virol 73:3108-3116.
30. Lobigs M. 1993. Flavivirus premembrane protein cleavage and spike heterodimer secretion require the function of the viral proteinase NS3. Proc Natl Acad Sci USA 90:6218-6222.
31. Amberg S M, Rice C M. 1999. Mutagenesis of the NS2B-NS3-mediated cleavage site in the flavivirus capsid protein demonstrates a requirement for coordinated processing. J Virol 73:8083-8094.
32. Ansarah-Sobrinho C, Nelson S, Jost C A, Whitehead S S, Pierson T C. 2008. Temperature-dependent production of pseudoinfectious dengue reporter virus particles by complementation. Virology 381:67-74.
33. Qing M, Liu W, Yuan Z, Gu F, Shi P Y. 2010. A high-throughput assay using dengue-1 virus-like particles for drug discovery. Antiviral Res 86:163-171.
34. Gromowski G D, Barrett A D. 2007. Characterization of an antigenic site that contains a dominant, type-specific neutralization determinant on the envelope protein domain III (ED3) of dengue 2 virus. Virology 366:349-360.
35. Gromowski G D, Barrett N D, Barrett A D. 2008. Characterization of dengue virus complex-specific neutralizing epitopes on envelope protein domain III of dengue 2 virus. J Virol 82:8828-8837.
36. Zhang W, Chipman P R, Corver J, Johnson P R, Zhang Y, Mukhopadhyay S, Baker T S, Strauss J H, Rossmann M G, Kuhn R J. 2003. Visualization of membrane protein domains by cryo-electron microscopy of dengue virus. Nat Struct Biol 10:907-912.
37. Wang P G, Kudelko M, Lo J, Siu L Y, Kwok K T, Sachse M, Nicholls J M, Bruzzone R, Altmeyer R M, Nal B. 2009. Efficient assembly and secretion of recombinant subviral particles of the four dengue serotypes using native prM and E proteins. PLoS One 4:e8325.
38. Zhang S, Liang M, Gu W, Li C, Miao F, Wang X, Jin C, Zhang L, Zhang F, Zhang Q, Jiang L, Li M, Li D. 2011. Vaccination with dengue virus-like particles induces humoral and cellular immune responses in mice. Virol J 8:333.
39. Konishi E, Fujii A. 2002. Dengue type 2 virus subviral extracellular particles produced by a stably transfected mammalian cell line and their evaluation for a subunit vaccine. Vaccine 20:1058-1067.
40. Zhang X, Sheng J, Plevka P, Kuhn R J, Diamond M S, Rossmann M G. 2013. Dengue structure differs at the temperatures of its human and mosquito hosts. Proc Natl Acad Sci USA 110:6795-6799.
41. Fibriansah G, Ng T S, Kostyuchenko V A, Lee J, Lee S, Wang J, Lok S M. 2013. Structural changes in dengue virus when exposed to a temperature of 37 degrees C. J Virol 87:7585-7592.
42. Rouvinski A, Guardado-Calvo P, Barba-Spaeth G, Duquerroy S, Vaney M C, Kikuti C M, Navarro Sanchez M E, Dejnirattisai W, Wongwiwat W, Haouz A, Girard-Blanc C, Petres S, Shepard W E, Despres P, Arenzana-Seisdedos F, Dussart P, Mongkolsapaya J, Screaton G R, Rey F A. 2015. Recognition determinants of broadly neutralizing human antibodies against dengue viruses. Nature 520:109-113.
43. Dowd K A, DeMaso C R, Pierson T C. 2015. Genotypic Differences in Dengue Virus Neutralization Are Explained by a Single Amino Acid Mutation That Modulates Virus Breathing. MBio 6:e01559-01515.
44. de Alwis R, Smith S A, Olivarez N P, Messer W B, Huynh J P, Wahala W M, White L J, Diamond M S, Baric R S, Crowe J E, Jr., de Silva A M. 2012. Identification of human neutralizing antibodies that bind to complex epitopes on dengue virions. Proc Natl Acad Sci USA 109:7439-7444.
45. Fibriansah G, Tan J L, Smith S A, de Alwis R, Ng T S, Kostyuchenko V A, Jadi R S, Kukkaro P, de Silva A M, Crowe J E, Lok S M. 2015. A highly potent human antibody neutralizes dengue virus serotype 3 by binding across three surface proteins. Nat Commun 6:6341.
46. Gallichotte E N, Widman D G, Yount B L, Wahala W M, Durbin A, Whitehead S, Sariol C A, Crowe J E, Jr., de Silva A M, Baric R S. 2015. A new quaternary structure epitope on dengue virus serotype 2 is the target of durable type-specific neutralizing antibodies. MBio 6:e01461-01415.

SEQUENCES

Exemplary sequences are shown below. It will be apparent that the same proteins can be used from any flavivirus, for example by aligning the sequences to those disclosed herein. The particular amino acid residues identified herein are numbered relative to the indicated sequences but their relative numbering in other flavivirus proteins can be readily determined, for example by alignment.

```
Dengue virus 2 Strain 168861 (GenBank U87411.1)
1. DEN-2 CprME wild-type nucleotide sequence
                                            (SEQ ID NO: 1)
ATGAATAACCAACGGAAAAAGGCGAAAAACACGCCTTTCAATATGCTGA

AACGCGAGAGAAACCGCGTGTCGACTGTGCAACAGCTGACAAAGAGATT

CTCACTTGGAATGCTGCAGGGACGAGGACCATTAAAACTGTTCATGGCCC

TGGTGGCGTTCCTTCGTTTCCTAACAATCCCACCAACAGCAGGGATATTGA

AGAGATGGGGAACAATTAAAAAATCAAAAGCTATTAATGTTTTGAGAGGG

TTCAGGAAAGAGATTGGAAGGATGCTGAACATCTTGAATAGGAGACGCA

GATCTGCAGGCATGATCATTATGCTGATTCCAACAGTGATGGCGTTCCATT

TAACCACACGTAACGGAGAACCACACATGATCGTCAGCAGACAAGAGAA

AGGGAAAAGTCTTCTGTTTAAAACAGAGGATGGCGTGAACATGTGTACCC

TCATGGCCATGGACCTTGGTGAATTGTGTGAAGACACAATCACGTACAAG

TGTCCCCTTCTCAGGCAGAATGAGCCAGAAGACATAGACTGTTGGTGCAA

CTCTACGTCCACGTGGGTAACTTATGGGACGTGTACCACCATGGGAGAAC

ATAGAAGAGAAAAAAGATCAGTGGCACTCGTTCCACATGTGGGAATGGG

ACTGGAGACACGAACTGAAACATGGATGTCATCAGAAGGGGCCTGGAAA
```

-continued

```
CATGTCCAGAGAATTGAAACTTGGATCTTGAGACATCCAGGCTTCACCAT
GATGGCAGCAATCCTGGCATACACCATAGGAACGACACATTTCCAAAGAG
CCCTGATTTTCATCTTACTGACAGCTGTCACTCCTTCAATGACAATGCGTT
GCATAGGAATGTCAAATAGAGACTTTGTGGAAGGGGTTTCAGGAGGAAGC
TGGGTTGACATAGTCTTAGAACATGGAAGCTGTGTGACGACGATGGCAAA
AAACAAACCAACATTGGATTTTGAACTGATAAAAACAGAAGCCAAACAG
CCTGCCACCCTAAGGAAGTACTGTATAGAGGCAAAGCTAACCAACACAAC
AACAGAATCTCGCTGCCCAACACAAGGGGAACCCAGCCTAAATGAAGAG
CAGGACAAAAGGTTCGTCTGCAAACACTCCATGGTAGACAGAGGATGGG
GAAATGGATGTGGACTATTTGGAAAGGGAGGCATTGTGACCTGTGCTATG
TTCAGATGCAAAAAGAACATGGAAGGAAAAGTTGTGCAACCAGAAAACT
TGGAATACACCATTGTGATAACACCTCACTCAGGGGAAGAGCATGCAGTC
GGAAATGACACAGGAAAACATGGCAAGGAAATCAAAATAACACCACAGA
GTTCCATCACAGAAGCAGAATTGACAGGTTATGGCACTGTCACAATGGAG
TGCTCTCCAAGAACGGGCCTCGACTTCAATGAGATGGTGTTGCTGCAGAT
GGAAAATAAAGCTTGGCTGGTGCACAGGCAATGGTTCCTAGACCTGCCGT
TACCATGGTTGCCCGGAGCGGACACACAAGGGTCAAATTGGATACAGAAA
GAGACATTGGTCACTTTCAAAAATCCCCATGCGAAGAAACAGGATGTTGT
TGTTTTAGGATCCCAAGAAGGGGCCATGCACACAGCACTTACAGGGGCCA
CAGAAATCCAAATGTCATCAGGAAACTTACTCTTCACAGGACATCTCAAG
TGCAGGCTGAGAATGGACAAGCTACAGCTCAAAGGAATGTCATACTCTAT
GTGCACAGGAAAGTTTAAAGTTGTGAAGGAAATAGCAGAAACACAACAT
GGAACAATAGTTATCAGAGTGCAATATGAAGGGGACGGCTCTCCATGCAA
GATCCCTTTTGAGATAATGGATTTGGAAAAAAGACATGTCTTAGGTCGCCT
GATTACAGTCAACCCAATTGTGACAGAAAAAGATAGCCCAGTCAACATAG
AAGCAGAACCTCCATTCGGAGACAGCTACATCATCATAGGAGTAGAGCCG
GGACAACTGAAGCTCAACTGGTTTAAGAAAGGAAGTTCTATCGGCCAAAT
GTTTGAGACAACAATGAGGGGGGCGAAGAGAATGGCCATTTTAGGTGAC
ACAGCCTGGGATTTTGGATCCTTGGGAGGAGTGTTTACATCTATAGGAAA
GGCTCTCCACCAAGTCTTTGGAGCAATCTATGGAGCTGCCTTCAGTGGGGT
TTCATGGACTATGAAAATCCTCATAGGAGTCATTATCACATGGATAGGAA
TGAATTCACGCAGCACCTCACTGTCTGTGACACTAGTATTGGTGGGAATTG
TGACACTGTATTTGGGAGTCATGGTGCAGGCC
```

2. DEN-2 CprME wild-type amino acid sequence (SEQ ID NO: 2)

```
MNNQRKKAKNTPFNMLKRERNRVSTVQQLTKRFSLGMLQGRGPLKLFMALV
AFLRFLTIPPTAGILKRWGTIKKSKAINVLRGFRKEIGRMLNILNRRRRSA
GMIIMLIPTVMAFHLTTRNGEPHMIVSRQEKGKSLLFKTEDGVNMCTLMAM
DLGELCEDTITYKCPLLRQNEPEDIDCWCNSTSTWVTYGTCTTMGEHRREK
RSVALVPHVGMGLETRTETWMSSEGAWKHVQRIETWILRHPGFTMMAAILA
YTIGTTHFQRALIFILLTAVTPSMTMRCIGMSNRDFVEGVSGGSWVDIVLE
HGSCVTTMAKNKPTLDFELIKTEAKQPATLRKYCIEAKLTNTTTESRCPTQ
GEPSLNEEQDKRFVCKHSMVDRGWGNGCGLFGKGGIVTCAMFRCKKNMEGK
VVQPENLEYTIVITPHSGEEHAVGNDTGKHGKEIKITPQSSITEAELTGYG
TVTMECSPRTGLDFNEMVLLQMENKAWLVHRQWFLDLPLPWLPGADTQGSN
WIQKETLVTFKNPHAKKQDVVVLGSQEGAMHTALTGATEIQMSSGNLLFTG
HLKCRLRMDKLQLKGMSYSMCTGKFKVVKEIAETQHGTIVIRVQYEGDGSP
CKIPFEIMDLEKRHVLGRLITVNPIVTEKDSPVNIEAEPPFGDSYIIIGVE
PGQLKLNWFKKGSSIGQMFETTMRGAKRMAILGDTAWDFGSLGGVFTSIGK
ALHQVFGAIYGAAFSGVSWTMKILIGVIITWIGMNSRSTSLSVTLVLVGIV
TLYLGVMVQA
```

3. DEN-2 CprME wild-type nucleotide sequence with Mutations (SEQ ID NO: 3)

ATGAATAACCAACGGAAAAAGGCGAAAAACACGCCTTTCAATATGCTGA
AACGCGAGAGAAACCGCGTGTCGACTGTGCAACAGCTGACAAAGAGATT
CTCACTTGGAATGCTGCAGGGACGAGGACCATTAAAACTGTTCATGGCCC
TGGTGGCGTTCCTTCGTTTCCTAACAATCCCACCAACAGCAGGGATATTGA
AGAGATGGGGAACAATTAAAAAATCAAAAGCTATTAATGTTTTGAGAGGG
TTCAGGAAAGAGATTGGAAGGATGCTGAACATCTTGAATAGGAGACGCA
GATCTGCAGGCATGATCATTATGCTGATTCCAACAGTGATGGCGTTCCATT
TAACCACACGTAACGGAGAACCACACATGATCGTCAGCAGACAAGAGAA
AGGGAAAAGTCTTCTGTTTAAAACAGAGGATGGCGTGAACATGTGTACCC
TCATGGCCATGGACCTTGGTGAATTGTGTGAAGACACAATCACGTACAAG
TGTCCCCTTCTCAGGCAGAATGAGCCAGAAGACATAGACTGTTGGTGCAA
CTCTACGTCCACGTGGGTAACTTATGGGACGTGTACCACCATGGGAGAAC
ATAGAAGAGCAAAAAGATCAGTGGCACTCGTTCCACATGTGGGAATGGG
ACTGGAGACACGAACTGAAACATGGATGTCATCAGAAGGGGCCTGGAAA
CATGTCCAGAGAATTGAAACTTGGATCTTGAGACATCCAGGCTTCACCAT
GATGGCAGCAATCCTGGCATACACCATAGGAACGACACATTTCCAAAGAG
CCCTGATTTTCATCTTACTGACAGCTGTCACTCCTTCAATGACAATGCGTT
GCATAGGAATGTCAAATAGAGACTTTGTGGAAGGGGTTTCAGGAGGAAGC
TGGGTTGACATAGTCTTAGAACATGGAAGCTGTGTGACGACGATGGCAAA
AAACAAACCAACATTGGATTTTGAACTGATAAAAACAGAAGCCAAACAG
CCTGCCACCCTAAGGAAGTACTGTATAGAGGCAAAGCTAACCAACACAAC
AACAGAATCTCGCTGCCCAACACAAGGGGAACCCAGCCTAAATGAAGAG
CAGGACAAAAGGTTCGTCTGCAAACACTCCATGGTAGACAGAGGATGGG
GAAATGGATGTGGACTATTTGGAAAGGGAGGCATTGTGACCTGTGCTATG
TTCAGATGCAAAAAGAACATGGAAGGAAAAGTTGTGCAACCAGAAAACT
TGGAATACACCATTGTGATAACACCTCACTCAGGGGAAGAGCATGCAGTC
GGAAATGACACAGGAAAACATGGCAAGGAAATCAAAATAACACCACAGA
GTTCCATCACAGAAGCAGAATTGACAGGTTATGGCACTGTCACAATGGAG
TGCTCTCCAAGAACGGGCCTCGACTTCAATGAGATGGTGTTGCTGCAGAT
GGAAAATAAAGCTTGGCTGGTGCACAGGCAATGGTTCCTAGACCTGCCGT

-continued

TACCATGGTTGCCCGGAGCGGACACACAAGGGTCAAATTGGATACAGAAA
GAGACATTGGTCACTTTCAAAAATCCCCATGCGAAGAAACAGGATGTTGT
TGTTTTAGGATCCCAAGAAGGGGCCATGCACACAGCACTTACAGGGGCCA
CAGAAATCCAAATGTCATCAGGAAACTTACTCTTCACAGGACATCTCAAG
TGCAGGCTGAGAATGGACAAGCTACAGCTCAAAGGAATGTCATACTCTAT
GTGCACAGGAAAGTTTAAAGTTGTGAAGGAAATAGCAGAAACACAACAT
GGAACAATAGTTATCAGAGTGCAATATGAAGGGGACGGCTCTCCATGCAA
GATCCCTTTTGAGATAATGGATTTGGAAAAAAGACATGTCTTAGGTCGCCT
GATTACAGTCAACCCAATTGTGACAGAAAAAGATAGCCCAGTCAACATAG
AAGCAGAACCTCCATTCGGAGACAGCTACATCATCATAGGAGTAGAGCCG
GGACAACTGAAGCTCAACTGGTTTAAGAAAGGAAGTTCTTTGGGCCAAGC

CTTTGAGACAACAATGAGGGGGGCGAAGAGATTGGCCATTTTAGGTGACA

CAGCCTGGGATTTTGGATCCTTGGGAGGAGTGTTTACATCTATAGGAAAG
GCTCTCCACCAAGTCTTTGGAGCAATCTATGGAGCTGCCTTCAGTGGGGTT
TCATGGACTATGAAAATCCTCATAGGAGTCATTATCACATGGATAGGAAT
GAATTCACGCAGCACCTCACTGTCTGTGACACTAGTATTGGTGGGAATTGT
GACACTGTATTTGGGAGTCATGGTGCAGGCCTAG

4. DEN-2 CprME codon optimized nucleotide sequence with Mutations (SEQ ID NO: 4)

ATGAACAACCAGCGCAAGAAGGCCAAAAACACTCCGTTCAATATGCTCAA

GAGAGAGCGCAATCGGGTTTCTACGGTACAGCAGCTGACGAAGAGATTCT

CCCTGGGCATGCTGCAAGGTCGCGGACCACTGAAGCTGTTCATGGCCCTT

GTTGCATTTCTTAGGTTTCTTACAATTCCCCCCACTGCTGGAATCCTGAAG

CGGTGGGGCACCATCAAAAAGTCCAAGGCTATTAATGTCCTCAGGGGGTT

CAGGAAAGAGATTGGGCGGATGCTGAACATCCTTAATAGACGCAGACGGT

CCGCTGGCATGATAATCATGCTGATCCCAACCGTCATGGCCTTCCACCTGA

CTACCCGAAATGGAGAGCCCCACATGATCGTGAGCAGACAAGAGAAGGG

GAAGAGTCTCCTGTTCAAGACAGAAGATGGCGTGAACATGTGCACACTGA

TGGCCATGGATCTCGGCGAACTGTGTGAAGACACTATCACCTACAAATGC

CCTCTCCTCCGCCAAAATGAACCAGAAGATATTGACTGTTGGTGTAATTCA

ACAAGTACATGGGTGACCTATGGCACCTGTACCACCATGGGTGAACATCG

ACGGGCGAAGAGAAGTGTGGCCCTCGTCCCTCATGTCGGCATGGGGTTGG

AGACCAGAACAGAAACCTGGATGAGCTCCGAGGGCGCCTGGAAACACGT

GCAGCGGATCGAAACATGGATTTTGCGGCACCCTGGATTTACTATGATGG

CTGCCATTCTGGCTTACACAATAGGCACCACACACTTTCAGCGGGCGCTTA

TCTTTATCCTCCTGACAGCAGTAACACCCTCTATGACCATGAGGTGCATCG

GGATGTCAAACCGGGACTTTGTTGAGGGGGTCAGCGGTGGATCTTGGGTG

GATATCGTGCTGGAACACGGATCTTGCGTGACCACCATGGCAAAGAATAA

GCCCACACTTGATTTTGAATTGATTAAAACCGAGGCAAAACAGCCAGCCA

CTCTTCGCAAATACTGCATCGAGGCCAAGCTGACCAACACAACCACAGAA

TCCCGATGCCCTACCCAAGGTGAGCCTTCTCTTAACGAAGAGCAGGACAA

-continued

ACGGTTCGTGTGTAAGCATTCCATGGTGGACAGGGGGTGGGGGAATGGAT

GCGGGCTCTTCGGGAAGGGCGGGATCGTCACATGTGCAATGTTTAGATGT

AAGAAAAATATGGAAGGCAAAGTTGTGCAGCCAGAGAATCTGGAATATA

CTATTGTGATAACGCCTCACTCAGGTGAAGAGCACGCTGTAGGCAACGAT

ACCGGCAAGCACGGAAAGGAAATCAAGATAACTCCACAGTCAAGCATCA

CGGAAGCTGAGTTGACAGGGTACGGCACTGTCACCATGGAGTGCAGCCCA

CGCACTGGTCTGGACTTCAATGAGATGGTGCTTCTCCAGATGGAAAACAA

AGCCTGGCTGGTTCATAGGCAATGGTTTCTTGATCTTCCTTTGCCCTGGCT

GCCTGGAGCAGATACACAGGGTTCTAATTGGATCCAAAAGGAAACCCTTG

TGACCTTCAAGAACCCGCATGCAAAGAAGCAGGATGTGGTGGTCCTCGGC

TCTCAGGAGGGAGCCATGCACACCGCCCTTACCGGAGCCACAGAGATCCA

GATGAGCTCTGGTAACCTCCTCTTTACCGGGCATCTGAAGTGTCGCCTTAG

AATGGATAAACTGCAGCTCAAAGGTATGTCCTACAGCATGTGCACAGGTA

AATTCAAAGTGGTGAAGGAAATAGCTGAGACTCAGCACGGCACAATCGTC

ATCCGAGTTCAATATGAGGGTGACGGAAGCCCATGTAAAATCCCTTTCGA

AATTATGGACCTGGAAAAACGCCACGTGCTGGGCCGACTTATCACTGTTA

ATCCCATAGTCACAGAGAAGGACTCTCCAGTTAACATCGAGGCCGAGCCT

CCCTTCGGGGACTCCTATATCATCATCGGCGTTGAACCTGGCCAATTGAAG

CTGAACTGGTTCAAAAAGGGTTCCTCACTGGGACAGGCCTTCGAAACGAC

AATGAGAGGCGCAAAGAGACTGGCTATCCTCGGCGATACAGCATGGGACT

TCGGGTCCCTGGGAGGAGTATTCACAAGCATAGGGAAGGCCCTGCACCAA

GTGTTCGGTGCGATCTATGGTGCGGCCTTCTCAGGAGTCAGTTGGACCATG

AAGATTCTGATTGGCGTCATAATTACGTGGATTGGTATGAATTCAAGGTCT

ACATCTTTGTCCGTGACTCTGGTCCTGGTGGGAATTGTGACTTTGTATCTC

GGCGTGATGGTGCAAGCCTAG

5. DEN-2 CPrME amino acid sequence with mutations (SEQ ID NO: 5)

MNNQRKKAKNTPFNMLKRERNRVSTVQQLTKRFSLGMLQGRGPLKLFMALV

AFLRFLTIPPTAGILKRWGTIKKSKAINVLRGFRKEIGRMLNILNRRRRSA

GMIIMLIPTVMAFHLTTRNGEPHMIVSRQEKGKSLLFKTEDGVNMCTLMAM

DLGELCEDTITYKCPLLRQNEPEDIDCWCNSTSTWVTYGTCTTMGEHRRAK

RSVALVPHVGMGLETRTETWMSSEGAWKHVQRIETWILRHPGFTMMAAILA

YTIGTTHFQRALIFILLTAVTPSMTMRCIGMSNRDFVEGVSGGSWVDIVLE

HGSCVTTMAKNKPTLDFELIKTEAKQPATLRKYCIEAKLTNTTTESRCPTQ

GEPSLNEEQDKRFVCKHSMVDRGWGNGCGLFGKGGIVTCAMFRCKKNMEGK

VVQPENLEYTIVITPHSGEEHAVGNDTGKHGKEIKITPQSSITEAELTGYG

TVTMECSPRTGLDFNEMVLLQMENKAWLVHRQWFLDLPLPWLPGADTQGSN

WIQKETLVTFKNPHAKKQDVVVLGSQEGAMHTALTGATEIQMSSGNLLFTG

HLKCRLRMDKLQLKGMSYSMCTGKFKVVKEIAETQHGTIVIRVQYEGDGSP

CKIPFEIMDLEKRHVLGRLITVNPIVTEKDSPVNIEAEPPFGDSYIIIGVE

PGQLKLNWFKKGSSLGQAFETTMRGAKRLAILGDTAWDFGSLGGVFTSIGK

ALHQVFGAIYGAAFSGVSWTMKILIGVIITWIGMNSRSTSLSVTLVLVGIV

TLYLGVMVQA

6. DEN-2 NS2BNS3 wild-type nucleotide sequence
(SEQ ID NO: 6)
AGCTGGCCATTAAATGAGGCTATCATGGCAGTCGGGATGGTGAGCATTTT

AGCCAGTTCTCTCCTAAAAAATGATATTCCCATGACAGGACCATTAGTGG

CTGGAGGGCTCCTCACTGTGTGCTACGTGCTCACTGGACGATCGGCCGATT

TGGAACTGGAGAGAGCAGCCGATGTCAAATGGGAAGACCAGGCAGAGAT

ATCAGGAAGCAGTCCAATCCTGTCAATAACAATATCAGAAGATGGTAGCA

TGTCGATAAAAAATGAAGAGGAAGAACAAACACTGACCATACTCATTAG

AACAGGATTGCTGGTGATCTCAGGACTTTTTCCTGTATCAATACCAATCAC

GGCAGCAGCATGGTACCTGTGGGAAGTGAAGAAACAACGGGCCGGAGTA

TTGTGGGATGTTCCTTCACCCCCACCCATGGGAAAGGCTGAACTGGAAGA

TGGAGCCTATAGAATTAAGCAAAAAGGGATTCTTGGATATTCCCAGATCG

GAGCCGGAGTTTACAAAGAAGGAACATTCCATACAATGTGGCATGTCACA

CGTGGCGCTGTTCTAATGCATAAAGGAAAGAGGATTGAACCATCATGGGC

GGACGTCAAGAAAGACCTAATATCATATGGAGGAGGCTGGAAGTTAGAA

GGAGAATGGAAGGAAGGAGAAGAAGTCCAGGTATTGGCACTGGAGCCTG

GAAAAAATCCAAGAGCCGTCCAAACGAAACCTGGTCTTTTCAAAACCAAC

GCCGGAACAATAGGTGCTGTATCTCTGGACTTTTCTCCTGGAACGTCAGGA

TCTCCAATTATCGACAAAAAAGGAAAAGTTGTGGGTCTTTATGGTAATGG

TGTTGTTACAAGGAGTGGAGCATATGTGAGTGCTATAGCCCAGACTGAAA

AAAGCATTGAAGACAACCCAGAGATCGAAGATGACATTTTCCGAAAGAG

AAGACTGACCATCATGGACCTCCACCCAGGAGCGGGAAAGACGAAGAGA

TACCTTCCGGCCATAGTCAGAGAAGCTATAAAACGGGGTTTGAGAACATT

AATCTTGGCCCCCACTAGAGTTGTGGCAGCTGAAATGGAGGAAGCCCTTA

GAGGACTTCCAATAAGATACCAGACCCCAGCCATCAGAGCTGAGCACACC

GGGCGGGAGATTGTGGACCTAATGTGTCATGCCACATTTACCATGAGGCT

GCTATCACCAGTTAGAGTGCCAAACTACAACCTGATTATCATGGACGAAG

CCCATTTCACAGACCCAGCAAGTATAGCAGCTAGAGGATACATCTCAACT

CGAGTGGAGATGGGTGAGGCAGCTGGGATTTTTATGACAGCCACTCCCCC

GGGAAGCAGAGACCCATTTCCTCAGAGCAATGCACCAATCATAGATGAAG

AAAGAGAAATCCCTGAACGTTCGTGGAATTCCGGACATGAATGGGTCACG

GATTTTAAAGGGAAGACTGTTTGGTTCGTTCCAAGTATAAAAGCAGGAAA

TGATATAGCAGCTTGCCTGAGGAAAAATGAAAGAAAGTGATACAACTCA

GTAGGAAGACCTTTGATTCTGAGTATGTCAAGACTAGAACCAATGATTGG

GACTTCGTGGTTACAACTGACATTTCAGAAATGGGTGCCAATTTCAAGGCT

GAGAGGGTTATAGACCCCAGACGCTGCATGAAACCAGTCATACTAACAGA

TGGTGAAGAGCGGGTGATTCTGGCAGGACCTATGCCAGTGACCCACTCTA

GTGCAGCACAAAGAAGAGGGAGAATAGGAAGAAATCCAAAAAATGAGA

ATGACCAGTACATATACATGGGGGAACCTCTGGAAAATGATGAAGACTGT

GCACACTGGAAAGAAGCTAAAATGCTCCTAGATAACATCAACACGCCAGA

AGGAATCATTCCTAGCATGTTCGAACCAGAGCGTGAAAAGGTGGATGCCA

TTGATGGCGAATACCGCTTGAGAGGAGAAGCAAGGAAAACCTTTGTAGAC

TTAATGAGAAGAGGAGACCTACCAGTCTGGTTGGCCTACAGAGTGGCAGC

TGAAGGCATCAACTACGCAGACAGAAGGTGGTGTTTTGATGGAGTCAAGA

ACAACCAAATCCTAGAAGAAAACGTGGAAGTTGAAATCTGGACAAAAGA

AGGGGAAAGGAAGAAATTGAAACCCAGATGGTTGGATGCTAGGATCTATT

CTGACCCACTGGCGCTAAAAGAATTTAAGGAATTTGCAGCCGGAAGAAAG

7. DEN-2 NS2B/NS3 wild-type amino acid sequence
(SEQ ID NO: 7)
MSWPLNEAIMAVGMVSILASSLLKNDIPMTGPLVAGGLLTVCYVLTGRSAD

LELERAADVKWEDQAEISGSSPILSITISEDGSMSIKNEEEEQTLTILIRT

GLLVISGLFPVSIPITAAAWYLWEVKKQRAGVLWDVPSPPPMGKAELEDGA

YRIKQKGILGYSQIGAGVYKEGTFHTMWHVTRGAVLMHKGKRIEPSWADVK

KDLISYGGGWKLEGEWKEGEEVQVLALEPGKNPRAVQTKPGLFKTNAGTIG

AVSLDFSPGTSGSPIIDKKGKVVGLYGNGVVTRSGAYVSAIAQTEKSIEDN

PEIEDDIFRKRRLTIMDLHPGAGKTKRYLPAIVREAIKRGLRTLILAPTRV

VAAEMEEALRGLPIRYQTPAIRAEHTGREIVDLMCHATFTMRLLSPVRVPN

YNLIIMDEAHFTDPASIAARGYISTRVEMGEAAGIFMTATPPGSRDPFPQS

NAPIIDEEREIPERSWNSGHEWVTDFKGKTVWFVPSIKAGNDIAACLRKNG

KKVIQLSRKTFDSEYVKTRTNDWDFVVTTDISEMGANFKAERVIDPRRCMK

PVILTDGEERVILAGPMPVTHSSAAQRRGRIGRNPKNENDQYIYMGEPLEN

DEDCAHWKEAKMLLDNINTPEGIIPSMFEPEREKVDAIDGEYRLRGEARKT

FVDLMRRGDLPVWLAYRVAAEGINYADRRWCFDGVKNNQILEENVEVEIWT

KEGERKKLKPRWLDARIYSDPLALKEFKEFAAGR

8. DEN-2 NS2B/NS3Pro codon optimization nucleotide
sequence with mutations
(SEQ ID NO: 8)
ATGAGTTGGCCTCTGAACGAGGCAATAATGGCGGTGGGGATGGTGAGCAT

ACTTGCATCAAGCCTGCTGAAGAACGACATCCCTATGACTGGTCCCCTGGT

GGCCGGCGGCCTGCTGACGGTCTGTTATGTGCTGACCGGCAGGTCCGCAG

ACTTGGAGCTGGAAAGGGCTGCCGACGTCAAGTGGGAGGACCAGGCCGA

AATTTCAGGAAGCAGTCCCATCCTGAGTATCACAATTTCCGAGGACGGTT

CAATGTCCATCAAGAATGAAGAGGAAGAGCAGACACTGACCATACTGATT

CGCACCGGCCTGCTTGTTATTAGTGGCTTGTTCCCTGTATCTATCCCTATC

ACTGCCGCCGCCTGGTATCTCTGGGAAGTAAAGAAGCAGCGGGCAGGCGTA

CTCTGGGATGTGCCTTCCCCCCCACCTATGGGAAAGGCGGAACTGGAGGA

CGGTGCATACCGCATTAAGCAAAAAGGCATCCTCGGATACAGCCAGATCG

GAGCCGGGGTGTATAAAGAAGGAACCTTTCATACTATGTGGCACGTGACT

AGAGGGGCGGTGCTTATGCATAAGGGTAAAAGGATTGAACCATCCTGGGC

AGATGTGAAAAAAGACCTGATCTCCTACGGGGGTGGCTGGAAGCTGGAA

GGGGAATGGAAGGAAGGAGAGGAGGTTCAGGTCCTTGCCCTGGAACCAG

```
GTAAGAATCCCCGCGCCGTGCAGACAAAGCCGGGCGCTTTCAAGACTAAT
GCGGGAACCATCGGAGCTGTCTCCTTGGATTTCAGCCCAGGCACCTCCGG
TTCTCCCATCATCGACAAAAAGGGCAAAGTCGTTGGGCTCTATGGGAATG
GGGTGGTGACGCGCTCAGGAGCCTATGTTTCTGCAATAGCTCAGACCGAG
AAGTCAATCGAAGATAACCCGGAAATCGAAGATGATTAG
```

9. DEN-2 NS2B/NS3Pro amino acid sequence with mutations
(SEQ ID NO: 9)
```
MSWPLNEAIMAVGMVSILASSLLKNDIPMTGPLVAGGLLTVCYVLTGRSAD
LELERAADVKWEDQAEISGSSPILSITISEDGSMSIKNEEEEQTLTILIRT
GLLVISGLFPVSIPITAAAWYLWEVKKQRAGVLWDVPSPPPMGKAELEDGA
YRIKQKGILGYSQIGAGVYKEGTFHTMWHVTRGAVLMHKGKRIEPSWADVK
KDLISYGGGWKLEGEWKEGEEVQVLALEPGKNPRAVQTKPGAFKTNAGTIG
AVSLDFSPGTSGSPIIDKKGKVVGLYGNGVVTRSGAYVSAIAQTEKSIEDN
PEIEDD
```

10. DEN-2 NS2B codon optimized nucleotide sequence
(SEQ ID NO: 10)
```
ATGAGTTGGCCTCTGAACGAGGCAATAATGGCGGTGGGGATGGTGAGCAT
ACTTGCATCAAGCCTGCTGAAGAACGACATCCCTATGACTGGTCCCCTGGT
GGCCGGCGGCCTGCTGACGGTCTGTTATGTGCTGACCGGCAGGTCCGCAG
ACTTGGAGCTGGAAAGGGCTGCCGACGTCAAGTGGGAGGACCAGGCCGA
AATTTCAGGAAGCAGTCCCATCCTGAGTATCACAATTTCCGAGGACGGTT
CAATGTCCATCAAGAATGAAGAGGAAGAGCAGACACTGACCATACTGATT
CGCACCGGCCTGCTTGTTATTAGTGGCTTGTTCCCTGTATCTATCCCTATC
ACTGCCGCCGCCTGGTATCTCTGGGAAGTAAAGAAGCAGCGGTAG
```

11. DEN-2 NS2B amino acid sequence
(SEQ ID NO: 11)
```
MSWPLNEAIMAVGMVSILASSLLKNDIPMTGPLVAGGLLTVCYVLTGRSAD
LELERAADVKWEDQAEISGSSPILSITISEDGSMSIKNEEEEQTLTILIRT
GLLVISGLFPVSIPITAAAWYLWEVKKQR
```

12. DEN-2 NS3Pro codon optimized nucleotide sequence with mutation
(SEQ ID NO: 12)
```
GCAGGCGTACTCTGGGATGTGCCTTCCCCCCCACCTATGGGAAAGGCGGA
ACTGGAGGACGGTGCATACCGCATTAAGCAAAAAGGCATCCTCGGATACA
GCCAGATCGGAGCCGGGGTGTATAAAGAAGGAACCTTTCATACTATGTGG
CACGTGACTAGAGGGCGGTGCTTATGCATAAGGGTAAAAGGATTGAACC
ATCCTGGGCAGATGTGAAAAAAGACCTGATCTCCTACGGGGGTGGCTGGA
AGCTGGAAGGGGAATGGAAGGAAGGAGAGGAGGTTCAGGTCCTTGCCCT
GGAACCAGGTAAGAATCCCCGCGCCGTGCAGACAAAGCCGGGCGCTTTCA
AGACTAATGCGGGAACCATCGGAGCTGTCTCCTTGGATTTCAGCCCAGGC
ACCTCCGGTTCTCCCATCATCGACAAAAAGGGCAAAGTCGTTGGGCTCTA
TGGGAATGGGGTGGTGACGCGCTCAGGAGCCTATGTTTCTGCAATAGCTC
AGACCGAGAAGTCAATCGAAGATAACCCGGAAATCGAAGATGATTAG
```

13. DEN-2 NS3Pro amino acid sequence with mutation
(SEQ ID NO: 13)
```
AGVLWDVPSPPPMGKAELEDGAYRIKQKGILGYSQIGAGVYKEGTFHTMWH
VTRGAVLMHKGKRIEPSWADVKKDLISYGGGWKLEGEWKEGEEVQVLALEP
GKNPRAVQTKPGAFKTNAGTIGAVSLDFSPGTSGSPIIDKKGKVVGLYGNG
VVTRSGAYVSAIAQTEKSIEDNPEIEDD
```

14. DEN-2 NS1 wild-type nucleotide sequence
(SEQ ID NO: 14)
```
GATAGTGGTTGCGTTGTGAGCTGGAAAAACAAAGAACTGAAATGTGGCAG
TGGGATTTTCATCACAGACAACGTGCACACATGGACAGAACAATACAAGT
TCCAACCAGAATCCCCTTCAAAACTAGCTTCAGCTATCCAGAAAGCCCAT
GAAGAGGGCATTTGTGGAATCCGCTCAGTAACAAGACTGGAGAATCTGAT
GTGGAAACAAATAACACCAGAATTGAATCACATTCTATCAGAAAATGAGG
TGAAGTTAACTATTATGACAGGAGACATCAAAGGAATCATGCAGGCAGGA
AAACGATCTCTGCGGCCTCAGCCCACTGAGCTGAAGTATTCATGGAAAAC
ATGGGGCAAAGCAAAAATGCTCTCTACAGAGTCTCATAACCAGACCTTTC
TCATTGATGGCCCCGAAACAGCAGAATGCCCCAACACAAATAGAGCTTGG
AATTCGTTGGAAGTTGAAGACTATGGCTTTGGAGTATTCACCACCAATATA
TGGCTAAAATTGAAAGAAAAACAGGATGTATTCTGCGACTCAAAACTCAT
GTCAGCGGCCATAAAAGACAACAGAGCCGTCCATGCCGATATGGGTTATT
GGATAGAAAGTGCACTCAATGACACATGGAAGATAGAGAAAGCCTCTTTC
ATTGAAGTTAAAAAACTGCCACTGGCCAAAATCACACACCCTCTGGAGCAA
TGGAGTGCTAGAAAGTGAGATGATAATTCCAAAGAATCTCGCTGGACCAG
TGTCTCAACACAACTATAGACCAGGCTACCATACACAAATAACAGGACCA
TGGCATCTAGGTAAGCTTGAGATGGACTTTGATTTCTGTGATGGAACAAC
AGTGGTAGTGACTGAGGACTGCGGAAATAGAGGACCCTCTTTGAGAACAA
CCACTGCCTCTGGAAAACTCATAACAGAATGGTGCTGCCGATCTTGCACA
TTACCACCGCTAAGATACAGAGGTGAGGATGGGTGCTGGTACGGGATGGA
AATCAGACCATTGAAGGAGAAAGAAGAGAATTTGGTCAACTCCTTGGTCA
CAGCTGGACATGGGCAGG
```

15. DEN-2 NS1 wild-type amino acid sequence
(SEQ ID NO: 15)
```
DSGCVVSWKNKELKCGSGIFITDNVHTWTEQYKFQPESPSKLASAIQKAHE
EGICGIRSVTRLENLMWKQITPELNHILSENEVKLTIMTGDIKGIMQAGKR
SLRPQPTELKYSWKTWGKAKMLSTESHNQTFLIDGPETAECPNTNRAWNSL
EVEDYGFGVFTTNIWLKLKEKQDVFCDSKLMSAAIKDNRAVHADMGYWIES
ALNDTWKIEKASFIEVKNCHWPKSHTLWSNGVLESEMIIPKNLAGPVSQHN
YRPGYHTQITGPWHLGKLEMDFDFCDGTTVVVTEDCGNRGPSLRTTTASGK
LITEWCCRSCTLPPLRYRGEDGCWYGMEIRPLKEKEENLVNSLVTAGHGQ
```

16. DEN-2 NS2A wild-type nucleotide sequence
(SEQ ID NO: 16)
```
GACATGGGCAGGGTCGACAACTTTTCACTAGGAGTCTTGGGAATGGCATT
GTTCCTGGAGGAAATGCTTAGGACCCGAGTAGGAACGAAACATGCAATAC
TACTAGTTGCAGTTTCTTTTGTGACATTGATCACAGGGAACATGTCCTTTA
```

GAGACCTGGGAAGAGTGATGGTTATGGTAGGCGCCACTATGACGGATGAC
ATAGGTATGGGCGTGACTTATCTTGCCCTACTAGCAGCCTTCAAAGTCAGA
CCAACTTTTGCAGCTGGACTACTCTTGAGAAAGCTGACCTCCAAGGAATT
GATGATGACTACTATAGGAATTGTACTCCTCTCCCAGAGCACCATACCAG
AGACCATTCTTGAGTTGACTGATGCGTTAGCCTTAGGCATGATGGTCCTCA
AAATGGTGAGAAATATGGAAAAGTATCAATTGGCAGTGACTATCATGGCT
ATCTTGTGCGTCCCAAACGCAGTGATATTACAAAACGCATGGAAAGTGAG
TTGCACAATATTGGCAGTGGTGTCCGTTTCCCCACTGCTCTTAACATCCTC
ACAGCAAAAACAGATTGGATACCATTAGCATTGACGATCAAAGGTCTCA
ATCCAACAGCTATTTTTCTAACAACCCTCTCAAGAACCAGCAAGAAAAGG

17. DEN-2 NS2A wild-type amino acid sequence
(SEQ ID NO: 17)
GHGQVDNFSLGVLGMALFLEEMLRTRVGTKHAILLVAVSFVTLITGNMSFR

DLGRVMVMVGATMTDDIGMGVTYLALLAAFKVRPTFAAGLLLRKLTSKELM

MTTIGIVLLSQSTIPETILELTDALALGMMVLKMVRNMEKYQLAVTIIVIA

ILCVPNAVILQNAWKVSCTILAVVSVSPLLLTSSQQKTDWIPLALTIKGLN

PTAIFLTTLSRTSKKR

18. DEN-2 NS3 Full length nucleotide sequence
(SEQ ID NO: 18)

GCCGGAGTATTGTGGGATGTTCCTTCACCCCCACCCATGGGAAAGGCTGA

ACTGGAAGATGGAGCCTATAGAATTAAGCAAAAAGGGATTCTTGGATATT

CCCAGATCGGAGCCGGAGTTTACAAAGAAGGAACATTCCATACAATGTGG

CATGTCACACGTGGCGCTGTTCTAATGCATAAAGGAAAGAGGATTGAACC

ATCATGGGCGGACGTCAAGAAAGACCTAATATCATATGGAGGAGGCTGG

AAGTTAGAAGGAGAATGGAAGGAAGGAGAAGAAGTCCAGGTATTGGCAC

TGGAGCCTGGAAAAAATCCAAGAGCCGTCCAAACGAAACCTGGTCTTTTC

AAAACCAACGCCGGAACAATAGGTGCTGTATCTCTGGACTTTTCTCCTGG

AACGTCAGGATCTCCAATTATCGACAAAAAAGGAAAAGTTGTGGGTCTTT

ATGGTAATGGTGTTGTTACAAGGAGTGGAGCATATGTGAGTGCTATAGCC

CAGACTGAAAAAAGCATTGAAGACAACCCAGAGATCGAAGATGACATTTT

CCGAAAGAGAAGACTGACCATCATGGACCTCCACCCAGGAGCGGGAAAG

ACGAAGAGATACCTTCCGGCCATAGTCAGAGAAGCTATAAAACGGGGTTT

GAGAACATTAATCTTGGCCCCCACTAGAGTTGTGGCAGCTGAAATGGAGG

AAGCCCTTAGAGGACTTCCAATAAGATACCAGACCCCAGCCATCAGAGCT

GAGCACACCGGGCGGGAGATTGTGGACCTAATGTGTCATGCCACATTTAC

CATGAGGCTGCTATCACCAGTTAGAGTGCCAAACTACAACCTGATTATCA

TGGACGAAGCCCATTTCACAGACCCAGCAAGTATAGCAGCTAGAGGATAC

ATCTCAACTCGAGTGGAGATGGGTGAGGCAGCTGGGATTTTTATGACAGC

CACTCCCCCGGGAAGCAGAGACCCATTTCCTCAGAGCAATGCACCAATCA

TAGATGAAGAAAGAGAAATCCCTGAACGTTCGTGGAATTCCGGACATGAA

TGGGTCACGGATTTTAAAGGGAAGACTGTTTGGTTCGTTCCAAGTATAAA

AGCAGGAAATGATATAGCAGCTTGCCTGAGGAAAAATGGAAAGAAAGTG

ATACAACTCAGTAGGAAGACCTTTGATTCTGAGTATGTCAAGACTAGAAC

-continued

CAATGATTGGGACTTCGTGGTTACAACTGACATTTCAGAAATGGGTGCCA

ATTTCAAGGCTGAGAGGGTTATAGACCCCAGACGCTGCATGAAACCAGTC

ATACTAACAGATGGTGAAGAGCGGGTGATTCTGGCAGGACCTATGCCAGT

GACCCACTCTAGTGCAGCACAAAGAAGAGGGAGAATAGGAAGAAATCCA

AAAAATGAGAATGACCAGTACATATACATGGGGGAACCTCTGGAAAATG

ATGAAGACTGTGCACACTGGAAAGAAGCTAAAATGCTCCTAGATAACATC

AACACGCCAGAAGGAATCATTCCTAGCATGTTCGAACCAGAGCGTGAAAA

GGTGGATGCCATTGATGGCGAATACCGCTTGAGAGGAGAAGCAAGGAAA

ACCTTTGTAGACTTAATGAGAAGAGGAGACCTACCAGTCTGGTTGGCCTA

CAGAGTGGCAGCTGAAGGCATCAACTACGCAGACAGAAGGTGGTGTTTTG

ATGGAGTCAAGAACAACCAAATCCTAGAAGAAAACGTGGAAGTTGAAAT

CTGGACAAAAGAAGGGGAAAGGAAGAAATTGAAACCCAGATGGTTGGAT

GCTAGGATCTATTCTGACCCACTGGCGCTAAAAGAATTTAAGGAATTTGC

AGCCGGAAGAAAG

19. DEN-2 E protein amino acid sequence with mutations
(SEQ ID NO: 19)

MRCIGMSNRDFVEGVSGGSWVDIVLEHGSCVTTMAKNKPTLDFELIKTEAK

QPATLRKYCIEAKLTNTTTESRCPTQGEPSLNEEQDKRFVCKHSMVDRGWG

NGCGLFGKGGIVTCAMFRCKKNMEGKVVQPENLEYTIVITPHSGEEHAVGN

DTGKHGKEIKITPQSSITEAELTGYGTVTMECSPRTGLDFNEMVLLQMENK

AWLVHRQWFLDLPLPWLPGADTQGSNWIQKETLVTFKNPHAKKQDVVVLGS

QEGAMHTALTGATEIQMSSGNLLFTGHLKCRLRMDKLQLKGMSYSMCTGKF

KVVKEIAETQHGTIVIRVQYEGDGSPCKIPFEIMDLEKRHVLGRLITVNPI

VTEKDSPVNIEAEPPFGDSYIIIGVEPGQLKLNWFKKGSSLGQAFETTMRG

AKRLAILGDTAWDFGSLGGVFTSIGKALHQVFGAIYGAAFSGVSWTMKILI

GVIIITWIGMNSRSTSLSVTLVLVGIVTLYLGVMVQA

20. ZIKV CprME wild-type nucleotide sequence
(SEQ ID NO: 20)

ATGAAAAACCCAAAAAAGAAATCCGGAGGATTCCGGATTGTCAATATGCT

AAAACGCGGAGTAGCCCGTGTGAGCCCCTTTGGGGGCTTGAAGAGGCTGC

CAGCCGGACTTCTGCTGGGTCATGGGCCCATCAGGATGGTCTTGGCGATTC

TAGCCTTTTTGAGATTCACGGCAATCAAGCCATCACTGGGTCTCATCAATA

GATGGGGTTCAGTGGGGAAAAAAGAGGCTATGGAAATAATAAAGAAGTT

CAAGAAAGATCTGGCTGCCATGCTGAGAATAATCAATGCTAGGAAGGAG

AAGAAGAGACGAGGCGCAGATACTAGTGTCGGAATTGTTGGCCTCCTGCT

GACCACAGCTATGGCAGCGGAGGTCACTAGACGTGGGAGTGCATACTATA

TGTACTTGGACAGAAACGACGCTGGGGAGGCCATATCTTTTCCAACCACA

TTGGGGATGAATAAGTGTTATATACAGATCATGGATCTTGGACACATGTG

TGATGCCACCATGAGCTATGAATGCCCTATGCTGGATGAGGGGGTGGAAC

CAGATGACGTCGATTGTTGGTGCAACACGACGTCAACTTGGGTTGTGTAC

GGAACCTGCCATCACAAAAAAGGTGAAGCACGGAGATCTAGAAGAGCTG

TGACGCTCCCCTCCCATTCCACTAGGAAGCTGCAAACGCGGTCGCAAACC

-continued

TGGTTGGAATCAAGAGAATACACAAAGCACTTGATTAGAGTCGAAAATTG
GATATTCAGGAACCCTGGCTTCGCGTTAGCAGCAGCTGCCATCGCTTGGCT
TTTGGGAAGCTCAACGAGCCAAAAAGTCATATACTTGGTCATGATACTGC
TGATTGCCCCGGCATACAGCATCAGGTGCATAGGAGTCAGCAATAGGGAC
TTTGTGGAAGGTATGTCAGGTGGGACTTGGGTTGATGTTGTCTTGGAACAT
GGAGGTTGTGTCACCGTAATGGCACAGGACAAACCGACTGTCGACATAGA
GCTGGTTACAACAACAGTCAGCAACATGGCGGAGGTAAGATCCTACTGCT
ATGAGGCATCAATATCGGACATGGCTTCGGACAGCCGCTGCCCAACACAA
GGTGAAGCCTACCTTGACAAGCAATCAGACACTCAATATGTCTGCAAAAG
AACGTTAGTGGACAGAGGCTGGGGAAATGGATGTGGACTTTTTGGCAAAG
GGAGCCTGGTGACATGCGCTAAGTTTGCATGCTCCAAGAAAATGACCGGG
AAGAGCATCCAGCCAGAGAATCTGGAGTACCGGATAATGCTGTCAGTTCA
TGGCTCCCAGCACAGTGGGATGATCGTTAATGACACAGGACATGAAACTG
ATGAGAATAGAGCGAAGGTTGAGATAACGCCCAATTCACCAAGAGCCGA
AGCCACCCTGGGGGGTTTTGGAAGCCTAGGACTTGATTGTGAACCGAGGA
CAGGCCTTGACTTTTCAGATTTGTATTACTTGACTATGAATAACAAGCACT
GGTTGGTTCACAAGGAGTGGTTCCACGACATTCCATTACCTTGGCACGCTG
GGGCAGACACCGGAACTCCACACTGGAACAACAAAGAAGCACTGGTAGA
GTTCAAGGACGCACATGCCAAAAGGCAAACTGTCGTGGTTCTAGGGAGTC
AAGAAGGAGCAGTTCACACGGCCCTTGCTGGAGCTCTGGAGGCTGAGATG
GATGGTGCAAAGGGAAGGCTGTCCTCTGGCCACTTGAAATGTCGCCTGAA
AATGGATAAACTTAGATTGAAGGGCGTGTCATACTCCTTGTGTACCGCAG
CGTTCACATTCACCAAGATCCCGGCTGAAACACTGCACGGGACAGTCACA
GTGGAGGTACAGTACGCAGGGACAGATGGACCTTGCAAGGTTCCAGCTCA
GATGGCGGTGGACATGCAAACTCTGACCCCAGTTGGGAGGTTGATAACCG
CTAACCCCGTAATCACTGAAAGCACTGAGAACTCTAAGATGATGCTGGAA
CTTGATCCACCATTTGGGGACTCTTACATTGTCATAGGAGTCGGGGAGAA
GAAGATCACCCACCACTGGCACAGGAGTGGCAGCACCATTGGAAAAGCA
TTTGAAGCCACTGTGAGAGGTGCCAAGAGAATGGCAGTCTTGGGAGACAC
AGCCTGGGACTTTGGATCAGTTGGAGGCGCTCTCAACTCATTGGGCAAGG
GCATCCATCAAATTTTTGGAGCAGCTTTCAAATCATTGTTTGGAGGAATGT
CCTGGTTCTCACAAATTCTCATTGGAACGTTGCTGATGTGGTTGGGTCTGA
ACACAAAGAATGGATCTATTTCCCTTATGTGCTTGGCCTTAGGGGGAGTGT
TGATCTTCTTATCCACAGCTGTCTCTGCT

21. ZIKV CprME codon optimized nucleotide sequence
(SEQ ID NO: 21)
ATGAAGAACCCCAAGAAGAAGTCCGGCGGCTTCCGGATCGTGAACATGCT
GAAGAGAGGCGTGGCCAGAGTCAGCCCCTTCGGCGGACTGAAAAGACTG
CCTGCCGGACTGCTGCTGGGCCACGGCCCTATTAGAATGGTGCTGGCCAT
CCTGGCCTTTCTGCGGTTCACCGCCATCAAGCCCTCCCTGGGCCTGATCAA
CAGATGGGGCAGCGTGGGCAAGAAAGAAGCCATGGAAATCATCAAGAAG TTCAAGAAAGACCTGGCCGCCATGCTGCGGATCATCAACGCCCGGAAAGA
GAAGAAGCGCAGAGGCGCCGATACCTCCGTGGGCATTGTGGGCCTGCTGC
TGACAACAGCCATGGCCGCCGAAGTGACCAGAAGAGGCAGCGCCTACTA
CATGTACCTGGACCGGAATGACGCCGGCGAGGCCATCAGCTTTCCAACCA
CCCTGGGCATGAACAAGTGCTACATCCAGATCATGGACCTGGGCCACATG
TGCGACGCCACAATGAGCTACGAGTGCCCCATGCTGGACGAGGGCGTGGA
ACCCGACGATGTGGACTGCTGGTGCAACACCACCAGCACCTGGGTGGTGT
ACGGCACCTGTCACCACAAGAAGGGCGAAGCCCGCAGATCCAGACGGGC
CGTGACACTGCCTAGCCACAGCACCAGAAAGCTGCAGACCAGAAGCCAG
ACCTGGCTGGAAAGCAGAGAGTACACCAAGCACCTGATCCGGGTGGAAA
ACTGGATCTTCCGGAACCCCGGCTTTGCCCTGGCCGCTGCTGCTATTGCTT
GGCTGCTGGGAAGCAGCACCAGCCAGAAAGTGATCTACCTGGTCATGATC
CTGCTGATCGCCCCTGCCTACAGCATCCGGTGCATCGGCGTGTCCAACCGG
GACTTCGTGGAAGGCATGAGCGGCGGCACATGGGTGGACGTGGTGCTGGA
ACACGGCGGCTGTGTGACCGTGATGGCCCAGGATAAGCCCACCGTGGACA
TCGAGCTGGTCACCACCACCGTGTCCAATATGGCCGAAGTGCGGAGCTAC
TGCTACGAGGCCAGCATCAGCGACATGGCCAGCGACAGCAGATGCCCTAC
ACAGGGCGAGGCCTACCTGGACAAGCAGTCCGACACCCAGTACGTGTGCA
AGCGGACCCTGGTGGACAGAGGCTGGGGCAATGGCTGCGGCCTGTTTGGC
AAGGGCAGCCTCGTGACCTGCGCCAAGTTCGCCTGCAGCAAGAAGATGAC
CGGCAAGAGCATCCAGCCCGAGAACCTGGAATACCGGATCATGCTGAGCG
TGCACGGCAGCCAGCACTCCGGCATGATCGTGAATGACACCGGCCACGAG
ACAGACGAGAACCGGGCCAAGGTGGAAATCACCCCTAACAGCCCTAGAG
CCGAGGCCACACTGGGCGGCTTTGGATCTCTGGGCCTGGACTGCGAGCCC
CGGACCGGCCTGGATTTCAGCGACCTGTACTACCTGACCATGAACAACAA
GCACTGGCTGGTCCACAAAGAGTGGTTCCACGACATCCCTCTGCCCTGGC
ATGCCGGCGCTGATACAGGCACCCCTCACTGGAACAACAAAGAGGCCCTG
GTCGAGTTCAAGGACGCCCACGCCAAGAGGCAGACAGTGGTGGTCCTGGG
ATCTCAGGAAGGCGCCGTCCATACAGCTCTGGCTGGCGCCCTGGAAGCCG
AGATGGATGGCGCTAAGGGCAGACTGTCCAGCGGCCACCTGAAGTGCCGG
CTGAAGATGGACAAGCTGCGGCTGAAGGGCGTGTCCTACAGCCTGTGTAC
CGCCGCCTTCACCTTCACCAAGATCCCCGCCGAGACACTGCACGGCACCG
TGACCGTGGAAGTGCAGTATGCCGGCACCGATGGCCCATGCAAGGTGCCA
GCTCAGATGGCCGTGGATATGCAGACCCTGACCCCTGTGGGCCGGCTGAT
CACCGCCAATCCTGTGATCACCGAGAGCACCGAGAACAGCAAGATGATGC
TGGAACTGGACCCTCCATTCGGCGACAGCTACATCGTGATCGGAGTGGGC
GAGAAGAAGATCACCCACCACTGGCACAGAAGCGGCAGCACCATCGGCA
AGGCCTTCGAGGCTACAGTGCGGGGAGCAAGAGAATGGCCGTGCTGGG
CGATACCGCCTGGGATTTTGGTTCTGTGGGCGGAGCCCTGAACAGCCTGG
GCAAGGGAATCCACCAGATCTTCGGAGCCGCCTTTAAGAGCCTGTTCGGC
GGCATGTCCTGGTTCAGCCAGATCCTGATCGGCACCCTGCTGATGTGGCTG -continued

GGACTGAACACCAAGAACGGCAGCATCTCCCTGATGTGCCTGGCCCTGGG
CGGCGTGCTGATCTTTCTGAGCACAGCCGTGTCCGCCTGA

22. ZIKV CprME amino acid sequence (SEQ ID NO: 22)

MKNPKKKSGGFRIVNMLKRGVARVSPFGGLKRLPAGLLLGHGPIRMVLAIL

AFLRFTAIKPSLGLINRWGSVGKKEAMEIIKKFKKDLAAMLRIINARKEKK

RRGADTSVGIVGLLLTTAMAAEVTRRGSAYYMYLDRNDAGEAISFPTTLGM

NKCYIQIMDLGHMCDATMSYECPMLDEGVEPDDVDCWCNTTSTWVVYGTCH

HKKGEARRSRRAVTLPSHSTRKLQTRSQTWLESREYTKHLIRVENWIFRNP

GFALAAAAIAWLLGSSTSQKVIYLVMILLIAPAYSIRCIGVSNRDFVEGMS

GGTWVDVVLEHGGCVTVMAQDKPTVDIELVTTTVSNMAEVRSYCYEASISD

MASDSRCPTQGEAYLDKQSDTQYVCKRTLVDRGWGNGCGLFGKGSLVTCAK

FACSKKMTGKSIQPENLEYRIMLSVHGSQHSGMIVNDTGHETDENRAKVEI

TPNSPRAEATLGGFGSLGLDCEPRTGLDFSDLYYLTMNNKHWLVHKEWFHD

IPLPWHAGADTGTPHWNNKEALVEFKDAHAKRQTVVVLGSQEGAVHTALAG

ALEAEMDGAKGRLSSGHLKCRLKMDKLRLKGVSYSLCTAAFTFTKIPAETL

HGTVTVEVQYAGTDGPCKVPAQMAVDMQTLTPVGRLITANPVITESTENSK

MMLELDPPFGDSYIVIGVGEKKITHHWHRSGSTIGKAFEATVRGAKRMAVL

GDTAWDFGSVGGALNSLGKGIHQIFGAAFKSLFGGMSWFSQILIGTLLMWL

GLNTKNGSISLMCLALGGVLIFLSTAVSA

23. ZIKV NS2B/NS3 Full length nucleotide sequence (SEQ ID NO: 23)

AGCTGGCCCCCTAGCGAAGTACTCACAGCTGTTGGCCTGATATGCGCATT

GGCTGGAGGGTTCGCCAAGGCAGATATAGAGATGGCTGGGCCCATGGCCG

CGGTCGGTCTGCTAATTGTCAGTTACGTGGTCTCAGGAAAGAGTGTGGAC

ATGTACATTGAAAGAGCAGGTGACATCACATGGGAAAAAGATGCGGAAG

TCACTGGAAACAGTCCCCGGCTCGATGTGGCGCTAGATGAGAGTGGTGAT

TTCTCCCTGGTGGAGGATGACGGTCCCCCCATGAGAGAGATCATACTCAA

GGTGGTCCTGATGACCATCTGTGGCATGAACCCAATAGCCATACCCTTTGC

AGCTGGAGCGTGGTACGTATACGTGAAGACTGGAAAAAGGAGTGGTGCTC

TATGGGATGTGCCTGCTCCCAAGGAAGTAAAAAAGGGGGAGACCACAGA

TGGAGTGTACAGAGTAATGACTCGTAGACTGCTAGGTTCAACACAAGTTG

GAGTGGGAGTTATGCAAGAGGGGGTCTTTCACACTATGTGGCACGTCACA

AAAGGATCCGCGCTGAGAAGCGGTGAAGGGAGACTTGATCCATACTGGG

GAGATGTCAAGCAGGATCTGGTGTCATACTGTGGTCCATGGAAGCTAGAT

GCCGCCTGGGACGGGCACAGCGAGGTGCAGCTCTTGGCCGTGCCCCCCGG

AGAGAGAGCGAGGAACATCCAGACTCTGCCCGGAATATTTAAGACAAAG

GATGGGGACATTGGAGCGGTTGCGCTGGATTACCCAGCAGGAACTTCAGG

ATCTCCAATCCTAGACAAGTGTGGGAGAGTGATAGGACTTTATGGCAATG

GGGTCGTGATCAAAAATGGGAGTTATGTTAGTGCCATCACCCAAGGGAGG

AGGGAGGAAGAGACTCCTGTTGAGTGCTTCGAGCCTTCGATGCTGAAGAA

GAAGCAGCTAACTGTCTTAGACTTGCATCCTGGAGCTGGGAAAACCAGGA

-continued

GAGTTCTTCCTGAAATAGTCCGTGAAGCCATAAAAACAAGACTCCGTACT

GTGATCTTAGCTCCAACCAGGGTTGTCGCTGCTGAAATGGAGGAAGCCCT

TAGAGGGCTTCCAGTGCGTTATATGACAACAGCAGTCAATGTCACCCACT

CTGGAACAGAAATCGTCGACTTAATGTGCCATGCCACCTTCACTTCACGTC

TACTACAGCCAATCAGAGTCCCCAACTATAATCTGTATATTATGGATGAG

GCCCACTTCACAGATCCCTCAAGTATAGCAGCAAGAGGATACATTTCAAC

AAGGGTTGAGATGGGCGAGGCGGCTGCCATCTTCATGACCGCCACGCCAC

CAGGAACCCGTGACGCATTTCCGGACTCCAACTCACCAATTATGGACACC

GAAGTGGAAGTCCCAGAGAGAGCCTGGAGCTCAGGCTTTGATTGGGTGAC

GGATCATTCTGGAAAAACAGTTTGGTTTGTTCCAAGCGTGAGGAACGGCA

ATGAGATCGCAGCTTGTCTGACAAAGGCTGGAAAACGGGTCATACAGCTC

AGCAGAAAGACTTTTGAGACAGAGTTCCAGAAAACAAAACATCAAGAGT

GGGACTTTGTCGTGACAACTGACATTTCAGAGATGGGCGCCAACTTTAAA

GCTGACCGTGTCATAGATTCCAGGAGATGCCTAAAGCCGGTCATACTTGA

TGGCGAGAGAGTCATTCTGGCTGGACCCATGCCTGTCACACATGCCAGCG

CTGCCCAGAGGAGGGGGCGCATAGGCAGGAATCCCAACAAACCTGGAGA

TGAGTATCTGTATGGAGGTGGGTGCGCAGAGACTGACGAAGACCATGCAC

ACTGGCTTGAAGCAAGAATGCTCCTTGACAATATTTACCTCCAAGATGGC

CTCATAGCCTCGCTCTATCGACCTGAGGCCGACAAAGTAGCAGCCATTGA

GGGAGAGTTCAAGCTTAGGACGGAGCAAAGGAAGACCTTTGTGGAACTC

ATGAAAAGAGGAGATCTTCCTGTTTGGCTGGCCTATCAGGTTGCATCTGCC

GGAATAACCTACACAGATAGAAGATGGTGCTTTGATGGCACGACCAACAA

CACCATAATGGAAGACAGTGTGCCGGCAGAGGTGTGGACCAGACACGGA

GAGAAAAGAGTGCTCAAACCGAGGTGGATGGACGCCAGAGTTTGTTCAG

ATCATGCGGCCCTGAAGTCATTCAAGGAGTTTGCCGCTGGGAAAAGA

24. ZIK NS2B/NS3 full length amino acid sequence (SEQ ID NO: 24)

MSWPPSEVLTAVGLICALAGGFAKADIEMAGPMAAVGLLIVSYVVSGKSVD

MYIERAGDITWEKDAEVTGNSPRLDVALDESGDFSLVEDDGPPMREIILKV

VLMTICGMNPIAIPFAAGAWYVYVKTGKRSGALWDVPAPKEVKKGETTDGV

YRVMTRRLLGSTQVGVGVMQEGVFHTMWHVTKGSALRSGEGRLDPYWGDVK

QDLVSYCGPWKLDAAWDGHSEVQLLAVPPGERARNIQTLPGIFKTKDGDIG

AVALDYPAGTSGSPILDKCGRVIGLYGNGVVIKNGSYVSAITQGRREEETP

VECFEPSMLKKKQLTVLDLHPGAGKTRRVLPEIVREAIKTRLRTVILAPTR

VVAAEMEEALRGLPVRYMTTAVNVTHSGTEIVDLMCHATFTSRLLQPIRVP

NYNLYIMDEAHFTDPSSIAARGYISTRVEMGEAAAIFMTATPPGTRDAFPD

SNSPIMDTEVEVPERAWSSGFDWVTDHSGKTVWFVPSVRNGNEIAACLTKA

GKRVIQLSRKTFETEFQKTKHQEWDFVVTTDISEMGANFKADRVIDSRRCL

KPVILDGERVILAGPMPVTHASAAQRRGRIGRNPNKPGDEYLYGGGCAETD

EDHAHWLEARMLLDNIYLQDGLIASLYRPEADKVAAIEGEFKLRTEQRKTF

VELMKRGDLPVWLAYQVASAGITYTDRRWCFDGTTNNTIMEDSVPAEVWTR

HGEKRVLKPRWMDARVCSDHAALKSFKEFAAGKR

25. ZIK NS2B/NS3Pro codon optimized nucleotide
sequence
(SEQ ID NO: 25)
ATGTCTTGGCCTCCATCTGAGGTGCTGACCGCCGTGGGACTGATTTGTGCC

CTGGCTGGCGGATTCGCCAAGGCCGACATTGAGATGGCCGGACCTATGGC

CGCTGTGGGCCTGCTGATCGTGTCCTACGTGGTGTCCGGCAAGAGCGTGG

ACATGTACATCGAGAGAGCCGGCGACATCACCTGGGAGAAGGATGCCGA

AGTGACCGGCAACAGCCCCAGACTGGATGTGGCCCTGGACGAGAGCGGC

GATTTCAGCCTGGTGGAAGATGACGGCCCTCCCATGCGCGAGATCATCCT

GAAGGTGGTGCTGATGACCATCTGCGGAATGAACCCTATCGCCATCCCCT

TCGCCGCTGGCGCTTGGTACGTGTACGTGAAAACCGGCAAGCGGAGCGGA

GCCCTGTGGGACGTGCCAGCCCCTAAAGAAGTGAAGAAGGGCGAGACAA

CCGACGGCGTGTACAGAGTGATGACCAGACGGCTGCTGGGCAGCACACA

AGTCGGAGTGGGAGTGATGCAGGAAGGGGTCTTCCACACCATGTGGCACG

TGACCAAGGGCAGCGCCCTGAGATCTGGCGAAGGCAGACTGGACCCTTAC

TGGGGCGACGTGAAGCAGGACCTGGTGTCCTACTGCGGCCCCTGGAAACT

GGATGCCGCCTGGGATGGCCACAGCGAAGTGCAGCTGCTGGCTGTGCCTC

CCGGCGAGAGGGCCAGAAATATCCAGACCCTGCCCGGCATCTTCAAGACC

AAGGATGGCGACATCGGCGCCGTGGCTCTGGATTACCCTGCCGGCACATC

TGGCAGCCCCATCCTGGATAAGTGCGGCAGAGTGATCGGCCTGTACGGCA

ACGGCGTGGTCATCAAGAACGGCAGCTACGTGTCCGCCATCACCCAGGGC

AGACGCGAGGAAGAGACACCCGTGGAATGCTTCGAGTGA

26. ZIKV NS2B/NS3Pro amino acid sequence (SEQ ID NO: 26)

MSWPPSEVLTAVGLICALAGGF AKADIEMAGPMAAVGLLIVSYVVSGKSV

DMYIERAGDITWEKDAEVTGNSPRLDVALDESGDFSLVEDDGPPMREIILK

VVLMTICGMNPIAIPFAAGAWYVYVKTGKRSGALWDVPAPKEVKKGETTDG

VYRVMTRRLLGSTQVGVGVMQEGVFHTMWHVTKGSALRSGEGRLDPYWGDV

KQDLVSYCGPWKLDAAWDGHSEVQLLAVPPGERARNIQTLPGIFKTKDGDI

GAVALDYPAGTSGSPILDKCGRVIGLYGNGVVIKNGSYVSAITQGRREEET

PVECFE

27. DEN-2 NS3 wild-type amino acid sequence (SEQ ID NO: 27)

AGVLWDVPSPPPMGKAELEDGAYRIKQKGILGYSQIGAGVYKEGTFHTMWH

VTRGAVLMHKGKRIEPSWADVKKDLISYGGGWKLEGEWKEGEEVQVLALEP

GKNPRAVQTKPGLFKTNAGTIGAVSLDFSPGTSGSPIIDKKGKVVGLYGNG

VVTRSGAYVSAIAQTEKSIEDNPEIEDDIFRKRRLTIMDLHPGAGKTKRYL

PAIVREAIKRGLRTLILAPTRVVAAEMEEALRGLPIRYQTPAIRAEHTGRE

IVDLMCHATFTMRLLSPVRVPNYNLIIMDEAHFTDPASIAARGYISTRVEM

GEAAGIFMTATPPGSRDPFPQSNAPIIDEEREIPERSWNSGHEWVTDFKGK

TVWFVPSIKAGNDIAACLRKNGKKVIQLSRKTFDSEYVKTRTNDWDFVVTT

DISEMGANFKAERVIDPRRCMKPVILTDGEERVILAGPMPVTHSSAAQRRG

RIGRNPKNENDQYIYMGEPLENDEDCAHWKEAKMLLDNINTPEGIIPSMFE

PEREKVDAIDGEYRLRGEARKTFVDLMRRGDLPVWLAYRVAAEGINYADRR

WCFDGVKNNQILEENVEVEIWTKEGERKKLKPRWLDARIYSDPLALKEFKE

FAAGR

28. DEN-2 NS3 Helicase portion wild type nucleotide sequence (SEQ ID NO: 28)

ATTTTCCGAAAGAGAAGACTGACCATCATGGACCTCCACCCAGGAGCGGG

AAAGACGAAGAGATACCTTCCGGCCATAGTCAGAGAAGCTATAAAACGG

GGTTTGAGAACATTAATCTTGGCCCCCACTAGAGTTGTGGCAGCTGAAAT

GGAGGAAGCCCTTAGAGGACTTCCAATAAGATACCAGACCCCAGCCATCA

GAGCTGAGCACACCGGGCGGGAGATTGTGGACCTAATGTGTCATGCCACA

TTTACCATGAGGCTGCTATCACCAGTTAGAGTGCCAAACTACAACCTGATT

ATCATGGACGAAGCCCATTTCACAGACCCAGCAAGTATAGCAGCTAGAGG

ATACATCTCAACTCGAGTGGAGATGGGTGAGGCAGCTGGGATTTTTATGA

CAGCCACTCCCCCGGGAAGCAGAGACCCATTTCCTCAGAGCAATGCACCA

ATCATAGATGAAGAAAGAGAAATCCCTGAACGTTCGTGGAATTCCGGACA

TGAATGGGTCACGGATTTTAAAGGGAAGACTGTTTGGTTCGTTCCAAGTAT

AAAAGCAGGAAATGATATAGCAGCTTGCCTGAGGAAAAATGGAAAGAAA

GTGATACAACTCAGTAGGAAGACCTTTGATTCTGAGTATGTCAAGACTAG

AACCAATGATTGGGACTTCGTGGTTACAACTGACATTTCAGAAATGGGTG

CCAATTTCAAGGCTGAGAGGGTTATAGACCCCAGACGCTGCATGAAACCA

GTCATACTAACAGATGGTGAAGAGCGGGTGATTCTGGCAGGACCTATGCC

AGTGACCCACTCTAGTGCAGCACAAAGAAGAGGGAGAATAGGAAGAAAT

CCAAAAAATGAGAATGACCAGTACATATACATGGGGGAACCTCTGGAAA

ATGATGAAGACTGTGCACACTGGAAAGAAGCTAAAATGCTCCTAGATAAC

ATCAACACGCCAGAAGGAATCATTCCTAGCATGTTCGAACCAGAGCGTGA

AAAGGTGGATGCCATTGATGGCGAATACCGCTTGAGAGGAGAAGCAAGG

AAAACCTTTGTAGACTTAATGAGAAGAGGAGACCTACCAGTCTGGTTGGC

CTACAGAGTGGCAGCTGAAGGCATCAACTACGCAGACAGAAGGTGGTGTT

TTGATGGAGTCAAGAACAACCAAATCCTAGAAGAAAACGTGGAAGTTGA

AATCTGGACAAAAGAAGGGGAAAGGAAGAAATTGAAACCCAGATGGTTG

GATGCTAGGATCTATTCTGACCCACTGGCGCTAAAAGAATTTAAGGAATT

TGCAGCCGGAAGAAAG

29. DEN-2 NS3 Helicase wild type amino acid sequence (SEQ ID NO: 29)

IFRKRRLTIMDLHPGAGKTKRYLPAIVREAIKRGLRTLILAPTRVVAAEME

EALRGLPIRYQTPAIRAEHTGREIVDLMCHATFTMRLLSPVRVPNYNLIIM

DEAHFTDPASIAARGYISTRVEMGEAAGIFMTATPPGSRDPFPQSNAPIID

EEREIPERSWNSGHEWVTDFKGKTVWFVPSIKAGNDIAACLRKNGKKVIQL

SRKTFDSEYVKTRTNDWDFVVTTDISEMGANFKAERVIDPRRCMKPVILTD

GEERVILAGPMPVTHSSAAQRRGRIGRNPKNENDQYIYMGEPLENDEDCAH

WKEAKMLLDNINTPEGIIPSMFEPEREKVDAIDGEYRLRGEARKTFVDLMR

RGDLPVWLAYRVAAEGINYADRRWCFDGVKNNQILEENVEVEIWTKEGERK

KLKPRWLDARIYSDPLALKEFKEFAAGR

30. DEN-2 NS2B/NS3Pro wild-type nucleotide sequence
with Mutations
(SEQ ID NO: 30)
ATGAGCTGGCCATTAAATGAGGCTATCATGGCAGTCGGGATGGTGAGCAT

TTTAGCCAGTTCTCTCCTAAAAAATGATATTCCCATGACAGGACCATTAGT

GGCTGGAGGGCTCCTCACTGTGTGCTACGTGCTCACTGGACGATCGGCCG

ATTTGGAACTGGAGAGAGCAGCCGATGTCAAATGGGAAGACCAGGCAGA

GATATCAGGAAGCAGTCCAATCCTGTCAATAACAATATCAGAAGATGGTA

GCATGTCGATAAAAAATGAAGAGGAAGAACAAACACTGACCATACTCATT

AGAACAGGATTGCTGGTGATCTCAGGACTTTTTCCTGTATCAATACCAATC

ACGGCAGCAGCATGGTACCTGTGGGAAGTGAAGAAACAACGGGCCGGAG

TATTGTGGGATGTTCCTTCACCCCCACCCATGGGAAAGGCTGAACTGGAA

GATGGAGCCTATAGAATTAAGCAAAAAGGGATTCTTGGATATTCCCAGAT

CGGAGCCGGAGTTTACAAAGAAGGAACATTCCATACAATGTGGCATGTCA

CACGTGGCGCTGTTCTAATGCATAAAGGAAAGAGGATTGAACCATCATGG

GCGGACGTCAAGAAAGACCTAATATCATATGGAGGAGGCTGGAAGTTAG

AAGGAGAATGGAAGGAAGGAGAAGAAGTCCAGGTATTGGCACTGGAGCC

TGGAAAAAATCCAAGAGCCGTCCAAACGAAACCTGGTGCCTTCAAAACCA

ACGCCGGAACAATAGGTGCTGTATCTCTGGACTTTTCTCCTGGAACGTCAG

GATCTCCAATTATCGACAAAAAAGGAAAAGTTGTGGGTCTTTATGGTAAT

GGTGTTGTTACAAGGAGTGGAGCATATGTGAGTGCTATAGCCCAGACTGA

AAAAAGCATTGAAGACAACCCAGAGATCGAAGATGACTAG

31. DEN-2 Capsid (C) codon optimized nucleotide sequence (SEQ ID NO: 31)

ATGAACAACCAGCGCAAGAAGGCCAAAAACACTCCGTTCAATATGCTCAA

GAGAGAGCGCAATCGGGTTTCTACGGTACAGCAGCTGACGAAGAGATTCT

CCCTGGGCATGCTGCAAGGTCGCGGACCACTGAAGCTGTTCATGGCCCTT

GTTGCATTTCTTAGGTTTCTTACAATTCCCCCCACTGCTGGAATCCTGAAG

CGGTGGGGCACCATCAAAAAGTCCAAGGCTATTAATGTCCTCAGGGGGTT

CAGGAAAGAGATTGGGCGGATGCTGAACATCCTTAATAGACGCAGACGGT

CCGCTGGCATGATAATCATGCTGATCCCAACCGTCATGGCC

32. DEN-2 Capsid (C) amino acid sequence (SEQ ID NO: 32)

MNNQRKKAKNTPFNMLKRERNRVSTVQQLTKRFSLGMLQGRGPLKLFMALV

AFLRFLTIPPTAGILKRWGTIKKSKAINVLRGFRKEIGRMLNILNRRRRSA

GMIIMLIPTVMA

Dengue virus 1 Strain West Pac 94 Genbank M23027.1

33. DEN-1 prME wild type nucleotide sequence (SEQ ID NO: 33)

TTCCATCTGACCACCCGAGGGGGAGAGCCGCACATGATAGTTAGCAAGCA

GGAAAGAGGAAAATCACTTTTGTTTAAGACCTCTGCAGGTGTCAACATGT

GCACCCTTATTGCAATGGATTTGGGAGAGTTATGTGAGGACACAATGACC

TACAAATGCCCCCGGATCACTGAGACGGAACCAGATGACGTTGACTGTTG

-continued

GTGCAATGCCACGGAGACATGGGTGACCTATGGAACATGTTCTCAAACTG

GTGAACACCGACGAGACAAACGTTCCGTCGCACTGGCACCACACGTAGGG

CTTGGTCTAGAAACAAGAACCGAAACGTGGATGTCCTCTGAAGGCGCTTG

GAAACAAATACAAAAAGTGGAGACCTGGGCTCTGAGACACCCAGGATTC

ACGGTGATAGCCCTTTTTCTAGCACATGCCATAGGAACATCCATCACCCAG

AAAGGGATCATTTTTATTTTGCTGATGCTGGTAACTCCATCCATGGCCATG

CGGTGCGTGGGAATAGGCAACAGAGACTTCGTGGAAGGACTGTCAGGAG

CTACGTGGGTGGATGTGGTACTGGAGCATGGAAGTTGCGTCACTACCATG

GCAAAAGACAAACCAACACTGGACATTGAACTCTTGAAGACGGAGGTCA

CAAACCCTGCCGTCCTGCGCAAACTGTGCATTGAAGCTAAAATATCAAAC

ACCACCACCGATTCGAGATGTCCAACACAAGGAGAAGCCACGCTGGTGGA

AGAACAGGACACGAACTTTGTGTGTCGACGAACGTTCGTGGACAGAGGCT

GGGGCAATGGTTGTGGGCTATTCGGAAAAGGTAGCTTAATAACGTGTGCT

AAGTTTAAGTGTGTGACAAAACTGGAAGGAAAGATAGTCCAATATGAAA

ACTTAAAATATTCAGTGATAGTCACCGTACACACTGGAGACCAGCACCAA

GTTGGAAATGAGACCACAGAACATGGAACAACTGCAACCATAACACCTCA

AGCTCCCACGTCGGAAATACAGCTGACAGACTACGGAGCTCTAACATTGG

ATTGTTCACCTAGAACAGGGCTAGACTTTAATGAGATGGTGTTGTTGACA

ATGGAAAAAAAATCATGGCTCGTCCACAAACAATGGTTTCTAGACTTACC

ACTGCCTTGGACCTCGGGGGCTTCAACATCCCAAGAGACTTGGAATAGAC

AAGACTTGCTGGTCACATTTAAGACAGCTCATGCAAAAAAGCAGGAAGTA

GTCGTACTAGGATCACAAGAAGGAGCAATGCACACTGCGTTGACTGGAGC

GACAGAAATCCAAACGTCTGGAACGACAACAATTTTTGCAGGACACCTGA

AATGCAGACTAAAAATGGATAAACTGACTTTAAAAGGGATGTCATATGTA

ATGTGCACAGGGTCATTCAAGTTAGAGAAGGAAGTGGCTGAGACCCAGCA

TGGAACTGTTCTAGTGCAGGTTAAATACGAAGGAACAGATGCACCATGCA

AGATCCCCTTCTCGTCCCAAGATGAGAAGGGAGTAACCCAGAATGGGAGA

TTGATAACAGCCAACCCCATAGTCACTGACAAAGAAAAACCAGTCAACAT

TGAAGCGGAGCCACCTTTTGGTGAGAGCTACATTGTGGTAGGAGCAGGTG

AAAAAGCTTTGAAACTAAGCTGGTTCAAGAAGGGAAGCAGTATAGGGAA

AATGTTTGAAGCAACTGCCCGTGGAGCACGAAGGATGGCCATCCTGGGAG

ACACTGCATGGGACTTCGGTTCTATAGGAGGGGTGTTCACGTCTGTGGGA

AAACTGATACACCAGATTTTTGGGACTGCGTATGGAGTTTTGTTCAGCGGT

GTTTCTTGGACCATGAAGATAGGAATAGGGATTCTGCTGACATGGCTAGG

ATTAAACTCAAGGAGCACGTCCCTTTCAATGACGTGTATCGCAGTTGGCAT

GGTCACGCTGTACCTAGGAGTCATGGTTCAGGCG

34. DEN-1 prME wild type amino acid sequence (SEQ ID NO: 34)

MIVSKQERGKSLLFKTSAGVNMCTLIAMDLGELCEDTMTYKCPRITETEPD

DVDCWCNATETWVTYGTCSQTGEHRRDKRSVALAPHVGLGLETRTETWMSS

EGAWKQIQKVETWALRHPGFTVIALFLAHAIGTSITQKGIIFILLMLVTPS

```
MAMRCVGIGNRDFVEGLSGATWVDVVLEHGSCVTTMAKDKPTLDIELLKTE

VTNPAVLRKLCIEAKISNTTTDSRCPTQGEATLVEEQDTNFVCRRTFVDRG

WGNGCGLFGKGSLITCAKFKCVTKLEGKIVQYENLKYSVIVTVHTGDQHQV

GNETTEHGTTATITPQAPTSEIQLTDYGALTLDCSPRTGLDFNEMVLLTME

KKSWLVHKQWFLDLPLPWTSGASTSQETWNRQDLLVTFKTAHAKKQEVVVL

GSQEGAMHTALTGATEIQTSGTTTIFAGHLKCRLKMDKLTLKGMSYVMCTG

SFKLEKEVAETQHGTVLVQVKYEGTDAPCKIPFSSQDEKGVTQNGRLITAN

PIVTDKEKPVNIEAEPPFGESYIVVGAGEKALKLSWFKKGSSIGKMFEATA

RGARRMAILGDTAWDFGSIGGVFTSVGKLIHQIFGTAYGVLFSGVSWTMKI

GIGILLTWLGLNSRSTSLSMTCIAVGMVTLYLGVMVQA
```

35. TVXD021 (Capsid of DENV-2 and prME of DENV-1)
Codon Optimized nucleotide sequence with mutations
(SEQ ID NO: 35)
```
ATGAACAACCAGCGCAAGAAGGCCAAAAACACTCCGTTCAATATGCTCAA

GAGAGAGCGCAATCGGGTTTCTACGGTACAGCAGCTGACGAAGAGATTCT

CCCTGGGCATGCTGCAAGGTCGCGGACCACTGAAGCTGTTCATGGCCCTT

GTTGCATTTCTTAGGTTTCTTACAATTCCCCCACTGCTGGAATCCTGAAG

CGGTGGGGCACCATCAAAAAGTCCAAGGCTATTAATGTCCTCAGGGGGTT

CAGGAAAGAGATTGGGCGGATGCTGAACATCCTTAATAGACGCAGACGGT

CCGCTGGCATGATAATCATGCTGATCCCAACCGTCATGGCCTTTCACCTGA

CCACTAGGGGCGGTGAGCCACATATGATAGTTAGTAAACAGGAAAGGGG

TAAAAGTCTGCTTTTTAAAACTTCCGCCGGCGTAAATATGTGCACACTGAT

AGCCATGGACTTGGGCGAGCTTTGCGAGGATACCATGACATACAAATGCC

CCCGGATCACAGAGACAGAACCAGACGATGTTGACTGCTGGTGCAACGCC

ACCGAGACTTGGGTTACATACGGGACTTGCAGCCAAACGGGAGAACATAG

ACGCGCAAAGAGATCTGTAGCCCTTGCCCCACACGTAGGACTGGGACTCG

AGACAAGAACAGAAACCTGGATGAGTAGTGAAGGCGCTTGGAAAAGAT

CCAAAAGGTGGAAACTTGGGCTCTGCGACACCCTGGGTTCACAGTGATCG

CATTGTTTTTGGCCCATGCAATAGGAACTTCTATCACACAGAAAGGCATTA

TCTTCATCCTGCTGATGTTGGTTACACCTTCAATGGCCATGAGGTGCGTCG

GTATCGGAAACAGAGATTTCGTGGAAGGGCTGAGCGGGGCTACCTGGGTG

GATGTCGTCCTCGAACACGGATCATGTGTCACGACTATGGCAAAAGATAA

GCCTACCCTCGATATTGAGCTGTTGAAGACCGAGGTTACTAACCCTGCTGT

GCTGCGCAAACTGTGTATTGAAGCAAAGATTTCTAACACAACAACCGACA

GTAGATGCCCCACTCAGGGAGAAGCCACGCTGGTGGAAGAGCAGGACAC

CAACTTTGTATGTAGAAGAACCTTCGTCGATCGCGGATGGGGGAACGGGT

GCGGACTCTTCGGAAAAGGATCCCTGATTACTTGTGCAAAATTCAAATGC

GTGACTAAACTTGAAGGCAAAATCGTACAGTACGAAAATTTGAAGTACTC

TGTTATCGTTACCGTTCATACGGGAGATCAACACCAGGTTGGGAACGAGA

CCACCGAACACGGCACTACCGCAACGATTACACCTCAAGCCCCTACTTCC

GAAATACAACTCACCGACTATGGCGCCCTTACACTGGACTGTTCACCACG

CACTGGACTGGACTTCAACGAAATGGTCCTCCTGACAATGGAAAAGAAAA
```

```
GCTGGCTTGTACACAAGCAATGGTTCTTGGACCTGCCGCTCCCATGGACG

AGTGGCGCGAGTACTAGCCAGGAGACCTGGAACCGGCAGGACCTTCTGGT

AACATTCAAGACAGCACACGCTAAAAAACAAGAGGTGGTCGTTCTTGGAT

CCCAAGAGGGTGCAATGCACACAGCCCTCACAGGTGCAACCGAGATCCAG

ACTTCCGGAACTACCACTATCTTTGCAGGCCATCTCAAATGCAGACTGAA

AATGGATAAACTTACACTCAAGGGGATGTCATATGTCATGTGTACGGGGT

CTTTTAAACTTGAAAAGGAGGTCGCTGAAACACAACACGGAACTGTTCTG

GTGCAAGTCAAATACGAAGGTACGGATGCTCCCTGTAAAATTCCCTTCAG

CTCTCAGGACGAAAAGGTGTTACTCAGAATGGTAGGCTGATTACCGCTA

ATCCAATTGTAACCGATAAGGAGAAACCCGTGAATATTGAGGCAGAGCCC

CCCTTCGGTGAATCTTATATTGTAGTTGGAGCAGGAGAGAAGGCCCTTAA

ACTCAGTTGGTTCAAGAAGGGATCTTCCCTCGGAAAAGCATTTGAAGCTA

CGGCTCGGGGAGCGCGCAGGCTGGCTATCCTTGGGGACACGGCATGGGAC

TTTGGAAGCATTGGTGGCGTCTTTACATCCGTGGGAAAGTTGATACACCA

AATCTTCGGGACCGCGTACGGCGTGCTCTTTTCAGGAGTCTCTTGGACTAT

GAAGATCGGAATTGGCATACTCTTGACCTGGCTTGGCTTGAATTCCCGGTC

TACTTCTTTGAGTATGACTTGCATTGCTGTTGGCATGGTCACTCTCTACCT

CGGCGTGATGGTGCAGGCCTAG
```

36. TVXD021 amino acid sequence with mutations
(SEQ ID NO: 36)
```
MNNQRKKAKNTPFNMLKRERNRVSTVQQLTKRFSLGMLQGRGPLKLFMALV

AFLRFLTIPPTAGILKRWGTIKKSKAINVLRGFRKEIGRMLNILNRRRRSA

GMIIMLIPTVMAFHLTTRGGEPHMIVSKQERGKSLLFKTSAGVNMCTLIAM

DLGELCEDTMTYKCPRITETEPDDVDCWCNATETWVTYGTCSQTGEHRRDK

RSVALAPHVGLGLETRTETWMSSEGAWKQIQKVETWALRHPGFTVIALFLA

HAIGTSITQKGIIFILLMLVTPSMAMRCVGIGNRDFVEGLSGATWVDVVLE

HGSCVTTMAKDKPTLDIELLKTEVTNPAVLRKLCIEAKISNTTTDSRCPTQ

GEATLVEEQDTNFVCRRTFVDRGWGNGCGLFGKGSLITCAKFKCVTKLEGK

IVQYENLKYSVIVTVHTGDQHQVGNETTEHGTTATITPQAPTSEIQLTDYG

ALTLDCSPRTGLDFNEMVLLTMEKKSWLVHKQWFLDLPLPWTSGASTSQET

WNRQDLLVTFKTAHAKKQEVVVLGSQEGAMHTALTGATEIQTSGTTTIFAG

HLKCRLKMDKLTLKGMSYVMCTGSFKLEKEVAETQHGTVLVQVKYEGTDAP

CKIPFSSQDEKGVTQNGRLITANPIVTDKEKPVNIEAEPPFGESYIVVGAG

EKALKLSWFKKGSSLGKAFEATARGARRLAILGDTAWDFGSIGGVFTSVGK

LIHQIFGTAYGVLFSGVSWTMKIGIGILLTWLGLNSRSTSLSMTCIAVGMV

TLYLGVMVQA
```

Dengue virus 3 Strain CH53489 Genbank DQ863638.1
37. DEN-3 prME wild-type nucleotide sequence
(SEQ ID NO: 37)
```
TTCCACTTAACTTCACGAGATGGAGAGCCGCGCATGATTGTGGGAAGAA

TGAAAGAGGAAATCCCTACTTTTTAAGACAGCTTCTGGAATCAACATGT

GCACACTCATAGCCATGGACTTGGGAGAGATGTGTGATGACACGGTCACT

TACAAATGCCCCCACATTGCCGAAGTGGAACCTGAAGACATTGACTGCTG
```

-continued

GTGCAACCTTACATCGACATGGGTGACTTATGGAACGTGCAATCAAGCTG

GGGAGCACAGACGCGACAAGAGATCAGTGGCGTTAGCTCCCCATGTCGGC

ATGGGACTGGACACACGCACCCAAACCTGGATGTCGGCTGAAGGAGCTTG

GAGACAAGTCGAGAAGGTAGAGACATGGGCCCTTAGGCACCCAGGGTTC

ACCATACTAGCTCTATTTCTTGCCCATTACATAGGCACTTCCTTGACCCAG

AAAGTGGTTATTTTTATACTACTAATACTGGTCACTCCATCCATGGCAATG

AGATGCGTGGGAGTAGGAAACAGAGATTTTGTGGAAGGTCTATCGGGAGC

TACGTGGGTTGACGTGGTGCTCGAGCACGGTGGGTGTGTGACCACCATGG

CTAAGAACAAGCCCACGCTGGACATAGAGCTTCAGAAGACCGAGGCCAC

CCAACTGGCCACCCTAAGGAAGTTATGCATTGAGGGAAAAATTACCAACA

TAACAACTGACTCAAGGTGTCCTACCCAGGGGGAAGCGATTTTACCTGAG

GAGCAGGACCAGAACTACGTATGTAAGCATACATACGTGGATAGAGGCTG

GGGAAACGGTTGTGGTTTGTTTGGAAAAGGAAGCTTGGTGACATGCGCGA

AATTTCAATGCTTAGAATCAATAGAGGGAAAAGTGGTGCAACATGAGAAC

CTCAAATACACTGTCATCATTACAGTGCACACAGGAGACCAACACCAGGT

GGGAAATGAAACGCAGGGAGTCACGGCTGAGATAACACCCCAGGCATCA

ACCGTTGAAGCTATCTTGCCTGAATATGGAACCCTTGGGCTAGAATGCTCA

CCACGGACAGGTTTGGATTTCAATGAAATGATCTTATTGACAATGAAGAA

CAAAGCATGGATGGTACATAGACAATGGTTCTTTGACCTCCCCCTACCATG

GACATCAGGAGCTACAACAGAGACACCAACTTGGAACAGGAAAGAGCTT

CTTGTGACATTCAAAAATGCACATGCAAAAAAGCAAGAAGTAGTTGTCCT

TGGATCGCAAGAGGGAGCAATGCACACAGCGCTGACAGGAGCTACAGAG

ATCCAAAACTCAGGAGGCACAAGCATTTTTGCCGGGCACTTGAAATGTAG

ACTTAAGATGGACAAATTGGAACTCAAGGGGATGAGCTATGCAATGTGCT

TGAACACCTTTGTGTTGAAGAAAGAAGTCTCCGAGACGCAGCATGGGACA

ATACTCATTAAGGTTGAGTACAAAGGGGAAGATGCACCTTGCAAGATTCC

TTTCTCCACGGAGGATGGACAAGGGAAAGCTCACAATGGTAGACTGATCA

CAGCCAACCCAGTGGTGACCAAGAAGGAGGAGCCTGTCAACATTGAGGCT

GAACCTCCTTTTGGGGAAAGTAACATAGTGATTGGAATTGGAGACAAAGC

CTTGAAAATTAACTGGTACAAGAAGGGAAGCTCGATTGGGAAGATGTTCG

AGGCCACTGCCAGAGGTGCAAGGCGCATGGCCATCTTGGGAGACACAGCC

TGGGACTTTGGATCAGTGGGTGGTGTCTTGAATTCATTAGGGAAAATGGT

CCACCAAATATTTGGAAGTGCTTACACAGCCCTGTTTAGTGGAGTCTCATG

GATAATGAAAATTGGAATAGGTGTCCTCTTAACCTGGATAGGGTTGAATT

CAAAAAACACTTCCATGTCATTTTCATGTATTGCGATAGGAATTATTACAC

TCTATCTGGGAGCCGTGGTACAAGCT

DEN-3 prME wild type amino acid sequence
(SEQ ID NO: 48)

MIVGKNERGKSLLFKTASGINMCTLIAMDLGEMCDDTVTYKCPHIAEVEPE

DIDCWCNLTSTWVTYGTCNQAGEHRRDKRSVALAPHVGMGLDTRTQTWMSA

EGAWRQVEKVETWALRHPGFTILALFLAHYIGTSLTQKVVIFILLILVTPS

MAMRCVGVGNRDFVEGLSGATWVDVVLEHGGCVTTMAKNKPTLDIELQKTE

-continued

ATQLATLRKLCIEGKITNITTDSRCPTQGEAILPEEQDQNYVCKHTYVDRG

WGNGCGLFGKGSLVTCAKFQCLESIEGKVVQHENLKYTVIITVHTGDQHQV

GNETQGVTAEITPQASTVEAILPEYGTLGLECSPRTGLDFNEMILLTMKNK

AWMVHRQWFFDLPLPWTSGATTETPTWNRKELLVTFKNAHAKKQEVVVLGS

QEGAMHTALTGATEIQNSGGTSIFAGHLKCRLKMDKLELKGMSYAMCLNTF

VLKKEVSETQHGTILIKVEYKGEDAPCKIPFSTEDGQGKAHNGRLITANPV

VTKKEEPVNIEAEPPFGESNIVIGIGDKALKINWYKKGSSIGKMFEATARG

ARRMAILGDTAWDFGSVGGVLNSLGKMVHQIFGSAYTALFSGVSWIMKIGI

GVLLTWIGLNSKNTSMSFSCIAIGIITLYLGAVVQA

38. TVXDO23 (Capsid of DENV-2 and prME of DENV-3) Codon Optimized nucleotide sequence with mutations
(SEQ ID NO: 38)

ATGAACAACCAGCGCAAGAAGGCCAAAAACACTCCGTTCAATATGCTCAA

GAGAGAGCGCAATCGGGTTTCTACGGTACAGCAGCTGACGAAGAGATTCT

CCCTGGGCATGCTGCAAGGTCGCGGACCACTGAAGCTGTTCATGGCCCTT

GTTGCATTTCTTAGGTTTCTTACAATTCCCCCCACTGCTGGAATCCTGAAG

CGGTGGGGCACCATCAAAAAGTCCAAGGCTATTAATGTCCTCAGGGGGTT

CAGGAAAGAGATTGGGCGGATGCTGAACATCCTTAATAGACGCAGACGGT

CCGCTGGCATGATAATCATGCTGATCCCAACCGTCATGGCCTTTCATCTGA

CTTCTCGAGATGGAGAGCCTCGCATGATCGTTGGCAAGAATGAGCGCGGC

AAAAGTCTCCTGTTCAAAACGGCCTCTGGAATTAATATGTGTACCTTGATT

GCTATGGATCTGGGAGAGATGTGTGATGATACCGTTACCTACAAGTGCCC

GCACATTGCTGAGGTTGAGCCTGAAGACATAGACTGCTGGTGCAACTTGA

CAAGTACGTGGGTCACCTACGGGACCTGCAACCAAGCCGGCGAGCACAG

GCGCGCAAAGAGATCCGTTGCGCTGGCGCCACACGTAGGAATGGGCCTGG

ACACTCGCACTCAGACTTGGATGTCTGCTGAGGGCGCCTGGCGGCAGGTA

GAGAAAGTAGAGACATGGGCTCTCAGGCACCCAGGATTTACCATTCTGGC

TCTGTTTTTGGCCCACTATATCGGCACCTCCCTCACTCAGAAGGTCGTCAT

TTTCATACTCCTGATACTCGTGACCCCTTCTATGGCCATGCGGTGTGTCGG

GGTCGGCAATAGGGACTTCGTGGAAGGATTGAGTGGCGCAACTTGGGTCG

ATGTCGTGCTGGAACATGGAGGTTGTGTAACTACTATGGCGAAGAATAAA

CCAACTCTGGACATCGAGCTGCAAAAGACTGAGGCAACACAACTTGCAAC

TCTTAGAAAGCTGTGTATCGAAGGCAAAATAACTAATATCACCACAGATT

CCAGATGTCCCACCCAGGGGGAAGCTATCCTGCCAGAGGAGCAGGACCA

GAATTACGTGTGTAAGCATACCTATGTGGATCGGGGCTGGGGGAATGGAT

GTGGCCTCTTCGGTAAGGGTTCCCTCGTGACGTGCGCGAAATTCCAGTGTT

TGGAATCCATAGAAGGCAAAGTAGTACAACACGAAAACCTCAAATATAC

AGTTATTATCACTGTTCACACCGGGGACCAGCACCAAGTAGGGAATGAGA

CACAGGGCGTTACAGCCGAAATTACTCCACAAGCCAGTACAGTCGAGGCT

ATTCTGCCTGAATATGGTACTTTGGGACTCGAATGCTCACCGCGGACCGG

ACTGGACTTTAACGAAATGATACTGCTGACAATGAAGAACAAGGCCTGGA

TGGTACACCGCCAATGGTTCTTTGACCTGCCACTGCCATGGACATCCGGTG

CAACAACTGAAACTCCTACATGGAACCGAAAAGAACTGCTCGTCACTTTT
AAGAATGCCCATGCTAAAAAACAGGAGGTTGTCGTATTGGGTTCTCAGGA
AGGCGCAATGCATACTGCTCTTACAGGGGCCACCGAGATACAAAATTCAG
GGGGAACCAGCATCTTCGCAGGGCACTTGAAGTGTAGGCTGAAAATGGAC
AAGCTGGAGCTCAAGGGAATGAGTTACGCCATGTGCCTCAACACGTTTGT
TCTGAAAAAGGAGGTCAGCGAGACACAGCACGGAACAATACTGATTAAG
GTTGAGTATAAAGGAGAAGATGCCCCCTGCAAAATTCCTTTCAGCACCGA
AGACGGGCAAGGGAAAGCACACAACGGACGCCTGATTACTGCCAATCCC
GTCGTCACTAAGAAGGAGGAACCAGTGAATATTGAGGCCGAACCACCTTT
TGGGGAATCAACATTGTAATTGGGATTGAGACAAAGCATTGAAGATAA
ATTGGTACAAGAAGGGTTCATCTCTGGGCAAGGCTTTCGAGGCCACAGCG
AGAGGGGCAAGACGACTGGCCATTTTGGGGGATACAGCTTGGGACTTCGG
TAGCGTCGGCGGAGTGCTGAACTCCCTGGGGAAAATGGTGCACCAGATAT
TCGGTTCCGCCTACACTGCGCTGTTCTCTGGGGTTAGTTGGATTATGAAAA
TCGGTATCGGAGTGCTGCTCACGTGGATCGGACTCAACAGTAAGAACACC
TCTATGTCATTTAGTTGTATCGCAATTGGAATCATTACCTTGTATCTGGGA
GCCGTCGTGCAAGCCTAG

39. TVXD023 amino acid sequence with mutations
(SEQ ID NO: 39)
FHLTSRDGEPRMIVGKNERGKSLLFKTASGINMCTLIAMDLGEMCDDTVTY
KCPHIAEVEPEDIDCWCNLTSTWVTYGTCNQAGEHRRAKRSVALAPHVGMG
LDTRTQTWMSAEGAWRQVEKVETWALRHPGFTILALFLAHYIGTSLTQKVV
IFILLILVTPSMAMRCVGVGNRDFVEGLSGATWVDVVLEHGGCVTTMAKNK
PTLDIELQKTEATQLATLRKLCIEGKITNITTDSRCPTQGEAILPEEQDQN
YVCKHTYVDRGWGNGCGLFGKGSLVTCAKFQCLESIEGKVVQHENLKYTVI
ITVHTGDQHQVGNETQGVTAEITPQASTVEAILPEYGTLGLECSPRTGLDF
NEMILLTMKNKAWMVHRQWFFDLPLPWTSGATTETPTWNRKELLVTFKNAH
AKKQEVVVLGSQEGAMHTALTGATEIQNSGGTSIFAGHLKCRLKMDKLELK
GMSYAMCLNTFVLKKEVSETQHGTILIKVEYKGEDAPCKIPFSTEDGQGKA
HNGRLITANPVVTKKEEPVNIEAEPPFGESNIVIGIGDKALKINWYKKGSS
LGKAFEATARGARRLAILGDTAWDFGSVGGVLNSLGKMVHQIFGSAYTALF
SGVSWIMKIGIGVLLTWIGLNSKNTSMSFSCIAIGIITLYLGAVVQA Dengue virus 4 Strain P75215 Genbank EF457906

40. DEN-4 prME wild type nucleotide sequence (SEQ ID NO: 40)

TTCCACTTATCGTCAAGAGACGGCGAACCCCTCATGATAGTAGCGAAACA

CGAAAGGGGGAGACCTCTTTTGTTTAAGACAACGGAAGGAATCAACAGAT

GCACTCTCATTGCCATGGACGTGGGTGAAATGTGTGAGGACACCGTCACA

TATAAATGCCCCCTACTGGTCAACACTGAGCCTGAAGACATTGATTGCTG

GTGCAACTCCACATCCACTTGGGTCACGTATGGAACGTGTACCCAGAGTG

GGGAACGGAGACGGGAGAAGCGCTCAGTGGCACTGGCACCACATTCAGG

AATGGGATTGGAAACCAGGACAGAGACGTGGATGTCATCGGAGGGGGCA

TGGAAACATGCCCAGAGAGTGGAGAGCTGGATACTTAGAAATCCAGGATT

-continued

TGCACTCTTGGCAGGATTTATGGCTTACATGATTGGACAGACAGGAATTC

AACGAACAGTCTTCTTTGTCCTCATGATGTTGGTCGCTCCATCCTATGGAA

TGCGATGCGTGGGAGTGGGGAATAGAGATTTTGTGGAAGGAGTCTCAGGA

GGAACATGGGTCGACCTGGTGCTGGAACACGGAGGATGTGTTACAACCAT

GGCACAGGGAAAGCCAACCTTGGATTTTGAATTGATCAAGACAACAGCAA

AGGAGGTAGCTCTATTAAGAACTTATTGCATAGAGGCCTCAATATCAAAC

ATAACCACGGCAACAAGATGTCCAACACAAGGAGAACCTTATCTTAAAGA

GGAACAAGACCAGCAGTACATTTGCAGAAGAGACGTGGTAGACAGAGGA

TGGGGTAATGGCTGTGGCCTATTTGGAAAAGGAGGAGTTGTAACATGCGC

AAAGTTTTCATGCTCGGGGAAAATAACAGGCAACCTGGTCCAAGTTGAAA

ACCTTGAATACACAGTGGTTGTGACAGTTCATAATGGGGATGCCCACGCA

GTGGGAAACAGCACGTCCAATCATGGAGTAACAACCACAATAACCCCCAG

GTCACCATCGGTAGAAGTTAAACTACCAGATTATGGGGAACTGACACTCG

ATTGCGAACCCAGGTCCGGAATCGACTTTAACGAAATGATCCTGATGAAA

ATGAAAGGAAAAACATGGCTTGTGCACAAACAATGGTTCTTAGATCTACC

CCTGCCATGGACAGCAGGAGCTGACACATCAGAAGTCCATTGGAATTATA

AAGAGAGAATGGTGACGTTCAAAGTACCTCATGCCAAGAGACAGGATGTC

ACAGTGCTAGGATCCCAGGAAGGAGCCATGCACTCTGCCCTCACTGGAGC

TACGGAGGTGGATTCTGGTGACGGAAACCACATGTTTGCAGGGCACCTAA

AGTGCAAAGTGCGCATGGAAAAATTGAGGATCAAGGGAATGTCATACAC

GATGTGCTCAGGAAAGTTTTCCATCGACAAGGAAATGGCAGAAACGCAGC

ACGGGACAACAGTGGTGAAGGTCAAGTATGAAGGCACTGGGGCTCCATG

CAAAATTCCAATAGAAATAAAAGACATGAATAAGGAAAAAGTGGTTGGA

CGCATTATTTCATCTATTCCCTTTGCTGAAAACACCAACAGCATAACCAAT

ATTGAACTCGAACCCCCCTTTGGGGACAGCTACATAGTGATAGGCGCTGG

AGACAGTGCATTGACACTCCATTGGTTTAGGAAGGGAAGTTCTATCGGGA

AGATGTTTGAGTCCACTTATAGAGGTGCAAAAAGAATGGCCATTTTGGGT

GAAACAGCATGGGATTTTGGCTCCGTTGGTGGATTGTTTACATCATTAGGG

AAAGCTGTGCATCAGGTTTTTGGCAGTGTCTACACAACAATGTTTGGGGG

AGTCTCATGGATGATCAGAATTCTCATTGGGATTTTAGTATTGTGGATCGG

CACGAACTCAAGAAACACTTCAATGGCAATGTCATGCATAGCTGTTGGAG

GAATCACCTTATTTCTTGGTTTTACGGTCCAAGCA

41. DEN-4 prME wild type amino acid sequence (SEQ ID NO: 41)

MIVAKHERGRPLLFKTTEGINRCTLIAMDVGEMCEDTVTYKCPLLVNTEPE

DIDCWCNSTSTWVTYGTCTQSGERRREKRSVALAPHSGMGLETRTETWMSS

EGAWKHAQRVESWILRNPGFALLAGFMAYMIGQTGIQRTVFFVLMMLVAPS

YGMRCVGVGNRDFVEGVSGGTWVDLVLEHGGCVTTMAQGKPTLDFELIKTT

AKEVALLRTYCIEASISNITTATRCPTQGEPYLKEEQDQQYICRRDVVDRG

WGNGCGLFGKGGVVTCAKFSCSGKITGNLVQVENLEYTVVVTVHNGDAHAV

GNSTSNHGVTTTITPRSPSVEVKLPDYGELTLDCEPRSGIDFNEMILMKMK

```
GKTWLVHKQWFLDLPLPWTAGADTSEVEIWNYKERMVTFKVPHAKRQDVTV

LGSQEGAMHSALTGATEVDSGDGNHMFAGHLKCKVRMEKLRIKGMSYTMCS

GKFSIDKEMAETQHGTTVVKVKYEGTGAPCKIPIEIKDMNKEKVVGRIISS

IPFAENTNSITNIELEPPFGDSYIVIGAGDSALTLHWFRKGSSIGKMFEST

YRGAKRMAILGETAWDFGSVGGLFTSLGKAVHQVFGSVYTTMFGGVSWMIR

ILIGILVLWIGTNSRNTSMAMSCIAVGGITLFLGFTVQA
```

42. TVXD024 (Capsid of DENV-2 and prME of DENV-4)
Codon Optimized nucleotide sequence with mutations
(SEQ ID NO: 42)
```
ATGAACAACCAGCGCAAGAAGGCCAAAAACACTCCGTTCAATATGCTCAA

GAGAGAGCGCAATCGGGTTTCTACGGTACAGCAGCTGACGAAGAGATTCT

CCCTGGGCATGCTGCAAGGTCGCGGACCACTGAAGCTGTTCATGGCCCTT

GTTGCATTTCTTAGGTTTCTTACAATTCCCCCCACTGCTGGAATCCTGAAG

CGGTGGGGCACCATCAAAAAGTCCAAGGCTATTAATGTCCTCAGGGGGTT

CAGGAAAGAGATTGGGCGGATGCTGAACATCCTTAATAGACGCAGACGGT

CCGCTGGCATGATAATCATGCTGATCCCAACCGTCATGGCCTTTCATCTCA

GCTCCCGCGATGGAGAACCTTTGATGATAGTCGCAAAACACGAACGGGGC

AGGCCACTGCTTTTCAAGACTACTGAAGGCATCAACCGCTGCACCCTGAT

CGCAATGGACGTGGGTGAGATGTGCGAGGATACCGTGACTTATAAGTGCC

CACTTCTCGTAAACACAGAGCCAGAAGACATTGATTGTTGGTGCAATTCT

ACCTCTACCTGGGTAACCTATGGAACTTGCACACAAAGCGGAGAAAGGAG

AAGAGCCAAGCGGAGCGTTGCTCTGGCACCGCATTCCGGAATGGGACTTG

AAACTAGAACAGAAACTTGGATGAGTAGCGAAGGAGCCTGGAAACATGC

CCAACGGGTGGAAAGCTGGATTCTGCGCAACCCTGGATTCGCACTGCTTG

CCGGTTTTATGGCATACATGATTGGACAGACCGGAATCCAGAGAACCGTT

TTCTTTGTACTGATGATGCTGGTGGCTCCCTCTTATGGAATGCGATGTGTC

GGCGTGGGCAATCGAGATTTTGTGGAAGGGGTCAGCGGGGGCACTTGGGT

GGACCTCGTGCTGGAGCATGGAGGATGCGTTACAACCATGGCCCAAGGAA

AACCTACACTTGATTTTGAACTGATAAAGACAACAGCTAAGGAAGTAGCC

CTGTTGCGCACCTACTGTATCGAAGCTAGTATCTCTAACATCACTACAGCA

ACACGGTGCCCAACTCAGGGAGAACCCTATTTGAAGGAGGAGCAAGATC

AGCAGTATATCTGTCGCCGAGATGTCGTGGACCGAGGATGGGGGAACGGC

TGCGGGCTTTTTGGAAAAGGAGGCGTCGTGACCTGTGCTAAATTCAGTTGT

TCAGGAAAGATTACGGGGAACCTCGTGCAGGTGGAGAACCTGGAATACA

CGGTGGTAGTAACAGTTCATAATGGGGACGCACACGCCGTAGGAAATAGC

ACCTCCAACCACGGCGTTACCACTACAATTACACCTAGAAGCCCTTCCGTG

GAAGTTAAGCTGCCTGATTATGGGGAGCTCACCCTTGATTGCGAGCCCAG

AAGTGGCATTGACTTTAACGAAATGATACTCATGAAGATGAAAGGAAAAA

CCTGGCTGGTACATAAACAGTGGTTCCTCGACCTTCCGCTCCCATGGACAG

CAGGAGCCGACACCTCCGAGGTTCATTGGAATTACAAAGAGAGAATGGTT

ACTTTCAAGGTGCCACATGCGAAGCGCCAGGATGTGACAGTACTGGGATC

CCAAGAAGGCGCCATGCACTCTGCCCTGACAGGCGCTACTGAGGTGGACT
```

```
CCGGCGATGGAAATCACATGTTCGCGGGCCATCTGAAGTGTAAAGTAAGG

ATGGAGAAGCTGCGAATCAAAGGAATGTCCTATACGATGTGTTCAGGTAA

GTTTTCTATTGACAAAGAAATGGCAGAAACCCAACATGGTACTACTGTGG

TGAAGGTGAAATATGAAGGAACTGGAGCTCCATGTAAAATACCGATCGAG

ATCAAAGACATGAATAAGGAGAAAGTTGTGGGAAGAATCATAAGCAGCA

TTCCTTTTGCTGAGAATACTAACTCTATCACAAATATAGAACTTGAACCTC

CGTTCGGTGATTCCTACATAGTAATCGGAGCCGGCGATTCAGCACTTACTC

TGCACTGGTTCAGAAAAGGAAGTTCACTCGGAAAGGCTTTTGAGTCAACA

TATAGGGGCGCAAAGAGACTTGCAATTCTTGGGGAAACAGCTTGGGATTT

CGGGAGCGTCGGTGGTCTGTTTACTTCCCTTGGAAAGGCGGTTCATCAAGT

GTTTGGCTCAGTATACACCACAATGTTTGGGGGAGTGAGTTGGATGATCC

GCATTCTTATCGGTATACTTGTGCTGTGGATTGGAACAAATTCAAGAAATA

CCAGTATGGCAATGTCATGTATTGCTGTGGGGGGATAACTTTGTTTCTCG

GGTTTACCGTGCAGGCATAG
```

43. TVXD024 amino acid sequence
(SEQ ID NO: 43)
```
MNNQRKKAKNTPFNMLKRERNRVSTVQQLTKRFSLGMLQGRGPLKLFMALV

AFLRFLTIPPTAGILKRWGTIKKSKAINVLRGFRKEIGRMLNILNRRRRSA

GMIIMLIPTVMAFHLSSRDGEPLMIVAKHERGRPLLFKTTEGINRCTLIAM

DVGEMCEDTVTYKCPLLVNTEPEDIDCWCNSTSTWVTYGTCTQSGERRRAK

RSVALAPHSGMGLETRTETWMSSEGAWKHAQRVESWILRNPGFALLAGFMA

YMIGQTGIQRTVFFVLMMLVAPSYGMRCVGVGNRDFVEGVSGGTWVDLVLE

HGGCVTTMAQGKPTLDFELIKTTAKEVALLRTYCIEASISNITTATRCPTQ

GEPYLKEEQDQQYICRRDVVDRGWGNGCGLFGKGGVVTCAKFSCSGKITGN

LVQVENLEYTVVVTVHNGDAHAVGNSTSNHGVTTTITPRSPSVEVKLPDYG

ELTLDCEPRSGIDFNEMILMKMKGKTWLVHKQWFLDLPLPWTAGADTSEVH

WNYKERMVTFKVPHAKRQDVTVLGSQEGAMHSALTGATEVDSGDGNHMFAG

HLKCKVRMEKLRIKGMSYTMCSGKFSIDKEMAETQHGTTVVKVKYEGTGAP

CKIPIEIKDMNKEKVVGRIISSIPFAENTNSITNIELEPPFGDSYIVIGAG

DSALTLHWFRKGSSLGKAFESTYRGAKRLAILGETAWDFGSVGGLFTSLGK

AVHQVFGSVYTTMFGGVSWMIRILIGILVLWIGTNSRNTSMAMSCIAVGGI

TLFLGFTVQA
```

ZIKA
44. ZIKV NS2B/NS3Pro wild-type nucleotide sequence
(SEQ ID NO: 44)
```
AGCTGGCCCCCTAGCGAAGTACTCACAGCTGTTGGCCTGATATGCGCATT

GGCTGGAGGGTTCGCCAAGGCAGATATAGAGATGGCTGGGCCCATGGCCG

CGGTCGGTCTGCTAATTGTCAGTTACGTGGTCTCAGGAAAGAGTGTGGAC

ATGTACATTGAAAGAGCAGGTGACATCACATGGGAAAAAGATGCGGAAG

TCACTGGAAACAGTCCCCGGCTCGATGTGGCGCTAGATGAGAGTGGTGAT

TTCTCCCTGGTGGAGGATGACGGTCCCCCCATGAGAGAGATCATACTCAA

GGTGGTCCTGATGACCATCTGTGGCATGAACCCAATAGCCATACCCTTTGC

AGCTGGAGCGTGGTACGTATACGTGAAGACTGGAAAAAGGAGTGGTGCTC
```

TATGGGATGTGCCTGCTCCCAAGGAAGTAAAAAAGGGGGAGACCACAGA

TGGAGTGTACAGAGTAATGACTCGTAGACTGCTAGGTTCAACACAAGTTG

GAGTGGGAGTTATGCAAGAGGGGGTCTTTCACACTATGTGGCACGTCACA

AAAGGATCCGCGCTGAGAAGCGGTGAAGGGAGACTTGATCCATACTGGG

GAGATGTCAAGCAGGATCTGGTGTCATACTGTGGTCCATGGAAGCTAGAT

GCCGCCTGGGACGGGCACAGCGAGGTGCAGCTCTTGGCCGTGCCCCCGG

AGAGAGAGCGAGGAACATCCAGACTCTGCCCGGAATATTTAAGACAAAG

GATGGGACATTGGAGCGGTTGCGCTGGATTACCCAGCAGGAACTTCAGG

ATCTCCAATCCTAGACAAGTGTGGGAGAGTGATAGGACTTTATGGCAATG

GGGTCGTGATCAAAAATGGGAGTTATGTTAGTGCCATCACCCAAGGGAGG

AGGGAGGAAGAGACTCCTGTTGAGTGCTTCGAG

45. ZIKV NS3 Helicase wild type nucleotide sequence
(SEQ ID NO: 45)

CCTTCGATGCTGAAGAAGAAGCAGCTAACTGTCTTAGACTTGCATCCTGG

AGCTGGGAAAACCAGGAGAGTTCTTCCTGAAATAGTCCGTGAAGCCATAA

AAACAAGACTCCGTACTGTGATCTTAGCTCCAACCAGGGTTGTCGCTGCTG

AAATGGAGGAAGCCCTTAGAGGGCTTCCAGTGCGTTATATGACAACAGCA

GTCAATGTCACCCACTCTGGAACAGAAATCGTCGACTTAATGTGCCATGC

CACCTTCACTTCACGTCTACTACAGCCAATCAGAGTCCCCAACTATAATCT

GTATATTATGGATGAGGCCCACTTCACAGATCCCTCAAGTATAGCAGCAA

GAGGATACATTTCAACAAGGGTTGAGATGGGCGAGGCGGCTGCCATCTTC

ATGACCGCCACGCCACCAGGAACCCGTGACGCATTTCCGGACTCCAACTC

ACCAATTATGGACACCGAAGTGGAAGTCCCAGAGAGAGCCTGGAGCTCA

GGCTTTGATTGGGTGACGGATCATTCTGGAAAAACAGTTTGGTTTGTTCCA

AGCGTGAGGAACGGCAATGAGATCGCAGCTTGTCTGACAAAGGCTGAA

AACGGGTCATACAGCTCAGCAGAAAGACTTTTGAGACAGAGTTCCAGAAA

ACAAAACATCAAGAGTGGGACTTTGTCGTGACAACTGACATTTCAGAGAT

GGGCGCCAACTTTAAAGCTGACCGTGTCATAGATTCCAGGAGATGCCTAA

AGCCGGTCATACTTGATGGCGAGAGAGTCATTCTGGCTGGACCCATGCCT

GTCACACATGCCAGCGCTGCCCAGAGGAGGGGCGCATAGGCAGGAATC

CCAACAAACCTGGAGATGAGTATCTGTATGGAGGTGGGTGCGCAGAGACT

GACGAAGACCATGCACACTGGCTTGAAGCAAGAATGCTCCTTGACAATAT

TTACCTCCAAGATGGCCTCATAGCCTCGCTCTATCGACCTGAGGCCGACAA

AGTAGCAGCCATTGAGGGAGAGTTCAAGCTTAGGACGGAGCAAAGGAAG

ACCTTTGTGGAACTCATGAAAAGAGGAGATCTTCCTGTTTGGCTGGCCTAT

CAGGTTGCATCTGCCGGAATAACCTACACAGATAGAAGATGGTGCTTTGA

TGGCACGACCAACAACACCATAATGGAAGACAGTGTGCCGGCAGAGGTG

TGGACCAGACACGGAGAGAAAAGAGTGCTCAAACCGAGGTGGATGGACG

CCAGAGTTTGTTCAGATCATGCGGCCCTGAAGTCATTCAAGGAGTTTGCCG

CTGGGAAAAGA

46. ZIKV NS3 Helicase wild type amino acid sequence
(SEQ ID NO: 46)

PSMLKKKQLTVLDLHPGAGKTRRVLPEIVREAIKTRLRTVILAPTRVVAAE

MEEALRGLPVRYMTTAVNVTHSGTEIVDLMCHATFTSRLLQPIRVPNYNLY

IMDEAHFTDPSSIAARGYISTRVEMGEAAAIFMTATPPGTRDAFPDSNSPI

MDTEVEVPERAWSSGFDWVTDHSGKTVWFVPSVRNGNEIAACLTKAGKRVI

QLSRKTFETEFQKTKHQEWDFVVTTDISEMGANFKADRVIDSRRCLKPVIL

DGERVILAGPMPVTHASAAQRRGRIGRNPNKPGDEYLYGGGCAETDEDHAH

WLEARMLLDNIYLQDGLIASLYRPEADKVAAIEGEFKLRTEQRKTFVELMK

RGDLPVWLAYQVSAGITYTDRRWCFDGTTNNTIMEDSVPAEVWTRHGEKR

VLKPRWMDARVCSDHAALKSFKEFAAGKR

47. DEN-2 E protein wild-type amino acid sequence
(SEQ ID NO: 47)

MRCIGMSNRDFVEGVSGGSWVDIVLEHGSCVTTMAKNKPTLDFELIKTEAK

QPATLRKYCIEAKLTNTTTESRCPTQGEPSLNEEQDKRFVCKHSMVDRGWG

NGCGLFGKGGIVTCAMFRCKKNMEGKVVQPENLEYTIVITPHSGEEHAVGN

DTGKHGKEIKITPQSSITEAELTGYGTVTMECSPRTGLDFNEMVLLQMENK

AWLVHRQWFLDLPLPWLPGADTQGSNWIQKETLVTFKNPHAKKQDVVVLGS

QEGAMHTALTGATEIQMSSGNLLFTGHLKCRLRMDKLQLKGMSYSMCTGKF

KVVKEIAETQHGTIVIRVQYEGDGSPCKIPFEIMDLEKRHVLGRLITVNPI

VTEKDSPVNIEAEPPFGDSYIIIGVEPGQLKLNWFKKGSSIGQMFETTMRG

AKRMAILGDTAWDFGSLGGVFTSIGKALHQVFGAIYGAAFSGVSWTMKILI

GVIITWIGMNSRSTSLSVTLVLVGIVTLYLGVMVQA

---

What is claimed is:

1. A virus-like particle (VLP) comprising at least one flavivirus structural protein; and at least one non-structural flavivirus protein, wherein the at least one non-structural flavivirus protein comprises a truncated NS3 protein co-expressed with a truncated NS2B protein.

2. The VLP of claim 1, wherein the at least one structural protein comprises one or more of CPrME.

3. The VLP of claim 1, wherein the at least one structural protein consists of CPrME, PrME, CME, CPrE or ME.

4. The VLP of claim 1, wherein the truncated NS3 protein co-expressed with the truncated NS2B protein has a nucleotide sequence of SEQ ID NO: 8.

5. The VLP of claim 1, wherein the flavivirus is Dengue, Zika, yellow fever, Japanese encephalitis and/or West Nile virus.

6. The VLP of claim 1, wherein the VLP is: (i) a single bivalent VLP that displays on its surface an E antigen of two flavivirus virus serotypes or clades; or (ii) a multivalent VLP that displays on its surface an E antigen of multiple flavivirus serotypes or clades.

7. The VLP of claim 6, wherein the VLP comprises E antigens from at least two different flaviviruses.

8. A DNA construct comprising sequences encoding flavivirus viral proteins used to assemble the VLP of claim 1, the DNA construct comprising sequences encoding the at least one structural protein and at least one non-structural protein, wherein the at least one non-structural protein is operably linked directly to the at least one structural protein, and wherein the at least one structural protein consists of CprME, wherein the CprME comprises an amino acid sequence of SEQ ID NO: 2.

9. The DNA construct of claim 8, further comprising one or more sequences encoding a linker between one or more of the sequences encoding the structural and non-structural proteins.

10. The DNA construct of claim 9, wherein the linker comprises amino acids corresponding to amino acids 1 to 8 or 9 or 10 of NS1 (nucleotide sequence SEQ ID NO: 14 and amino acid sequence SEQ ID NO: 15) and amino acids corresponding to 186 or 187 or 188 or 189 to amino acids corresponding to 218 of NS2A (nucleotide sequence SEQ ID NO: 16 and amino acid sequence SEQ ID NO: 17); amino acid 1 to 8 or 9 or 10 of NS1(SEQ ID NO: 14), amino acids 1 to 24 or 25 or 26 or 27 or 10 28 or 29 or 30 or 31 or 32 of NS2A, amino acids 186 or 187 or 188 or 189 to 218 of NS2A (SEQ ID NO: 16); amino acids 190 or 191 or 192 or 193 to amino acids corresponding to 225 of NS2A (SEQ ID NO: 16); amino acids 190 or 191 or 192 or 193 to amino acids 225 of NS2A (SEQ ID NO: 16); amino acids 1 to 8 or 9 or 10 of NS1 (SEQ ID NO: 14) and the second transmembrane domain of NS2B (nucleotide sequence SEQ ID NO: 10 and amino acid sequence SEQ ID NO: 11); amino acid 1 to 8 or 9 or 10 of NS1 (SEQ ID NO: 14) and the first transmembrane domain of NS2A (amino acid 51 to 100 of nucleotide sequence SEQ ID NO: 16 and amino acid sequence SEQ ID NO: 17); and amino acid 1 to 8 or 9 or 10 of NS1 (SEQ ID NO: 14) and the C terminal portion of NS2B comprising the second transmembrane domain to the end of the protein (nucleotide sequence SEQ ID NO: 10 and amino acid sequence SEQ ID NO:11).

11. The DNA construct of claim 8, wherein the at least one non-structural protein comprises an NS3 of a dengue virus having a protease active site and wherein the NS3 protease active site is modified via a substitution of amino acid leucine at position 115 and thereby comprises an amino acid sequence of SEQ ID NO: 9, and wherein enzymatic activity of the NS3 protease active site is enhanced relative to enzymatic activity at an NS3 protease of a dengue virus without such modification at its active site.

12. The DNA construct of claim 8, wherein the CprME comprises an amino acid sequence of SEQ ID NO: 5, which comprises a pr protein and an M protein, and a furin protease cleavage site between the pr protein and the M protein, and wherein the furin protease cleavage site is modified by substituting amino acids residues at position P3 with a hydrophobic amino acid such that furin cleavage is enhanced, relative to furin cleavage at an unmodified cleavage site, and wherein the pr protein and the M protein are from a dengue virus.

13. The DNA construct of any of claims 8 to 10, wherein the sequence encoding the E protein is modified to enhance VLP assembly and release relative to VLP assembly and release with an unmodified E antigen, and wherein the E antigen is from a dengue virus and wherein the E antigen comprises an amino acid sequence of SEQ ID NO:47 that is modified at one or more of positions 398, 401, and 412.

14. A method of producing a VLP, the method comprising introducing into a host cell one or more DNA constructs according to claim 8 under conditions such that the cell produces the VLP.

15. The method of claim 14, wherein the host cell is a eukaryotic cell selected from the group consisting of mammalian, yeast, insect, plant, amphibian and avian cells.

16. An immunogenic composition comprising at least one VLP according to claim 1.

17. The immunogenic composition of claim 16, further comprising an adjuvant.

18. The immunogenic composition of claim 16, wherein the composition comprises at least two VLPs comprising different flavivirus E proteins.

* * * * *